United States Patent
Takahashi et al.

(10) Patent No.: US 12,297,268 B2
(45) Date of Patent: May 13, 2025

(54) ANTIBODY WHICH BINDS TO MYELIN OLIGODENDROCYTE GLYCOPROTEIN

(71) Applicants: Kyowa Kirin Co., Ltd., Tokyo (JP); KAGOSHIMA UNIVERSITY, Kagoshima (JP)

(72) Inventors: Nobuaki Takahashi, Tokyo (JP); Ryosuke Nakano, Tokyo (JP); Sayaka Maeda, Tokyo (JP); Yuji Ito, Kagoshima (JP)

(73) Assignees: KYOWA KIRIN CO., LTD., Tokyo (JP); KAGOSHIMA UNIVERSITY, Kagoshima (JP)

( * ) Notice: Subject to any disclaimer, the term of this patent is extended or adjusted under 35 U.S.C. 154(b) by 104 days.

(21) Appl. No.: 18/363,113

(22) Filed: Aug. 1, 2023

(65) Prior Publication Data

US 2024/0124577 A1  Apr. 18, 2024

Related U.S. Application Data

(60) Continuation of application No. 17/399,354, filed on Aug. 11, 2021, now abandoned, which is a division of application No. 16/473,482, filed as application No. PCT/JP2017/046445 on Dec. 25, 2017, now Pat. No. 11,117,963.

(30) Foreign Application Priority Data

Dec. 26, 2016  (JP) ................ 2016-251106

(51) Int. Cl.
C07K 16/28 (2006.01)
A61K 47/10 (2017.01)
A61K 47/36 (2006.01)
C12N 5/12 (2006.01)
G01N 33/563 (2006.01)

(52) U.S. Cl.
CPC .......... *C07K 16/2803* (2013.01); *A61K 47/10* (2013.01); *A61K 47/36* (2013.01); *C12N 5/12* (2013.01); *G01N 33/563* (2013.01); *C07K 2317/24* (2013.01); *C07K 2317/31* (2013.01); *C07K 2317/565* (2013.01)

(58) Field of Classification Search
None
See application file for complete search history.

(56) References Cited

U.S. PATENT DOCUMENTS

| 6,333,033 | B1 | 12/2001 | Genain et al. |
| 2002/0068058 | A1 | 6/2002 | Genain et al. |
| 2002/0072588 | A1 | 6/2002 | Budingen et al. |

FOREIGN PATENT DOCUMENTS

| CA | 2 623 841 | 4/2007 |
| JP | 5-170667 | 7/1993 |
| JP | 9-502346 | 3/1997 |
| JP | 2002-523472 | 7/2002 |
| JP | 2004-511570 | 4/2004 |
| WO | 95/06727 | 3/1995 |
| WO | 95/07096 | 3/1995 |
| WO | 2006/116155 | 11/2006 |
| WO | 2007/036021 | 4/2007 |
| WO | 2012/023623 | 2/2012 |
| WO | 2014/033074 | 3/2014 |
| WO | 2016/081640 | 5/2016 |
| WO | 2016/081643 | 5/2016 |

OTHER PUBLICATIONS

Office Action issued Mar. 20, 2024 in corresponding European Patent Application No. 17885914.6.
Dondelinger, M. et al., "Understanding the Significance and Implications of Antibody Numbering and Antigen-Binding Surface/Residue Definition", 2018, Frontiers in Immunology, vol. 9, Article 2278, pp. 1-15.
Rogers et al., "Therapeutic monoclonal antibodies and derivatives: Historical perspectives and future directions", Biotechnology Advances, 34: 1149-1158 (2016).
Partridge, "Re-Engineering Biopharmaceuticals for Delivery to Brain with Molecular Trojan Horses", Bioconjugate Chemistry, 19(7): 1327-1338 (2008).
Wang et al., "Monoclonal Antibody Pharmacokinetics and Pharmacodynamics", Clin. Pharma. Ther., 84(5): 548-558 (2008).
Garg et al., "Investigation of the Influence of FcRn on the Distribution of IgG to the Brain", The AAPS Journal, 11(3): 553-557 (2009).
Blennow et al., "Effect of Immunotherapy with Bapineuzumab on Cerebrospinal Fluid Biomarker Levels in Patients With Mild to Moderate Alzheimer Disease", Arch Neurol, 69(8): 1002-1010 (2012).
Wraith et al., "Enzyme Replacement Therapy for Mucopolysaccharidosis I: A randomized, double-blinded, placebo-controlled, multinational study of recombinant human a-L-Iduronidase (Laronidase)", J. Pediatrics, 144(5): 581-588 (2004).

(Continued)

*Primary Examiner* — Kimberly Ballard
*Assistant Examiner* — Stacey N Macfarlane
(74) *Attorney, Agent, or Firm* — Wenderoth, Lind & Ponack, L.L.P.

(57) ABSTRACT

The invention relates to an antibody which binds to myelin oligodendrocyte glycoprotein (MOG), an antibody fragment thereof, a hybridoma which produces the antibody or the antibody fragment, a nucleic acid containing a nucleotide sequence which encodes the antibody or the antibody fragment, a transformant cell containing a vector containing the nucleic acid, a method for producing the antibody or the antibody fragment, a composition containing the antibody or the antibody fragment and a method for detecting or measuring an antigen that is present in the brain, a method for diagnosing or treating a brain disease, a method for improving the property of an antibody of accumulating in the brain and a method for increasing the amount of an antibody in the brain which use the antibody or the antibody fragment.

12 Claims, 27 Drawing Sheets

Specification includes a Sequence Listing.

(56) References Cited

OTHER PUBLICATIONS

Muenzer et al., "A phase II/III clinical study of enzyme replacement therapy with idursulfase in mucopolysaccharidosis II (Hunter Syndrome)", Genetics in Medicine 8(8): 465-473 (2006).
Document attached to intravenous infusion 2.9 mg of Aldurazyme (registered trademark) (Jul. 2016, 8th edition), with partial English translation.
Document attached to intravenous infusion 6 mg of Elaprase (registered trademark) (Jul. 2016, 6th edition), with partial English translation.
Brooks et al., "Significance of immune response to enzyme-replacement therapy for patients with a lysosomal storage disorder", Trends in Molecular Medicine, 9(10): 450-453 (2003).
Sorrentino et al., "Brain Targeting in MPS-IIIA", Pediatric Endocrinology Reviews (PER), 13(Supplement 1): 630-638 (2016).
Couch et al., "Addressing Safety Liabilities of TfR Bispecific Antibodies That Cross the Blood-Brain Barrier", Science Translation Medicine, 5(183): 1-12 (2013).
Yu et al., "Therapeutic bispecific antibodies cross the blood-brain barrier in nonhuman primates", Science Translation Medicine, 6(261): 1-10 (2014).
Niewoehner et al., "Increased Brain Penetration and Potency of a Therapeutic Antibody Using a Monovalent Molecular Shuttle", Neuron, 81: 49-60 (2014).
Yue et al., Fluorescence-Labeled Immunomicelles: Preparation, in vivo Biodistribution, and Ability to Cross the Blood-Brain Barrier, Macromol. Biosci., 12: 1209-1219 (2012).
Partridge et al., "Reengineering Biopharmaceuticals for Targeted Delivery Across the Blood-Brain Barrier", Methods in Enzymology, 503: 269-292 (2012).
Boado et al., "Comparison of Blood-Brain Barrier Transport of Glial-Derived Neurotrophic Factor (GDNF) and an IgG- GDNF Fusion Protein in the Rhesus Monkey", Drug Metabolism and Disposition, 37(12): 2299-2304 (2009).
Boado et al., "Drug Targeting in Erythropoietin Across the Primate Blood-Brain Barrier with an IgG Molecular Trojan Horse", The Journal of Pharmacology and Experimental Therapeutics, 333(3): 961-969 (2010).
Boado et al., "IgG-Enzyme Fusion Protein: Pharmacokinetics and Anti-Drug Antibody Response in Rhesus Monkeys", Bioconjugate Chemistry, 24: 97-104 (2013).
Zhang et al., "Delivery of ß-Galactosidase to Mouse Brain via the Blood-Brain Barrier Transferrin Receptor", The Journal of Pharmacology and Experimental Therapeutics, 313(3): 1075-1081 (2005).
Abulrob et al., "The blood-brain barrier transmigrating single domain antibody: mechanisms of transport and antigenic epitopes in human brain endothelial cells", Journal of Neurochemistry, 95: 1201-1214 (2005).
Farrington et al., "A novel platform for engineering blood-brain barrier-crossing bispecific biologics", The FASEB Journal, 28: 4764-4778 (2014).
Webster et al., "Brain penetration, target engagement, and disposition of the blood-brain barrier-crossing bispecific antibody antagonist of metabotropic glutamate receptor type 1", The FASEB Journal, 30: 1927-1940 (2016).
Zhang et al., "Mediated efflux of IgG molecules from brain to blood across the blood-brain barrier", Journal of Neuroimmunology, 114: 168-172 (2001).
Cooper et al., "Efflux of monoclonal antibodies from rat brain by neonatal Fc receptor, FcRn", Brain Research, 1534: 13-21 (2013).
Brunner et al., "Differential Ultrastructural Localization of Myelin Basic Protein, Myelin/Oligodendroglial Glycoprotein, and 2',3'-Cyclic Nucleotide 3'-Phosphodiesterase in the CNS of Adult Rats", Journal of Neurochemistry, 52(1): 296-304 (1989).
Pham-Dinh et al., "Myelin/oligodendrocyte glycoprotein is a member of a subset of the immunoglobulin superfamily encoded within the major histocompatibility complex", Proc. Natl. Acad. Sci. USA, 90: 7990-7994 (1993).
Gardinier et al., "Myelin/Oligodendrocyte Glycoprotein Is a Unique Member of the Immunoglobulin Superfamily", Journal of Neuroscience Research, 33: 177-187 (1992).
Urich et al., Autoantibody-mediated demyelination depends on complement activation but not activatory Fc-receptors, PNAS, 103(49): 18697-18702 (2006).
Reindl et al., "Antibodies against the myelin oligodendrocyte glycoprotein and the myelin basic protein in multiple sclerosis and other neurological diseases: a comparative study", Brain, 122: 2047-2056 (1999).
Shimizu et al., "Disruption of blood-brain barrier in multiple sclerosis and neuromyelitis optica", Nippon Rinsho, 72(11): 1949-1954 (2014).
Sinmaz et al., "Autoantibodies in movement and psychiatric disorders: updated concepts in detection methods, pathogenicity, and CNS entry", Annals of the New York Academy of Sciences, 1351: 22-38 (2015).
Quintana et al., "Antigen microarrays identify CNS-produced autoantibodies in RRMS", Neurology, 78: 532-539 (2012).
Gold et al., "Understanding pathogenesis and therapy of multiple sclerosis via animal models: 70 years of merits and culprits in experimental autoimmune encephalomyelitis research", Brain, 129: 1953-1971 (2006).
Morris-Downes et al., "Pathological and regulatory effects of anti-myelin antibodies in experimental allergic encephalomyelitis in mice", Journal of Neuroimmunology, 125: 114-124 (2002).
Locatelli et al., "Primary oligodendrocyte death does not elicit anti-CNS immunity", Nature Neuroscience, 15(4): 543-551 (2012).
Schluesener et al., "A monoclonal antibody against a myelin oligodendrocyte glycoprotein induces relapses and demyelination in central nervous system autoimmune disease", The Journal of Immunology, 139(12): 4016-4021 (1987).
Tokuhara et al., "N-type Calcium Channel in the Pathogenesis of Experimental Autoimmune Encephalomyelitis", Journal of Biological Chemistry, 285(43): 33294-33306 (2010).
International Search Report (ISR) and Written Opinion of the International Searching Authority, Issued Mar. 27, 2018 in corresponding International Patent Application No. PCT/JP2017/046445, with English language translation of the ISR.
Extended European Search Report issued Nov. 25, 2020 in corresponding European Patent Application No. 17885914.6.
Von Budingen et al., "Molecular characterization of antibody specificities against myelin/oligodendrocyte glycoprotein in autoimmune demyelination", PNAS 99(12):8207-8212 (2002).
Nakano et al., "A new technology for increasing therapeutic protein levels in the brain over extended periods", PLOS ONE 14(4): e0214404, pp. 1-16 (2019).
Rudikoff et al., Proc Natl Acad Sci, USA, 1982, vol. 79, p. 1979 (Year: 1982).

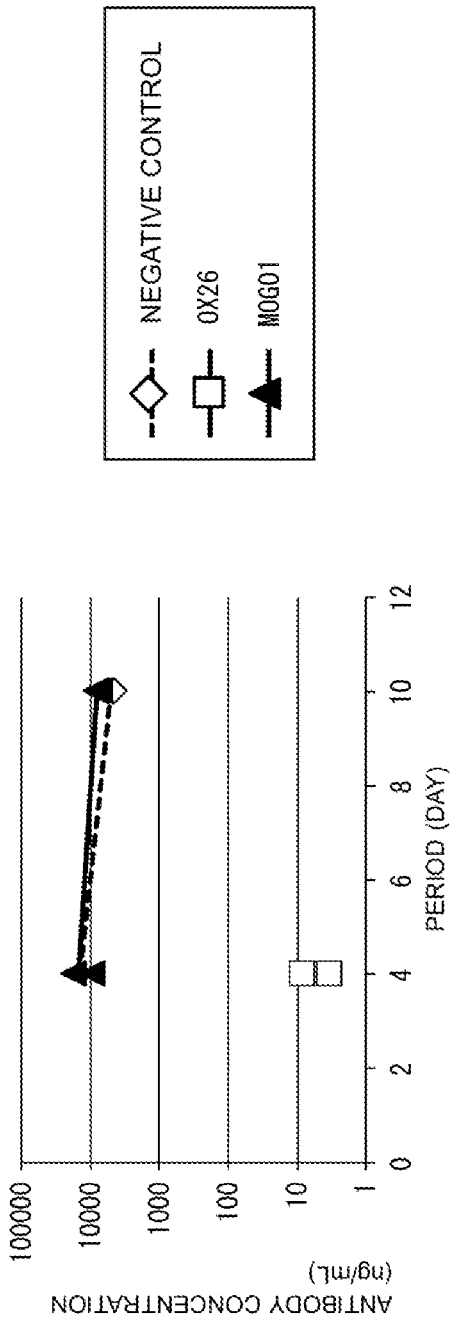
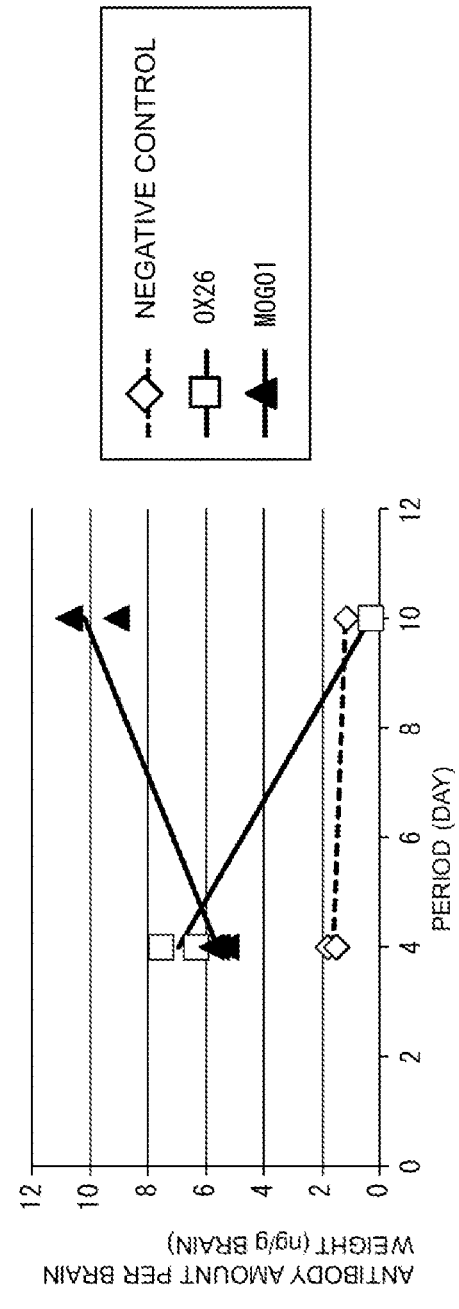

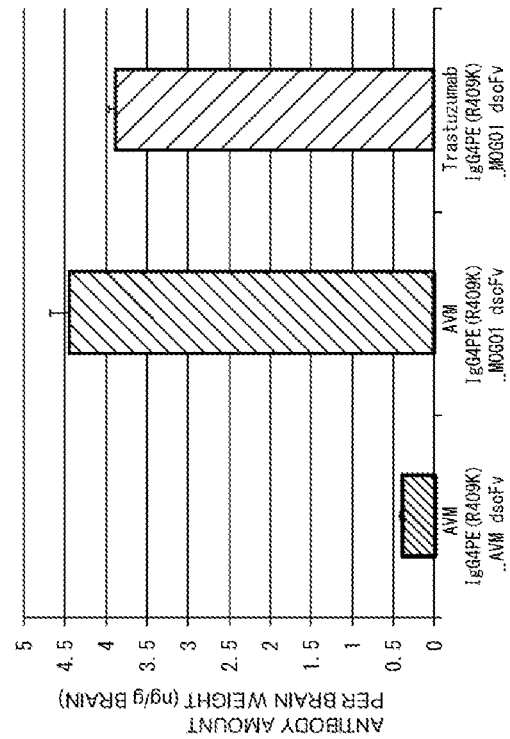
Fig. 7B BRAIN
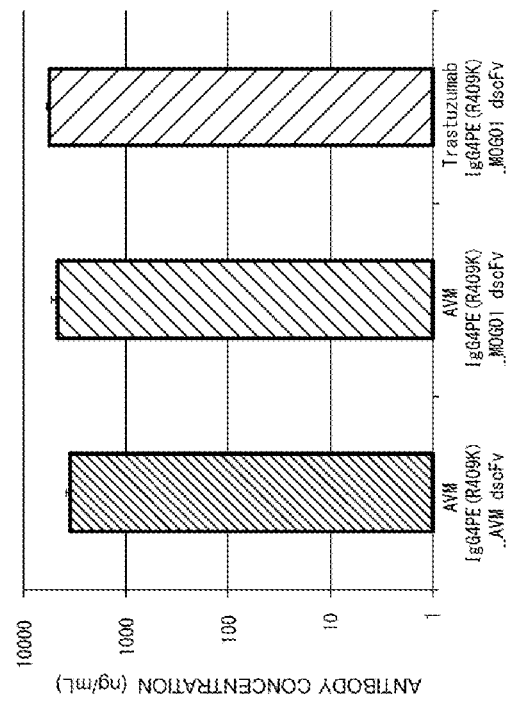
Fig. 7A SERUM

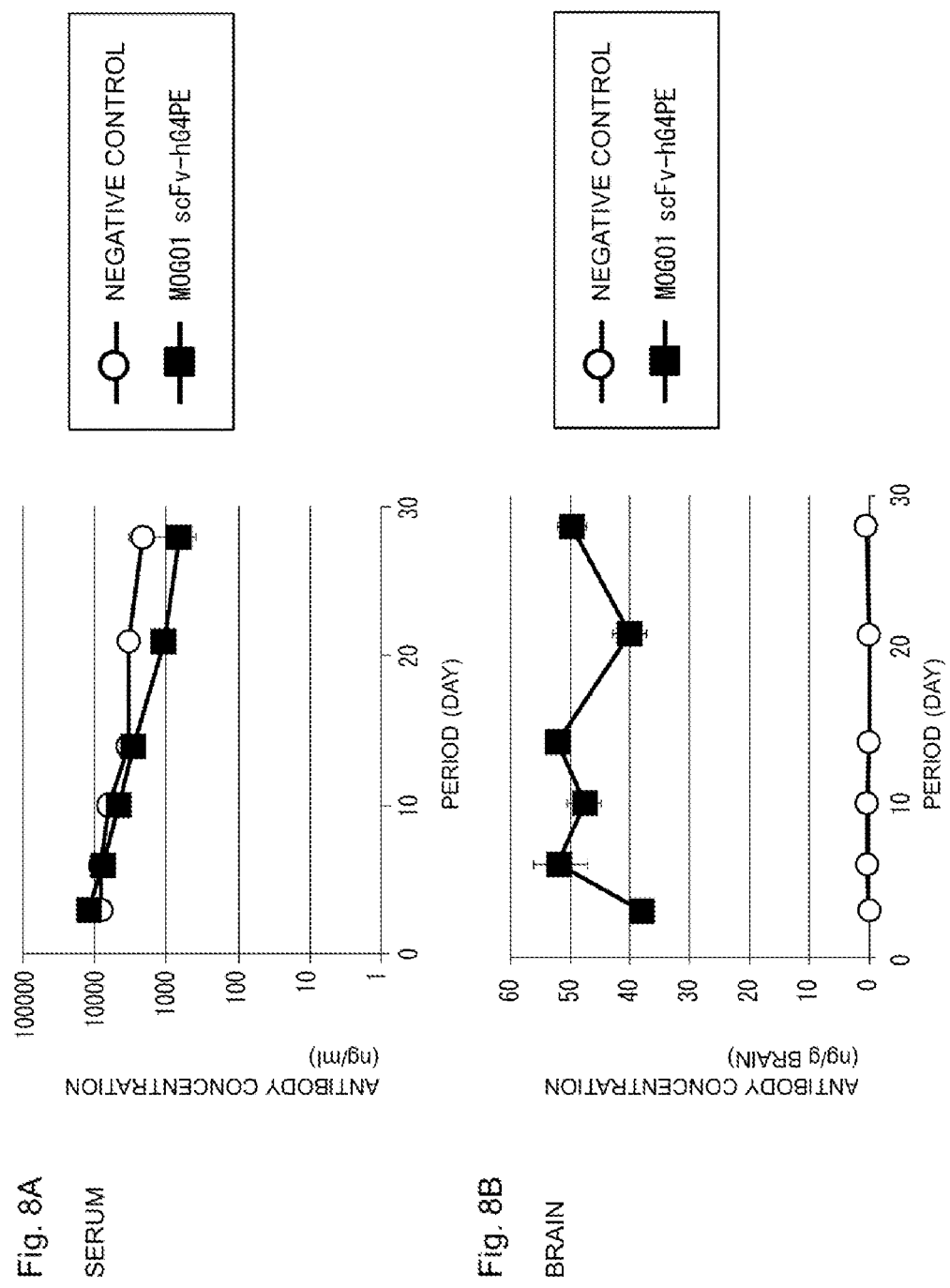

Fig. 9C
Fig. 9A
AFTER 6 DAYS
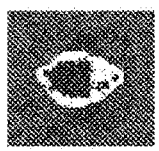
AF488-AVM IgG4PE ANTIBODY
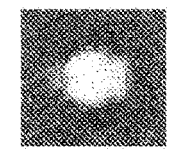
AF488-MOG01 IgG4PE ANTIBODY
Fig. 9B
AFTER 14 DAYS
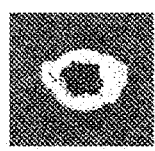
AF488-AVM IgG4PE ANTIBODY
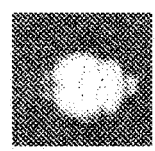
AF488-MOG01 IgG4PE ANTIBODY

Fig. 10A

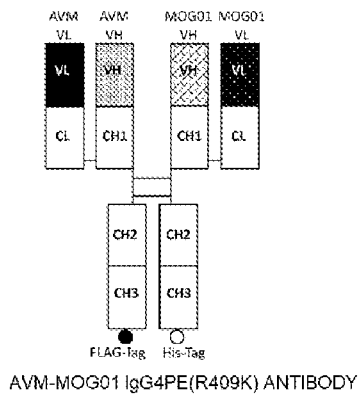

AVM-MOG01 IgG4PE(R409K) ANTIBODY

Fig. 10B

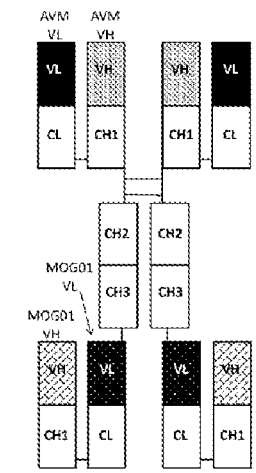

AVM IgG4PE(R409K)_MOG01 Fab ANTIBODY

Fig. 10C

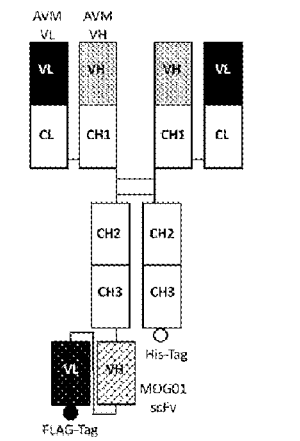

AVM IgG4PE(R409K)_MOG01sscFv ANTIBODY

Fig. 11A

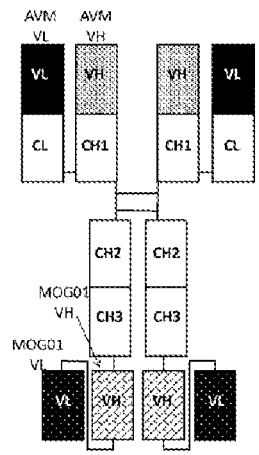

AVM IgG4PE(R409K)_MOG01dscFv ANTIBODY
AVM IgG4PE(R409K)_MOG01dscFv2 ANTIBODY
AVM IgG4PE(R409K)_MOG01dscFv4 ANTIBODY

Fig. 11B

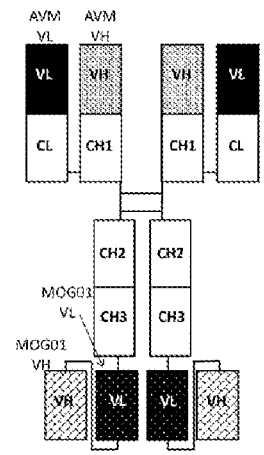

AVM IgG4PE(R409K)_MOG01dscFv3 ANTIBODY
AVM IgG4PE(R409K)_MOG01dscFv5 ANTIBODY
AVM IgG4PE(R409K)_MOG01dscFv6 ANTIBODY
AVM IgG4PE(R409K)_MOG01dscFv7 ANTIBODY
AVM IgG4PE(R409K)_MOG01dscFv8 ANTIBODY
AVM IgG4PE(R409K)_MOG01dscFv9 ANTIBODY
AVM IgG4PE(R409K)_MOG01dscFv10 ANTIBODY
AVM IgG4PE(R409K)_MOG01dscFv11 ANTIBODY

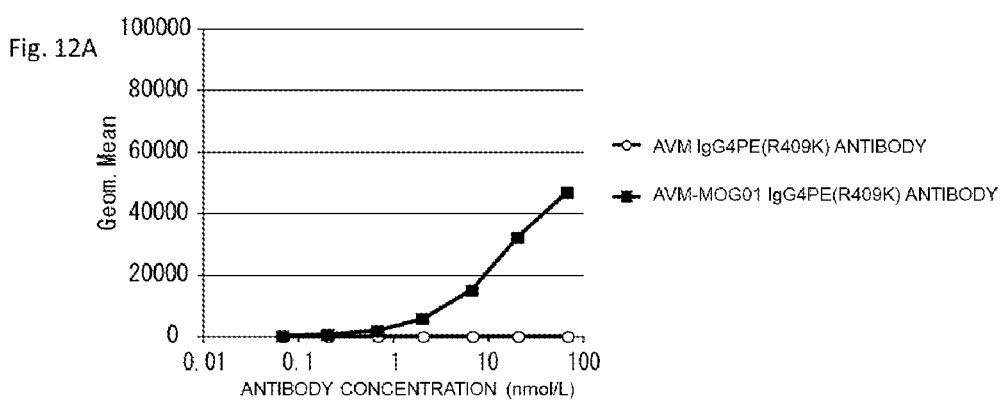
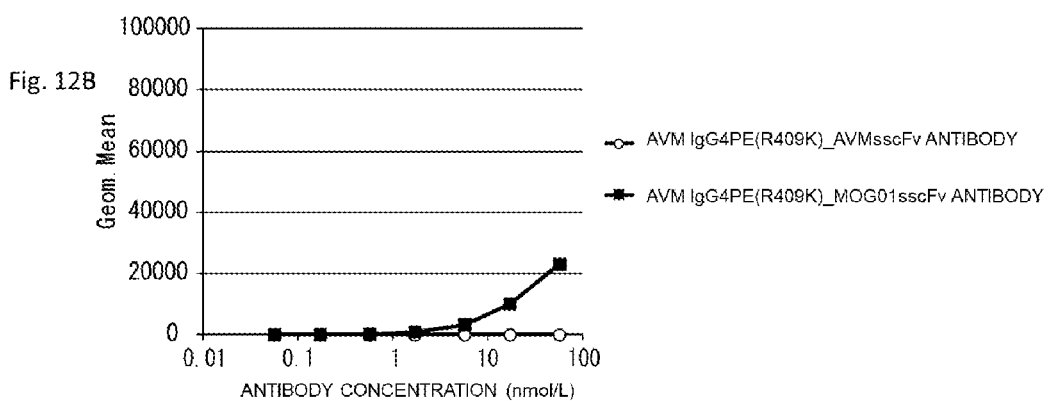
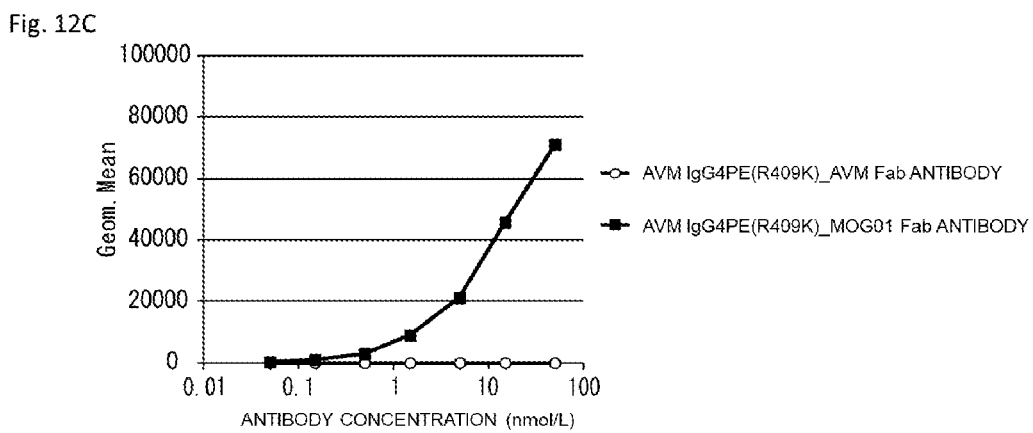

SERUM

BRAIN

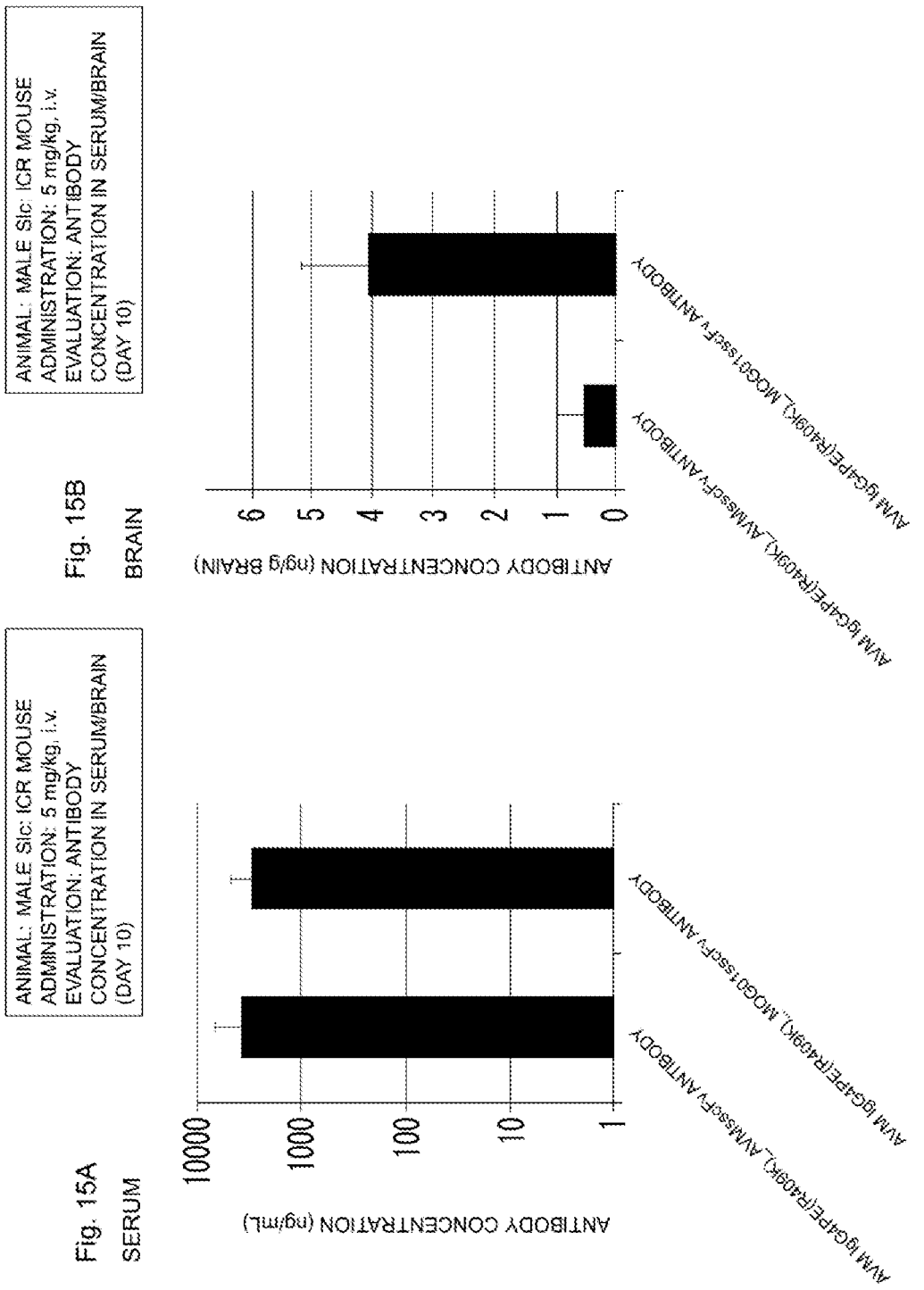

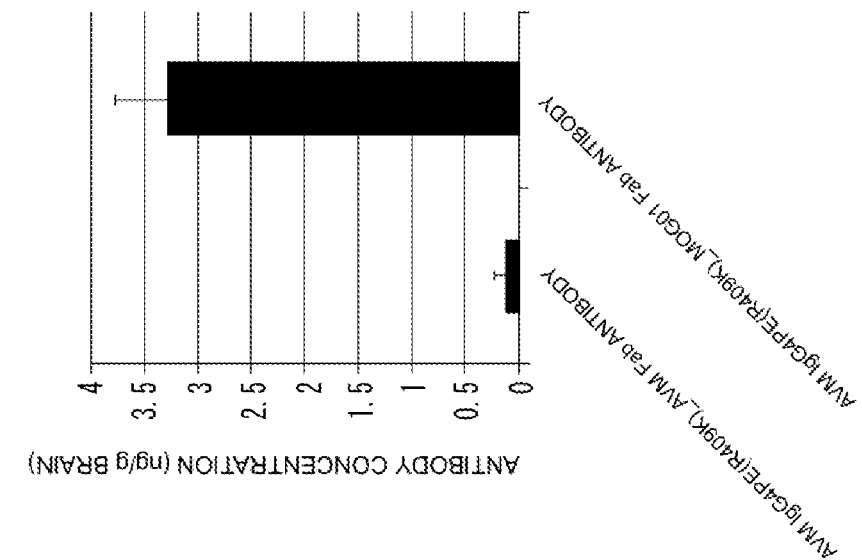
Fig. 16A SERUM
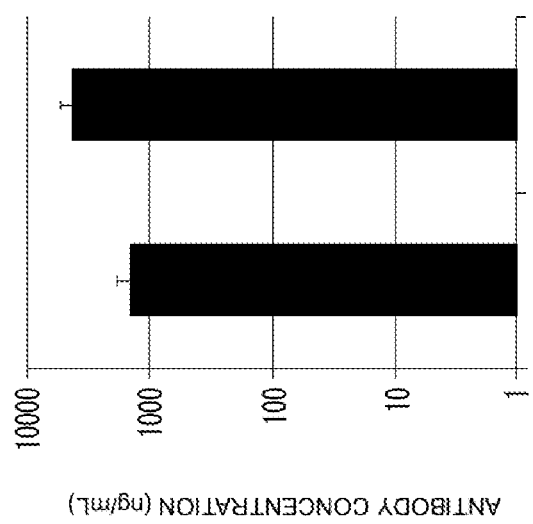
Fig. 16B BRAIN

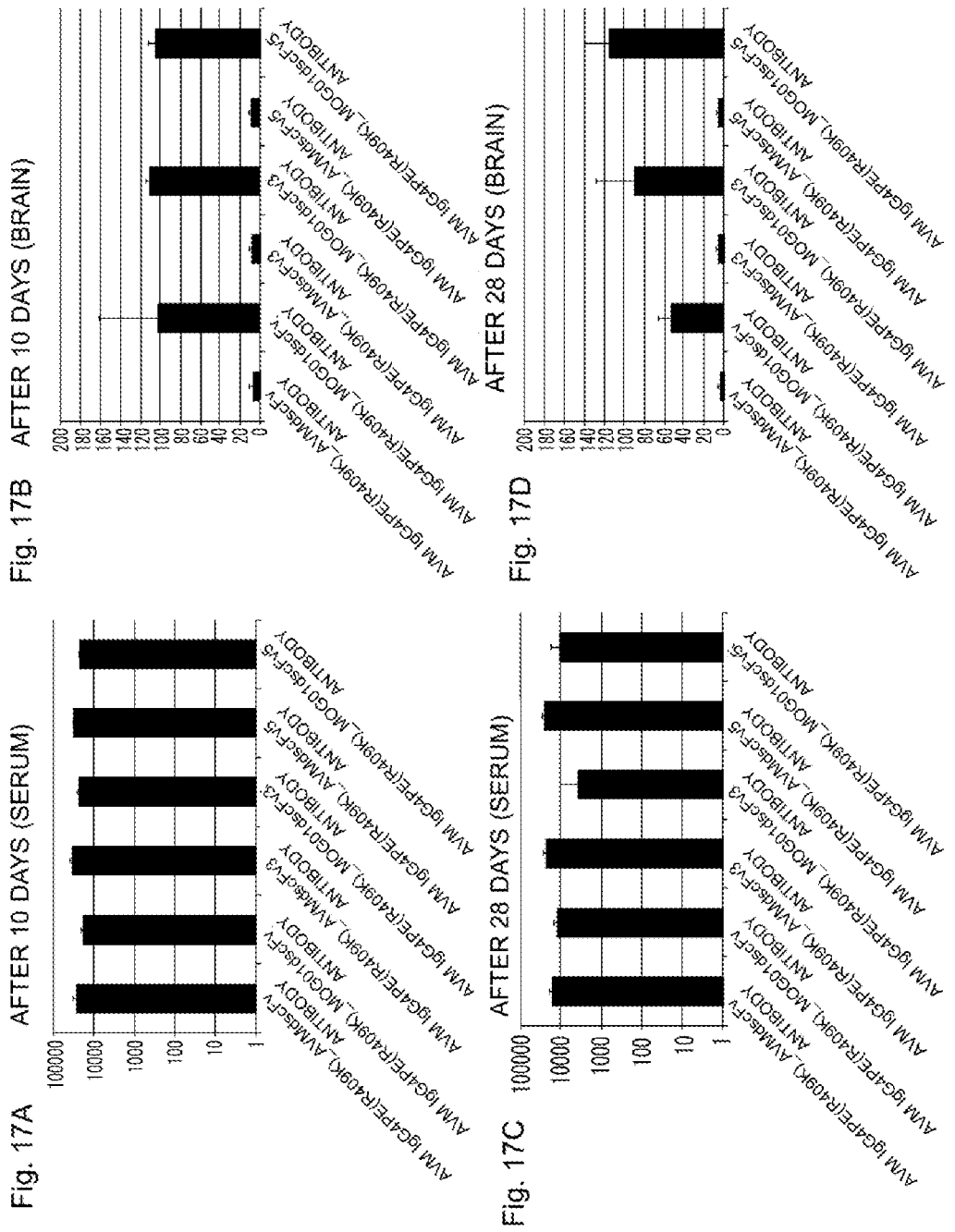

Fig. 18

CLONES SIMILAR TO MOG301 ANTIBODY

```
MOG#426  QVQLVQSGAEVKKPGASVKVSCKASGYSFNSYGINWVRQAPGQGLEWMGWISAYTGKTSY
MOG#428  EVQLVQSGAEVKKPGASVKVSCKASGYSFNSYGINWVRQAPGQGLEWMGWISAYTGKTSY
MOG#301  QVQLVQSGAEVKKPGASVKVSCKASGYSFTSYGINWVRQAPGQGLEWMGWISAYNGYTNY

MOG#426  AQKVQGRVTMTTDRSTSTAYMELRSLRSDDTAMYYCAREYDILTGYSDAFDTWGQGTMVT
MOG#428  AQKVQGRVTMTTDRSTSTAYMELRSLRSDDTAMYYCAREYDILTGYSDAFDTWGQGTMVT
MOG#301  AQKVQGRVTMTRDTSTRTAYMELRSLRSDDTAYYCAREYDILTGYSDAFDTWGQGTVT

MOG#426  VSSGGGGSGGRASGGGGSEIVLTQSPXTLSLSPGERATLSCRASQSVSS-YLAWYQQKPG
MOG#428  VSSGGGGSGGRASGGGGSEIVLTQSPGTLSLSPGERATLSCRASQSVSSSYLAWYQQKPG
MOG#301  VSSGGGGSGGRASGGGGSEIVXTQSPGTLSLSPGERATLSCRASQSVSSSYLAWYQQKPG

MOG#426  QAPRLLIYDASNRATGIPARFSGSGSGTDFTLTISSLEPEDFAVYYCQQRGNWPLTFGGG
MOG#428  QAPRLLIYGASSRATGIPDRFSGSGSGTDFTLTISRLEPEDFAVYYCQQYGSSPRTFGQG
MOG#301  QAPRLLIYGASSRATGIPDRFSGSGSGTDFTLTISRLEPEDFAVYYCQQYGSSPLTFGGG

MOG#426  TKLEIK
MOG#428  TKLEIK
MOG#301  TKLEIK
```

Fig. 19

CLONES SIMILAR TO MOG303 ANTIBODY

```
MOG#303  EVQLVESGGGLVQPGGSLRLSCAASGFTFSSYAMGWVRQAPGKGLEWVSAISGSGGSTYY
MOG#476  EVQLVESGGGLVQPGGSLRLSCAASGFTFSSYAMNWVRQAPGKGLEWVSAISYSGRSTYY
MOG#314  QVQLVESGGGLVQPGGSLRLSCAASGFTFSSYAMSWVRQAPGKGLEWVSAISGRGSSTYY
MOG#315  EVQLVESGGGLVQPGGSLRLSCAASGFTFSIYAMSWVRQAPGKGLEWVSAISGSGVSTYY
MOG#313  QVQLVESGGGLVQPGGSLRLSCAASGFTFSSYAMSWVRQAPGKGLEWVSVISGSGGSTYY
MOG#357  EVQLVESGGGLVQPGGSLRLSCAASGFTFSSYAMSWVRQAPGKGLEWVSDINHSGGSTYY
MOG#331  EVQLVESGGGLVYPGGSLRLSCAASGFTFSSYAMSWVRQAPGKGLEWVSAISGSGGSTYY

MOG#303  ADSVKGRFTISRDNSKNTLYLQMNSLRAEDTAVYYCARGYDILTGYFFDYWGQGTTVTV
MOG#476  ADSVKGRFTISRDNSKNTLYLQMNSLRAEDTAVYYCAKLYDILTGGGFDYWGQGTLVTV
MOG#314  ADSVKGRFTISRDNSKNTLYLQMNSLRAEDTAVYYCAKYYDILTGSFFDYWGQGTLVTV
MOG#315  ADSVKGRFTISRDNSKNTLYLQMNSLRAEDTAVYYCARYYDILTGNFLDYWGQGTLVTV
MOG#313  ADSVKGRFTISRDNSKNTLYLQMNSLRAEDTAVYYCAKYYDILTGSLFDSWGQGTLVTV
MOG#357  ADSVKGRFTISRDNSKHTLYLQMNSLRAEDTAVYYCAKDYDILTGSFFDYWGQGTLVTV
MOG#331  ADSVKGRFTISRDNSKNTLYLQMNSLRAEDTAVYYCARYYDILTGSFFDYWGQGTLVTV

MOG#303  SSGGGGSGGRASGGGGSAIQMTQSPSSLSASVGDRVTITCRASQGISSALAWYQQKPGKA
MOG#476  SSGGGGSGGRASGGGGSDIQMTQSPSSLSASVGDRVTITCRASQGISSALAWYQQKPGKA
MOG#314  SSGGGGSGGRASGGGGSDIQITQSPSSLSASVGDRVTITCRASQGISSALAWYQQKPGKA
MOG#315  SSGGGGSGGRASGGGGSAIQITQSPSSLSASVGDRVTITCRASQGISSALAWYQQKPGKA
MOG#313  SSGGGGSGGRASGGGGSDIVMTQSPSSLSASVGDRVTITCRASQGISSALAWYQQKPGKA
MOG#357  SSGGGGSGGRASGGGGSDIVMTQSPSSLSASVGDRVTITCRASQGISSALAWYQQKPGKA
MOG#331  SSGGGGSGGRASGGGGSIIVMTQSPALSLSPGERATLSCRASQSVSSYLAWYQQKPGQA

MOG#303  PKLLIYDASSLESGVPSRFSGSGSGTDFTLTISSLQPEDFATYYCQQFNSYPFTFGPGT
MOG#476  PKLLIYDASSLESGVPSRFSGSGSGTDFTLTISSLQPEDFATYYCQQFNSYPSTFGQGT
MOG#314  PKLLIYDASSLESGVPSRFSGSGSGTDFTLTISSLQPEDFATYYCQQFNSYPYTFGQGTK
MOG#315  PKLLIYDASSLESGVPSRFSGSGSGTDFTLTISSLQPEDFATYYCQQFNSYPLTFGGGTK
MOG#313  PKLLIYDASSLESGVPSRFSGSGSGTDFTLTISSLQPEDFATYYCQQFNSYPLTFGGGTK
MOG#357  PKLLIYDASSLESGVPSRFSGSGSGTDFTLTISSLQPEDFATYYCQQFNSYPWTFGQGTK
MOG#331  PKLLIYDASNRATGIPARFSGSGSGTDFTLTISRLEPEDFAVYYCQQGSSPLTFGGGTK

MOG#303  LEIK
MOG#476  LEIK
MOG#314  LEIK
MOG#315  LEIK
MOG#313  LEIK
MOG#357  LEIK
MOG#331  LEIK
```

Fig. 20

CLONES SIMILAR TO MOG307 ANTIBODY

```
MOG#307  RITLRESGPTLVKPTQTLTLTCTFSGFSLSTSGVGVGWIRQPPGKALEWLALIFWDDDSH
MOG#323  RITLRESGPTLVKPTQTLTLTCTFSGFSLSTSGVGVGWIRQPPGKALEWLALIFWDDDSH
MOG#341  RITLKESGPTLVKPTQTLTLTCTFSGFSLSTSGVGVGWIRQPPGKALEWLALISWDDDKH
MOG#354  RITLRESGPTLVKPTQTLTLTCTSSGLSLSTSGVGVGWIRQPPGKALEWLALIFWDDDSH
MOG#355  RITLRESGPTLVKPTQTLTLTCTSSGLSLSTSGVGVGWIRQPPGKALEWLALIFWDDDSH

MOG#307  YSPSLKSRLTITKDTSKNQVVLTMTNMDPVDTATYYCARYYFGSGSYFPSYWYFDLWGRG
MOG#323  YSPSLKSRLTITKDTSKNQVVLTMTNMDPVDTATYYCARYYFGSGSYFPSYWYFDLWGRG
MOG#341  YSPSLKSRLTITKDTSKNQVVLTMTNMDPVDTATYYCARYYFGSGSYSPSYWYFDLWGRG
MOG#354  YSPSLKSRLTITKDTSKNQVVLTMTNMDPVDTATYYCARYYFGSGSYFPSYWYFDLWGRG
MOG#355  YSPSLKSRLTITKDTSKNQVVLTMTNMDPVDTATYYCARYYFGSGSYFPSYWYFDLWGRG

MOG#307  TLVTVSSGGGGSGGRASGGGGSEIVMTQSPATLSLSPGERATLSCRASQSVSSYLAWYQQ
MOG#323  TLVTVSSGGGGSGGRASGGGGSEIVMTQSPATLSLSPGERATLSCRASQSVSSYLAWYQQ
MOG#341  TLVTVSSGGGGSGGRASGGGGSEIVITQSPATLSLSPGERATLSCRASQSVSSYLAWYQQ
MOG#354  TLVTVSSGGGGSGGRASGGGGSEIVMTQSPATLSLSPGERATLSCRASQSVSSYLAWYQQ
MOG#355  TLVTVSSGGGGSGGRASGGGGSEIVITQSPATLSLSPGERATLSCRASQSVSSYLAWYQQ

MOG#307  KPGQAPRLLIYDASNRATGIPARFSGSGSGTDFTLTISSLEPEDFAVYYCQQRSNWPPTF
MOG#323  KPGQAPRLLIYDASNRATGIPARFSGSGSGTDFTLTISSLEPEDFAVYYCQQRSNWPPTF
MOG#341  KPGQAPRLLIYDASNRATGIPARFSGSGSGTDFTLTISSLEPEDFAVYYCQQRSNWPPTF
MOG#354  KPGQAPRLLIYDASNRATGIPARFSGSGSGTDFTLTISSLEPEDFAVYYCQQRSNWPLTF
MOG#355  KPGQAPRLLIYDASNRATGIPARFSGSGSGTDFTLTISSLEPEDFAVYYCQQRSNWPLTF

MOG#307  GQGTKVEIK
MOG#323  GGGTKLEIK
MOG#341  GGGTKVEIK
MOG#354  GGGTKVEIK
MOG#355  GGGTKLEIK
```

Fig. 21

CLONES SIMILAR TO MOG310 ANTIBODY

```
MOG#308  EVQLVQSGAEVKKSGSSVKVSCKASGGTFSRYAISWVRQAPGQGLEWMGGIIPMFSTTNY
MOG#338  QVQLVQSGAEVKKPGSSVKVSCKASGGTFSRYAISWVRQAPGQGLEWMGGIIPMFNTANY
MOG#319  QVQLVQSGAEVKKPGSSVKVSCKASGGTFSRYAISWVRQAPGQGLEWMGGIIPMFSTANY
MOG#320  QVQLVQSGAEVKKPGSSVKVSCKASGGTFSRYAINWVRQAPGQGLEWMGGIIPMFSTVNY
MOG#310  QVQLVQSGAEVKKPGSSVKVSCKASGGTFSRYAISWVRQAPGQGLEWMGGIIPMFSTANY
MOG#359  EVQLVQSGAEVKKPGSSVKVSCKASGGTFSRYAISWVRQAPGQGLEWMGGIIPMFNTANY
MOG#478  EVQLVQSGAEVKKPGSSVKVSCKASGGTFSRYAISWVRQAPGQGLEWMGGIIPMFATANY
MOG#316  EVQLVQSGAEVKKPGSSVKVSCKASGGTFSRYAISWVRQAPGQGLEWMGGIIPMFNTANY
MOG#352  EVQLVQSGAEVKKPGSSVKVSCKASGGTFSRYAINWVRQAPGQGLEWMGGIIPMFSTVNY

MOG#308  AQKFQGRVTITADESTSTAYMELSSLRSEDTAVYYCARDWAVAGMGFAYWGQGTLVTVSS
MOG#338  AQKFQGRVTITADESTSTAYMELSSLRSEDTAVYYCARDWAVAGMGFDPWGQGTLVTVSS
MOG#319  AQKFQGRVTITADESTSTAYMELSSLRSDDTAVYYCARDWAVAGMGFNYWGQGTLVTVSS
MOG#320  AQKFQGRVTITADESTSTAYMELSSLRSEDTAVYYCARDWAVAGMGFDYWGQGTLVTVSS
MOG#310  AQKFQGRVTITADESTSTAYMELSSLRSEDTAVYYCARDWAVAGMGFNYWGQGTLVTVSS
MOG#359  AQKFQGRVTITADESTSTAYMELSSLRSEDTAVYYCARDWAVAGMGFNYWGQGTLVTVSS
MOG#478  AQKFQRVTITADESTSTAYMELSSLRSEDTVYYCARDWAVAMGFAHWGQGTLVTVSS
MOG#316  AQKFQGRVTITADESTSTAYMELSSLRSEDTAVYYCARDWAVAGMGFNYWGQGTLVTVSS
MOG#352  AQKFQGRVTITADESTSTAYMELSSLRSEDTAVYYCARDWAVAGMGFDYWGQGTLVTVSS

MOG#308  GGGGSGGRASGGGGSEIVLTQSPATLSLSPGERATLSCRASQSVSS-YLAWYQQKPGQAP
MOG#338  GGGGSGGRASGGGGSEIVLTQSPATLSLSPGERATLSCRASQSVSS-YLAWYQQKPGQAP
MOG#319  GGGGSGGRASGGGGSEIVLTQSPGTLSLSPGERATLSCRASQSVSSSYLAWYQQKPGQAP
MOG#320  GGGGSGGRASGGGGSEIVLTQSPGTLSLSPGERATLSCRASQSVSSSYLAWYQQKPGQAP
MOG#310  GGGGSGGRASGGGGSEIVLTQSPGTLSLSPGERATLSCRASQSVSSSYLAWYQQKPGQAP
MOG#359  GGGGSGGRASGGGGSEIVLTQSPGTLSLSPGERATLSCRASQSVSSSYLAWYQQKPGQAP
MOG#478  GGGGSGGRASGGGGSEIVTQSPGTLSLSPGERATLSCRASQSVSSSYLAWYQQKPGQAP
MOG#316  GGGGSGGRASGGGSEIQTQSPSLSASVGRVTCRASQGINS-ALAWYQQKPGKAP
MOG#352  GGGGSGGRASGGGSAIQTQSPSSASVGRVTCRASQGISS-YLAWYQHKPGKAP

MOG#308  RLLIYDASNRATGIPARFSGSGSGTDFTLTISSLEPEDFAVYYCQQRSNWPPTFGQGTKV
MOG#338  RLLIYDASNRATGIPARFSGSGSGTDFTLTISSLEPEDFAVYYCQQRNNWPTFGGGTK
MOG#319  RLLIYGASSRATGIPDRFSGSGSGTDFTLTISRLEPEDFAVYYCQQYGSSPFTFGPGTKV
MOG#320  RLLIYGASSRATGIPDRFSGSGSGTDFTLTISRLEPEDFAVYYCQQYGSSPFTFGPGTKV
MOG#310  RLLIYGASSRATGIPDRFSGSGSGTDFTLTISRLEPEDFAVYYCQQYGSSPYTFGQGTKV
MOG#359  RLLIYGASSRATGIPDRFSGSGSGTDFTLTISRLEPEDFAVYYCQQYGSSPTFGGGTK
MOG#478  RLLIYGASSRATGIPDRFSGSGSGTDFTLTISRLEPEDFAVYYCQQYGSSPTFGQGT
MOG#316  LLIYASSLQGPSRFSGSGSGTDFTLTISSLQPEDFATYYCQQYNSYPTFGQGT
MOG#352  KSLIYASSLQGPSRFSGSGSGTDFTLTISSLQPEDFATYYCQQYNSYPTFGGGTKV

MOG#308  IK
MOG#338  EIK
MOG#319  EIK
MOG#320  IK
MOG#310  IK
MOG#359  EIK
MOG#478  EIK
MOG#316  EIK
MOG#352  IK
```

Fig. 22A

CLONE SIMILAR TO MOG329 ANTIBODY

```
MOG#329  QVQLVESGGGLVQPGGSLRLSCAASGFAFRNYAMNWVRQAPGKGLEWVSAISGSGGSTYY
MOG#470  QVQLVESGGGLVQPGGSLRLSCAASGFTFSSYAMNWVRQAPGKGLEWVSAISGSGGSTYY

MOG#329  ADSVKGRFTISRDNSKNTLYLQMNSLRAEDTAVYYCARDYGGISPFDYWGQGTLVTVSSG
MOG#470  ADSVKGRFTISRDNSKNTLYLQMNSLRAEDTAVYYCARDYGGISPFDYWGQGTLVTVSSG

MOG#329  GGGSGGRASGGGGSIQLTQSPSSLSASVGDRVTITCRASQGISSALAWYQQKPGKAPKL
MOG#470  GGGSGGRASGGGGSIVMTQSPATLSLSPGERATLSCRASQSVSSYLAWYQQKPGQAPRL

MOG#329  LIYDASSLESGVPSRFSGSGSGTDFTLTISSLQPEDFATYYCQQFNSYPHTFGQGTKVEI
MOG#470  LIYDASNRATGIPARFSGSGSGTDFTLTISRLEPEDFAVYYCQQYGSSPYTFGQGTKLEI

MOG#329  K
MOG#470  K
```

Fig. 22B

CLONE SIMILAR TO MOG456 ANTIBODY

```
MOG#418  QVYLVQSGGGLVKPGGSLRLSCAASGFTFSSYSMHWVRQAPGKGLEWVSSISHSSSYISY
MOG#456  EVQLVESGGGLVKPGGSLRLSCAASGFTFSSYSMHWVRQAPGKGLEWVSSIGSRSRYIYY

MOG#418  ADSVKGRFTISRDNAKNSLYLQMNSLRAEDTAVYYCAKGYYDILTGSLFDYWGQGTLVTV
MOG#456  ADSVKGRFTISRDNAKNSLYLQMNSLRAEDTAVYYCAKGYYDILTGSLFDYWGQGTLVTV

MOG#418  SSGGGGSGGRASGGGGSIVMTQSPATLSLSPGERATLSCRASQSVSSYLAWYQQKPGQA
MOG#456  SSGGGGSGGRASGGGGSIVLTQSPSSLSASVGDRVTITCRASQGISSALAWYQQKPGKA

MOG#418  PRLLIYDASNRATGIPARFSGSGSGTDFTLTISRLEPEDFAVYYCQQYGSSPTFGPGTK
MOG#456  PKLLIYDASSLESGVPSRFSGSGSGTDFTLTISSLQPEDFATYYCQQFNSYPTFGQGTK

MOG#418  VEIK
MOG#456  VEIK
```

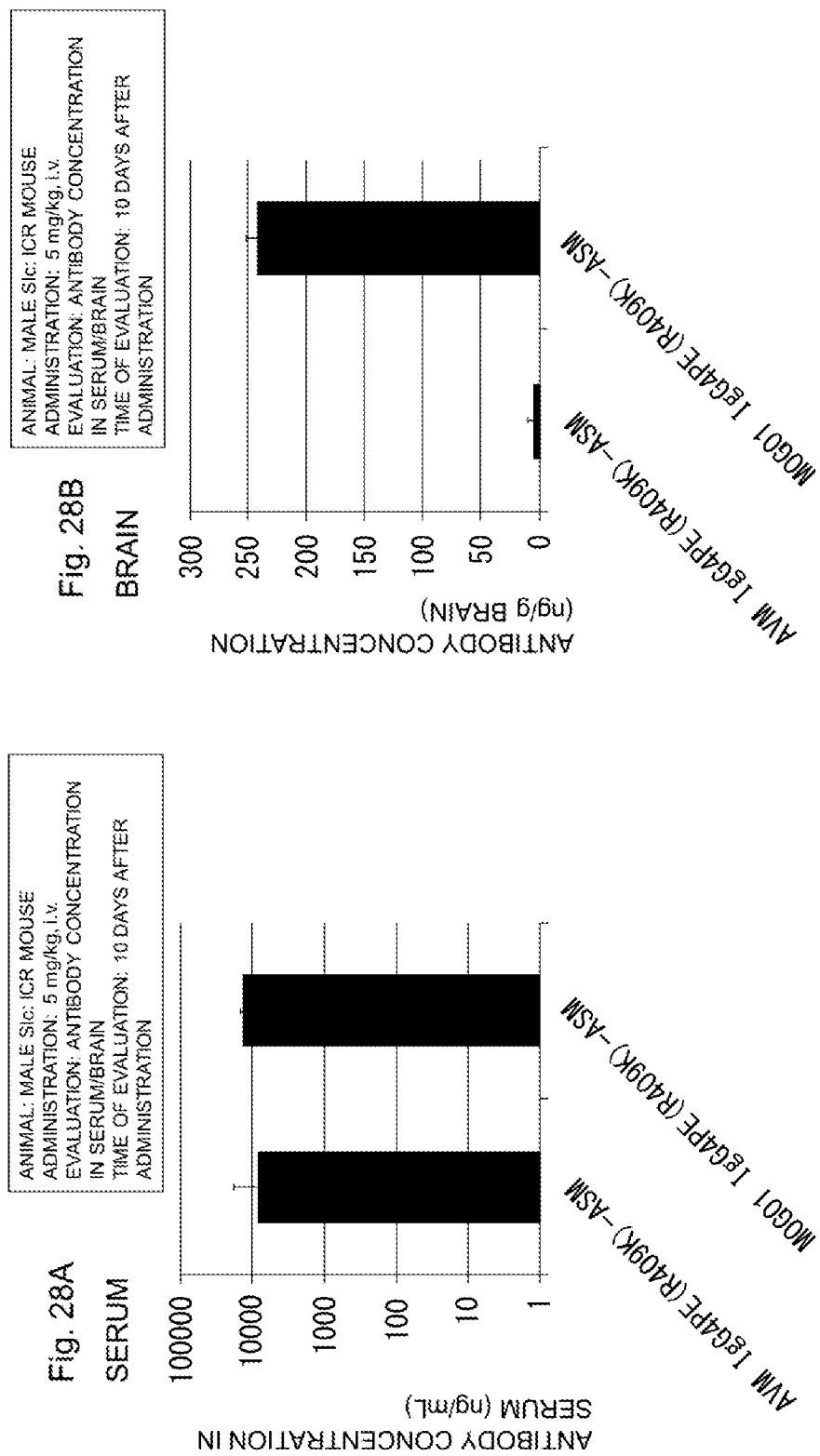

ANTIBODY WHICH BINDS TO MYELIN OLIGODENDROCYTE GLYCOPROTEIN

SEQUENCE LISTING

A sequence listing in electronic (XML file) format is filed with this application and incorporated herein by reference. The name of the ASCII text file is "2023-1209.xml"; the file was created on Aug. 1, 2023; the size of the file is 570,775 bytes.

TECHNICAL FIELD

The present invention relates to an antibody which binds to myelin oligodendrocyte glycoprotein (MOG), an antibody fragment thereof, a hybridoma which produces the antibody or the antibody fragment, a nucleic acid containing a nucleotide sequence which encodes the antibody or the antibody fragment, a transformant cell containing a vector containing the nucleic acid, a method for producing the antibody or the antibody fragment, a composition containing the antibody or the antibody fragment and a method for detecting or measuring an antigen that is present in the brain, a method for diagnosing or treating a brain disease, a method for improving the property of an antibody of accumulating in the brain and a method for increasing the amount of an antibody in the brain which use the antibody or the antibody fragment.

BACKGROUND ART

Since the approval of a mouse anti-CD3 antibody, muromonab-CD3 (OKT3) as the first antibody drug by FDA in 1986, many antibody drugs have been developed. In 1994, a chimeric antibody, abciximab, in which a variable region of a mouse antibody and a constant region of a human antibody are linked to reduce the antigenicity of the mouse antibody, has been approved.

To further reduce the antigenicity, humanized antibody technique in which a complementarity determining region (CDR below), which plays an important role in binding to an antigen, of a variable region of a mouse antibody is inserted to the frame work region (FR below) of a human antibody has been developed, and a humanized anti-CD20 antibody, dacizumab has been approved in 1997.

Moreover, phage display technique using a human antibody sequence library has been used, and a fully human anti-TNF α antibody, adalimumab, which is the first antibody using the phage display technique that has been approved, has been approved in 2002. Sixty or more antibody drugs targeting antigens such as CD20, CD52, TNF α, HER2 and EGFR have already been approved (NPL 1).

In this manner, antibodies are a widely recognized drug format. Most of the antibody drugs that have been approved so far are those for cancers and immune diseases, which account for about 75% or more of all the antibody drugs.

The importance of biologics such as antibodies is increasing also in the treatment of central nervous system diseases, and it is reported that a monoclonal antibody to amyloid p is studied in Alzheimer's disease and that neurotrophic factors (brain-derived neurotrophic factor BDNF and glial-derived neurotrophic factor GDNF) having neuroprotective effect exhibit neuroprotective effect in central nervous system diseases in an animal model (NPL 2).

However, when an antibody is peripherally administered, the amount sent to the central nervous system is lower than those to the other organs, and the antibody migration rate (the ratio of the concentration in the cerebrospinal fluid (CSF) to the serum concentration) is reported to be 0.1-0.3% (NPLs 3-5).

A reason why the drug delivery amount decreases in the central nervous system including the brain and the bone marrow is the mechanism which is called the blood brain barrier (BBB) and which limits the transportation of a substance between the tissue liquids of the blood and the brain. The blood brain barrier has a physical/nonspecific control mechanism due to the intercellular adhesion of the vascular endothelial cells and a substrate-specific efflux mechanism due to efflux transporters. The blood brain barrier protects the central nervous system from foreign matters or drugs and plays an important role in maintaining the homeostasis.

However, due to the existence of the blood brain barrier, the effective concentration of drug administration is not easily obtained in the central nervous system, and the drug development is difficult. For example, although enzyme replacement therapy is conducted by intravenously administering α-L-iduronidase to Hurler syndrome (mucopolysaccharidosis-I) or iduronate-2-sulfatase to Hunter syndrome (mucopolysaccharidosis-II), the enzymes do not pass through the blood brain barrier due to their high molecular weights, and no efficacy on conditions in the central nervous system has been found (NPLs 6-9). Moreover, it is reported that side effects such as production of a neutralizing antibody are caused because a certain amount of a recombinant enzyme is continuously administered regularly (NPL 10).

Moreover, attempts to directly administer biologics into the medullary cavity or the brain have been made to increase the concentration in the brain. For example, a method of administering iduronate-2-sulfatase into the brain of patients with Hunter syndrome (mucopolysaccharidosis-II) to prevent the progress of brain disorder of the patients is reported (PTL 1). However, direct administration into the medullary cavity or the brain is highly invasive (NPL 11).

Therefore, various delivery techniques have been studied to increase the concentrations of substances with high molecular weights such as biologics in the brain. For example, methods for allowing a substance with a high molecular weight to pass through the blood brain barrier through endocytosis by binding the substance and a membrane protein which is expressed in the brain vascular endothelial cells and by forming a complex of the substance with a high molecular weight and the membrane protein are reported.

Most of the reported techniques use receptor-mediated transcytosis (RMT below), and the target receptors expressed in the brain vascular endothelium are, for example, transferrin receptors, insulin receptors, insulin-like growth factor receptors and the low-density lipoprotein receptor family (LDLRf).

Techniques for passing the blood brain barrier through a transferrin receptor by producing a fused protein of an anti-transferrin receptor antibody and a nerve growth factor are reported. Reported techniques using an anti-transferrin receptor antibody are bispecific antibodies of an anti-transferrin receptor antibody and an anti-beta secretase (BACE1) antibody (PTLs 2 and 3 and NPLs 12 and 13) and fused antibodies obtained by fusing a monovalent anti-transferrin receptor antibody to the carboxyl terminus of an anti-amyloid p antibody (PTL 4 and NPL 14).

It is reported that, regarding the brain delivery using a bispecific antibody of an anti-transferrin receptor antibody and an anti-BACE1 antibody, the amount of the antibody taken into the brain increases to about four times the amount of the control when the antibody is administered to a mouse at 20 mg/kg body weight (NPL 13).

Furthermore, a technique for allowing a drug to pass through the blood brain barrier by encapsulating the drug with a liposome having an anti-transferrin receptor antibody on its surface is reported. It is reported that the amount taken into the rat brain increases to about two to five times when an anti-rat transferrin receptor antibody fused to immunomicelle is used (NPL 9).

Techniques for passing through the blood brain barrier through an insulin receptor by producing a fused protein of a neurotrophic factor, an enzyme or an anti-amyloid antibody fused to the carboxyl terminus of an anti-insulin receptor antibody are reported (NPLs 16-19).

It is reported that when a fused antibody of a labeled anti-human insulin receptor antibody and GDNF is administered to a rhesus monkey, the amount taken into the brain after two hours is about 15 times compared to that of GDNF (NPL 17).

However, because transferrin receptors and insulin receptors are expressed not only in the brain vascular endothelial cells but also in the whole body including the liver and the like, a drug is delivered also to the liver and the like as the amount of the drug delivered to the central nervous system increases in these techniques (NPL 20). Moreover, because the antigen is expressed in the whole body, the half-life of the antibody in the blood is short (NPL 12).

Moreover, it is reported that an antibody (Fc5) to TMEM30A, which is an antigen expressed in the brain vascular endothelial membrane, shows an RMT-like activity (PTL 5 and NPLs 21 and 22). Fc5 is an antibody of a variable domain of heavy chain of heavy chain antibody (VHH below) of a single domain derived from llama, and it is shown in an in vitro BBB model and in a rat in vivo model that the amount of Fc5 fused with human Fe delivered to the brain is higher than that of the control IgG.

It is reported that the CSF exposure of a Fc5-derived single chain antibody (scFv) fused with a metabotropic glutamate receptor type I (mGluRI below) antibody is higher than that of a control single chain antibody fused with a mGluRI antibody in a rat model, but the increase in the amount is around five times (NPL 23).

It is also reported that an IgG antibody is rapidly discharged from the brain to the circulating blood by neonatal Fc receptor (FcRn) (NPLs 24 and 25), and for example, the half-life of IgG in the brain after the administration into the brain is as short as 48 minutes in rats (NPL 24).

MOG is a protein belonging to the immunoglobulin superfamily and constitutes myelin. Whole human MOG consists of 218 amino acids, and human MOG is expressed in the outermost layer of myelin in the central nervous system and plays a role in the cell adhesion and the cell surface interaction (NPLs 26-28).

MOG is considered as a candidate of an autoantigen in inflammatory diseases in which the glial cells in the central nerves are attacked by the autoimmunity, such as multiple sclerosis (MS) (NPLs 29 and 30). It is reported that, although the concentrations of anti-MOG antibodies in the serum are low in MS patients, anti-MOG antibodies are detected also in the central nerves (NPL 29).

As a reason for this, it is reported that the blood brain barrier breaks due to leakage of humoral factors and entry of inflammatory cells in pathological conditions such as MS and that antibodies easily migrate to the central nervous system (NPLs 30 and 31). It is also reported that autoantibodies are produced locally in the central nervous system due to B cells and plasma cells infiltrated to the central nervous system (NPLs 30, 32 and 33).

Experimental autoimmune encephalomyelitis (EAE) and MS have many pathological conditions in common, and thus EAE is a model used for studying the pathological conditions of MS. It is reported that EAE can be induced by immunizing an animal with MOG protein or peptide (NPL 34).

It is also reported that the EAE score deteriorates when an anti-MOG antibody is administered to an animal in which EAE has been induced (NPLs 29 and 35). However, the EAE score reaches its peak one to two days (NPL 29) or four days (NPL 35) after the administration of the antibody, and the deterioration is temporal. On the other hand, it is also reported that EAE does not develop even when an anti-MOG antibody alone is administered to a normal animal (NPLs 36 and 37).

CITATION LIST

Patent Literature

PTL 1: International Publication No. 2012/023623
PTL 2: International Publication No. 2016/081640
PTL 3: International Publication No. 2016/081643
PTL 4: International Publication No. 2014/033074
PTL 5: Canadian Patent No. 2623841

Non Patent Literature

NPL 1: Kyla R R. and Richard C C., Biotechnol Adv, pii: S0734-9750 (16), 30091-X, 2016
NPL 2: Pardridge W M., Bioconjugate Chem., 19, 1327-1338, 2008
NPL 3: Wang W., et al., Clin. pharmacol. Ther., 84, 548-558, 2008
NPL 4: Garg A., et al., AAPSJ., 11, 553-557, 2009
NPL 5: Kaj B., et al., Arch. Neurol., 69 (8), 1002-1010, 2012
NPL 6: Wraith J E. et al., J. Pediatr. 144 (5), 581-588, 2004
NPL 7: Muenzer J. et al., Genet Med. 8 (8), 465-473, 2006
NPL 8: Document attached to intravenous infusion 2.9 mg of Aldurazyme (registered trademark) (July, 2016, 8th edition)
NPL 9: Document attached to intravenous infusion 6 mg of Elaprase (registered trademark) (July, 2016, 6th edition)
NPL 10: Brooks, D. A. et al., Trends Mol. Med. 9, 450-453, 2003
NPL 11: Sorrentino N C. et al., Pediatr Endocrinol Rev. 1, 630-638, 2016
NPL 12: Couch J A., et al., Science Translational Medicine, 5, 183ra57, 2013
NPL 13: Yu Y J., et al., Science Translational Medicine, 6, 261ra154, 2014
NPL 14: Niewoehner J., et al., Neuron. 81, 49-60, 2014
NPL 15: Jun Y, et al., Macromol. Biosci. 12, 1209-1219, 2012
NPL 16: Pardridge W M. and Boado R J., Methods in Enzymology, 503, 269-292, 2012
NPL 17: Boado R J., et al., Drug Metab. Dispos., 37 (12), 2299-2304, 2009
NPL 18: Boado R J., et al., J. Pharmacol. Exp. Ther., 333 (3), 961-969, 2010
NPL 19: Boado R J., et al., Bioconjugate Chem., 1, 97-104, 2012
NPL 20: Yun Zhang. et al., J. Pharmacol. Exp. Ther., 313 (3), 1075-1081, 2005

NPL 21: Abulrob A., et al., J. Neuyrochem., 95 (4), 1201-1214, 2005
NPL 22: Farrington G K., et al., FASEB J., 28, 4764-4778, 2014
NPL 23: Webster C I., et al., FASEB J., 30, 1927-1940, 2016
NPL 24: Zhang Y, et al., J. Neuroimmunol., 114(1-2), 168-172, 2001
NPL 25: Philip R C., et al., Brain Research, 1534, 13-21, 2013
NPL 26: Brunner C., et al., J. Neurochem, 52, 296-394, 1989
NPL 27: Pham-Dinh D., et al., Proc. Natl. Acad. Sci. USA, 90, 7990-7994, 1993
NPL 28: Gardinier M V, et al., J. Neurosci. Res., 33, 177-187, 1992
NPL 29: Eduard Urich, et al., PNAS, 103, 18697-18702, 2006
NPL 30: Markus Reindl, et al., Brain, 122, 2047-2056, 1999
NPL 31: Shimizu F., et al., Nihon Rinsho. 72(11), 1949-1954, 2014
NPL 32: Nese Sinmaz., et al., Ann. N.Y Acad. Sci., 1351, 22-38, 2015
NPL 33: F. J. Quintana, Neurology, 78, 532-539, 2012
NPL 34: Ralf Gold., et al., Brain, 129, 1953-1971, 2006
NPL 35: Margaret M., et al., J. Neuroimmunology, 125, 114-124, 2002
NPL 36: G. Locatelli, et al., Nature Neuro Science, 15(4), 543-551, 2012
NPL 37: H J Schluesener, et al., J. Immunol., 139, 4016-4021, 1987

SUMMARY OF INVENTION

Technical Problem

Although it is disclosed in NPLs 29 and 35 that an anti-MOG antibody is detected in the brain when the antibody is administered to an EAE model, there is no report on an anti-MOG antibody which can be detected in the brain when the anti-MOG antibody is peripherally administered to a normal animal.

The invention relates to a myelin oligodendrocyte glycoprotein (MOG)-binding molecule which binds to MOG and methods using the molecule. Specifically, an object is to provide an antibody which binds to MOG, an antibody fragment thereof, a hybridoma which produces the antibody or the antibody fragment, a nucleic acid containing a nucleotide sequence which encodes the antibody or the antibody fragment, a transformant cell containing a vector containing the nucleic acid, a method for producing the antibody or the antibody fragment, a composition containing the antibody or the antibody fragment and a method for detecting or measuring an antigen that is present in the brain, a method for diagnosing or treating a brain disease, a method for improving the property of an antibody of accumulating in the brain and a method for increasing the amount of an antibody in the brain which use the antibody or the antibody fragment.

Solution to Problem

As means for solving the problems, the invention provides a MOG-binding molecule which binds to MOG and methods using the molecule and specifically provides an antibody or an antibody fragment thereof.
That is, the invention relates to (1) to (22) below.
(1) An antibody which binds to myelin oligodendrocyte glycoprotein (referred to as MOG below) or an antibody fragment thereof.
(2) The antibody or the antibody fragment according to (1), wherein the antibody has a property of accumulating in a brain.
(3) The antibody or the antibody fragment according to (1) or (2), wherein the antibody is selected from the group consisting of (a) to (r) below.
  (a) an antibody in which the amino acid sequences of complementarity determining regions (CDRs below) 1 to 3 of a heavy chain variable region (referred to as VH below) contain the amino acid sequences of SEQ ID NOs: 4, 5 and 6, respectively, and in which the amino acid sequences of CDRs 1 to 3 of a light chain variable region (VL) contain the amino acid sequences of SEQ ID NOs: 10, 11 and 12, respectively,
  (b) an antibody in which the amino acid sequences of CDRs 1 to 3 of VH contain the amino acid sequences of SEQ ID NOs: 16, 17 and 18, respectively, and in which the amino acid sequences of CDRs 1 to 3 of VL contain the amino acid sequences of SEQ ID NOs: 22, 23 and 24, respectively,
  (c) an antibody in which the amino acid sequences of CDRs 1 to 3 of VH contain the amino acid sequences of SEQ ID NOs: 28, 29 and 30, respectively, and in which the amino acid sequences of CDRs 1 to 3 of VL contain the amino acid sequences of SEQ ID NOs: 34, 35 and 36, respectively,
  (d) an antibody fragment in which the amino acid sequences of CDRs 1 to 3 of a heavy chain variable region of a heavy chain antibody (referred to as VHH below) contain the amino acid sequences of SEQ ID NOs: 40, 41 and 42, respectively,
  (e) an antibody in which the amino acid sequences of CDRs 1 to 3 of VH contain the amino acid sequences of SEQ ID NOs: 153, 154 and 155, respectively, and in which the amino acid sequences of CDRs 1 to 3 of VL contain the amino acid sequences of SEQ ID NOs: 158, 159 and 160, respectively,
  (f) an antibody in which the amino acid sequences of CDRs 1 to 3 of VH contain the amino acid sequences of SEQ ID NOs: 163, 164 and 165, respectively, and in which the amino acid sequences of CDRs 1 to 3 of VL contain the amino acid sequences of SEQ ID NOs: 168, 169 and 170, respectively,
  (g) an antibody in which the amino acid sequences of CDRs 1 to 3 of VH contain the amino acid sequences of SEQ ID NOs: 173, 174 and 175, respectively, and in which the amino acid sequences of CDRs 1 to 3 of VL contain the amino acid sequences of SEQ ID NOs: 178, 179 and 180, respectively,
  (h) an antibody in which the amino acid sequences of CDRs 1 to 3 of VH contain the amino acid sequences of SEQ ID NOs: 183, 184 and 185, respectively, and in which the amino acid sequences of CDRs 1 to 3 of VL contain the amino acid sequences of SEQ ID NOs: 188, 189 and 190, respectively,
  (i) an antibody in which the amino acid sequences of CDRs 1 to 3 of VH contain the amino acid sequences of SEQ ID NOs: 193, 194 and 195, respectively, and in which the amino acid sequences of CDRs 1 to 3 of VL contain the amino acid sequences of SEQ ID NOs: 198, 199 and 200, respectively,
  (i) an antibody in which the amino acid sequences of CDRs 1 to 3 of VH contain the amino acid sequences of SEQ ID NOs: 203, 204 and 205, respectively, and in which the amino acid sequences of CDRs 1 to 3 of VL contain the amino acid sequences of SEQ ID NOs: 208, 209 and 210, respectively, (k) an antibody in which the amino acid sequences of CDRs 1 to 3 of VH contain the amino acid sequences of SEQ ID NOs: 213, 214 and 215, respectively, and in which the amino acid sequences of CDRs 1 to 3 of VL contain the amino acid sequences of SEQ ID NOs: 218, 219 and 220, respectively, (l) an antibody in which the amino acid sequences of CDRs 1 to 3 of VH contain the amino acid sequences of SEQ ID NOs: 223, 224 and 225, respectively, and in which the amino acid sequences of CDRs 1 to 3 of VL contain the amino acid sequences of SEQ ID NOs: 228, 229 and 230, respectively, (m) an antibody in which the amino acid sequences of CDRs 1 to 3 of VH contain the amino acid sequences of SEQ ID NOs: 233, 234 and 235, respectively, and in which the amino acid sequences of CDRs 1 to 3 of VL contain the amino acid sequences of SEQ ID NOs: 238, 239 and 240, respectively, (n) an antibody in which the amino acid sequences of CDRs 1 to 3 of VH contain the amino acid sequences of SEQ ID NOs: 243, 244 and 245, respectively, and in which the amino acid sequences of CDRs 1 to 3 of VL contain the amino acid sequences of SEQ ID NOs: 248, 249 and 250, respectively, (o) an antibody which competes in binding to MOG with at least one of the antibodies described in (a) to (n), (p) an antibody which binds to an epitope containing an epitope to which any one of the antibodies described in (a) to (n) binds, (q) an antibody which binds to the same epitope as an epitope to which any one of the antibodies described in (a) to (n) binds and (r) an antibody which contains an amino acid sequence having homology of 85% or higher to the amino acid sequence of any one of the antibodies described in (a) to (n).

(4) The antibody or the antibody fragment according to any one of (1) to (3), wherein the antibody is selected from the group consisting of (a) to (n), (o1) to (o22) and (p) below, (a) an antibody in which the amino acid sequence of VH contains the amino acid sequence of SEQ ID NO: 3 and in which the amino acid sequence of VL contains the amino acid sequence of SEQ ID NO: 9, (b) an antibody in which the amino acid sequence of VH contains the amino acid sequence of SEQ ID NO: 15 and in which the amino acid sequence of VL contains the amino acid sequence of SEQ ID NO: 21, (c) an antibody in which the amino acid sequence of VH contains the amino acid sequence of SEQ ID NO: 27 and in which the amino acid sequence of VL contains the amino acid sequence of SEQ ID NO: 33, (d) an antibody fragment in which the amino acid sequence of VHH contains the amino acid sequence of SEQ ID NO: 39, (e) an antibody in which the amino acid sequence of VH contains the amino acid sequence of SEQ ID NO: 152 and in which the amino acid sequence of VL contains the amino acid sequence of SEQ ID NO: 157, (f) an antibody in which the amino acid sequence of VH contains the amino acid sequence of SEQ ID NO: 162 and in which the amino acid sequence of VL contains the amino acid sequence of SEQ ID NO: 167, (g) an antibody in which the amino acid sequence of VH contains the amino acid sequence of SEQ ID NO: 172 and in which the amino acid sequence of VL contains the amino acid sequence of SEQ ID NO: 177, (h) an antibody in which the amino acid sequence of VH contains the amino acid sequence of SEQ ID NO: 182 and in which the amino acid sequence of VL contains the amino acid sequence of SEQ ID NO: 187, (i) an antibody in which the amino acid sequence of VH contains the amino acid sequence of SEQ ID NO: 192 and in which the amino acid sequence of VL contains the amino acid sequence of SEQ ID NO: 197, (j) an antibody in which the amino acid sequence of VH contains the amino acid sequence of SEQ ID NO: 202 and in which the amino acid sequence of VL contains the amino acid sequence of SEQ ID NO: 207, (k) an antibody in which the amino acid sequence of VH contains the amino acid sequence of SEQ ID NO: 212 and in which the amino acid sequence of VL contains the amino acid sequence of SEQ ID NO: 217, (l) an antibody in which the amino acid sequence of VH contains the amino acid sequence of SEQ ID NO: 222 and in which the amino acid sequence of VL contains the amino acid sequence of SEQ ID NO: 227, (m) an antibody in which the amino acid sequence of VH contains the amino acid sequence of SEQ ID NO: 232 and in which the amino acid sequence of VL contains the amino acid sequence of SEQ ID NO: 237, (n) an antibody in which the amino acid sequence of VH contains the amino acid sequence of SEQ ID NO: 242 and in which the amino acid sequence of VL contains the amino acid sequence of SEQ ID NO: 247, (o1) an antibody in which the amino acid sequence of VH contains the amino acid sequence of SEQ ID NO: 252 and in which the amino acid sequence of VL contains the amino acid sequence of SEQ ID NO: 254, (o2) an antibody in which the amino acid sequence of VH contains the amino acid sequence of SEQ ID NO: 256 and in which the amino acid sequence of VL contains the amino acid sequence of SEQ ID NO: 258, (o3) an antibody in which the amino acid sequence of VH contains the amino acid sequence of SEQ ID NO: 260 and in which the amino acid sequence of VL contains the amino acid sequence of SEQ ID NO: 262, (o4) an antibody in which the amino acid sequence of VH contains the amino acid sequence of SEQ ID NO: 264 and in which the amino acid sequence of VL contains the amino acid sequence of SEQ ID NO: 266, (o5) an antibody in which the amino acid sequence of VH contains the amino acid sequence of SEQ ID NO: 268 and in which the amino acid sequence of VL contains the amino acid sequence of SEQ ID NO: 270, (o6) an antibody in which the amino acid sequence of VH contains the amino acid sequence of SEQ ID NO: 272 and in which the amino acid sequence of VL contains the amino acid sequence of SEQ ID NO: 274, (o7) an antibody in which the amino acid sequence of VH contains the amino acid sequence of SEQ ID NO: 276 and in which the amino acid sequence of VL contains the amino acid sequence of SEQ ID NO: 278, (o8) an antibody in which the amino acid sequence of VH contains the amino acid sequence of SEQ ID NO: 280 and in which the amino acid sequence of VL contains the amino acid sequence of SEQ ID NO: 282, (o9) an antibody in which the amino acid sequence of VH contains the amino acid sequence of SEQ ID NO: 284 and in which the amino acid sequence of VL contains the amino acid sequence of SEQ ID NO: 286, (o10) an antibody in which the amino acid sequence of VH contains the amino acid sequence of SEQ ID NO:

288 and in which the amino acid sequence of VL contains the amino acid sequence of SEQ ID NO: 290, (o11) an antibody in which the amino acid sequence of VH contains the amino acid sequence of SEQ ID NO: 292 and in which the amino acid sequence of VL contains the amino acid sequence of SEQ ID NO: 294, (o12) an antibody in which the amino acid sequence of VH contains the amino acid sequence of SEQ ID NO: 296 and in which the amino acid sequence of VL contains the amino acid sequence of SEQ ID NO: 298, (o13) an antibody in which the amino acid sequence of VH contains the amino acid sequence of SEQ ID NO: 300 and in which the amino acid sequence of VL contains the amino acid sequence of SEQ ID NO: 302, (o14) an antibody in which the amino acid sequence of VH contains the amino acid sequence of SEQ ID NO: 304 and in which the amino acid sequence of VL contains the amino acid sequence of SEQ ID NO: 306, (o15) an antibody in which the amino acid sequence of VH contains the amino acid sequence of SEQ ID NO: 308 and in which the amino acid sequence of VL contains the amino acid sequence of SEQ ID NO: 310, (o16) an antibody in which the amino acid sequence of VH contains the amino acid sequence of SEQ ID NO: 312 and in which the amino acid sequence of VL contains the amino acid sequence of SEQ ID NO: 314, (o17) an antibody in which the amino acid sequence of VH contains the amino acid sequence of SEQ ID NO: 316 and in which the amino acid sequence of VL contains the amino acid sequence of SEQ ID NO: 318, (o18) an antibody in which the amino acid sequence of VH contains the amino acid sequence of SEQ ID NO: 320 and in which the amino acid sequence of VL contains the amino acid sequence of SEQ ID NO: 322, (o19) an antibody in which the amino acid sequence of VH contains the amino acid sequence of SEQ ID NO: 324 and in which the amino acid sequence of VL contains the amino acid sequence of SEQ ID NO: 326, (o20) an antibody in which the amino acid sequence of VH contains the amino acid sequence of SEQ ID NO: 328 and in which the amino acid sequence of VL contains the amino acid sequence of SEQ ID NO: 330, (o21) an antibody in which the amino acid sequence of VH contains the amino acid sequence of SEQ ID NO: 332 and in which the amino acid sequence of VL contains the amino acid sequence of SEQ ID NO: 334, (o22) an antibody in which the amino acid sequence of VH contains the amino acid sequence of SEQ ID NO: 336 and in which the amino acid sequence of VL contains the amino acid sequence of SEQ ID NO: 338 and (p) an antibody which contains an amino acid sequence having homology of 85% or higher to the amino acid sequence of any one of the antibodies described in (a) to (n) and (o1) to (o22).

(5) The antibody or the antibody fragment according to any one of (1) to (4), wherein the antibody or the antibody fragment is a bispecific antibody.

(6) The bispecific antibody according to (5), wherein the bispecific antibody binds to MOG and an antigen that is present in a brain.

(7) The bispecific antibody according to (5) or (6), wherein the bispecific antibody contains an antigen binding site which binds to MOG and an antigen binding site which binds to an antigen that is present in a brain.

(8) The antibody fragment according to any one of (1) to (7) which is selected from the group consisting of Fab, Fab', F(ab')2, a single chain antibody (scFv), a dimerized V region (diabody), a disulfide-stabilized V region (dsFv), VHH and, a peptide containing CDR.

(9) The antibody and the antibody fragment according to any one of (1) to (8), wherein the antibody is a genetically recombinant antibody.

(10) The antibody and the antibody fragment according to any one of (1) to (9), wherein the antibody is selected from the group consisting of a mouse antibody, a rat antibody, a rabbit antibody, an alpaca antibody, a camel antibody, a llama antibody, a chimeric antibody, a humanized antibody, and a human antibody.

(11) A fused antibody or a fused antibody fragment which is obtained by binding at least one selected from the group consisting of (a) to (c) below to the antibody which binds to MOG according to any one of (1) to (10) or the antibody fragment thereof,
(a) a hydrophilic polymer,
(b) an amphipathic polymer, and
(c) a functional molecule.

(12) A hybridoma which produces the antibody according to any one of (1) to (11).

(13) A nucleic acid which contains a nucleotide sequence which encodes the antibody according to any one of (1) to (11).

(14) A transformant cell which contains a vector containing the nucleic acid according to (13).

(15) A method for producing the antibody or the antibody fragment according to any one of (1) to (11), including culturing the hybridoma according to (12) or the transformant cell according to (14) and collecting the antibody or the antibody fragment according to any one of (1) to (11) from a culture solution.

(16) A composition which contains the antibody or the antibody fragment according to any one of (1) to (11).

(17) The composition according to (16), wherein the composition is a composition for detecting or measuring an antigen that is present in a brain.

(18) The composition according to (16), wherein the composition is a composition for diagnosing or treating a brain disease.

(19) A method for detecting or measuring an antigen that is present in a brain using the antibody or the antibody fragment according to any one of (1) to (11) or the composition according to (16).

(20) A method for diagnosing or treating a brain disease using the antibody or the antibody fragment according to any one of (1) to (11) or the composition according to (16).

(21) A method for improving the property of accumulating in the brain of an antibody, an antibody fragment thereof, a fused antibody or a fused antibody fragment using the antibody, the antibody fragment, the fused antibody or the fused antibody fragment according to any one of (1) to (11) or the composition according to (16).

(22) A method for increasing the amount of an antibody, the amount of an antibody fragment thereof, the amount of a fused antibody or the amount of a fused antibody fragment in a brain using the antibody, the antibody fragment, the fused antibody or the fused antibody fragment according to any one of (1) to (11) or the composition according to (16).

Advantageous Effects of Invention

The MOG-binding molecule of the invention improves the property of the binding molecule itself of accumulating in the brain by specifically binding to MOG, and the MOG-binding molecule can also be applied to the treatment of brain diseases because another molecule which is modified by the MOG-binding molecule is delivered and kept in the brain. A specific MOG-binding molecule of the invention is an antibody. The antibody or the antibody fragment of the invention relates to an antibody which binds to MOG in the brain and thus has a property of accumulating in the brain. Accordingly, the antibody or the antibody fragment of the invention can be used for a composition for detecting or measuring an antigen that is present in the brain (MOG, or MOG and another antigen that is present in the brain), a composition for diagnosing a brain disease and a pharmaceutical composition for treating a brain disease.

BRIEF DESCRIPTION OF DRAWINGS

FIG. 3A shows the antibody concentrations in the serum four days after administering the antibodies to rats. The vertical axis shows the antibody concentration (ng/mL), and the horizontal axis shows the administered antibodies. FIG. 3B shows the antibody concentrations in the brain tissues four days after administering the antibodies to rats. The vertical axis shows the antibody amount per brain weight (ng/g brain), and the horizontal axis shows the administered antibodies. In both figures, the white bars show the results of an anti-AVM antibody used as a negative control, and the black bars show the results of the anti-MOG antibodies.

FIGS. 4A and 4B show the results of evaluation of the rat brain migration property of an anti-MOG antibody. FIG. 4A shows the antibody concentrations in the serum four days and 10 days after administering the antibodies to rats. The vertical axis shows the antibody concentration (ng/mL), and the horizontal axis shows the period (day) after the administration of the antibodies. FIG. 4B shows the antibody concentrations in the brain tissues four days and 10 days after administering the antibodies to rats. The vertical axis shows the antibody amount per brain weight (ng/g brain), and the horizontal axis shows the period (day) after the administration of the antibodies. In both figures, the plots with white diamond markers show the results of an anti-AVM antibody used as a negative control. The plots with white square markers show the results of an anti-transferrin receptor antibody, OX26 antibody, and the plots with black triangle markers show the results of the anti-MOG antibody, MOG01 antibody.

FIGS. 7A and 7B show the results of evaluation of the rat brain migration properties of bispecific antibodies which bind to MOG. FIG. 7A shows the antibody concentrations in the serum 10 days after administering the antibodies to rats. The vertical axis shows the antibody concentration (ng/mL), and the horizontal axis shows the bispecific antibodies used. FIG. 7B shows the antibody concentrations in the brain tissues 10 days after administering the antibodies to rats. The vertical axis shows the antibody amount per brain weight (ng/g brain), and the horizontal axis shows the bispecific antibodies used.

FIGS. 8A and 8B show the results of evaluation of the mouse brain migration property of an anti-MOG01 antibody. FIG. 8A shows the antibody concentrations in the serum 3, 6, 10, 14, 21 and 28 days after administering the antibodies to mice. The vertical axis shows the antibody concentration (ng/mL), and the horizontal axis shows the time (day). FIG. 8B shows the antibody concentrations in the brain tissues 3, 6, 10, 14, 21 and 28 days after administering the antibodies to mice. The vertical axis shows the antibody concentration (ng/g brain), and the horizontal axis shows the time (day). In both figures, the plots with white circle markers show the results of an anti-AVM antibody used as a negative control, and the plots with black square markers show the results of MOG01 scFv-hG4PE.

FIGS. 9A to 9C show the results of evaluation of the mouse brain migration property imaging of an anti-MOG01 antibody. FIG. 9A shows the measurement data of the fluorescence intensities in the brain six days after administering an Alexa FluorR 488-labeled anti-AVM antibody as a negative control and an Alexa FluorR 488-labeled anti-MOG01 antibody to mice, and FIG. 9B shows the measurement data of the fluorescence intensities in the brain after 14 days. FIG. 9C shows the values obtained by correcting the fluorescence amounts in the brain after six days and 14 days using the fluorescence intensities of the administered antibodies. The vertical axis shows the fluorescence amount in brain/fluorescence amount of administered antibody (%), and the horizontal axis shows the administered antibodies.

FIGS. 10A to 10C show the structures of bispecific antibodies which bind to AVM and MOG. FIG. 10A shows the structure of AVM-MOG01 IgG4PE(R409K) antibody, and FIG. 10B shows the structure of AVM IgG4PE (R409K)_ MOG01 Fab antibody. FIG. 10C shows the structure of AVM IgG4PE(R409K)_MOG01sscFv antibody.

FIGS. 11A and 11B show the structures of bispecific antibodies which bind to AVM and MOG. FIG. 11A shows the structure of AVM IgG4PE(R409K)_MOG01dscFv antibody, AVM IgG4PE(R409K)_MOG01dscFv2 antibody and AVM IgG4PE(R409K)_MOG01dscFv4 antibody, and FIG. 11B shows the structure of AVM IgG4PE(R409K)_ MOG01dscFv3 antibody and AVM IgG4PE(R409K)_ MOG01dscFv5 antibody to AVM IgG4PE(R409K)_ MOG01dscFv11antibody.

FIGS. 12A to 12C show the results of analysis using a flow cytometer of the affinities of bispecific antibodies to human MOG/L929 cells. The vertical axis shows the average fluorescence intensity, and the horizontal axis shows the antibody concentration. In FIG. 12A, the plot with white circle markers shows the results of AVM IgG4PE(R409K) antibody (negative control), and the plot with black square markers shows the results of AVM-MOG01 IgG4PE (R409K) antibody. In FIG. 12B, the plot with white circle markers shows the results of AVM IgG4PE(R409K)_ AVMsscFv antibody (negative control), and the plot with black square markers shows the results of AVM IgG4PE (R409K)_MOG01sscFv antibody. In FIG. 12C, the plot with white circle markers shows the results of AVM IgG4PE (R409K)_AVM Fab antibody (negative control), and the plot with black square markers shows the results of AVM IgG4PE(R409K)_MOG01 Fab antibody.

In FIG. 13A, the plot with white square markers shows the results of AVM IgG4PE(R409K)_ MOG01dscFv antibody, the plot with white circle markers shows the results of AVM IgG4PE(R409K)_MOG01dscFv2 antibody, and the plot with white triangle markers shows the results of AVM IgG4PE(R409K)_MOG01dscFv4 antibody. In FIG. 13B, the plot with white diamond markers shows the results of AVM IgG4PE(R409K)_MOG01dscFv3 antibody, the plot with black diamond markers shows the results of AVM IgG4PE(R409K)_MOG01dscFv5 antibody, the plot with white circle markers shows the results of AVM IgG4PE (R409K)_MOG01dscFv6 antibody, the plot with black circle markers shows the results of AVM IgG4PE(R409K)_ MOG01dscFv7 antibody, the plot with white triangle markers shows the results of AVM IgG4PE(R409K)_ MOG01dscFv8 antibody, the plot with black triangle markers shows the results of AVM IgG4PE(R409K)_ MOG01dscFv9 antibody, the plot with white square markers shows the results of AVM IgG4PE(R409K)_ MOG01dscFv10 antibody, and the plot with black square markers shows the results of AVM IgG4PE(R409K)_ MOG01dscFv11 antibody.

FIGS. 14A and 14B show the antibody concentrations in the serum and in the brain tissues, respectively, 10 days after the administration of AVM IgG4PE(R409K) antibody (negative control) and AVM-MOG01 IgG4PE(R409K) antibody.

FIGS. 15A and 15B show the results of evaluation of the mouse brain migration properties of bispecific antibodies. The vertical axis shows the antibody concentration, and the horizontal axis shows the bispecific antibodies used. FIGS. 15A and 15B show the antibody concentrations in the serum and in the brain tissues, respectively, 10 days after the administration of AVM IgG4PE(R409K)_AVMsscFv antibody (negative control) and AVM IgG4PE(R409K)_ MOG01sscFv antibody.

FIGS. 16A and 16B show the results of evaluation of the mouse brain migration properties of bispecific antibodies. The vertical axis shows the antibody concentration, and the horizontal axis shows the bispecific antibodies used. FIGS. 16A and 16B show the antibody concentrations in the serum and in the brain tissues, respectively, 10 days after the administration of AVM IgG4PE(R409K) AVM Fab antibody (negative control) and AVM IgG4PE(R409K)_MOG01 Fab antibody.

FIGS. 17A to 17D show the results of evaluation of the mouse brain migration properties of bispecific antibodies. The vertical axis shows the antibody concentration, and the horizontal axis shows the bispecific antibodies used. The negative control corresponding to AVM IgG4PE(R409K)_ MOG01dscFv antibody is AVM IgG4PE(R409K)_AVMdscFv antibody, and the negative control corresponding to AVM IgG4PE(R409K)_MOG01dscFv3 antibody is AVM IgG4PE(R409K)_AVMdscFv3 antibody. The negative control corresponding to AVM IgG4PE(R409K)_ MOG01dscFv5 antibody is AVM IgG4PE(R409K)_AVMdscFv5 antibody. FIG. 17A shows the antibody concentrations in the serum 10 days after the administration of the antibodies. FIG. 17B shows the antibody concentrations in the brain tissues 10 days after the administration of the antibodies. FIG. 17C shows the antibody concentrations in the serum 28 days after the administration of the antibodies. FIG. 17D shows the antibody concentrations in the brain tissues 28 days after the administration of the antibodies.

FIG. 18 shows the amino acid sequences of scFv of clones similar to a MOG antibody and shows clones similar to MOG301 antibody.

FIG. 19 shows the amino acid sequences of scFv of clones similar to a MOG antibody and shows clones similar to MOG303 antibody.

FIG. 20 shows the amino acid sequences of scFv of clones similar to a MOG antibody and shows clones similar to MOG307 antibody.

FIG. 21 shows the amino acid sequences of scFv of clones similar to a MOG antibody and shows clones similar to MOG310 antibody.

FIGS. 22A and 22B show the amino acid sequences of scFv of clones similar to MOG antibodies. FIG. 22A shows a clone similar to MOG329 antibody, and FIG. 22B shows a clone similar to MOG456 antibody.

FIGS. 28A and 28B show the results of evaluation of the mouse brain migration properties of enzyme-fused antibodies, MOG01 IgG4PE(R409K)-ASM and AVM IgG4PE (R409K)-ASM. The vertical axis shows the antibody concentration, and the horizontal axis shows the enzyme-fused antibodies used. FIG. 28A shows the antibody concentrations in the serum 10 days after the administration of the antibodies. FIG. 28B shows the antibody concentrations in the brain tissues 10 days after the administration of the antibodies.

DESCRIPTION OF EMBODIMENTS

Figure 1:
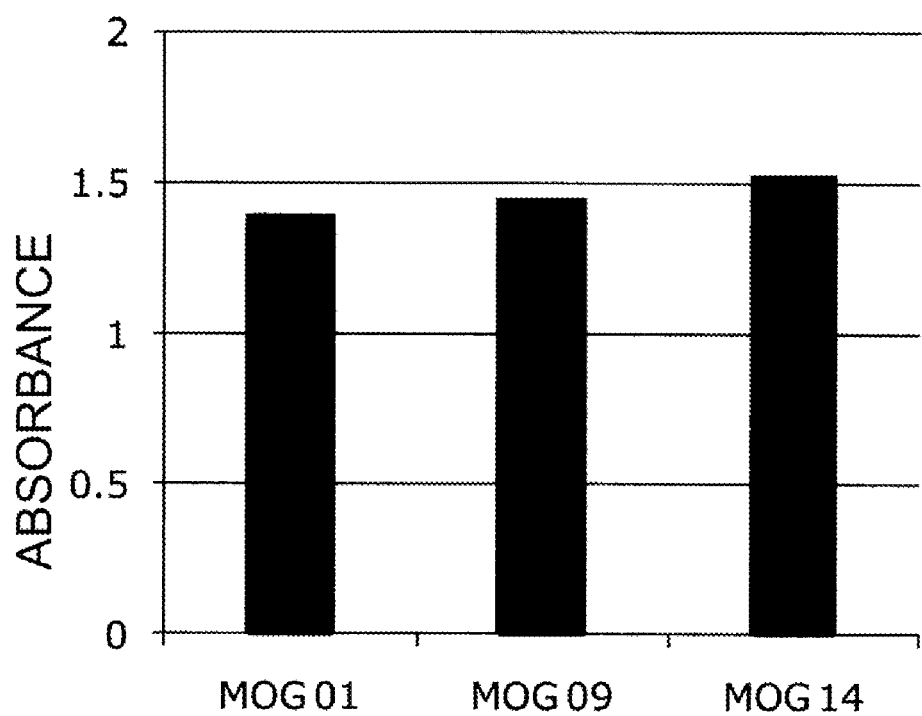
FIG. 1 shows the results of analysis by ELISA of the affinities to rMOG-FLAG_Fc of phage clones displaying scFv that binds to MOG. The vertical axis shows the absorbance relative to rMOG-FLAG_Fc, and the horizontal axis shows the names of the scFv antibodies displayed by the phage clones.

The invention relates to an antigen-binding molecule which binds to myelin-oligodendrocyte glycoprotein (referred to as MOG below). More specifically, the invention relates to an antibody which binds to MOG or an antibody fragment thereof.

The MOG-binding molecule of the invention may be a molecule of any state as long as the molecule specifically binds to MOG and accumulates in the brain, and the MOG-binding molecule may be any of molecules such as proteins, nucleic acids and synthetic organic low-molecular-weight compounds/high-molecular-weight compounds. Specifically, the MOG-binding molecule may be any of recombinant proteins, antibodies, aptamers, low-molecular-weight compounds obtained by screening low-molecular-weight molecules and the like, but an antibody and an antibody fragment thereof are preferable. The MOG-binding molecule is preferably a molecule which binds to an extracellular region of MOG.

MOG is a protein belonging to the immunoglobulin superfamily and constitutes myelin. Whole human MOG, for example, consists of 218 amino acids, and human MOG is expressed in the outermost layer of myelin in the central nervous system and plays a role in the cell adhesion and the cell surface interaction.

The kinds of animal of MOG to which the MOG-binding molecule of the invention binds are mouse, rat, cynomolgus monkey, human and/or the like but are not particularly limited to these kinds, and an appropriate animal kind can be selected depending on the use of the antibody. For example, when the antibody of the invention is used for a pharmaceutical use for humans, the antibody is preferably an antibody which binds to at least human MOG.

In the invention, human MOG is a polypeptide which contains the amino acid sequence of SEQ ID NO: 78 or the amino acid sequence of NCBI accession No. AAB08088, a polypeptide which has the amino acid sequence of SEQ ID NO: 78 or the amino acid sequence of NCBI accession No. AAB08088, wherein one or more amino acids are deleted, substituted or added, and which has a function of human MOG, a polypeptide which has an amino acid sequence having homology of 60% or higher, preferably 80% or higher, further preferably 90% or higher, most preferably 95% or higher to the amino acid sequence of SEQ ID NO: 78 or the amino acid sequence of NCBI accession No. AAB08088 and which has a function of human MOG or the like.

The polypeptide which has the amino acid sequence of SEQ ID NO: 78 or the amino acid sequence of NCBI accession No. AAB08088, wherein one or more amino acids are deleted, substituted or added, can be obtained by introducing a site-specific mutation for example to DNA that encodes a polypeptide containing the amino acid sequence of SEQ ID NO: 78 using the site-directed mutagenesis [Molecular Cloning, A Laboratory Manual, Second Edition, Cold Spring Harbor Laboratory Press (1989), Current Protocols in Molecular Biology, John Wiley & Sons (1987-1997), Nucleic acids Research, 10, 6487 (1982), Proc. Natl. Acad. Sci. USA, 79, 6409 (1982), Gene, 34, 315 (1985), Nucleic Acids Research, 13, 4431 (1985) and Proc. Natl. Acad. Sci. USA, 82, 488 (1985)] or the like.

The number of amino acids that are deleted, substituted or added is not particularly limited but is preferably one to tens, for example, 1 to 20, more preferably one to a few, for example, one to five amino acids.

The same applies to the amino acid sequence of mouse MOG [SEQ ID NO: 74 and NCBI accession No. NP_034944], the amino acid sequence of rat MOG [SEQ ID NO: 68 and NCBI accession No. AAA41628] and the amino acid sequence of cynomolgus monkey MOG [SEQ ID NO: 76 and NCBI accession No. NP_001271785].

Genes which encode human MOG are the nucleotide sequence of SEQ ID NO: 77 and the nucleotide sequence of NCBI accession No. U64564. A gene containing DNA which has the nucleotide sequence of SEQ ID NO: 77 or the nucleotide sequence of NCBI accession No. U64564, wherein one or more bases are deleted, substituted or added, and which encodes a polypeptide having a function of MOG, a gene containing DNA which has a nucleotide sequence having homology of at least 60% or higher to the nucleotide sequence of SEQ ID NO: 77 or the nucleotide sequence of NCBI accession No. U64564, preferably a nucleotide sequence having homology of 80% or higher or further preferably a nucleotide sequence having homology of 95% or higher and which encodes a polypeptide having a function of MOG, a gene which contains DNA that hybridizes with DNA containing the nucleotide sequence of SEQ ID NO: 77 or the nucleotide sequence of NCBI accession No. U64564 under stringent conditions and which encodes a polypeptide having a function of MOG and another gene are also included as the genes that encode MOG in the invention.

The DNA that hybridizes under stringent conditions means hybridizable DNA that is obtained by a colony hybridization method, a plaque hybridization method, a southern blot hybridization method, a DNA microarray method or the like using DNA containing the nucleotide sequence of SEQ ID NO: 77 or the nucleotide sequence of NCBI accession No. U64564 as a probe.

Specifically, it is possible to exemplify DNA that can be identified by washing a filter or a glass slide under the condition of 65° C. using a SSC solution of the concentration of 0.1 to 2 times (the composition of the SSC solution with the concentration of 1 time is 150 mmol/L sodium chloride and 15 mmol/L sodium citrate), after performing hybridization [Molecular Cloning, A Laboratory Manual, Second Edition, Cold Spring Harbor Laboratory Press (1989), Current Protocols in Molecular Biology, John Wiley & Sons (1987-1997) and DNA Cloning 1: Core Techniques, A Practical Approach, Second Edition, Oxford University, (1995)] at 65° C. in the presence of 0.7 to 1.0 mol/L sodium chloride using a filter or a glass slide on which DNA derived from a hybridized colony or plaque or a PCR product or DNA oligo having the sequence is fixed.

Examples of the hybridizable DNA include DNA having homology of at least 60% or higher to the nucleotide sequence of SEQ ID NO: 77 or the nucleotide sequence of NCBI accession No. U64564, preferably DNA having homology of 80% or higher and further preferably DNA having homology of 95% or higher.

The same applies to the nucleotide sequence of mouse MOG [SEQ ID NO: 73 and NCBI accession No. NM_010814], the nucleotide sequence of rat MOG [SEQ ID NO: 67 and NCBI accession No. M99485] and the nucleotide sequence of cynomolgus monkey MOG [SEQ ID NO: 75 and NCBI accession No. NM_001284856].

The function of MOG is involvement in the cell adhesion, the cell surface interaction and the like on myelin.

Genetic polymorphism is often recognized in a nucleotide sequence of a gene that encodes a protein of a eukaryote. The genes that encode MOG in the invention also include genes in which small scale mutations arise in the nucleotide sequences by such polymorphism in the genes used in the invention.

A value of homology in the invention may be a value calculated using a homology detection program known to those skilled in the art unless particularly specified. Regarding a nucleotide sequence, there are a value calculated using a default parameter of BLAST [J. Mol. Biol., 215, 403 (1990)] and the like. Regarding an amino acid sequence, there are a value calculated using a default parameter of BLAST2 [Nucleic Acids Res., 25, 3389 (1997), Genome Res., 7, 649 (1997) and http://www.ncbi.nlm.nih.gov/Education/BLASTinfo/information3.htmL] and the like.

Regarding the default parameters, G (Cost to open gap) is 5 for a nucleotide sequence and 11 for an amino acid sequence, -E (Cost to extend gap) is 2 for a nucleotide sequence and 1 for an amino acid sequence, -q (Penalty for nucleotide mismatch) is -3, -r (reward for nucleotide match) is 1, -e (expect value) is 10, -W (wordsize) is 11 residues for a nucleotide sequence and 3 residues for an amino acid sequence, -y [Dropoff (X) for blast extensions in bits] is 20 for the blastn and 7 for programs other than the blastn, -X (X dropoff value for gapped alignment in bits) is 15, and -Z (final X dropoff value for gapped alignment in bits) is 50 for the blastn and 25 for programs other than the blastn (http://www.ncbi.nlm.nih.gov/blast/htmL/blastcgihelp.htmL).

A polypeptide containing a partial sequence of the amino acid sequence of any of the MOG kinds can be produced by a method known to those skilled in the art. Specifically, the polypeptide can be produced by deleting a part of DNA that encodes the amino acid sequence of any of the MOG kinds and culturing a transformant into which an expression vector including the DNA has been introduced. In addition, a polypeptide having the amino acid sequence of any of the MOG kinds in which one or more amino acids are deleted, substituted or added can be obtained by the same method as above.

Furthermore, a polypeptide that has the amino acid sequence of any of the MOG kinds or a polypeptide having the amino acid sequence of any of the MOG kinds in which one or more amino acids are deleted, substituted or added can be produced also using a chemical synthesis method such as a fluorenylmethyloxycarbonyl (Fmoc) method or a t-butyloxycarbonyl (tBoc) method.

In the invention, the extracellular region of human MOG is the amino acid sequence of from position 30 to position 154 or from position 232 to position 247 in the amino acid sequence of SEQ ID NO: 78 or NCBI accession No. AAB08088 and is preferably the amino acid sequence of from position 30 to position 154.

The extracellular region of mouse MOG is the amino acid sequence of from position 30 to position 157 or from position 232 to position 247 in the amino acid sequence of SEQ ID NO: 74 or NCBI accession No. NP_034944 and is preferably the amino acid sequence of from position 30 to position 157. The extracellular region of rat MOG is the amino acid sequence of from position 28 to position 155 or from position 230 to 245 in the amino acid sequence of SEQ ID NO: 68 or NCBI accession No. AAA41628 and is preferably the amino acid sequence of from position 28 to position 155.

The extracellular region of cynomolgus monkey MOG is the amino acid sequence of from position 30 to position 154 or from position 232 to position 247 in the amino acid sequence of SEQ ID NO: 76 or NCBI accession No. NP_001271785 and is preferably the amino acid sequence of from position 30 to position 154.

That the antibody of the invention binds to an extracellular region of MOG can be confirmed by measuring the affinity of the antibody of the invention to MOG-expressing cells or a recombinant MOG protein using ELISA, flow cytometry, surface plasmon resonance method or the like. Moreover, binding of the antibody can be confirmed also using a combination of known immunological detection methods [Monoclonal Antibodies-Principles and practice, Third edition, Academic Press (1996), Antibodies-A Laboratory Manual, Cold Spring Harbor Laboratory (1988) and A manual for monoclonal antibody experiments, Kodansha scientific books (1987)] and the like.

The MOG-binding molecule of the invention is a molecule which specifically binds to MOG in the brain and which thus has a property of accumulating in the brain, and for example, the antibody is an antibody which binds to MOG in the brain and which thus has a property of accumulating in the brain. Moreover, the antibody of the invention is an antibody which passes through the blood brain barrier in the brain from the peripheral part, migrates to the brain and binds to MOG in the brain when peripherally administered to an animal and which thus has a property of accumulating in the brain. The antibody of the invention is preferably an antibody having an excellent property of accumulating in the brain or an antibody having an improved property of accumulating in the brain.

In the invention, the property of accumulating in the brain is a property of a subject of accumulating in the brain when the subject is administered to an animal to be tested. That is, the property means that the concentration in the brain (or the amount in the brain) of the subject increases or that the subject exists at a certain detectable concentration due to at least any one cause selected from an increase in the migration into the brain, an increase in the accumulation in the brain, a decrease in the migration to outside from the brain, a decrease in the discharge to outside from the brain and a decrease in the decomposition in the brain.

In the invention, that the property of accumulating in the brain is excellent, that the property of accumulating in the brain is high or that the property of accumulating in the brain is improved means that the concentration in the brain (or the amount in the brain) of the subject increases or that the subject exists in the brain at a certain concentration (amount) which is detectable for a long time when the subject is administered to an animal to be tested, as compared to a control after a same period (day) after the administration.

The phenomena are caused by at least any one of an increase in the migration of the subject into the brain, an increase in the accumulation in the brain, a decrease in the migration to outside from the brain, a decrease in the discharge to outside from the brain and a decrease in the decomposition in the brain as compared to a control.

In the invention, that the property of accumulating in the brain is excellent, that the property of accumulating in the brain is high or that the property of accumulating in the brain is improved means, for example, that, when the subject is administered to an animal to be tested, the concentration (amount) of the subject in the brain is higher than that of a control 1 to 10 days after the administration, preferably 2 to 10 days or 3 to 10 days, more preferably 4 to 10 days after the administration or that the peak of the concentration in the brain (or the amount in the brain) of the subject is seen on day 4 or later after the administration, preferably on day 5 or later, day 6 or later, day 7 or later, day 8 or later or day 9 or later, more preferably on day 10 or later after the administration.

The antibody having an excellent property of accumulating in the brain, the antibody having a high property of accumulating in the brain or the antibody having an improved property of accumulating in the brain may be any antibody as long as the antibody is an antibody whose antibody concentration (antibody amount) in the brain is higher than that of a control antibody or an antibody having the characteristic of existing in the brain for a long time.

Examples include antibodies having the characteristic that the migration rate to the brain and/or the accumulation rate in the brain are higher than those of a control antibody, the characteristic that the migration rate to outside from the brain, the discharge rate and/or the decomposition rate in the brain are lower and the characteristic that the migration rate to the brain and/or the accumulation rate in the brain are higher than the migration rate to outside from the brain, the discharge rate and/or the decomposition rate in the brain.

Accordingly, the antibody or the antibody fragment of the invention is, for example an antibody or an antibody fragment thereof whose antibody concentration (or the antibody amount) in the brain is higher than that of a control antibody after a same period (day) after the administration when the antibody or the antibody fragment is administered to an animal or an antibody or an antibody fragment thereof which can exist in the brain for a long time.

The change in the antibody concentration (or the antibody amount) in the brain may be any change, and examples include a case in which the antibody concentration gradually decreases after the antibody concentration in the brain once reaches its peak during the measurement period, a case in which after the antibody concentration in the brain reaches its peak, the antibody concentration is maintained, a case in which the antibody concentration in the brain continues to increase after the administration of the antibody or another case.

The antibody or the antibody fragment of the invention is, for example, an antibody whose antibody concentration or antibody amount in the brain is higher than that of a control antibody on day 4 or day 10 after the administration to a rat, an antibody whose antibody concentration or antibody amount in the brain is maintained or increases from day 4 to day 10 after the administration to a rat, an antibody whose existence in the brain can be clearly confirmed on day 10 or later after the administration to a rat or another antibody but is not limited to these examples.

The control antibody may be any antibody as long as the control antibody is an antibody of the same species or subclass as that of the antibody to be tested, but for example, an anti-avermectin (AVM) antibody and the like can be used.

In the invention, the term "in the brain" is, for example, in the brain parenchyma, in a cerebral ventricle, in the cerebrospinal fluid or the like but is not limited to these examples.

In the invention, the method for administering an antibody to an animal is, for example, intravenous administration, intraventricular administration, intraperitoneal administration, subcutaneous administration, intradermal administration, nasal administration, intrathecal administration or the like but is not limited to these methods.

In the invention, the method for measuring the property of an antibody of accumulating in the brain is, for example, a method of collecting brain tissues several days after administering the antibody to an animal, measuring the antibody concentration of the supernatant obtained after homogenization and centrifugation and calculating the antibody amount per unit brain weight, a method of detecting the antibody using a known immunological method using the collected brain tissues, a method of administering the antibody which has been labeled to an animal and detecting the antibody by an in vivo imaging system sequentially or another method.

The antibody of the invention may be an antibody selected from the group consisting of (a) to (q) below, (a) an antibody in which the amino acid sequences of CDRs 1 to 3 of VH are the amino acid sequences of SEQ ID NOs: 4, 5 and 6, respectively, and in which the amino acid sequences of CDRs 1 to 3 of VL contain the amino acid sequences of SEQ ID NOs: 10, 11 and 12, respectively, (b) an antibody in which the amino acid sequences of CDRs 1 to 3 of VH are the amino acid sequences of SEQ ID NOs: 16, 17 and 18, respectively, and in which the amino acid sequences of CDRs 1 to 3 of VL contain the amino acid sequences of SEQ ID NOs: 22, 23 and 24, respectively, (c) an antibody in which the amino acid sequences of CDRs 1 to 3 of VH are the amino acid sequences of SEQ ID NOs: 28, 29 and 30, respectively, and in which the amino acid sequences of CDRs 1 to 3 of VL contain the amino acid sequences of SEQ ID NOs: 34, 35 and 36, respectively, (d) an antibody fragment in which the amino acid sequences of CDRs 1 to 3 of VHH contain the amino acid sequences of SEQ ID NOs: 40, 41 and 42, respectively, (e) an antibody in which the amino acid sequences of CDRs 1 to 3 of VH contain the amino acid sequences of SEQ ID NOs: 153, 154 and 155, respectively, and in which the amino acid sequences of CDRs 1 to 3 of VL contain the amino acid sequences of SEQ ID NOs: 158, 159 and 160, respectively, (f) an antibody in which the amino acid sequences of CDRs 1 to 3 of VH contain the amino acid sequences of SEQ ID NOs: 163, 164 and 165, respectively, and in which the amino acid sequences of CDRs 1 to 3 of VL contain the amino acid sequences of SEQ ID NOs: 168, 169 and 170, respectively, (g) an antibody in which the amino acid sequences of CDRs 1 to 3 of VH contain the amino acid sequences of SEQ ID NOs: 173, 174 and 175, respectively, and in which the amino acid sequences of CDRs 1 to 3 of VL contain the amino acid sequences of SEQ ID NOs: 178, 179 and 180, respectively, (h) an antibody in which the amino acid sequences of CDRs 1 to 3 of VH contain the amino acid sequences of SEQ ID NOs: 183, 184 and 185, respectively, and in which the amino acid sequences of CDRs 1 to 3 of VL contain the amino acid sequences of SEQ ID NOs: 188, 189 and 190, respectively, (i) an antibody in which the amino acid sequences of CDRs 1 to 3 of VH contain the amino acid sequences of SEQ ID NOs: 193, 194 and 195, respectively, and in which the amino acid sequences of CDRs 1 to 3 of VL contain the amino acid sequences of SEQ ID NOs: 198, 199 and 200, respectively, (j) an antibody in which the amino acid sequences of CDRs 1 to 3 of VH contain the amino acid sequences of SEQ ID NOs: 203, 204 and 205, respectively, and in which the amino acid sequences of CDRs 1 to 3 of VL contain the amino acid sequences of SEQ ID NOs: 208, 209 and 210, respectively, (k) an antibody in which the amino acid sequences of CDRs 1 to 3 of VH contain the amino acid sequences of SEQ ID NOs: 213, 214 and 215, respectively, and in which the amino acid sequences of CDRs 1 to 3 of VL contain the amino acid sequences of SEQ ID NOs: 218, 219 and 220, respectively, (l) an antibody in which the amino acid sequences of CDRs 1 to 3 of VH contain the amino acid sequences of SEQ ID NOs: 223, 224 and 225, respectively, and in which the amino acid sequences of CDRs 1 to 3 of VL contain the amino acid sequences of SEQ ID NOs: 228, 229 and 230, respectively, (m) an antibody in which the amino acid sequences of CDRs 1 to 3 of VH contain the amino acid sequences of SEQ ID NOs: 233, 234 and 235, respectively, and in which the amino acid sequences of CDRs 1 to 3 of VL contain the amino acid sequences of SEQ ID NOs: 238, 239 and 240, respectively, (n) an antibody in which the amino acid sequences of CDRs 1 to 3 of VH contain the amino acid sequences of SEQ ID NOs: 243, 244 and 245, respectively, and in which the amino acid sequences of CDRs 1 to 3 of VL contain the amino acid sequences of SEQ ID NOs: 248, 249 and 250, respectively, (o) an antibody which competes in binding to MOG with at least one of the antibodies described in (a) to (n), (p) an antibody which binds to an epitope containing an epitope to which any one of the antibodies described in (a) to (n) binds and (q) an antibody which binds to the same epitope as an epitope to which any one of the antibodies described in (a) to (n) binds.

As the antibody of the invention, an antibody having amino acid sequences of CDRs 1 to 3 of VH and CDRs 1 to 3 of VL of an antibody having homology of 85% or higher, preferably 90% or higher to the amino acid sequences of CDRs 1 to 3 of VH and CDRs 1 to 3 of VL of any one of the antibodies described in (a) to (n) is included. The homology of 90% or higher is more preferably homology of 91%, 92%, 93%, 94%, 95%, 96%, 97%, 98% or 99% or the like.

In the invention, embodiments of the antibodies described in (a) to (n) include human anti-MOG monoclonal antibodies, MOG01 antibody, MOG09 antibody and MOG14 antibody and an alpaca anti-MOG monoclonal VHH antibody, iMOG-3Rim1-S32 antibody. In addition, embodiments include a human chimeric antibody of iMOG-3Rim1-S32, a humanized antibody of iMOG-3Rim1-S32 and the like.

In the invention, the antibody of (o) is a second antibody which inhibits binding of a first antibody and MOG, wherein the antibody described in any of (a) to (n) is the first antibody.

In the invention, the antibody of (p) is a second antibody which binds to a second epitope containing a first epitope, wherein the antibody described in any of (a) to (n) is a first antibody, and the epitope to which the first antibody binds is the first epitope.

Moreover, the antibody of (q) of the invention is a second antibody which binds to a first epitope, wherein the antibody described in any of (a) to (n) is a first antibody, and the epitope to which the first antibody binds is the first epitope.

Furthermore, the antibody of the invention may be specifically an antibody selected from the group consisting of (a) to (n) and (o1) to (o22) below, (a) an antibody in which the amino acid sequence of VH is the amino acid sequence of SEQ ID NO: 3 and in which the amino acid sequence of VL contains the amino acid sequence of SEQ ID NO: 9, (b) an antibody in which the amino acid sequence of VH is the amino acid sequence of SEQ ID NO: 15 and in which the amino acid sequence of VL contains the amino acid sequence of SEQ ID NO: 21, (c) an antibody in which the amino acid sequence of VH is the amino acid sequence of SEQ ID NO: 27 and in which the amino acid sequence of VL contains the amino acid sequence of SEQ ID NO: 33, (d) an antibody fragment in which the amino acid sequence of VHH contains the amino acid sequence of SEQ ID NO: 39, (e) an antibody in which the amino acid sequence of VH contains the amino acid sequence of SEQ ID NO: 152 and in which the amino acid sequence of VL contains the amino acid sequence of SEQ ID NO: 157, (f) an antibody in which the amino acid sequence of VH contains the amino acid sequence of SEQ ID NO: 162 and in which the amino acid sequence of VL contains the amino acid sequence of SEQ ID NO: 167, (g) an antibody in which the amino acid sequence of VH contains the amino acid sequence of SEQ ID NO: 172 and in which the amino acid sequence of VL contains the amino acid sequence of SEQ ID NO: 177, (h) an antibody in which the amino acid sequence of VH contains the amino acid sequence of SEQ ID NO: 182 and in which the amino acid sequence of VL contains the amino acid sequence of SEQ ID NO: 187, (i) an antibody in which the amino acid sequence of VH contains the amino acid sequence of SEQ ID NO: 192 and in which the amino acid sequence of VL contains the amino acid sequence of SEQ ID NO: 197, (j) an antibody in which the amino acid sequence of VH contains the amino acid sequence of SEQ ID NO: 202 and in which the amino acid sequence of VL contains the amino acid sequence of SEQ ID NO: 207, (k) an antibody in which the amino acid sequence of VH contains the amino acid sequence of SEQ ID NO: 212 and in which the amino acid sequence of VL contains the amino acid sequence of SEQ ID NO: 217, (l) an antibody in which the amino acid sequence of VH contains the amino acid sequence of SEQ ID NO: 222 and in which the amino acid sequence of VL contains the amino acid sequence of SEQ ID NO: 227, (m) an antibody in which the amino acid sequence of VH contains the amino acid sequence of SEQ ID NO: 232 and in which the amino acid sequence of VL contains the amino acid sequence of SEQ ID NO: 237, (n) an antibody in which the amino acid sequence of VH contains the amino acid sequence of SEQ ID NO: 242 and in which the amino acid sequence of VL contains the amino acid sequence of SEQ ID NO: 247, (o1) an antibody in which the amino acid sequence of VH contains the amino acid sequence of SEQ ID NO: 252 and in which the amino acid sequence of VL contains the amino acid sequence of SEQ ID NO: 254, (o2) an antibody in which the amino acid sequence of VH contains the amino acid sequence of SEQ ID NO: 256 and in which the amino acid sequence of VL contains the amino acid sequence of SEQ ID NO: 258, (o3) an antibody in which the amino acid sequence of VH contains the amino acid sequence of SEQ ID NO: 260 and in which the amino acid sequence of VL contains the amino acid sequence of SEQ ID NO: 262, (o4) an antibody in which the amino acid sequence of VH contains the amino acid sequence of SEQ ID NO: 264 and in which the amino acid sequence of VL contains the amino acid sequence of SEQ ID NO: 266, (o5) an antibody in which the amino acid sequence of VH contains the amino acid sequence of SEQ ID NO: 268 and in which the amino acid sequence of VL contains the amino acid sequence of SEQ ID NO: 270, (o6) an antibody in which the amino acid sequence of VH contains the amino acid sequence of SEQ ID NO: 272 and in which the amino acid sequence of VL contains the amino acid sequence of SEQ ID NO: 274, (o7) an antibody in which the amino acid sequence of VH contains the amino acid sequence of SEQ ID NO: 276 and in which the amino acid sequence of VL contains the amino acid sequence of SEQ ID NO: 278, (o8) an antibody in which the amino acid sequence of VH contains the amino acid sequence of SEQ ID NO: 280 and in which the amino acid sequence of VL contains the amino acid sequence of SEQ ID NO: 282, (o9) an antibody in which the amino acid sequence of VH contains the amino acid sequence of SEQ ID NO: 284 and in which the amino acid sequence of VL contains the amino acid sequence of SEQ ID NO: 286, (o10) an antibody in which the amino acid sequence of VH contains the amino acid sequence of SEQ ID NO: 288 and in which the amino acid sequence of VL contains the amino acid sequence of SEQ ID NO: 290, (o1) an antibody in which the amino acid sequence of VH contains the amino acid sequence of SEQ ID NO: 292 and in which the amino acid sequence of VL contains the amino acid sequence of SEQ ID NO: 294, (o12) an antibody in which the amino acid sequence of VH contains the amino acid sequence of SEQ ID NO: 296 and in which the amino acid sequence of VL contains the amino acid sequence of SEQ ID NO: 298, (o13) an antibody in which the amino acid sequence of VH contains the amino acid sequence of SEQ ID NO: 300 and in which the amino acid sequence of VL contains the amino acid sequence of SEQ ID NO: 302, (o14) an antibody in which the amino acid sequence of VH contains the amino acid sequence of SEQ ID NO: 304 and in which the amino acid sequence of VL contains the amino acid sequence of SEQ ID NO: 306, (o15) an antibody in which the amino acid sequence of VH contains the amino acid sequence of SEQ ID NO: 308 and in which the amino acid sequence of VL contains the amino acid sequence of SEQ ID NO: 310, (o16) an antibody in which the amino acid sequence of VH contains the amino acid sequence of SEQ ID NO: 312 and in which the amino acid sequence of VL contains the amino acid sequence of SEQ ID NO: 314, (o17) an antibody in which the amino acid sequence of VH contains the amino acid sequence of SEQ ID NO: 316 and in which the amino acid sequence of VL contains the amino acid sequence of SEQ ID NO: 318, (o18) an antibody in which the amino acid sequence of VH contains the amino acid sequence of SEQ ID NO: 320 and in which the amino acid sequence of VL contains the amino acid sequence of SEQ ID NO: 322, (o19) an antibody in which the amino acid sequence of VH contains the amino acid sequence of SEQ ID NO: 324 and in which the amino acid sequence of VL contains the amino acid sequence of SEQ ID NO: 326, (o20) an antibody in which the amino acid sequence of VH contains the amino acid sequence of SEQ ID NO: 328 and in which the amino acid sequence of VL contains the amino acid sequence of SEQ ID NO: 330, (o21) an antibody in which the amino acid sequence of VH contains the amino acid sequence of SEQ ID NO: 332 and in which the amino acid sequence of VL contains the amino acid sequence of SEQ ID NO: 334 and (o22) an antibody in which the amino acid sequence of VH contains the amino acid sequence of SEQ ID NO: 336 and in which the amino acid sequence of VL contains the amino acid sequence of SEQ ID NO: 338.

As the antibody of the invention, an antibody having amino acid sequences of VH and VL of an antibody having homology of 85% or higher, preferably 90% or higher to the amino acid sequences of VH and VL of any one of the antibodies described in (a) to (n) and (o1) to (o22) is included. The homology of 90% or higher is more preferably homology of 91%, 92%, 93%, 94%, 95%, 96%, 97%, 98% or 99% or the like.

In the invention, embodiments of the antibodies described in (a) to (n) and (o1) to (o22) include human anti-MOG monoclonal antibodies, MOG01 antibody, MOG09 antibody and MOG14 antibody and an alpaca anti-MOG monoclonal VHH antibody, iMOG-3Rim1-S32 antibody. In addition, embodiments include an iMOG-3Rim1-S32 human chimeric antibody, an iMOG-3Rim1-S32 humanized antibody and the like.

In the invention, the EU index refers to the position of an amino acid residue according to Sequences of Proteins of Immunological Interest, Fifth edition (1991). The positions of the amino acid residues shown below are all the positions of the amino acid residues according to the EU index unless particularly described.

An antibody molecule is also called an immunoglobulin (referred to as Ig below), and its basic structure is a tetramer having two polypeptides called heavy chains (referred to as H chains below) and two polypeptides called light chains (referred to as L chains below).

Each H chain is composed of a H chain variable region (also referred to as VH) and a H chain constant region (also referred to as CH) from the N-terminus side, and each L chain is composed of a L chain variable region (also referred to as VL) and a L chain constant region (also referred to as CL) from the N-terminus side.

For CH, α, δ, ε, γ and μ chains are known for each subclass. CH is further composed of a CH1 domain, a hinge domain, a CH2 domain and a CH3 domain from the N-terminus side.

A domain is a functional structural unit which constitutes a polypeptide of an antibody molecule. The CH2 domain and the CH3 domain are together called a Fc (Fragment, crystallizable) region or simply Fc. For CL, $C_\lambda$ chain and $C_\kappa$ chain are known.

The subclasses of antibody in which CH is α, δ, ε, γ and μ chains are called IgA, IgD, IgE, IgG and IgM, respectively. There are sometimes isotypes for a subclass of an antibody depending on the animal. In human, there are isotypes IgA1 and IgA2 for IgA, and there are isotypes IgG1, IgG2, IgG3 and IgG4 for IgG.

The CH1 domain, the hinge domain, the CH2 domain, the CH3 domain and the Fc region in the invention can be identified by the positions of the amino acid residues from the N-terminus according to the EU index.

Specifically, CH1 is identified as the amino acid sequence of from position 118 to position 215 according to the EU index, and the hinge is identified as the amino acid sequence of from position 216 to position 230 according to the EU index. CH2 is identified as the amino acid sequence of from position 231 to position 340 according to the EU index, and CH3 is identified as the amino acid sequence of from position 341 to position 447 according to the EU index. The Fc region is identified as the amino acid sequence of from position 231 to position 447 according to the EU index.

As the antibody of the invention, a polyclonal antibody, a monoclonal antibody and an oligoclonal antibody are all included. A polyclonal antibody is a group of antibody molecules that are secreted by antibody-producing cells of different clones. A monoclonal antibody is an antibody that is secreted by antibody-producing cells of a single clone and recognizes only one epitope (also called an antigenic determinant). The amino acid sequences (primary sequences) of same monoclonal antibodies are the same. An oligoclonal antibody is a group of antibody molecules in which different monoclonal antibodies are mixed.

The monoclonal antibody of the invention may be an antibody that is produced from a hybridoma or a genetically recombinant antibody that is produced by a transformant transformed with an expression vector containing the antibody genes.

The epitope may be a single amino acid sequence, a three-dimensional structure made of an amino acid sequence, an amino acid sequence modified after translation, a three-dimensional structure made of an amino acid sequence modified after translation which the monoclonal antibody recognizes and binds to or the like.

The amino acid sequence modified after translation may be an O-linked glycan in which sugar chains are attached to Tyr and Ser having OH substituents, an N-linked glycan in which sugar chains are attached to Gln and Asn having $NH_2$ substituents or a tyrosine sulfated amino acid sequence in which a sulfuric acid molecule is attached to Tyr having OH substituents.

The epitope of MOG to which the antibody of the invention binds can be identified by an antibody-binding test using a deletion variant of MOG in which some domains are lost, a mutant in which some domains are replaced with domains derived from another protein, a partial peptide fragment of MOG or the like. The antibody-binding test can also be conducted using cells expressing the deletion variant or the mutant.

Alternatively, the epitope of MOG to which the antibody of the invention binds can also be identified by adding the antibody of the invention to peptide fragments of MOG obtained by decomposition using a protease and conducting epitope mapping using a known mass spectrometry.

As the antibody of the invention, genetically recombinant antibodies of a mouse antibody, a rat antibody, a hamster antibody, a rabbit antibody, a llama antibody, a camel antibody, an alpaca antibody, a chimeric antibody, a humanized antibody (also called a "Complementarity Determining Region (CDR)-inserted antibody"), a human antibody and the like are also included.

In the invention, the chimeric antibody is an antibody in which VH and VL are derived from a different animal kind from that of CH and CL. An antibody composed of VH and VL of an antibody of an animal other than human (a non-human animal) and CH and CL of a human antibody is called a human chimeric antibody, and an antibody composed of VH and VL of an antibody of an animal other than mouse and CH and CL of a mouse antibody is called a mouse chimeric antibody. Other chimeric antibodies are named in the same manner.

As the non-human animal, any animal such as mouse, rat, hamster, rabbit, llama, camel or alpaca can be used as long as a hybridoma can be produced or an antibody phage library can be produced.

A hybridoma is a cell which is obtained by cell fusion of a B cell obtained by immunizing a non-human animal with an antigen and a myeloma cell derived from a mouse or the like and which produces a monoclonal antibody having a desired antigen specificity.

An antibody phage library is a library produced by cloning the genes of immunoglobulin variable regions to a phage and expressing an antigen-binding molecule on its surface. The phages used are M13 phage and the like but are not particularly limited.

The antigen-binding molecule which is displayed on a phage may be in any form but is preferably an antibody fragment such as scFv, Fab or VHH.

In the invention, the antibody phage library may be any library of an immune library, a naive library and a synthetic library.

An immune library is an antibody phage library which is constructed based on the antibody genes derived from lymphocytes of an animal immunized with an antigen or a patient. A naive library is an antibody phage library which is constructed based on the antibody genes derived from lymphocytes of a normal animal or a healthy human. A synthetic library is a library in which CDRs of a V gene in genome DNA or a reconstructed functional V gene are replaced with oligonucleotides that encode any amino acid sequences of appropriate lengths.

As a method for producing a chimeric antibody, a method for producing a human chimeric antibody is described below. Other chimeric antibodies can also be produced by the same method.

A human chimeric antibody can be produced by obtaining cDNAs that encode VH and VL from a hybridoma derived from a non-human animal cell producing a monoclonal antibody, inserting the cDNAs into an expression vector for animal cells having DNA that encodes CH and CL of a human antibody, thereby constructing a human chimeric antibody expression vector, introducing the vector to an animal cell and expressing the antibody.

A human chimeric antibody can also be produced by cloning the genes that encode VH and VL from an antibody phage library derived from a non-human animal, inserting the genes into an expression vector for animal cells having DNA that encodes CH and CL of a human antibody, thereby constructing a human chimeric antibody expression vector, introducing the vector to an animal cell and expressing the antibody.

A humanized antibody is an antibody in which the amino acid sequences of CDRs of VH and VL of an antibody of a non-human animal are implanted to the corresponding CDRs of VH and VL of a human antibody. The region other than the CDRs of VH and VL is called a framework region (referred to as FR below).

A humanized antibody can be produced by constructing cDNA that encodes the amino acid sequence of VH formed from the amino acid sequences of CDRs of VH of an antibody of a non-human animal and the amino acid sequence of FR of VH of any human antibody and cDNA that encodes the amino acid sequence of VL formed from the amino acid sequences of CDRs of VL of an antibody of a non-human animal and the amino acid sequence of FR of VL of any human antibody, inserting the cDNAs into an expression vector for animal cells having DNA that encodes CH and CL of a human antibody, thereby constructing a humanized antibody expression vector, introducing the vector to an animal cell and expressing the antibody.

A human antibody is originally an antibody that naturally exists in the human body, but antibodies obtained from a human antibody phage library and a human antibody-producing transgenic animal and the like are also included.

A human antibody can be obtained by immunizing a mouse having a human immunoglobulin gene (Tomizuka K. et al., Proc Natl Acad Sci USA. 97, 722-7, 2000.) with a desired antigen. A human antibody can be obtained also without immunization by selecting a human antibody having a desired binding activity using a phage display library obtained by amplifying antibody genes from human-derived B cells (Winter G. et al., Annu Rev Immunol. 12:433-55. 1994).

Moreover, a human antibody can be obtained by producing cells which produce a human antibody having a desired binding activity by immortalizing human B cells using EB virus (Rosen A. et al., Nature 267, 52-54.1977).

A human antibody phage library is a library in which antibody fragments such as Fab, scFv and VHH are expressed on the surface of phages by inserting an antibody gene produced from lymphocytes of a human (a healthy individual or a patient) to phage genes. It is possible to collect phages on which antibody fragments having a desired antigen binding activity are expressed using binding activity to a substrate to which an antigen is fixed as an index from the library. The antibody fragments can be further converted to a human antibody molecule formed from two whole H chains and two whole L chains using the genetic engineering technique.

A human antibody-producing transgenic animal is an animal in which a human antibody gene is incorporated into the chromosomes of the host animal. Specifically, a human antibody-producing transgenic animal can be produced by introducing a human antibody gene to mouse ES cells, implanting the ES cells to an early embryo of another mouse and then causing development.

A human antibody can be produced from a human antibody-producing transgenic animal by culturing a human antibody-producing hybridoma obtained by a general hybridoma production method performed for mammals other than human, producing and accumulating the human antibody in the culture and purifying the antibody from the culture.

The antibody of the invention includes a heavy chain antibody composed of heavy chains only. Heavy chain antibodies are an antibody obtained from a Camelidae animal such as llama, camel and alpaca and a genetically recombinant antibody produced based on the antibody.

In the invention, the antibody fragment is a fragment of an antibody which has an antigen binding activity. Examples include Fab, Fab', F(ab')2, single chain Fv (scFv), diabody, dsFv, a peptide containing CDRs, VHH and the like. The antibody fragment of the invention also includes any antibody fragment as long as the antibody fragment contains a partial fragment of an antibody and has a MOG binding activity, such as an antibody fragment obtained by fusing the whole or a part of a constant region or Fc of an antibody to the antibody fragment or an antibody fragment containing a constant region or Fc.

Fab is an antibody fragment which has an antigen binding activity and a molecular weight of approximately fifty thousand and in which about a half of the H chain in the N-terminus side and the entire L chain are linked to each other through disulfide bonds (S—S bonds) (cleaved at the 224th amino acid residue in the H chain), of the fragments obtained by treating IgG antibody with a protease, papain.

$F(ab')_2$ is an antibody fragment which has an antigen binding activity and a molecular weight of approximately hundred thousand and which is slightly larger than the one in which Fabs are bound through the S—S bond in the hinge region (cleaved at the 234th amino acid residue in the H chain), of the fragments obtained by treating IgG with a protease, pepsin.

Fab' is an antibody fragment which has an antigen binding activity and a molecular weight of approximately fifty thousand and in which the S—S bond in the hinge region of the above $F(ab')_2$ is cleaved.

scFv is a VH-P-VL or VL-P-VH polypeptide in which one VH and one VL are linked using an appropriate peptide linker (P) such as a linker peptide of any number of connected linkers each having four Gly residues and one Ser residue (G4S) and is an antibody fragment having an antigen binding activity.

Diabody is an antibody fragment in which scFvs having same or different antigen binding specificities form a dimer and is an antibody fragment having a divalent antigen binding activity to a same antigen or specific antigen binding activities to different antigens.

dsFv is a fragment in which polypeptides obtained by substituting one amino acid residue in VH and that in VL with cysteine residues are bound through the S—S bond between the cysteine residues.

A peptide containing CDR is composed of and contains at least one or more regions of CDRs of VH or VL. In a peptide containing CDRs, the CDRs can be bound directly or through an appropriate peptide linker.

Production can be performed by constructing DNA that encodes CDRs of VH and VL of the antibody of the invention, inserting the DNA into an expression vector for a prokaryote or an expression vector for a eukaryote and introducing the expression vector into a prokaryote or a eukaryote for expression. In addition, a peptide containing CDR can also be produced by a chemical synthesis method such as the Fmoc method or the tBoc method.

VHH is a variable region of a heavy chain antibody and is also called a nanobody.

The antibody fragment of the invention includes any antibody fragment as long as the antibody fragment contains any of the antibody fragments described above or a partial fragment thereof and has a MOG binding activity.

In the invention, an antibody having one antigen binding site or an antibody fragment thereof is called a monovalent antibody. The formats of a monovalent antibody are the formats of an antibody having one antigen binding site or an antibody fragment thereof described in International Publication No. 2014/054804, International Publication No. 2011/090754, International Publication No. 2007/048037, International Publication No. 2012/116927 and the like and other formats.

In the invention, an antibody of one molecule which binds to three or more different antigens or epitopes or an antibody fragment thereof is called a multispecific antibody. In the invention, an antibody of one molecule which binds to two different antigens or epitopes or an antibody fragment thereof is called a bispecific antibody.

The formats of a multispecific antibody or a bispecific antibody are the formats described in International Publication No. 2009/131239, International Publication No. 2014/054804, International Publication No. 01/077342, US Patent Application Publication No. 2007/0071675, International Publication No. 2007/024715, Wu et al., [Nature Biotechnology, 2007, 25(11), p. 1290-1297], Labrijn et al., [PNAS 2013, vol. 110, no. 13, p 5145-5150], Jong et al., [http://dx.doi.org/10.1371/journal.pbio.1002344], Kontermann et al., [mAbs 2012, vol. 4, issue 2, p 182-197], Spiess et al., [Molecular Immunology 67 (2015) 95-106], Ridgway et al., [Protein engineering, 1996 vol. 9 no. 7 pp 617-621, International Publication No. 2009/080251, International Publication No. 2010/151792, International Publication No. 2014/033074 and the like and other formats.

The bispecific antibody may be specifically any of the bispecific antibodies described below and the like.

(1) A bispecific antibody in which amino acid modifications S354C/T366W are introduced to CH3 of one of the two heavy chains of an antibody (heavy chain A) and in which amino acid modifications Y349C/T366S/L368A/Y407V are introduced to CH3 of the other heavy chain (heavy chain B).

(2) A bispecific antibody in which an antibody fragment is fused to a C-terminus of an antibody.

(3) A bispecific antibody in which an antibody fragment is fused to a N-terminus of an antibody.

The bispecific antibody described in (1) may be a bispecific antibody in which the antigen binding site containing VH of heavy chain A binds to MOG and in which the antigen binding site containing VH of heavy chain B binds to an antigen that is present in the brain or one in which the bindings are the other way around.

The bispecific antibody described in (2) may be any bispecific antibody of a bispecific antibody in which an antibody fragment is bound to the C-terminus of one of the two heavy chains constituting the antibody and a bispecific antibody in which antibody fragments are bound to both of the two heavy chains. Moreover, an appropriate linker may be between the C-terminus of the heavy chain of the antibody and the antibody fragment.

The antibody fragment(s) that the bispecific antibody described in (2) has is preferably scFv, Fab, VHH or the like but is not particularly limited to these fragments.

The bispecific antibody described in (2) may be a bispecific antibody in which the antigen binding site at the N-terminus binds to MOG and in which the antigen binding site at the C-terminus binds to an antigen that is present in the brain or one in which the bindings are the other way around.

The bispecific antibody described in (3) is a bispecific antibody in which an antibody fragment is bound to the N-terminus of at least any one of the two heavy chains or the light chains constituting the antibody. Moreover, an appropriate linker may be between the N-terminus of the heavy chain and/or the light chain of the antibody and the antibody fragment. The antibody fragment that the bispecific antibody described in (3) has is preferably scFv, Fab, VHH or the like but is not particularly limited to these fragments.

The bispecific antibody described in (3) is a bispecific antibody having a structure $VH_1$-CH1-$VH_2$-CH1-hinge-CH2-CH3 from the N-terminus of a heavy chain, a bispecific antibody which has the heavy chain structure and in which $VH_1$ and $VH_2$ each form an antigen binding site with VL or the like. The VLs with which $VH_1$ and $VH_2$ form antigen binding sites may have a same amino acid sequence or different amino acid sequences.

In the invention, the multispecific antibody or the bispecific antibody may be any antibody as long as the antibody is a multispecific antibody or a bispecific antibody which binds to MOG. Of such antibodies, a multispecific antibody or a bispecific antibody which binds to MOG and an antigen that is present in the brain is preferable, and a multispecific antibody or a bispecific antibody containing an antigen binding site which binds to MOG and an antigen binding site which binds to an antigen that is present in the brain is more preferable.

In the invention, the antigen that is present in the brain is a protein, a sugar chain, a lipid or the like and is preferably a protein of these antigens.

Examples of the protein that is present in the brain include MOG, Prion, 5T4, AFP, ADAM-10, ADAM-12, ADAM17, AFP, AXL, BSG, C5, C5R, CA9, CA72-4, CCL11, CCL2, CCR1, CCR4, CCR5, CCR6, CD2, CD3E, CD4, CD5, CD6, CD8, CD11, CD18, CD19, CD20, CD22, CD24, CD25, CD29, CD30, CD32B, CD33, CD37, CD38, CD40, CD40LG, CD44, CD47, CD52, CD55SC1, CD56, CD66E, CD71, CD72, CD74, CD79a, CD79b, CD80, CD86, CD95, CD98, CD137, CD147, CD138, CD168, CD200, CD248, CD254, CD257, CDH3, CEA, CEACAM1, CEACAM5, CEACAM6, CEACAM8, Claudin3, Claudin4, c-Met, CS-1, CSF2RA, CSPG-4, CTLA4, CRF-1, Cripto, CXCR4, CXCR5, DLL4, DR4, DR5, ED-B, EFNA2, EGFR, EGFRvIII, ETBR, ENPP3, EPCAM, EphA2, ERBB2, ERBB3, ERBB4, FAPα, FAS, FcγRI, FCER2, FGFR1, FGFR2, FGFR3, FGFR4, FLT1, FOLH1, FOLR1, GDF2, GFR, GLP1R, glypican-3, GPNMB, GRP78, HB-EGF, HGF, HLA-DRβ, ICAM1, IFNA1, IFNA1, IgE, IgE-Fc, IGF1R, IL10, IL12B, IL13, IL15, IL17A, ILiA, IL1B, IL2RA, IL4, IL5, IL5RA, IL6, IL6R, IL9, IL2Rα, IL2Rβ, IL2Rγ, INSR, ITGA2, ITGA2B2, ITGB3, ITGA4, ITGB7, ITGA5, ITGAL, ITGAV, ITGB3, ITGB2, KDR, LiCAM, mesothelin, MMP14, MMP15, MST1R, MSTN, MUC1, MUC4, MUC16, MUCSAC, myostatin, NECTIN4, NGF, NOTCH, NRG1, NRP, OX40, OX40L, PDGFA, PDGFB, PDGFRA, PDGFRB, PD1, PDL1, PSCA, SLAM7, SLC44A4, TAG-72, TCR, TGFB1, TGFB2, TGFBR, TNF, TNFR, TNFRSF10A, TNFRSF10B, TNFRSF12A, TNFSF13, TNFSF14, TNFSF2, TNFSF7, TRAILR2, TRKA, TRKB, TRKC, VEGF, VEGFR, VLA-4, CGRP, alpha-synuclein, TDP-43, Tau, FUS, Amyloid-beta (A3), APP, BACE1, Presenilin, LINGO-1, Nogo, polyQ, androgen receptor, huntingtin, ataxin 1, ataxin 2, RGMA, Phospho-Tau, Phospho-alpha-synuclein and the like, but the protein is not limited to these proteins.

Examples of the sugar chain that is present in the brain include Lewis-x, Lewis-y, CD15 and the like, but the sugar chain is not limited to these sugar chain.

Examples of the lipid that is present in the brain include GD1a, GD2, GD3, GM1, GM2, GM3, phosphatidylserine and the like, but the lipid is not limited to these lipids.

The antibody or the antibody fragment of the invention also includes an antibody containing any amino acid that is modified after translation. Examples of the modification after translation include deletion of the lysine residue at the C-terminus of a H chain (lysine clipping), conversion of the glutamine residue at the N-terminus of a polypeptide into pyroglutamine (puroGlu) and the like [Beck et al, Analytical Chemistry, 85, 715-736(2013)].

An amino acid residue in the Fc region of the antibody or the antibody fragment of the invention may be modified. Examples of the amino acid modification in the Fc region include amino acid modification for stabilizing the antibody or regulating the half-life in the blood and the like. Specific examples of the amino acid modification in the Fc region include those in International Publication No. 2006/033386, International Publication No. 2006/075668, International Publication No. 2011/122011, International Publication No. 2009/125825 and the like.

The antibody or the antibody fragment of the invention also includes a fused antibody or a fused antibody fragment in which an antibody or an antibody fragment is modified. The method for modifying an antibody is not particularly limited, and any method which can modify a desired amino acid residue and a sugar chain can be used.

Examples include chemical modification using chemical reaction [Introduction to Antibody Engineering, Chijinshokan Co., Ltd. (1994); and Kolb et al., Angew Chem Int Ed Engl. 40. 2004-21, 2001], modification by the genetic engineering technique in which a recombinant protein expression vector is introduced to an appropriate host cell for expression using genetic recombination technology and the like.

In the invention, examples of the molecule which modifies the antibody or the antibody fragment include a hydrophilic polymer, an amphipathic polymer, a functional molecule and the like. Examples of the hydrophilic polymer and the amphipathic polymer include a polyoxyalkylene, a molecule containing a polyol or a polysaccharide and the like.

Examples of the polyoxyalkylene include linear or branched chain polyethylene glycol (referred to as PEG below), polypropylene glycol, polypropylene ethylene glycol and the like.

Examples of the molecule containing a polyol or a polysaccharide include homo- or hetero-polysaccharides such as amylose, dextran, pullulan or glycogen composed of linear or branched chain polyglycerol and the like.

The molecular weight of the molecule containing a hydrophilic polymer or an amphipathic polymer is not particularly limited but is preferably 100 Da or more, preferably for example 100 Da to 100 kDa.

Examples of the functional molecule include an antigen-binding molecule, a fragment thereof, a drug, a bioactive peptide, a bioactive protein, a nucleic acid, a radiolabeling compound, a sugar chain, a lipid, a fluorescent compound and the like. A molecule which has double specificity as a result of modification with a functional molecule such as an antigen-binding molecule is a bispecific antibody.

Examples of the antigen-binding molecule include an antibody, a receptor, a ligand and the like.

The fragment of the antigen-binding molecule may be any fragment as long as the fragment is a fragment of the antigen-binding molecule and has an antigen binding activity.

Examples of the drug include anti-cancer drugs such as alkylating agents, nitrosoureas, antimetabolites, antiviral agents, antibiotics, plant alkaloids, topoisomerase inhibitors, tubulin polymerization inhibitors, hormonal therapy agents, hormone antagonists, aromatase inhibitors, P-glycoprotein inhibitors, platinum complex derivatives, M cycle inhibitor or kinase inhibitors [Clinical oncology, Cancer and chemotherapy (1996)], anti-inflammatory agents such as steroids such as hydrocortisone or prednisone, nonsteroidal drugs such as aspirin or indomethacin, immune modulating drugs such as gold thiomalate or penicillamine, immunosuppressive drugs such as cyclophosphamide or azathioprine, antihistamine drugs such as chlorpheniramine maleate or clemastine [Inflammation and anti-inflammatory therapy, Ishiyaku Pub, Inc. (1982)] and the like.

Examples of the anti-cancer drugs include mertansine, emtansine, amifostine (Ethyol), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (Adriamycin), epirubicin, gemcitabine (Gemzar), daunorubicin, procarbazine, mitomycin, cytarabine, etoposide, 5-fluorouracil, fluorouracil, vinblastine, vincristine, bleomycin, daunomycin, peplomycin, estramustine, paclitaxel (Taxol), docetaxel (Taxotere), Aldesleukin, asparaginase, busulfan, carboplatin, oxaliplatin, nedaplatin, cladribine, camptothecin, 7-ethyl-10-hydroxycamptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacitidine, UFT, oxaloplatin, gefitinib (Iressa), imatinib (STI571), erlotinib, FMS-like tyrosine kinase 3 (Flt3) inhibitor, vascular endothelial growth factor receptor (VEGFR) inhibitor, fibroblast growth factor receptor (FGFR) inhibitor, epidermal growth factor receptor (EGFR) inhibitor such as Tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestins, estrogens, anastrozole (Arimidex), Leuplin, Aspirin, indomethacin, celecoxib, azathioprine, penicillamine, gold thiomalate, chlorpheniramine maleate, chlorpheniramine, clemastine, tretinoin, bexarotene, arsenic, bortezomib, allopurinol, calicheamicin, ibritumomab tiuxetan, targretin, ozogamine, clarithromycin, leucovorin, ketoconazole, aminoglutethimide, suramin, methotrexate, maytansinoid, derivatives thereof and the like.

Examples of the method for binding the drug and the antibody or the antibody fragment include a method of binding the drug to an amino group of the antibody through glutaraldehyde, a method of binding an amino group of the drug to a carboxyl group of the antibody through water-soluble carbodiimide and the like in addition to the above method.

Examples of the bioactive peptide or the bioactive protein include interferon (referred to as IFN below)-α, IFN-β, IFN-γ, interleukin (referred to as IL below)-2, IL-12, IL-15, IL-18, IL-21, IL-23, granulocyte colony stimulating factor (G-CSF), granulocyte-macrophage colony stimulating factor (GM-CSF), macrophage colony stimulating factor (M-CSF), cytokines or growth factors which activate immunocompetent cells such as NK cells, macrophages or neutrophils, proteases such as hydrase, lyase and isomerase, enzymes such as acid sphingomyelinase, toxins including bacterial toxins and phytotoxins such as ricin, diphtheria toxin or ONTAK, antimicrobial peptides having cytomembrane-damaging activity, peptides having cytomembrane-binding affinity or permeability to cytomembrane, derivatives thereof and the like.

The nucleic acid may be any molecule as long as it is a molecule in which nucleotides or molecules having equivalent function to that of nucleotides are polymerized, and examples include siRNA, microRNA, antisense RNA, DNA aptamers and the like.

The radiolabeling compound may be any nuclide that is used for applications for diagnoses or treatment, and examples include $^{3}$H, $^{14}$C, $^{32}$P, $^{33}$P, $^{35}$S $^{51}$Cr, $^{57}$CO, $^{18}$F, $^{153}$Gd, $^{159}$Gd, $^{64}$Cu, $^{68}$Ge, $^{166}$Ho, $^{115}$In, $^{113}$In, $^{112}$In, $^{111}$In, $^{131}$I, $^{125}$I, $^{123}$I, $^{121}$I, $^{140}$La, $^{177}$Lu, $^{54}$Mn, $^{99}$Mo, $^{103}$Pd, $^{142}$Pr, $^{149}$Pm, $^{186}$Re, $^{188}$Re, $^{211}$At, $^{105}$Rh, $^{97}$Ru, $^{153}$Sm, $^{47}$Sc, $^{75}$Se, $^{85}$Sr, $^{99}$Tc, $^{201}$Ti, $^{113}$Sn, $^{117}$Sn, $^{133}$Xe, $^{169}$Y, $^{175}$Y, $^{90}$Y, $^{65}$Zn and compounds containing the nuclides.

The radiolabeling compound can be directly bound to the antibody by the chloramine T method or the like. In addition, a substance that chelates the radiolabeling compound may be bound to the antibody. Examples of the chelating agent include DOTA, PA-DOTA, TRITA, DTPA and the like, and an antibody modified with the chelating agent and a modified antibody which is labeled with the radiolabeling compound through the chelating agent are also included in the antibody of the invention.

Examples of the sugar chain include monosaccharides, disaccharides or oligosaccharides such as fucose, mannose, glucose, allose, aldose, gulose, idose, galactose, talose, ribose, arabinose, xylose, lyxose, erythose, erythrose, threose, cellobiose, maltose, isomaltose, lactose, lipoarabinomannan, Lewis X trisaccharide and sialyl-Lewis X tetrasaccharide and the like. Moreover, the sugar chain may be a natural product containing a sugar chain known as immunoadjuvant and may be β(1→3) glucan (lentinan or schizophyllan), α-galactosylceramide (KRN7000) or the like.

Examples of the lipid include simple lipids (neutral lipids), which are esters of fatty acids and alcohols and analogues thereof. Examples include fats (for example, triacylglycerol), wax (for example, fatty acid esters of higher alcohols), sterol esters, cholesterol esters, fatty acid esters and the like of vitamins, complex lipids having a polar group such as phosphoric acid, saccharide, sulfuric acid or amine in addition to a fatty acid and an alcohol such as phospholipids (for example, glycerophospholipids, sphingophospholipids and the like) and glycolipids (for example, glyceroglycolipids, sphingoglycolipids and the like), derived lipids which are lipid-soluble compounds of compounds produced by hydrolysis of simple lipids and complex lipids such as fatty acids, higher alcohols, lipid-soluble vitamins, steroids and carbohydrates and the like.

Examples of the fluorescent compound include fluorescent dyes such as fluorescein series like fluorescein isothiocyanate (FITC), rhodamine series, Cy3, Cy5, eosine series, Alexa Fluor series and NBD series, light-emitting substances such as acridinium esters or lophine, fluorescent proteins such as green fluorescent protein (GFP) and the like.

The antibody or the antibody fragment of the invention can be bound to the hydrophilic polymer, the amphipathic polymer or the functional molecule directly or through an appropriate linker. Examples of the linker include esters, disulfides, hydrazones, dipeptides and the like.

When a fused antibody or a fused antibody fragment is produced by modifying the antibody or the antibody fragment of the invention by the genetic engineering technique, a fused antibody or a fused antibody fragment can be produced by linking cDNA encoding a protein to cDNA encoding an antibody to construct DNA that encodes the fused antibody or the fused antibody fragment, inserting the DNA into an expression vector for a prokaryote or a eukaryote, introducing the expression vector into a prokaryote or a eukaryote and expressing the fused antibody or the fused antibody fragment.

The composition of the invention may be any composition as long as the composition contains the antibody or the antibody fragment of the invention. The composition may contain an appropriate carrier or an additive such as a stabilizing agent in addition to the antibody or the antibody fragment.

Examples of the composition of the invention includes a composition for detection or measurement containing the antibody or the antibody fragment of the invention and the like. Examples of the composition of the invention include a pharmaceutical composition (a therapeutic agent) containing the antibody or the antibody fragment of the invention as an active ingredient and the like, and pharmaceutical formulation with a desired dosage form is prepared together with a pharmacologically acceptable carrier.

In the invention, the composition for detection or measurement may be any composition as long as the composition contains the antibody or the antibody fragment of the invention and can detect or measure an antigen to which the antibody or the antibody fragment of the invention specifically binds. The antigen to which the antibody or the antibody fragment of the invention specifically binds is MOG, MOG and an antigen that is present in the brain or the like.

The antibody or the antibody fragment of the invention has a property of binding to MOG in the brain and accumulating in the brain when administered to an animal. Therefore, when the composition for detection or measurement containing the antibody or the antibody fragment is used, the antibody can be maintained in the brain, or the antibody concentration in the brain can be improved. Thus, MOG or MOG and an antigen that is present in the brain can be detected or measured for a long time, and/or MOG or MOG and an antigen that is present in the brain can also be detected or measured with high sensitivity.

For example, when the composition for detection or measurement is a composition containing a bispecific antibody which binds to MOG and an antigen that is present in the brain, MOG and the antigen in the brain, to which the bispecific antibody binds, can be detected or measured for a long time, and/or MOG and the antigen that is present in the brain can be detected or measured with high sensitivity.

Moreover, for example, when the composition for detection or measurement is a composition containing a fused antibody or a fused antibody fragment which is labeled with a radiolabeling compound or a fluorescent dye and which binds to MOG, MOG can be detected or measured for a long time, and/or MOG can be detected or measured with high sensitivity.

The pharmaceutical composition (therapeutic agent) containing the antibody of the invention may be a therapeutic agent for any disease as long as the antigen to which the antibody or the antibody fragment of the invention specifically binds is expressed in the disease but is preferably a therapeutic agent for a brain disease.

Examples of the brain disease include Alzheimer's disease, the prodromal stage of Alzheimer's disease, Huntington disease, Parkinson's disease, brain tumors, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, cerebrovascular disease, epilepsy, migraine, hyperactivity disorder, Creutzfeldt-Jakob disease, corticobasal degeneration, lysosomal storage disease, depression, dystonia and the like.

The antibody of the invention has a property of binding to MOG in the brain and accumulating in the brain when administered to an animal. Therefore, when the therapeutic agent containing the antibody or the antibody fragment is used, the antibody or the antibody fragment can be maintained in the brain for a long time, and the antibody concentration in the brain can be improved. Thus, therapeutic effects on the diseases can be exhibited.

For example, when the therapeutic agent is a therapeutic agent containing a bispecific antibody which binds to MOG and an antigen that is present in the brain, a therapeutic effect on a brain disease related to the antigen in the brain, to which the bispecific antibody binds, can be exhibited.

Moreover, for example, when the therapeutic agent is a fused antibody or a fused antibody fragment which is modified with a low molecular weight drug and which binds to MOG, a therapeutic effect on a brain disease targeted by the low molecular weight drug can be exhibited. At this point, the therapeutic effect is preferably higher when the therapeutic agent of the invention is used compared to the effect of the low molecular weight drug alone.

The therapeutic agent containing the antibody or the antibody fragment of the invention may be an agent that contains only the antibody or the antibody fragment as an active ingredient, but the agent is generally desirably mixed with one or more pharmacologically acceptable carriers and provided as medicinal formulation that is produced by any method known in the technical field of pharmaceutical science.

As the route of administration, it is preferable to use the most effective route for the treatment, and examples include oral administration or parenteral administration such as intraoral, airway, intrarectal, subcutaneous, intradermal, intramuscular, intraventricular, intraspinal cord, intranasal, intraperitoneal or intravenous administration. Intravenous or intraventricular administration or the like is particularly preferable. Examples of the form of administration include a spray, a capsule, a tablet, a powder, a granule, a syrup, an emulsion, a suppository, an injection, an ointment, a tape and the like.

The dose or the frequency of administration varies according to the desired therapeutic effect, administration method, treatment period, age, body weight and the like but is usually 10 µg/kg to 20 mg/kg per day for adult.

The invention also includes a method for keeping an antibody in the brain, a method for improving the property of an antibody of accumulating in the brain and a method for increasing the antibody concentration (or the antibody amount) in the brain which use the antibody or the antibody fragment of the invention.

The invention also relates to a peptide which binds to MOG, a nucleic acid containing a nucleotide sequence which encodes the peptide, a transformant cell which contains a vector containing the nucleic acid, a method for producing the peptide including culturing the transformant cell and collecting the peptide from the culture solution, a composition containing the peptide or a method for detecting or measuring an antigen that is present in the brain, a method for diagnosing or treating a brain disease, a method for improving the property of a peptide of accumulating in the brain or a method for increasing the peptide amount in the brain that uses the peptide or the composition.

The peptide of the invention includes a fused peptide obtained by modifying a peptide.

The definitions of the terms related to the peptide which binds to MOG and the like are the same as the definitions of the terms described for the antibody which binds to MOG and the like above unless particularly described.

The method for producing the antibody or the antibody fragment of the invention, the method for treating a disease, the method for diagnosing a disease and the like are specifically explained below.

1. Production Method of Antibody
(1) Preparation of Antigen

MOG as an antigen or a MOG-expressing cell can be obtained by introducing an expression vector containing cDNA that encodes the full length of MOG or a partial length thereof to E. coli, yeast, insect cells, animal cells or the like. In addition, MOG can also be obtained by purifying MOG from an animal cell line, an animal cell or an animal tissue of various kinds and the like in which MOG is expressed in a large amount.

In addition, the animal cell line, the animal cell, the animal tissue and the like can also be used as they are as an antigen. Furthermore, a synthetic peptide having a partial sequence of MOG can be prepared using a chemical synthesis method such as the Fmoc method or the tBoc method and used as an antigen.

A known tag such as FLAG or His may be added to the C-terminus or the N-terminus of MOG or the synthetic peptide having a partial sequence of MOG.

MOG used in the invention can be produced using the method described in Molecular Cloning, A Laboratory Manual, Second Edition, Cold Spring Harbor Laboratory Press (1989), Current Protocols In Molecular Biology, John Wiley & Sons (1987-1997) or the like or another method by expressing DNA that encodes MOG in a host cell for example by the following method.

First, a recombinant vector is produced by inserting the full-length cDNA containing the part that encodes MOG into downstream of a promoter in an appropriate expression vector. A DNA fragment of an appropriate length which contains the part that encodes the polypeptide and which is prepared based on the full-length cDNA may be used in place of the full-length cDNA. Next, a transformant that produces the polypeptide can be obtained by introducing the obtained recombinant vector into a host cell suitable for the expression vector.

As the expression vector, any vector can be used as long as it can replicate autonomously or can be inserted into a chromosome in a host cell to be used and which contains a suitable promoter in the position that enables the transcription of DNA that encodes the polypeptide. As the host cell, any cell, such as a microorganism belonging to the genus *Escherichia* such as *E. coli*, yeast, an insect cell or an animal cell, can be used as long as it enables the expression of a target gene.

In a case where a prokaryote such as *E. coli* is used as a host cell, the expression vector is preferably a vector that can replicate autonomously in the prokaryote and that contains a promoter, a ribosomal binding sequence, DNA containing the part encoding human MOG and a transcription termination sequence. In addition, the transcription termination sequence is not essentially needed for the expression vector, but the transcription termination sequence is preferably placed immediately after the structural gene. Furthermore, the recombinant vector may contain a gene controlling the promoter.

As the expression vector, it is preferable to use a plasmid in which the distance between the Shine-Dalgarno sequence (also called SD sequence) that is a ribosomal binding sequence and the initiation codon is appropriately adjusted (to, for example, 6 to 18 nucleotides).

In addition, regarding the nucleotide sequence of DNA that encodes MOG, a nucleotide can be substituted in a manner that the codon becomes optimum for the expression in a host, which enables the enhancement in the production rate of target MOG.

As the expression vector, any vector can be used as long as it can exhibit its function in a host cell to be used. Examples thereof include pBTrp2, pBTac1 and pBTac2 (manufactured by Roche Diagnostics K.K.), pKK233-2 (manufactured by Pharmacia), pSE280 (manufactured by Invitrogen), pGEMEX-1 (manufactured by Promega Corporation), pQE-8 (manufactured by QIAGEN), pKYP10 (JP-A-S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene Corporation), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), JP-A-S60-221091], pGKA2 [prepared from *Escherichia co/i* IGKA2 (FERM BP-6798), JP-A-S60-221091], pTerm2 (U.S. Pat. Nos. 4,686,191, 4,939,094 and U.S. Pat. No. 160,735), pSupex, pUB110, pTP5, pC194, pEG400 [J. Bacteriol., 172, 2392 (1990)], pGEX (manufactured by Pharmacia), pET System (manufactured by Novagen), pME18SFL3 and the like.

As the promoter, any promoter may be used as long as it can exhibit its function in a host cell to be used. Examples thereof include promoters such as a trp promoter (Ptrp), a lac promoter, a PL promoter, a PR promoter or a T7 promoter, which are derived from *E. coli*, a phage or the like. In addition, examples thereof also include promoters such as a tandem promoter with two tandemly arrayed Ptrps, a tac promoter, a lacT7 promoter or a let I promoter, which are artificially designed and altered.

Examples of the host cell include *E. coli* XL1-Blue, *E. coli* XL2-Blue, *E. coli* DH1, *E. coli* MC1000, *E. coli* KY3276, *E. coli* W1485, *E. coli* JM109, *E. coli* HB101, *E. coli* No. 49, *E. coli* W3110, *E. coli* NY49, *E. coli* DH5α, and the like.

As a method for introducing a recombinant vector into a host cell, any method can be used as long as it is a method by which DNA is introduced into a host cell to be used. Examples thereof include a method using calcium ions [Proc. Natl. Acad. Sci. USA, 69, 2110 (1972), Gene, 17, 107 (1982) and Molecular & General Genetics, 168, 111 (1979)].

In a case of using an animal cell as a host, as the expression vector, any vector can be used as long as it can exhibit its function in the animal cell. Examples thereof include pcDNAI, pCDM8 (manufactured by Funakoshi Co., Ltd.), pAGE107 [JP-A-H3-22979; and Cytotechnology, 3, 133 (1990)], pAS3-3 (JP-A-H2-227075), pCDM8 [Nature, 329, 840 (1987)], pcDNAI/Amp (manufactured by Invitrogen), pcDNA3.1 (manufactured by Invitrogen), pREP4 (manufactured by Invitrogen), pAGE103 [J. Biochemistry, 101, 1307 (1987)], pAGE210, pME18SFL3, pKANTEX93 (International Publication No. 97/10354), N5KG1val (U.S. Pat. No. 6,001,358), INPEP4 (manufactured by Biogen-IDEC), pCI (manufactured by Promega Corporation), a transposon vector (International Publication No. 2010/143698) and the like.

As the promoter, any promoter can be used as long as it can exhibit its function in the animal cell. Examples thereof include a promoter of cytomegalovirus (CMV) immediate early (IE) gene, an early promoter of SV40, a retroviral promoter, a metallothionein promoter, a heat-shock promoter, a SRα promoter, a promoter of Moloney murine leukemia virus or an enhancer. In addition, an enhancer of human CMV IE gene may be used together with the promoter.

Examples of the host cell include a human leukemia cell Namalwa, a monkey cell COS, a Chinese hamster ovary cell CHO [Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci., 60, 1275 (1968); Cell, 6, 121 (1975); and Molecular Cell Genetics, Appendix I, II (pp. 883-900)]; a CHO cell which lacks dihydrofolate reductase gene (referred to as dhfr below) (CHO/DG44 cell) [Proc. Natl. Acad. Sci. USA, 77, 4216(1980)], CHO-K1 (ATCC CCL-61), DUkXB11 (ATCC CCL-9096), Pro-5 (ATCC CCL-1781), CHO-S (Life Technologies, Cat #11619), Pro-3, a rat myeloma cell YB2/3HL.P2.G11.16Ag.20 (also called YB2/0), a mouse myeloma cell NS0, a mouse myeloma cell SP2/0-Agl4, a Syrian hamster cell BHK, HBT5637 (JP-A-S63-000299) and the like.

As a method for introducing an expression vector into a host cell, any method can be used as long as it is a method by which DNA is introduced into an animal cell. Examples thereof include the electroporation [Cytotechnology, 3, 133 (1990)], the calcium phosphate transfection method (JP-A-H2-227075), the lipofection [Proc. Natl. Acad. Sci. USA, 84, 7413 (1987)] and the like.

MOG can be produced by culturing a transformant derived from a microorganism, an animal cell or the like having the expression vector into which DNA that encodes MOG has been introduced and which is obtained as above in a medium, generating and accumulating MOG in the culture solution and then collecting MOG from the culture solution. A method of culturing the transformant in a medium can be performed according to a usual method used for a host culture.

In a case of expression in the cells derived from a eukaryote, MOG added with sugars or sugar chains can be obtained.

When culturing a microorganism that has been transformed by an expression vector using an inducible promoter, an inducer may be added to the medium if necessary. For example, isopropyl-β-D-thiogalactopyranoside or the like may be added to the medium for a case of culturing a microorganism that has been transformed by an expression vector using a lac promoter, and indoleacrylic acid or the like may be added to the medium for a case of culturing a microorganism that has been transformed by an expression vector using a trp promoter.

Examples of the medium in which the transfectant obtained using an animal cell as a host is cultured include RPMI 1640 Medium [The Journal of the American Medical Association, 199, 519 (1967)], Eagle's MEM Medium [Science, 122, 501 (1952)], Dulbecco's Modified MEM Medium [Virology, 8, 396 (1959)], Medium 199 [Proc. Soc. Exp. Biol. Med., 73, 1 (1950)], Iscove's Modified Dulbecco's Medium (IMDM), which are generally used, or a medium in which fetal bovine serum (FBS) or the like is added to such a medium. Culture is usually performed under the conditions of pH 6 to 8 and 30 to 40° C. in the presence of 5% $CO_2$ for 1 to 7 days. In addition, during the culture, antibiotics such as kanamycin or penicillin may be added to the medium, if necessary.

Examples of the method for expressing a gene that encodes MOG include a method such as secretory production or fused protein expression [Molecular Cloning, A Laboratory Manual, Second Edition, Cold Spring Harbor Laboratory Press (1989)] in addition to direct expression.

Examples of the method for producing MOG include a method of producing in a host cell, a method of secretion out of a host cell and a method of producing on the outer membrane of a host cell. An appropriate method can be selected by changing the host cell to be used or the structure of MOG to be produced.

In a case where MOG is produced in a host cell or on the outer membrane of a host cell, MOG can be actively secreted outside the host cell using the method by Paulson et al. [J. Biol. Chem., 264, 17619 (1989)], the method by Lowe et al. [Proc. Natl. Acad. Sci., USA, 86, 8227 (1989) and Genes Develop., 4, 1288 (1990)] or the method described in JP-A-H05-336963, International Publication No. 94/23021 or the like. In addition, the amount of production of MOG can also be increased using the gene amplification using dihydrofolate reductase gene or the like (JP-A-H2-227075).

Obtained MOG can be isolated and purified as follows for example. In a case where MOG is expressed in the cells in a dissolved state, the cells are collected by centrifugation after completing culture and suspended in an aquatic buffer solution, followed by crushing of the cells using an ultrasonic crusher, a French press, a Manton Gaulin homogenizer, a Dyno mill or the like, and therefore cell-free extract is obtained. A purified sample can be obtained from a supernatant obtained by centrifugation of the cell-free extract using a method such as a general method for isolation and purification of proteins, that is, a solvent extraction method, a salting-out method using ammonium sulfate or the like, a desalting method, a precipitation method using an organic solvent, anion-exchange chromatography using a resin such as Diethylaminoethyl (DEAE)-Sepharose or DIAION HPA-75 (manufactured by Mitsubishi Chemical Corporation), cation-exchange chromatography using a resin such as S—Sepharose FF (manufactured by Pharmacia), hydrophobic interaction chromatography method using a resin such as Butyl Sepharose or Phenyl Sepharose, a gel filtration method using molecular decoration, affinity chromatography, a chromatofocusing method, electrophoresis such as isoelectric focusing electrophoresis and the like alone or in combination.

In a case where MOG forms an insoluble complex and expressed in the cells, the cells are collected and then crushed in the same manner as above, followed by centrifugation, and then an insoluble complex of MOG is collected as a precipitated fraction. The collected insoluble complex of MOG is solubilized with a protein denaturant. A purified sample of the polypeptide can be obtained by the same method for isolation and purification as above, after returning MOG back to the normal three-dimensional structure through dilution or dialysis of the solubilized solution.

In a case where MOG or a derivative thereof such as a sugar-modified complex is extracellularly secreted, MOG or the derivative thereof such as a sugar-modified complex can be collected in a culture supernatant. By subjecting the culture to procedures using a method such as centrifugation as in the same manner as above, thereby obtaining a soluble fraction, and then using the same method for isolation and purification as above, a purified sample can be obtained from the soluble fraction.

In addition, MOG used in the invention can be produced also by a chemical synthesis method such as the Fmoc method or the tBoc method. MOG can be also chemically synthesized using a peptide synthesizer manufactured by Advanced Chemtech, PerkinElmer, Inc., Pharmacia, Protein Technology Instrument, Inc., Shinseserubega Co., Perceptive, Shimadzu Corporation or the like.

(2) Immunization of Animal and Preparation of Antibody-Producing Cell for Fusion By immunizing a 3- to 20-week old animal such as a mouse, a rat, a rabbit or a hamster with the antigen obtained in (1), antibody-producing cells are collected from the spleen, lymph nodes or peripheral blood of the animal. In addition, an animal such as a llama, an alpaca or a camel can also be used as the animal to be immunized.

Immunization is performed by administering the antigen for example together with an appropriate adjuvant such as Freund's complete adjuvant, aluminum hydroxide gel or *Bordetella pertussis* vaccine subcutaneously, intravenously or intraperitoneally to the animal. In a case where the antigen is a partial peptide, a conjugate of the antigen with a carrier protein such as BSA (bovine serum albumin) or KLH (Keyhole Limpet hemocyanin) is produced and used as an immunogen.

When a mouse or a rat is immunized, the administration of the antigen is performed 5 to 10 times every 1 to 2 weeks after the first administration. On the $3^{rd}$ to $7^{th}$ day after each administration, the blood is collected from a venous plexus of the fundus of the eye, and the antibody valency of the serum is measured using an enzyme immunoassay method [Antibodies—A Laboratory Manual, Cold Spring Harbor Laboratory (1988)] or the like. An animal in which the serum exhibited sufficient antibody valency with respect to the antigen used for the immunization is used as a supply source for the antibody-producing cells for fusion.

On the $3^{rd}$ to $7^{th}$ day after a final administration of the antigen, tissues including the antibody-producing cells such as the spleen are extracted from the immunized animal, and the antibody-producing cells are collected. In a case of using the spleen cells, the spleen is shredded and loosened, followed by centrifugation, and then erythrocytes are removed. The antibody-producing cells for fusion are thus obtained.

Other animals to be immunized can also be immunized by the same method, and antibody-producing cells can be obtained. Appropriate conditions for the interval of immunizations and the period between the final immunization and the collection of the tissues can be determined depending on the kind of the animal to be immunized.

(3) Preparation of Myeloma Cells

As the myeloma cells, established cells obtained from a mouse are used, and for example, a 8-azaguanine resistant mouse (BALB/c derived) myeloma cell line, P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], P3-X63-Ag8 (X63) [Nature, 256, 495 (1975)] or the like is used.

The myeloma cells are subjected to subculturing with a normal medium [RPMI1640 medium supplemented with glutamine, 2-mercaptoethanol, gentamicin, FBS and 8-azaguanine] and subjected to subculturing with a normal medium 3 to 4 days before the cell fusion, and $2 \times 10^7$ or more cells are acquired on the day of the fusion.

(4) Cell Fusion and Preparation of Monoclonal Antibody-Producing Hybridoma

The antibody-producing cells for fusion obtained in (2) and the myeloma cells obtained in (3) are thoroughly washed with the Minimum Essential Medium (MEM) or PBS (disodium phosphate 1.83 g, monopotassium phosphate 0.21 g, salt 7.65 g, distilled water 1 liter, pH 7.2), mixed at cell numbers of antibody-producing cells for fusion:myeloma cells of 5:1 to 10:1 and centrifuged, and then the supernatant is removed.

After the precipitated cell clusters are loosened thoroughly, a mixture of polyethylene glycol-1000 (PEG-1000), MEM and dimethylsulfoxide is added thereto while stirring at 37° C. Furthermore, 1 to 2 mL of MEM is added thereto every 1 to 2 minutes for several times, and then MEM is added so that the total amount becomes 50 mL.

After centrifugation, the supernatant is removed. The precipitated cell clusters are loosened gently, and then the cells are suspended gently in the HAT medium [normal medium supplemented with hypoxanthine, thymidine and aminopterin]. This suspension is cultured in a 5% $CO_2$ incubator at 37° C. for 7 to 14 days.

After culturing, a part of the culture supernatant is taken, and cell clusters which react with MOG and which do not react with antigens other than MOG are selected by a method for selecting a hybridoma such as the binding assay described below. Next, after cloning by the limiting dilution method, a hybridoma which stably shows potent antibody valency is selected as a monoclonal antibody-producing hybridoma.

(5) Preparation of Purified Monoclonal Antibody

The monoclonal antibody-producing hybridoma obtained in (4) is intraperitoneally injected into an 8- to 10-week old mouse or nude mouse which has been treated by pristane treatment [by intraperitoneally administering 2,6,10,14-tetramethylpentadecane (Pristane) 0.5 mL and breeding for 2 weeks]. In 10 to 21 days, the hybridoma becomes an ascites tumor.

The ascites are collected from this mouse, and the solid is removed by centrifugation. Then, by salting out with 40 to 50% ammonium sulfate and purifying by caprylic acid precipitation method, a DEAE-Sepharose column, a protein A-column or a gel filtration column, an IgG or IgM fraction is collected to obtain a purified monoclonal antibody.

Moreover, the monoclonal antibody-producing hybridoma obtained in (4) is cultured in RPMI1640 medium supplemented with 10% FBS or the like, and then the supernatant is removed by centrifugation. The hybridoma is suspended in Hybridoma SFM medium and cultured for 3 to 7 days.

A purified monoclonal antibody can also be obtained by centrifuging the obtained cell suspension, purifying from the obtained supernatant by a protein A-column or a protein G-column and collecting an IgG fraction. In this regard, 5% Daigo's GF21 can be added to Hybridoma SFM medium.

The subclass of the antibody is determined by the enzyme immunoassay method using a subclass typing kit. The protein mass is determined by the Lowry method or by calculating from the absorbance at 280 nm.

(6) Selection of Antibody

The antibody is selected for example by measuring the affinity of the antibody to MOG-expressing cells using flow cytometry as shown below. The MOG-expressing cells may be any cells as long as MOG is expressed on the cell surface, and examples include animal cells, an animal cell line, the MOG forcibly-expressing cell line obtained in (1) and the like.

After dispensing the MOG-expressing cells to a plate such as a 96-well plate, the substances to be tested such as serum, culture supernatants of hybridomas or purified antibodies are dispensed as the first antibodies and reacted. The cells after the reaction are thoroughly washed with PBS containing 1 to 10% bovine serum albumin (BSA) (referred to as BSA-PBS below) or the like, and an anti-immunoglobulin antibody labeled with a fluorescent reagent or the like is then dispensed as the second antibody and reacted. After thoroughly washing with BSA-PBS or the like, the fluorescence amounts of the labeled antibody are measured using a flow cytometer, and an antibody which specifically reacts with the MOG-expressing cells is thus selected.

Moreover, the antibody can also be selected by measuring the affinity of the monoclonal antibody to MOG-expressing cells, a MOG protein or the like using ELISA or surface plasmon resonance described below. The MOG protein may be a protein composed of some domains of MOG or a protein to which a tag such as GST is added.

In ELISA, after dispensing the MOG-expressing cells or the MOG protein to a plate such as a 96-well plate, the wells are blocked with BSA-PBS, and the substances to be tested such as serum, culture supernatants of hybridomas or purified antibodies are dispensed as the first antibodies and reacted. Next, after thoroughly washing with PBS or the like, an anti-immunoglobulin antibody labeled with a fluorescent reagent or the like is dispensed as the second antibody and reacted.

Then, after thoroughly washing with PBS or the like, a chromogenic reagent is added. At the end, the chromogenic reaction is stopped with a solution for stopping the reaction, and the absorbances of the wells are measured with a microplate reader. An antibody which specifically reacts with the MOG-expressing cells or the MOG protein is thus selected.

In surface plasmon resonance, using a known protocol, the affinity of an antibody which binds to MOG can be measured by immobilizing the antibody on an appropriate sensor chip and using a MOG protein as the analyte.

Using the affinity of the antibody obtained, an antibody having desired affinity to a MOG protein can be selected. The affinity of an antibody which binds to MOG can also be measured by immobilizing a MOG protein on a sensor chip and using the antibody as the analyte.

In addition, an antibody which competes in binding to MOG with the antibody of the invention can be obtained by adding an antibody to be tested to the assay system using flow cytometry or ELISA described above and reacting. That is, by selecting an antibody which inhibits binding of the antibody of the invention and MOG when the antibody to be tested is added by screening, an antibody that competes with the antibody of the invention in binding to the amino acid sequence of MOG or the three-dimensional structure thereof can be obtained.

An antibody which binds to an epitope containing the epitope to which the antibody of the invention binds can be obtained by identifying the epitope of an antibody obtained by the screening method described above by a known method, producing a synthetic peptide containing the identified epitope, a synthetic peptide which mimics the three-dimensional structure of the epitope or the like and immunizing.

An antibody which binds to the same epitope as the epitope to which the antibody of the invention binds can be obtained by identifying the epitope of an antibody obtained by the screening method described above, producing a partial synthetic peptide of the identified epitope, a synthetic peptide which mimics the three-dimensional structure of the epitope or the like and immunizing.

(7) Acquisition of Antibody by Phage Display Method (7-1) Production Method of Antibody Phage Library In the invention, as the antibody phage library, an immune library, a naive library and a synthetic library can be used. The methods for producing the libraries are described below.

Lymphocytes derived from an animal immunized by the same method as that of (1) or a patient are collected for an immune library, and lymphocytes derived from a normal animal or a healthy human are collected for a naive library. RNA is extracted from the lymphocytes, and cDNA is synthesized by reverse transcription reaction.

A fragment of an antibody gene amplified by PCR using the cDNA as a template is inserted to a phagemid vector, and E. coli is transformed by the phagemid vector. When the obtained transformant is infected with a helper phage, an antibody phage library of the antibody gene can be obtained.

With respect to a synthetic library, CDR of a V gene in the genome DNA or a reconstructed functional V gene is substituted with an oligonucleotide that encodes any amino acid sequence of an appropriate length, and E. coli is transformed by a phagemid vector into which the V gene has been inserted. When the obtained transformant is infected with a helper phage, an antibody phage library can be obtained.

As the cDNA derived from lymphocytes and the antibody phage library, those which are commercially available can also be used.

As the phagemid vector, pCANTAB 5E (Amersham Pharmacia Biotech Inc.), pUC118/pUC119 vector (TaKaRa), pBlueScript II Phagemid Vector (Agilent Technologies), pKSTV-02 (Miyazaki et al, J. Biochem. 2015; 1) and the like can be used.

As the helper phage, M13KO7 helper phage (Invitrogen), VCSM13 Interference Resistant Helper Phage (Agilent Technologies), R408 Interference Resistant Helper Phage (Agilent Technologies) and the like can be used.

A phage vector can also be used for phage display. There are a peptide phage library in which filamentous bacteriophage g3p is a displayed molecule (manufactured by New England Biolabs and the like), a method in which g7p, g8p or g9p is a displayed molecule and the like.

Moreover, phage display using T7 phage can also be used. A display system for T7 phage is T7 Select vector (Novagen) or the like.

(7-2) Selection of Antibody Phage Clone

An antibody phage clone can be selected from the antibody phage libraries produced in (7-1) using the ELISA method shown below.

MOG is immobilized in an immuno tube, and the tube is blocked with a blocking buffer. The antibody phage libraries produced in (7-1) are added to the wells of the tube and reacted. Next, the wells are washed, and a fluorescently labeled anti-phage antibody is added and reacted. Then, the wells are washed again, and a chromogenic solution is added. Then, the chromogenic reaction is stopped with a solution for stopping the reaction, and the absorbances of the wells are measured with a microplate reader. In this manner, an antibody phage clone which binds to MOG is selected.

2. Production of Genetically Recombinant Antibody

As examples for producing a genetically recombinant antibody, methods for producing a human chimeric antibody and a humanized antibody are described below. Genetically recombinant mouse antibody, rat antibody, rabbit antibody, hamster antibody, camel antibody, llama antibody, alpaca antibody and human antibody, chimeric antibodies, a heavy chain antibody and the like can also be produced by the same method.

(1) Construction of Expression Vector for Genetically Recombinant Antibody

An expression vector for a genetically recombinant antibody is an expression vector for animal cells in which DNA that encodes CH and CL of a human antibody has been incorporated and can be constructed by cloning DNAs that encode CH and CL of a human antibody into an expression vector for animal cells.

As the C region of a human antibody, CH and CL of any human antibody can be used. For example, CH of γ1 subclass and CL of K class of a human antibody and the like are used. As the DNAs that encode CH and CL of the human antibody, cDNA is used, but chromosomal DNA consisting of exons and introns can also be used.

As the expression vector for animal cells, any vector can be used as long as it is capable of incorporating and expressing a gene that encodes the C region of a human antibody. For example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)] and the like are used.

The promoter and the enhancer of the expression vector for animal cells are the early promoter of SV40 [J. Biochem., 101, 1307 (1987)], the Moloney murine leukemia virus LTR [Biochem. Biophys. Res. Commun., 149, 960 (1987)] or the promoter of immunoglobulin H chain [Cell, 41, 479 (1985)] and the enhancer [Cell, 33, 717 (1983)] or the like.

As the expression vector for the genetically recombinant antibody, an expression vector for a genetically recombinant antibody of a type in which the antibody H chains and L chains are on the same vector (tandem type) [J. Immunol. Methods, 167, 271 (1994)] is used from the viewpoints of ease of construction of the expression vector for the genetically recombinant antibody, ease of introduction into animal cells, balanced expression levels of the antibody H chains and L chains in animal cells and the like, but a type in which the antibody H chains and L chains are on different vectors can also be used. As the tandem type expression vector for a genetically recombinant antibody, pKANTEX93 (International Publication No. 97/10354), pEE18 [Hybridoma, 17, 559 (1998)] and the like are used.

(2) Acquisition of cDNA Encoding V Region of Antibody Derived from Animal Other than Human and Analysis of Amino Acid Sequence cDNA that encodes VH and VL of a non-human antibody can be obtained, and the amino acid sequence can be analyzed as follows.

(2-1) When Antibody is Obtained by Hybridoma Method mRNA is extracted from hybridoma cells producing a non-human antibody, and cDNA is synthesized. The synthesized cDNA is cloned into a vector such as a phage or a plasmid to produce a cDNA library.

Recombinant phages or recombinant plasmids having cDNAs that encode VH or VL are isolated from the libraries using DNAs that encode the C region and the V region of the non-human antibody as probes. The entire nucleotide sequences of VH or VL of the target non-human antibody on the recombinant phages or the recombinant plasmids are determined, and then the entire amino acid sequences of VH or VL are deduced from the nucleotide sequences.

As the animal other than human which produces the hybridoma cells producing the non-human antibody, a mouse, a rat, a hamster, a rabbit, a llama, a camel, an alpaca or the like is used, but any animal can be used as long as hybridoma cells can be produced.

For the preparation of total RNA from hybridoma cells, the guanidine thiocyanate-cesium trifluoroacetate method [Methods in Enzymol., 154, 3 (1987)], a kit such as RNA easy Kit (manufactured by QIAGEN) or the like is used.

To prepare mRNA from total RNA, oligo (dT) immobilized cellulose column chromatography [Molecular Cloning, A Laboratory Manual, Second Edition, Cold Spring Harbor Laboratory Press (1989)], a kit such as Oligo-dT30<Super> mRNA Purification (registered trademark) Kit (manufactured by Takara Bio Inc.) or the like is used. Furthermore, mRNA can also be prepared from hybridoma cells using a kit such as Fast Track mRNA Isolation (registered trademark) Kit (manufactured by Invitrogen) or QuickPrep mRNA Purification (registered trademark) Kit (manufactured by Pharmacia).

For the synthesis of cDNA and the production of a cDNA library, a known method [Molecular Cloning, A Laboratory Manual, Second Edition, Cold Spring Harbor Laboratory Press (1989) and Current Protocols in Molecular Biology, Supplement 1, John Wiley & Sons (1987-1997)], a kit such as SuperScript Plasmid System for cDNA Synthesis and Plasmid Cloning (manufactured by Invitrogen) or ZAP-cDNA Synthesis (registered trademark) Kit (manufactured by Stratagene) or the like is used.

When a cDNA library is produced, any vector capable of incorporating the cDNA can be used as a vector into which the cDNA synthesized using mRNA extracted from the hybridoma cells as a template is incorporated. For example, ZAP Express [Strategies, 5, 58 (1992)], pBluescript II SK (+) [Nucleic Acids Research, 17, 9494 (1989)], λZAPII (manufactured by Stratagene), λgt 10 and λgt 11 [DNA Cloning: A Practical Approach, I, 49 (1985)], Lambda Blue Mid (manufactured by Clontech Laboratories, Inc.), λExCell, pT7T3-18U (manufactured by Pharmacia), pCD2 [Mol. Cell. Biol., 3, 280 (1983)], pUC18 [Gene, 33, 103 (1985)] or the like is used.

Any *Escherichia coli* can be used as *Escherichia coli* into which a cDNA library constructed by a phage or a plasmid vector is introduced as long as the cDNA library can be introduced, expressed and maintained. For example, XL1-Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], JM105 [Gene, 38, 275 (1985)] or the like is used.

For the selection of the cDNA clone that encodes VH or VL of the non-human antibody from the cDNA libraries, a colony hybridization method using an isotope- or fluorescently labeled probe, the plaque hybridization method [Molecular Cloning, A Laboratory Manual, Second Edition, Cold Spring Harbor Laboratory Press (1989)] or the like is used.

In addition, the cDNA that encodes VH or VL can also be prepared by preparing primers and performing the polymerase chain reaction method [referred to as PCR method below, Molecular Cloning, A Laboratory Manual, Second Edition, Cold Spring Harbor Laboratory Press (1989) and Current Protocols in Molecular Biology, Supplement 1, John Wiley & Sons (1987-1997)] using the cDNA synthesized from mRNA or a cDNA library as a template.

The selected cDNA is cleaved with an appropriate restriction enzyme or the like and then cloned into a plasmid such as pBluescript SK (−) (manufactured by Stratagene), and the nucleotide sequence of the cDNA is determined by a commonly used nucleotide sequence analysis method or the like. For the nucleotide sequence analysis method, for example, after performing a reaction such as the dideoxy method [Proc. Natl. Acad. Sci. USA, 74, 5463 (1977)], an automatic nucleotide sequence analyzer such as ABI PRISM3700 (manufactured by PE Biosystems) or A.L.F. DNA sequencer (manufactured by Pharmacia) or the like is used.

(2-2) When Antibody is Obtained by Phage Display Method

The entire nucleotide sequences of VH or VL are determined from the plasmid vectors of the selected phage clones using DNAs that encode the vector region or the V region as probes, and then the entire amino acid sequences of VH or VL can be deduced from the nucleotide sequences.

In both of the hybridoma method and the phage display method, by deducing the entire amino acid sequences of VH and VL from the determined nucleotide sequences and comparing with the entire amino acid sequences of VH and VL of a known antibody [Sequences of Proteins of Immunological Interest, US Dept. Health and Human Services (1991)], it is confirmed whether the obtained cDNA encodes the complete amino acid sequences of VH and VL of an antibody containing a secretion signal sequence.

Regarding the complete amino acid sequences of VH and VL of the antibody containing a secretion signal sequence, by comparing with the entire amino acid sequences of VH and VL of a known antibody [Sequences of Proteins of Immunological Interest, US Dept. Health and Human Services (1991)], the length of the secretion signal sequence and the N-terminus amino acid sequence can be deduced, and the subgroup to which they belong can be found.

In addition, the amino acid sequences of the CDRs of VH and VL can also be determined by comparing with the amino acid sequences of VH and VL of a known antibody [Sequences of Proteins of Immunological Interest, US Dept. Health and Human Services (1991)].

Furthermore, using the obtained complete amino acid sequences of VH and VL, it is possible to confirm whether the complete amino acid sequences of VH and VL are new by carrying out homology search by the BLAST method [J. Mol. Biol., 215, 403 (1990)] or the like using any database such as SWISS-PROT or PIR-Protein.

(3) Construction of Human Chimeric Antibody Expression Vector

By cloning cDNAs that encode VH and VL of a non-human antibody in the upstream of the respective genes that encode CH and CL of a human antibody in the expression vector for a genetically recombinant antibody obtained in (1), a human chimeric antibody expression vector can be constructed.

In order to link the 3' terminus sides of the cDNAs that encode VH or VL of the non-human antibody with the respective 5' terminus sides of CH or CL of the human antibody, cDNAs of VH and VL in which the nucleotide sequences of the linking parts are designed to encode an appropriate amino acid and to become an appropriate restriction enzyme recognition sequence are produced.

The produced cDNAs of VH and VL are cloned in the upstream of the respective genes that encode CH or CL of the human antibody in the expression vector for a genetically recombinant antibody obtained in (1) in a manner that they are expressed in an appropriate form, and therefore a human chimeric antibody expression vector is constructed.

In addition, each of the cDNAs that encode VH or VL of the non-human antibody can be amplified by the PCR method using synthetic DNA having an appropriate restriction enzyme recognition sequence at both ends and cloned into the expression vector for a genetically recombinant antibody obtained in (1).

(4) Construction of cDNA Encoding V Region of Humanized Antibody

A cDNA that encodes VH or VL of a humanized antibody can be constructed as follows.

Amino acid sequences of the FRs of VH and VL of a human antibody for the insertion of the amino acid sequences of the CDRs of VH and VL of a non-human antibody are selected. Any amino acid sequences derived from a human antibody can be used as the selected amino acid sequences of the FRs.

For example, an amino acid sequence of FR of a human antibody registered in a database such as Protein Data Bank, a common amino acid sequence of the subgroups of FR of a human antibody [Sequences of Proteins of Immunological Interest, US Dept. Health and Human Services (1991)] or the like is used. In order to suppress a decrease in binding activity of the antibody, an amino acid sequence of FR having as high homology (at least 60% or more) as possible to the amino acid sequence of the FR of VH or VL of the original antibody is selected.

Next, the amino acid sequences of the CDRs of the original antibody are inserted to the respective selected amino acid sequences of the FRs of VH and VL of the human antibody, and the amino acid sequences of VH and VL of a humanized antibody are designed. By converting the designed amino acid sequences into DNA sequences in consideration of the use frequency of codons found in the nucleotide sequences of the antibody genes [Sequences of Proteins of Immunological Interest, US Dept. Health and Human Services (1991)], DNA sequences encoding the amino acid sequences of VH and VL of a humanized antibody are designed.

Based on the designed DNA sequences, several synthetic DNAs having lengths of around 100 bases are synthesized, and the PCR reaction is carried out using the DNAs. In this case, due to the reaction efficiency of the PCR reaction and the synthesizable lengths of DNAs, 6 synthetic DNAs are preferably designed for each of the VH and VL.

Furthermore, by introducing an appropriate restriction enzyme recognition sequence at the 5' or 3' terminus of the synthetic DNAs located at both ends, cDNA that encodes VH or VL of a humanized antibody can be easily cloned into the expression vector for a genetically recombinant antibody obtained in (1).

After the PCR reaction, the amplified products are each cloned into a plasmid such as pBluescript SK (−) (manufactured by Stratagene), and the nucleotide sequences are determined by the same method as the method described in (2). A plasmid having the DNA sequence that encodes the amino acid sequence of VH or VL of a desired humanized antibody is thus obtained.

Alternatively, the entire VH and the entire VL each synthesized as a long chain DNA based on the designed DNA sequences can also be used instead of the PCR amplified products. Moreover, by introducing an appropriate restriction enzyme recognition sequence at both ends of the synthesized long chain DNAs, cDNAs that encode VH and VL of the humanized antibody can be easily cloned into the expression vector for a genetically recombinant antibody obtained in (1).

(5) Modification of Amino Acid Sequence of V Region of Humanized Antibody

When only the CDRs of VH and VL of a non-human antibody are merely inserted into the FRs of VH and VL of a human antibody, the antigen binding activity of the humanized antibody is lower than that of the original non-human antibody [BIO/TECHNOLOGY, 9, 266 (1991)].

In a humanized antibody, by identifying the amino acid residues directly related to antigen binding, the amino acid residues interacting with the amino acid residues of the CDRs and the amino acid residues which maintain the three-dimensional structure of the antibody and which are indirectly related to antigen binding, in the amino acid sequences of the FRs of VH and VL of a human antibody, and by substituting these amino acid residues with the amino acid residues of the original non-human antibody, the lowered antigen binding activity can be increased.

In order to identify the amino acid residues of FR related to the antigen binding activity, the three-dimensional structure of the antibody can be constructed and analyzed using X-ray crystallography [J. Mol. Biol., 112, 535 (1977)], computer modeling [Protein Engineering, 7, 1501 (1994)] or the like. Furthermore, a humanized antibody having necessary antigen binding activity can be obtained by producing various types of variants for each antibody and repeatedly examining their correlation with the antigen binding activities and through trial and error.

Amino acid residues of the FRs of VH and VL of a human antibody can be modified by carrying out the PCR reaction described in (4) using synthetic DNA for the modification. The nucleotide sequence of the amplified product after the PCR reaction is determined, and whether the intended modification has been carried out is confirmed by the method described in (2).

(6) Construction of Expression Vector for Humanized Antibody

By cloning the cDNAs that encode VH and VL of the constructed genetically recombinant antibody in the upstream of the respective genes that encode CH and CL of the human antibody in the expression vector for a genetically recombinant antibody obtained in (1), an expression vector for a humanized antibody can be constructed.

For example, the cDNAs are cloned in the upstream of the respective genes that encode CH and CL of the human antibody in the expression vector for a genetically recombinant antibody obtained in (1) in a manner that the cDNAs are expressed in an appropriate form by introducing an appropriate restriction enzyme recognition sequence at the 5' or 3' terminus of the synthetic DNAs located at both ends of the synthetic DNAs used for constructing the VH and VL of the humanized antibody obtained in (4) and (5).

(7) Transient Expression of Genetically Recombinant Antibody

By transiently expressing genetically recombinant antibodies using the expression vectors of a genetically recombinant antibody obtained in (3) and (6) or modified expression vectors thereof, the antigen binding activities of the produced various human chimeric antibodies and humanized antibodies can be efficiently evaluated.

As a host cell into which an expression vector is introduced, any cell can be used as long as it is a host cell capable of expressing a genetically recombinant antibody, but for example, COS-7 cells [American Type Culture Collection (ATCC) number: CRL1651] are used [Methods in Nucleic Acids Res., CRC press, 283 (1991)].

For introduction of an expression vector into COS-7 cells, the DEAE-dextran method [Methods in Nucleic Acids Res., CRC press (1991)], the lipofection method [Proc. Natl. Acad. Sci. USA, 84, 7413 (1987)] or the like is used.

After the introduction of the expression vector, the expression level and the antigen binding activity of the genetically recombinant antibody in a culture supernatant are measured using the enzyme immunoassay method [Monoclonal Antibodies-Principles and practice, Third edition, Academic Press (1996), Antibodies-A Laboratory Manual, Cold Spring Harbor Laboratory (1988) and A manual for monoclonal antibody experiments, Kodansha scientific books (1987)] or the like.

(8) Acquisition of Stable Expression Transformant of Genetically Recombinant Antibody and Preparation of Genetically Recombinant Antibody By introducing the expression vector for a genetically recombinant antibody obtained in (3) or (6) into an appropriate host cell, a transformant stably expressing the genetically recombinant antibody can be obtained.

For the introduction of the expression vector into a host cell, the electroporation method [JP-A-H2-257891 and Cytotechnology, 3, 133 (1990)] or the like is used.

As the host cell into which the expression vector for a genetically recombinant antibody is introduced, any cell can be used as long as it is a host cell capable of expressing the genetically recombinant antibody. For example, CHO-K1 (ATCC CCL-61), DUKXB11 (ATCC CCL-9096), Pro-5 (ATCC CCL-1781), CHO-S (Life Technologies, Cat #11619), rat myeloma cells YB2/3HL.P2.G11.16Ag.20 (ATCC No. CRL1662, also called YB2/0), mouse myeloma cells NS0, mouse myeloma cells SP2/0-Ag14 (ATCC No. CRL1581), mouse P3X63-Ag8.653 cells (ATCC No. CRL1580), CHO cells in which the dihydrofolate reductase gene (referred to as dhfr below) is deficient (CHO/DG44 cells) [Proc. Natl. Acad. Sci. USA, 77, 4216 (1980)] and the like are used.

In addition, a host cell in which the activity of a protein such as enzymes related to intracellular synthesis of sugar nucleotide GDP-fucose, a protein such as enzymes related to glycosylation modification in which the 1-position of fucose is α-bonded to the 6-position of N-acetylglucosamine at the reducing terminus of a N-glycoside-linked complex type sugar chain, a protein related to intracellular transport of sugar nucleotide GDP-fucose to the Golgi body or the like is reduced or lost, for example, CHO cells in which the α1,6-fucosyltransferase gene is deficient (International Publication No. 2005/035586 and International Publication No. 02/31140), Lec13 having lectin resistance [Somatic Cell and Molecular genetics, 12, 55 (1986)] and the like can also be used.

After the introduction of the expression vector, a transformant stably expressing a genetically recombinant antibody is selected by culturing the transformant in a medium for animal cell culture containing a drug such as G418 sulfate (referred to as G418 below) (JP-A-H2-257891).

As the medium for animal cell culture, RPMI 1640 medium (manufactured by Invitrogen), GIT medium (manufactured by Nippon Pharmaceutical Co., Ltd.), EX-CELL 301 medium (manufactured by Jay Earl H., Inc.), IMDM medium (manufactured by Invitrogen), Hybridoma-SFM medium (manufactured by Invitrogen), a medium in which various additives such as FBS are added to any of these media or the like is used.

A genetically recombinant antibody is expressed and accumulated in a culture supernatant by culturing the obtained transformant in the medium. The expression level and the antigen binding activity of the genetically recombinant antibody in the culture supernatant can be measured by the ELISA method or the like. In addition, the expression level of the genetically recombinant antibody produced by the transformant can be increased using the dhfr gene amplification system (JP-A-H2-257891) or the like.

The genetically recombinant antibody is purified using a protein A-column from the culture supernatant of the transformant [Monoclonal Antibodies—Principles and practice, Third edition, Academic Press (1996) and Antibodies—A Laboratory Manual, Cold Spring Harbor Laboratory (1988)]. In addition, a method used for purifying proteins, such as gel filtration, ion exchange chromatography and ultrafiltration, can also be combined.

The molecular weights of the H chains, the L chains or the whole antibody molecule of the purified genetically recombinant antibody can be measured using polyacrylamide gel electrophoresis [Nature, 227, 680 (1970)], western blotting method [Monoclonal Antibodies—Principles and practice, Third edition, Academic Press (1996) and Antibodies—A Laboratory Manual, Cold Spring Harbor Laboratory (1988)] or the like.

(9) Production Method of Antibody Fragment

The antibody fragment of the invention can be produced according to a known method. The antibody fragment of the invention may be produced by cleaving an antibody produced according to the method described in (1) to (8) using an enzyme or the like or may be produced by the genetic engineering technique after preparing a nucleotide sequence which encodes a desired antibody fragment.

(10) Production Method of Monovalent Antibody

In the invention, a monovalent antibody can be produced by the method described in International Publication No. 2014/054804, International Publication No. 2011/090754, International Publication No. 2007/048037, International Publication No. 2012/116927 or the like or another method.

(11) Production Method of Bispecific Antibody or Multispecific Antibody

The bispecific antibody or the multispecific antibody of the invention can be produced according to the production method of the antibody described above. For example, the bispecific antibody or the multispecific antibody can be produced using the method described in International Publication No. 2009/131239, International Publication No. 2014/054804, International Publication No. 01/077342, US Patent Application Publication No. 2007/0071675, International Publication No. 2007/024715, Wu et al., [Nature Biotechnology, 2007, 25(11), p. 1290-1297], Labrijn et al., [PNAS 2013, vol. 110, no. 13, p 5145-5150], Jong et al., [http://dx.doi.org/10.1371/journal.pbio.1002344], Kontermann et al., [mAbs 2012, vol. 4, issue 2, p 182-197], Spiess et al., [Molecular Immunology 67 (2015) 95-106], Ridgway et al., [Protein engineering, 1996 vol. 9 no. 7 pp 617-621, International Publication No. 2009/080251, International Publication No. 2010/151792, International Publication No. 2014/033074 or the like.

For example, an expression vector of a bispecific antibody in which scFv that binds to MOG is fused to the C-terminus of an IgG antibody that binds to an antigen that is present in the brain can be produced by the method described below, and the bispecific antibody can be produced according to the expression method of the antibody and the purification method of the antibody described above. In addition, a bispecific antibody in which an antibody fragment is fused to the C-terminus of an antibody can also be produced by the same methods.

A gene fragment of a CH1-Hinge-CH2-CH3-linker domain is amplified by the PCR method using a synthetic gene of a heavy chain constant region of an IgG antibody which binds to an antigen that is present in the brain as a template. Next, using the nucleotide sequence of an antibody which binds to MOG as a template, the nucleotide sequence of a scFv domain in which VH and VL of the antibody are linked with an appropriate linker is prepared using the PCR method or the like. The two domains are linked by the PCR method or the like, and the obtained gene fragment is inserted to an appropriate vector such as pCI vector.

Moreover, a gene fragment of a light chain domain (VL and CL) of an IgG antibody which binds to an antigen that is present in the brain and a gene fragment of VH of the antibody are amplified by the PCR method using appropriate templates and are inserted into the appropriate position of the vector.

In addition, the bispecific antibody of the invention can also be produced by binding an antigen binding site containing an antibody fragment to an IgG antibody by a chemical method.

3. Evaluation of Activity of Antibody or Antibody Fragment Thereof

In the invention, the activity of an antibody or an antibody fragment thereof can be evaluated as follows.

(1) Binding Activity to MOG

The binding activity of the antibody or the antibody fragment of the invention to MOG is measured using flow cytometry, ELISA or surface plasmon resonance detection described in 1-(6) above or the like. Moreover, the binding activity can also be measured using a fluorescent antibody method [Cancer Immunol. Immunother., 36, 373 (1993)].

Also when the antibody or the antibody fragment of the invention is a monovalent antibody which binds to MOG, the binding activity of the monovalent antibody to MOG can be measured by the same method. Also when the antibody or the antibody fragment of the invention is a bispecific antibody or a multispecific antibody which binds to MOG and an antigen that is present in the brain, the binding activity of the bispecific antibody or the multispecific antibody to MOG or the antigen that is present in the brain can be measured by the same method.

(2) Measurement Method of Property of Accumulating in Brain

The property of the antibody or the antibody fragment of the invention of accumulating in the brain can be measured by the method described below.

A method of collecting brain tissues several days after administering the antibody or the antibody fragment to an animal, homogenizing the brain tissues, measuring the concentration of the antibody or the antibody fragment in the supernatant after centrifugation and calculating the amount of the antibody or the antibody fragment per unit brain weight, a method of detecting the presence of the antibody or the antibody fragment by a known immunological method using the collected brain tissues or the like is used. Moreover, a method of administering the antibody or the antibody fragment to which a pharmacologically acceptable label has been attached to an animal and detecting the presence of the antibody or the antibody fragment by in vivo imaging system sequentially or the like is used.

As the animal used, an animal suitable for the use of the antibody or the antibody fragment of the invention can be selected.

(3) Measurement Method of ADCC and CDC

The CDC or the ADCC of the antibody or the antibody fragment of the invention to human MOG-expressing cells or cells in which MOG and the antigen that is present in the brain are expressed can be measured by a known measurement method [Cancer Immunol. Immunother., 36, 373 (1993); and Current protocols in Immunology, Chapter 7. Immunologic studies in humans, Editor, John E, Coligan et al., John Wiley & Sons, Inc., (1993)].

4. Method for Controlling Effector Activity of Antibody or Antibody Fragment

As the method for controlling the effector activity of the antibody or the antibody fragment of the invention, a method for controlling the amount of α1,6-fucose (also called a core fucose) binding to N-acetylglucosamine (GlcNAc) present on the reducing terminal of the N-linked complex sugar chain that bind to the $297^{th}$ asparagine (Asn) in the Fc region of the antibody or the antibody fragment containing Fc (International Publication No. 2005/035586, International Publication No. 2002/31140 and International Publication No. 00/61739), a method for controlling by modifying an amino acid residue in the Fc region of the antibody or the antibody fragment and the like are known. The effector activity of the antibody or the antibody fragment of the invention can be controlled using any of the methods.

The effector activity refers to the antibody-dependent activity that is caused through the Fc region of the antibody or the antibody fragment, and ADCC, CDC, Antibody-dependent phagocytosis (ADP) that is caused by phagocytes such as macrophages or dendritic cells and the like are known.

As the method for measuring the effector activity, for example, the effector activity can be measured by mixing the target cells, human peripheral blood mononuclear cells (PBMCs) as the effector and a target cell-specific antibody or an antibody fragment thereof, incubating the mixture for around four hours and then measuring the released lactate dehydrogenase (LDH) as an index of the cytotoxicity. In addition, the effector activity can also be measured by $^{51}$Cr-release method, flow cytometry method or the like.

The effector activity of an antibody or an antibody fragment containing Fc can be increased or decreased by controlling the core fucose content of the N-linked complex sugar chain of Fc of the antibody. Regarding the method for reducing the amount of fucose that binds to the N-linked complex sugar chain binding to Fc of the antibody or the antibody fragment, an antibody or an antibody fragment thereof to which fucose is not bound can be obtained by expressing the antibody or the antibody fragment using CHO cells in which the α1,6-fucosyltransferase gene is deficient. An antibody or an antibody fragment thereof to which fucose is not bound has high ADCC.

On the other hand, as the method for increasing the amount of fucose that binds to the N-linked complex sugar chain binding to Fc of the antibody or the antibody fragment, an antibody or an antibody fragment thereof to which fucose is bound can be obtained by expressing the antibody or the antibody fragment using host cells into which the α1,6-fucosyltransferase gene has been introduced. An antibody or an antibody fragment thereof to which fucose is bound has lower ADCC than that of an antibody or an antibody fragment thereof to which fucose is not bound.

Moreover, by modifying an amino acid residue in the Fc region of the antibody or the antibody fragment, the ADCC or the CDC can be increased or reduced. For example, the CDC of the antibody or the antibody fragment can be increased using the amino acid sequence of the Fc region described in US Patent Application Publication No. 2007/0148165.

Furthermore, the ADCC or the CDC can be increased or decreased by the amino acid modifications described in U.S. Pat. Nos. 6,737,056, 7,297,775 or 7,317,091.

The antibody or the antibody fragment of the invention also includes an antibody or an antibody fragment thereof whose half-life in the blood is controlled by controlling the reactivity with Fc receptor, for example through the amino acid modifications described in JP-A-2013-165716, JP-A-2012-021004 or the like in accordance with the amino acid modifications or the sugar chain modifications in the constant region contained in the antibody or the antibody fragment.

Moreover, when a combination of the above methods is applied to one antibody or an antibody fragment thereof, an antibody or an antibody fragment thereof whose effector activity and the half-life in the blood are controlled can be obtained.

5. Method for Treating Disease Using Antibody or Antibody Fragment of Invention

The antibody or the antibody fragment of the invention can be used for treating a brain disease of an animal in which MOG is expressed in the brain.

Examples of the brain disease include Alzheimer's disease, the prodromal stage of Alzheimer's disease, Huntington disease, Parkinson's disease, brain tumors, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, cerebrovascular disease, epilepsy, migraine, hyperactivity disorder, Creutzfeldt-Jakob disease, corticobasal degeneration, lysosomal storage disease, depression, dystonia and the like.

The brain disease that the antibody or the antibody fragment of the invention can treat differs with the antigen to which the antibody or the antibody fragment of the invention binds, the kind of the molecule which modifies the antibody or the antibody fragment in the fused antibody or the fused antibody fragment of the invention and the like.

The therapeutic agent containing the antibody or the antibody fragment of the invention may contain only the antibody or the antibody fragment as an active ingredient, but the agent is generally mixed with one or more pharmacologically acceptable carriers and provided as medicinal formulation that is produced by a method known in the technical field of pharmaceutical science.

Examples of the route of administration include oral administration or parenteral administration such as intraoral, airway, intrarectal, subcutaneous, intramuscular, intraventricular, intraperitoneal, intradermal, intranasal, intrathecal or intravenous administration. Examples of the form of administration include a spray, a capsule, a tablet, a powder, a granule, a syrup, an emulsion, a suppository, an injection, an ointment, a tape and the like.

Formulations suitable for oral administration are emulsions, syrups, capsules, tablets, powders, granules and the like.

Liquid preparations such as emulsions or syrups are produced using water, sugars such as sucrose, sorbitol or fructose, glycols such as polyethylene glycol or propylene glycol, oils such as sesame oil, olive oil or soybean oil, preservatives such as p-hydroxybenzoic acid esters, flavors such as strawberry flavor or peppermint or the like as an additive.

The capsules, the tablets, the powders, the granules and the like are produced using excipients such as lactose, glucose, sucrose or mannitol, disintegrating agents such as starch or sodium alginate, lubricants such as magnesium stearate or talc, binders such as polyvinyl alcohol, hydroxypropyl cellulose or gelatin, surfactants such as a fatty acid ester, plasticizers such as glycerin or the like as an additive.

Formulations suitable for parenteral administration are injections, suppositories, sprays and the like. The injections are produced using a salt solution, a glucose solution, a carrier formed of a mixture of these solutions or the like. The suppositories are produced using carriers such as cocoa butter, hydrogenated fats or carboxylic acids.

The sprays are produced using a carrier which does not stimulate the oral and respiratory mucosa of a recipient and which enables dispersion of the antibody or the antibody fragment of the invention as fine particles and easy absorption or the like. As the carrier, for example, lactose, glycerin or the like is used. In addition, it can also be produced as an aerosol or a dry powder. Furthermore, also for the above parenteral preparations, the components exemplified as the additives for the formulations suitable for oral administration can also be added.

6. Method for Detecting or Measuring Antigen Present in Brain or Method for Diagnosing Disease Using Antibody or Antibody Fragment of Invention Using the antibody or the antibody fragment of the invention, MOG or MOG and an antigen that is present in the brain can be detected or measured. Moreover, by detecting or measuring MOG or MOG and an antigen that is present in the brain, a brain disease of an animal in which MOG is expressed in the brain can be diagnosed.

Examples of the brain disease include Alzheimer's disease, the prodromal stage of Alzheimer's disease, Huntington disease, Parkinson's disease, brain tumors, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, cerebrovascular disease, epilepsy, migraine, hyperactivity disorder, Creutzfeldt-Jakob disease, corticobasal degeneration, lysosomal storage disease, depression, dystonia and the like. The brain disease that the antibody or the antibody fragment of the invention can diagnose differs with the antigen to which the antibody or the antibody fragment of the invention binds, the kind of the molecule which modifies the antibody or the antibody fragment in the fused antibody or the fused antibody fragment of the invention and the like.

The brain disease of an animal in which MOG is expressed in the brain can be diagnosed for example by detecting or measuring MOG that is present in the brain of the patient or the patient animal by an immunological method. Moreover, the brain disease can be diagnosed by detecting MOG that is expressed or present in the cells in the brain of the patient or the patient animal using an immunological method such as flow cytometry.

When a monovalent antibody which binds to MOG is used as the antibody or the antibody fragment of the invention, MOG in the brain can be measured by the same method as that described above. When a bispecific antibody or a multispecific antibody which binds to MOG and an antigen that is present in the brain is used as the antibody or the antibody fragment of the invention, MOG in the brain or the antigen that is present in the brain can be detected or measured by the same method as that described above.

The immunological method is a method of detecting or measuring the amount of an antibody or the amount of an antigen using a labeled antigen, antibody or the like. For example, the radioactive material labeled immune antibody method, the enzyme immunoassay method, the fluorescence immunoassay method, the luminescence immunoassay method, the western blotting method, the physicochemical method or the like is used.

In the radioactive material labeled immune antibody method, for example, the antibody or the antibody fragment of the invention is reacted with an antigen, cells expressing an antigen or the like and then reacted with an anti-immunoglobulin antibody or an antibody fragment thereof subjected to radiolabeling, followed by measurement with a scintillation counter or the like.

In the enzyme immunoassay method, for example, the antibody or the antibody fragment of the invention is reacted with an antigen, cells expressing an antigen or the like and then reacted with an anti-immunoglobulin antibody or an antibody fragment thereof subjected to labeling with an enzyme or the like, followed by addition of a substrate and measurement of the absorbance of the reaction solution with an absorptiometer. For example, a sandwich ELISA method or the like is used. As a labeling substance used in the enzyme immunoassay method, a known [Enzyme Immunoassay Method, Igaku-Shoin Ltd. (1987)] enzyme label can be used.

For example, alkaline phosphatase label, peroxidase label, luciferase label, biotin label or the like is used. The sandwich ELISA method is a method in which after binding an antibody to a solid phase, a target antigen to be detected or to be measured is trapped, and then a second antibody is reacted with the trapped antigen.

In the ELISA method, two kinds of antibodies which recognize the antigen to be detected or measured and which have different antigen recognition sites are prepared, and among these, a first antibody is adsorbed on a plate (for example, a 96-well plate) in advance, followed by labeling the second antibody with a fluorescent substance such as FITC, an enzyme such as peroxidase, biotin or the like.

The plate on which the first antibody is adsorbed is allowed to react with cells or a lysate thereof, tissues or a lysate thereof, a cell culture supernatant, serum, pleural effusion, ascites, intraocular fluid or the like separated from the living body and then to react with the second antibody, followed by the detection reaction according to the labeling material. From a calibration curve prepared by serially diluting the antigen of a known concentration, the antigen concentration in the test sample is calculated.

As the antibodies used in the sandwich ELISA method, either a polyclonal antibody or a monoclonal antibody may be used. Antibody fragments such as Fab, Fab' and F(ab)$_2$ may be used instead of the antibodies. The combination of the two kinds of antibodies used in the sandwich ELISA method may be a combination of monoclonal antibodies or antibody fragments thereof which recognize different epitopes or may be a combination of a polyclonal antibody, a monoclonal antibody and antibody fragments thereof.

In the fluorescence immunoassay method, measurement is carried out by the method described in documents [Monoclonal Antibodies-Principles and practice, Third edition, Academic Press (1996) and A manual for monoclonal antibody experiments, Kodansha scientific books (1987)] or the like. As the labeling substance used in the fluorescence immunoassay method, a known [Fluorescent Antibody Method, Soft Science (1983)] fluorescent label can be used. For example, FITC, RITC or the like is used.

In the luminescence immunoassay method, measurement is carried out by the method described in a document [Bioluminescence and Chemiluminescence, Clinical Test 42, Hirokawa-Shoten Ltd. (1998)] or the like. As the labeling substance used in the luminescence immunoassay method, a known luminescent label is used, and an acridinium ester, a lophine or the like is used.

In the western blotting method, measurement is carried out by after fractionating antigens, cells expressing an antigen or the like by SDS (sodium dodecyl sulfate)—PAGE (polyacrylamide gel) [Antibodies—A Laboratory Manual Cold Spring Harbor Laboratory (1988)], blotting the gel on a polyvinylidene fluoride (PVDF) membrane or a nitrocellulose membrane, reacting an antibody or an antibody fragment that recognizes the antigen with the membrane, further reacting it with an anti-mouse IgG antibody or a binding fragment subjected to labeling with a fluorescent substance such as FITC, labeling with an enzyme such as peroxidase, biotin labeling or the like and then visualizing the label. An example is shown below.

Cells or tissues expressing a polypeptide having the amino acid sequence of MOG are lysed, and 0.1 to 30 µg as a protein amount per lane is subjected to electrophoresis by the SDS-PAGE method under reducing conditions. The electrophoresed proteins are transferred to a PVDF membrane and reacted with PBS containing 1 to 10% BSA (referred to as BSA-PBS below) for 30 minutes at room temperature to perform blocking operation.

The antibody or the antibody fragment of the invention is reacted therewith, and the membrane is washed with PBS containing 0.05 to 0.1% Tween-20 (referred to as Tween-PBS below) and reacted with a goat anti-mouse IgG labeled with peroxidase for 2 hours at room temperature.

By washing with Tween-PBS and detecting a band to which the antibody or the antibody fragment of the invention is bound using ECL Western Blotting Detection Reagents (manufactured by Amersham) or the like, the polypeptide having the amino acid sequence of MOG is detected.

As the antibody or the antibody fragment used for detection by western blotting, an antibody or an antibody fragment thereof capable of binding to a polypeptide that does not retain the natural three-dimensional structure is used.

The physicochemical method is carried out, for example, by binding MOG, which is the antigen, with the antibody or the antibody fragment of the invention to form an aggregate and detecting the aggregate. As another physicochemical method, a capillary tube method, a one-dimensional immunodiffusion method, an immunoturbidimetric method, a latex immunoturbidimetric method [Outline of Clinical Examination Method, KANEHARA & Co., LTD. (1998)] or the like can also be used.

In the latex immunoturbidimetric method, when a carrier such as a polystyrene latex having a particle size of approximately 0.1 to 1 µm sensitized with an antibody or an antigen is used to cause the antigen-antibody reaction with a corresponding antigen or antibody, the scattered light is increased in a reaction solution, and the transmitted light is decreased. The antigen concentration and the like in the test sample are measured by detecting this change as absorbance or integrating sphere turbidity.

For detection or measurement of cells expressing MOG, a known immunological detection method can be used, but of known methods, the immunoprecipitation method, the immunocytostaining method, the immunohistochemical staining method, the fluorescent antibody staining method or the like is preferably used.

In the immunoprecipitation method, after reacting cells expressing MOG or the like with the antibody or the antibody fragment of the invention, a carrier having specific binding ability to an immunoglobulin such as Protein G-Sepharose is added thereto, and therefore an antigen-antibody complex is precipitated. Alternatively, the method can also be carried out by the following method.

The antibody or the antibody fragment of the invention described above is immobilized on a 96-well plate for ELISA and then blocked with BSA-PBS. When the antibody is an antibody which is not purified such as a hybridoma culture supernatant for example, the hybridoma culture supernatant is dispensed and bound after immobilizing anti-mouse immunoglobulin, anti-rat immunoglobulin, protein-A, protein-G or the like on a 96-well plate for ELISA in advance and blocking the plate with BSA-PBS.

Next, after discarding BSA-PBS and thoroughly washing with PBS, lysates of cells or tissues expressing human MOG are reacted therewith. Immunoprecipitates are extracted from the plate after thoroughly washing with a sample buffer for SDS-PAGE and detected by the above western blotting.

The immunocytostaining method or the immunohistochemical staining method is a method in which cells, tissues or the like expressing an antigen are treated with a surfactant, methanol or the like in order to improve passing of the antibody in some cases, then reacted with the antibody of the invention and further reacted with an anti-immunoglobulin antibody or a binding fragment thereof subjected to fluorescent labeling with FITC or the like, labeling with an enzyme such as peroxidase, biotin labeling or the like and in which the label is then visualized and observed with a microscope.

In addition, detection can be carried out by the fluorescent antibody staining method in which a fluorescently-labeled antibody is reacted with cells and analyzed with a flow cytometer [Monoclonal Antibodies—Principles and practice, Third edition, Academic Press (1996) and A manual for monoclonal antibody experiments, Kodansha scientific books (1987)]. In particular, the antibody or the antibody fragment of the invention can detect cells in which the antigen is expressed and retains the natural three-dimensional structure by the fluorescent antibody staining method.

In addition, when the FMAT 8100 HTS system (manufactured by Applied Biosystems) or the like of the fluorescent antibody staining methods is used, the amount of an antigen or the amount of an antibody can be measured without separating the formed antibody-antigen complex from the free antibody or antigen that is not involved in formation of the antibody-antigen complex.

Hereinafter, the invention will be explained in more detail by Examples, but the invention is not limited to the following Examples.

EXAMPLES

[Example 1] Acquisition of Anti-MOG Antibodies (1) Acquisition of Antibodies Using Human Antibody Phage Libraries A VH gene fragment and a VL gene fragment were amplified from human PBMC-derived cDNA by PCR. The VH gene fragment and the VL gene fragment were inserted to a phagemid vector pCANTAB 5E (manufactured by Amersham Pharmacia Biotech), and a plasmid was obtained by transforming *Escherichia coli* TG1 (manufactured by Lucigen).

The obtained plasmid was infected with M13KO7 Helper Phage (manufactured by Invitrogen), and a human antibody M13 phage library of the VH gene and the VL gene was thus obtained.

Using the human antibody M13 phage libraries, anti-rat MOG (rMOG) monoclonal antibodies were obtained using the phage display method described below. rMOG-FLAG_Fc of Example 4 described below was immobilized on a MAXISORP STARTUBE (manufactured by NUNC), and the sites to which rMOG-FLAG_Fc was not bound were blocked using SuperBlock Blocking Buffer (manufactured by Thermo Fisher Scientific Inc.).

A human antibody M13 phage library was reacted with the tube at room temperature for an hour, and the phage was eluted with 0.1 M Gly-HCl (pH 2.2) after washing with PBS or PBS containing 0.1% Tween 20 (referred to as PBS-T below). The eluate was neutralized by adding Tris-HCl (pH 8.5). TG1 competent cells were infected with the eluted phage, and the phage was amplified.

Then, the reaction with rMOG-FLAG_Fc immobilized on a MAXISORP STARTUBE was conducted again, and washing and elution were conducted. This procedure was repeated, and phages displaying scFv which specifically binds to rMOG-FLAG_Fc were concentrated. The concentrated phages were monocloned, and three clones having affinity to rMOG-FLAG_Fc were selected by ELISA.

In ELISA, rMOG-FLAG_Fc was immobilized on MAXISORP (manufactured by NUNC), and the sites to which rMOG-FLAG_Fc was not bound were blocked using SuperBlock Blocking Buffer (manufactured by Thermo Fisher Scientific Inc.). As the negative control, a plate in which FLAG_Fc was immobilized was also prepared.

The phage clones were added to separate wells and reacted at room temperature for 30 minutes, and then the wells were washed with PBS-T. Subsequently, a solution obtained by diluting horseradish peroxidase-labeled anti-M13 antibody (manufactured by GE Healthcare) with PBS-T containing 10% Block Ace (manufactured by Dainippon Pharma Co., Ltd.) was added to the wells, and the plates were incubated at room temperature for 30 minutes.

After washing the microplates three times with PBS-T, a TMB chromogenic substrate solution (manufactured by DAKO) was added, and the plates were incubated at room temperature. The chromogenic reaction was stopped by adding 0.5 M sulfuric acid to the wells, and the absorbances at the wavelength of 450 nm (reference wavelength of 570 nm) were measured with a microplate reader (manufactured by Molecular Devices). The results obtained are shown in FIG. 1.

As shown in FIG. 1, it could be confirmed that the three phage clones all bind to rMOG-FLAG_Fc. On the other hand, none of the phage clones bound to FLAG Fc (data not shown).

The sequences of the clones which bound to rMOG-FLAG_Fc were analyzed, and anti-MOG antibody phagemid vectors, pCANTAB_MOG01, pCANTAB_MOG09 and pCANTAB_MOG14 were obtained.

In the following paragraphs, the names of the anti-MOG scFv antibodies displayed by the phages expressed using pCANTAB_MOG01, pCANTAB_MOG09 and pCANTAB_MOG14 are referred to as MOG01 antibody, MOG09 antibody and MOG14 antibody, respectively. The nucleotide sequences which encode VH or VL of the anti-MOG scFv antibodies, and the amino acid sequences deduced from the nucleotide sequences are shown in Table 1.

TABLE 1

Sequence Information of Anti-MOG scFv Antibodies (MOG01 Antibody, MOG09 Antibody and MOG14 Antibody)

| Clone Name | MOG01 | MOG09 | MOG14 |
| --- | --- | --- | --- |
| Nucleotide sequence encoding VH (including signal sequence) | SEQ ID NO: 1 | SEQ ID NO: 13 | SEQ ID NO: 25 |

TABLE 1-continued

Sequence Information of Anti-MOG scFv Antibodies (MOG01 Antibody, MOG09 Antibody and MOG14 Antibody)

| Clone Name | MOG01 | MOG09 | MOG14 |
|---|---|---|---|
| Amino acid sequence of VH (including signal sequence) | SEQ ID NO: 2 | SEQ ID NO: 14 | SEQ ID NO: 26 |
| Amino acid sequence of VH (excluding signal sequence) | SEQ ID NO: 3 | SEQ ID NO: 15 | SEQ ID NO: 27 |
| Amino acid sequence of HCDR1 | SEQ ID NO: 4 | SEQ ID NO: 16 | SEQ ID NO: 28 |
| Amino acid sequence of HCDR2 | SEQ ID NO: 5 | SEQ ID NO: 17 | SEQ ID NO: 29 |
| Amino acid sequence of HCDR3 | SEQ ID NO: 6 | SEQ ID NO: 18 | SEQ ID NO: 30 |
| Nucleotide sequence encoding VL (including signal sequence) | SEQ ID NO: 7 | SEQ ID NO: 19 | SEQ ID NO: 31 |
| Amino acid sequence of VL (including signal sequence) | SEQ ID NO: 8 | SEQ ID NO: 20 | SEQ ID NO: 32 |
| Amino acid sequence of VL (excluding signal sequence) | SEQ ID NO: 9 | SEQ ID NO: 21 | SEQ ID NO: 33 |
| Amino acid sequence of LCDR1 | SEQ ID NO: 10 | SEQ ID NO: 22 | SEQ ID NO: 34 |
| Amino acid sequence of LCDR2 | SEQ ID NO: 11 | SEQ ID NO: 23 | SEQ ID NO: 35 |
| Amino acid sequence of LCDR3 | SEQ ID NO: 12 | SEQ ID NO: 24 | SEQ ID NO: 36 |

(2) Acquisition of Antibodies Using Alpaca Antibody Libraries

An emulsion of rMOG-FLAG_Fc and complete adjuvant for the first immunization and an emulsion of rMOG-FLAG_Fc and incomplete adjuvant for the second and third immunization were produced as immunogens, and an alpaca was immunized.

Lymphocytes ($2 \times 10^7$ cells) were collected from the blood (50 mL) of the immunized alpaca, and RNA was extracted from the obtained cells using RNA IsoPlus (manufactured by TAKARA). After synthesizing cDNA by reverse transcription reaction using SuperScript (registered trademark) III First-Strand Synthesis System for RT-PC (manufactured by Invitrogen), VHH gene was amplified using primers specific to alpaca IgG2 (Short hinge-heavy chain antibody) and IgG3 (Long hinge-heavy chain antibody).

The VHH gene fragment was inserted to a phagemid vector pKSTV-02 (described in Miyazaki et al, J. Biochem. 2015; 1), and Escherichia coli TG1 was transformed by electroporation using a MicroPulser electroporator (manufactured by BioRad) (the IgG2 titer of the transformant was $2.6 \times 10^7$, and the IgG3 titer was $3.2 \times 10^7$).

The obtained transformant was infected with M13KO7 Helper Phage (manufactured by Invitrogen), and an alpaca antibody M13 phage library of the VHH gene was thus obtained.

Using the alpaca antibody M13 phage libraries, anti-MOG antibodies were obtained using the biopanning method described below. rMOG-GST (4 µg/2 mL) was immobilized on an immuno tube, and the sites to which rMOG-GST was not bound were blocked using 0.5% BSA.

The alpaca antibody M13 phage library was reacted with the tube at room temperature for an hour, and the phage was eluted with 0.1 M Gly-HCl (pH 2.7) after washing with PBS-T. The eluant was neutralized by adding Tris-HCl (pH 9.1). Escherichia coli TG1 was infected with the eluted phage, and then the phage was amplified. Then, the reaction with rMOG-GST immobilized on an immuno tube was conducted again, and washing and elution were conducted.

The procedure was repeated three times for IgG2 and twice for IgG3, and phages displaying VHH which specifically binds to rMOG-GST were concentrated. From the concentrated phages, 96 phage clones displaying VHH of IgG2 and 96 phage clones displaying VHH of IgG3 were monocloned, and clones having affinity to rMOG-GST were selected by ELISA.

In ELISA, rMOG-GST was immobilized (50 ng/50 µL) on MAXISORP (manufactured by NUNC), and the sites to which rMOG-GST was not bound were blocked using 0.5% BSA. The phage clones were added to separate wells and reacted at room temperature for an hour, and then the wells were washed five times with PBS-T.

Subsequently, 50 µL of a biotinylated anti-M13 phage antibody (manufactured by Abcam) and horseradish peroxidase-labeled streptavidin (manufactured by Vector) were added to the wells, and the plate was incubated at room temperature for an hour.

After washing the microplate with PBS-T, a TMB chromogenic substrate solution (manufactured by CAL-BIOCHEM) was added to the wells, and the plate was incubated at room temperature. The chromogenic reaction was stopped by adding 1 M hydrochloric acid to the wells, and the absorbances at the wavelength of 450 nm (reference wavelength of 570 nm) were measured with a microplate reader (Model 680XR, manufactured by BioRad).

The sequences of the clones which bound to rMOG-GST were analyzed, and an anti-MOG VHH antibody, iMOG-3Rim1-S32 antibody was obtained. The nucleotide sequence encoding VHH of iMOG-3Rim1-S32 antibody and the amino acid sequence deduced from the nucleotide sequence are shown in Table 2.

TABLE 2

Sequence Information of Anti-MOG VHH Antibody (iMOG-3Rim1-S32 Antibody)

| Clone Name | iMOG-3Rim1-S32 |
|---|---|
| Nucleotide sequence encoding VHH (including signal sequence) | SEQ ID NO: 37 |
| Amino acid sequence of VHH (including signal sequence) | SEQ ID NO: 38 |
| Amino acid sequence of VHH (excluding signal sequence) | SEQ ID NO: 39 |
| Amino acid sequence of CDR1 | SEQ ID NO: 40 |
| Amino acid sequence of CDR2 | SEQ ID NO: 41 |
| Amino acid sequence of CDR3 | SEQ ID NO: 42 |

[Example 2] Construction of Antibody Expression Vectors (1) Construction of Anti-MOG Antibody Expression Vectors To produce anti-MOG antibodies of human IgG type, expression vectors for anti-MOG antibodies in which the DNA sequences encoding the amino acid sequences of the variable regions of the human antibody phage library-derived anti-MOG scFv antibodies obtained in Example 1 were incorporated into a nucleotide sequence encoding the amino acid sequence of a constant region of human IgG antibody were produced by the method described below.

A nucleotide sequence encoding the lambda chain constant region of human IgG was synthesized and inserted to the BglII-EcoRI site of N5KG4PE vector (described in International Publication No. 2002/088186), and N5LG4PE vector was thus produced.

Expression vectors obtained by inserting nucleotide sequences encoding the amino acid sequences of VH and VL of MOG01 antibody and MOG09 antibody into N5LG4PE were named N5LG4PE_MOG01 and N5LG4PE_MOG09, respectively. Moreover, an expression vector obtained by inserting nucleotide sequences encoding the amino acid sequences of VH and VL of MOG14 antibody into N5KG4PE vector was named N5KG4PE_MOG14.

(1-1) MOG01 Antibody Expression Vector N5LG4PE_MOG01 Using phagemid vector pCANTAB_MOG01 as a template and using primer 1 (SEQ ID NO: 43) and primer 2 (SEQ ID NO: 44) and KOD plus DNA Polymerase (manufactured by Toyobo Co., Ltd.), a gene fragment of the VL region was amplified by PCR. In the PCR, 30 cycles of reaction of 30 seconds at 94° C., 30 seconds at 58° C. and 45 seconds at 68° C. were conducted. The PCR described in Example 2 was conducted under the conditions unless particularly described.

Using the PCR product as a template and using primer 3 (SEQ ID NO: 45) and primer 2 (SEQ ID NO: 44) and KOD plus DNA Polymerase (manufactured by Toyobo Co., Ltd.), a signal sequence was added to the gene fragment of the VL region by PCR.

The obtained gene fragment was inserted to the BglII-BlpI site of N5LG4PE vector, and N5LG4PE_MOG01VL was obtained. Next, using pCANTAB_MOG01 as a template and using primer 4 (SEQ ID NO: 46) and primer 5 (SEQ ID NO: 47) and KOD plus DNA Polymerase (manufactured by Toyobo Co., Ltd.), a gene fragment of the VH region was amplified by PCR.

Using the PCR product as a template and using primer 6 (SEQ ID NO: 48) and primer 5 (SEQ ID NO: 47) and KOD plus DNA Polymerase (manufactured by Toyobo Co., Ltd.), a signal sequence was added to the gene fragment of the VH region by PCR. The obtained gene fragment was inserted to the SalI-NheI site of N5LG4PE_MOG01VL vector, and N5LG4PE_MOG01 was obtained.

(1-2) MOG09 Antibody Expression Vector N5LG4PE_MOG09

N5LG4PE_MOG09 was produced by the same method as that of (1-1). A phagemid vector pCANTAB_MOG09 was used as a template. Primer 7 (SEQ ID NO: 49) and primer 8 (SEQ ID NO: 50) were used to amplify a gene fragment of the VL region, and primer 3 (SEQ ID NO: 45) and primer 8 (SEQ ID NO: 50) were used to add a signal sequence to the gene fragment of the VL region. Primer 9 (SEQ ID NO: 51) and primer 10 (SEQ ID NO: 52) were used to amplify a gene fragment of the VH region, and primer 6 (SEQ ID NO: 48) and primer 10 (SEQ ID NO: 52) were used to add a signal sequence to the gene fragment of the VH region.

(1-3) MOG14 Antibody Expression Vector N5KG4PE_MOG14

N5KG4PE_MOG14 was produced by the same method as that of (1-1). A phagemid vector pCANTAB_MOG14 was used as a template. Primer 11 (SEQ ID NO: 53) and primer 12 (SEQ ID NO: 54) were used to amplify a gene fragment of the VL region, and primer 3 (SEQ ID NO: 45) and primer 12 (SEQ ID NO: 54) were used to add a signal sequence to the gene fragment of the VL region. The obtained gene fragment of the VL region to which the signal sequence was added was inserted to the BglII-BsiWI site of N5KG4PE vector, and N5KG4PE_MOG14VL was obtained.

Next, pCANTAB_MOG14 was used as a template. Primer 13 (SEQ ID NO: 55) and primer 14 (SEQ ID NO: 56) were used to amplify a gene fragment of the VH region, and primer 6 (SEQ ID NO: 48) and primer 14 (SEQ ID NO: 56) were used to add a signal sequence to the gene fragment of the VH region. The obtained gene fragment of the VH region to which the signal sequence was added was inserted to the SalI-NheI site of N5KG4PE_MOG14VL, and N5KG4PE_MOG14 was obtained.

(1-4) iMOG-3Rim1-S32 Antibody Expression Vector N5G4PEFc_iMOG-3Rim1-S32

A sequence obtained by adding a signal sequence to the gene encoding the Fc region of human IgG4PE was synthesized, and a gene fragment of human Fc region was amplified by PCR using primer 25 (SEQ ID NO: 79) and primer 26 (SEQ ID NO: 80) and KOD plus DNA Polymerase (manufactured by Toyobo Co., Ltd.).

In the PCR, 30 cycles of reaction of 30 seconds at 94° C., 30 seconds at 58° C. and 60 seconds at 68° C. were conducted. The obtained Fc gene fragment was inserted to the BglII-BamHI site of N5KG4PE vector, and N5G4PEFc vector was produced.

An expression vector obtained by inserting a nucleotide sequence encoding the amino acid sequence of VHH of iMOG-3Rim1-S32 to N5G4PEFc was named N5G4PEFc_iMOG-3Rim1-S32. The VHH-Fc expression vector was produced by the method described below.

The nucleotide sequence of VHH of iMOG-3Rim1-S32 was synthesized, and a gene fragment of the VHH region was amplified by PCR using primer 15 (SEQ ID NO: 57) and primer 16 (SEQ ID NO: 58) and KOD plus DNA Polymerase (manufactured by Toyobo Co., Ltd.). In the PCR, 30 cycles of reaction of 30 seconds at 94° C., 30 seconds at 58° C. and 60 seconds at 68° C. were conducted. The obtained VHH gene fragment was inserted to the EcoRI-BglII site of N5G4PEFc vector, and N5G4PEFc_iMOG-3Rim1-S32 was obtained.

(2) Anti-Avermectin Antibody Expression Vector N5LG4PE_AVM As a negative control antibody, a chimeric anti-Avermectin (AVM) antibody was produced by the same method as that of (1-1). An expression vector obtained by inserting nucleotide sequences encoding the amino acid sequences of VH and VL of an AVM antibody to N5LG4PE was named N5LG4PE_AVM.

An SD rat was immunized with AVM, and an anti-AVM antibody-producing hybridoma was established by a general method. The variable region of the anti-AVM antibody derived from the hybridoma was used as a template. Primer 29 (SEQ ID NO: 83) and primer 30 (SEQ ID NO: 84) were used to amplify a gene fragment of the VL region, and primer 3 (SEQ ID NO: 45) and primer 30 (SEQ ID NO: 84) were used to add a signal sequence to the gene fragment of the VL region.

Primer 31 (SEQ ID NO: 85) and primer 32 (SEQ ID NO: 86) were used to amplify a gene fragment of the VH region, and primer 6 (SEQ ID NO: 48) and primer 32 (SEQ ID NO: 86) were used to add a signal sequence to the gene fragment of the VH region.

(3) Anti-Rat Transferrin Receptor Antibody OX26 Antibody Expression Vector N5KG4PE(R409K)_OX26

As a positive control antibody of an anti-rat transferrin receptor antibody, the anti-rat transferrin receptor antibody, OX26 antibody described in [Protein Engineering, 12, 787-796, 1999] was produced. An expression vector obtained by inserting nucleotide sequences encoding the amino acid sequences of VH and VL of OX26 antibody to N5KG4PE (R409K) (described in International Publication No. 2002/088186) was produced by the same method as that of (1-1) and named N5KG4PE(R409K)_OX26.

The gene encoding the amino acid sequence of VL of OX26 antibody was synthesized and used as a template. Primer 40 (SEQ ID NO: 94) and primer 41 (SEQ ID NO: 95) were used to amplify a gene fragment of the VL region, and primer 42 (SEQ ID NO: 96) and primer 43 (SEQ ID NO: 97) were used to amplify a gene fragment of the VH region.

[Example 3] Construction of Bispecific Antibody Expression Vectors (1) Production of Vector Expressing Bispecific Antibody Binding to Her2 and MOG A vector expressing a bispecific antibody binding to HER2 and MOG, pCI-Trastuzumab-hKG4PE(R409K)_MOG01scFv was produced by the following method. In the bispecific antibody, scFv of an anti-MOG antibody is fused to the C-terminuses of the two H chains of IgG of an anti-HER2 antibody.

Using a synthetic gene of the heavy chain constant region as a template and using primer 17 (SEQ ID NO: 59) and primer 18 (SEQ ID NO: 60) and KOD plus DNA Polymerase (manufactured by Toyobo Co., Ltd.), a gene fragment of the CH1-Hinge-CH2-CH3-linker region was amplified by PCR.

In the PCR, 30 cycles of reaction of 30 seconds at 94° C., 30 seconds at 58° C. and two minutes at 68° C. were conducted. Using a phagemid vector pCANTAB_MOG01 as a template and using primer 19 (SEQ ID NO: 61) and primer 20 (SEQ ID NO: 62) and KOD plus DNA Polymerase (manufactured by Toyobo Co., Ltd.), a gene fragment of the scFv region (referred to as MOG01scFv below) was amplified by PCR.

In the PCR, 30 cycles of reaction of 30 seconds at 94° C., 30 seconds at 58° C. and 90 seconds at 68° C. were conducted. Next, using the CH1-Hinge-CH2-CH3 region and the MOG01scFv region as templates and using primer 17 (SEQ ID NO: 59) and primer 20 (SEQ ID NO: 62) and KOD plus DNA Polymerase (manufactured by Toyobo Co., Ltd.), CH1-Hinge-CH2-CH3-MOG01scFv was amplified.

In the PCR, 30 cycles of reaction of 30 seconds at 94° C., 30 seconds at 58° C. and two minutes at 68° C. were conducted. The obtained gene fragment was inserted to pCI vector (manufactured by Promega Corporation), and pCI-hG4PE(R409K)_MOG01scFv vector was produced.

The gene encoding the amino acid sequence of VL of an anti-HER2 antibody (Trastuzumab) (described in International Publication No. 1999/57134) was synthesized and used as a template, and a gene fragment of the VL region was amplified by PCR using primer 21 (SEQ ID NO: 63) and primer 22 (SEQ ID NO: 64) and KOD plus DNA Polymerase (manufactured by Toyobo Co., Ltd.).

In the PCR, 30 cycles of reaction of 30 seconds at 94° C., 30 seconds at 58° C. and 45 seconds at 68° C. were conducted. Using N5KG4PE vector (described in International Publication No. 2002/088186) as a template and using primer 27 (SEQ ID NO: 81) and primer 28 (SEQ ID NO: 82) and KOD plus DNA Polymerase (manufactured by Toyobo Co., Ltd.), a gene fragment of the CL region was amplified by PCR.

In the PCR, 30 cycles of reaction of 30 seconds at 94° C., 30 seconds at 58° C. and 45 seconds at 68° C. were conducted. Using the obtained gene fragments VL and CL as templates and using primer 21 (SEQ ID NO: 63) and primer 28 (SEQ ID NO: 82) and KOD plus DNA Polymerase (manufactured by Toyobo Co., Ltd.), a gene fragment was amplified by PCR.

In the PCR, 30 cycles of reaction of 30 seconds at 94° C., 30 seconds at 58° C. and 90 seconds at 68° C. were conducted. The obtained gene fragment was inserted to pCI-hG4PE(R409K)_MOG01scFv, and pCI-TrastuzumabVL-hKG4PE(R409K)_MOG01scFv was obtained.

Next, the gene encoding the amino acid sequence of VH of Trastuzumab was synthesized and used as a template, and a gene fragment of the VH region was amplified by PCR using primer 23 (SEQ ID NO: 65) and primer 24 (SEQ ID NO: 66) and KOD plus DNA Polymerase (manufactured by Toyobo Co., Ltd.). In the PCR, 30 cycles of reaction of 30 seconds at 94° C., 30 seconds at 58° C. and 45 seconds at 68° C. were conducted.

The obtained gene fragment was inserted to pCI-TrastuzumabVL-hKG4PE(R409K)_MOG01scFv, and pCI-Trastuzumab-hKG4PE(R409K)_MOG01scFv was obtained.

(2) Production of Vector Expressing Bispecific Antibody Binding to AVM and MOG

Moreover, a vector expressing a bispecific antibody binding to AVM and MOG, pCI-AVM-hLG4PE(R409K)_MOG01scFv was produced by the method described below. In the bispecific antibody, scFv of an anti-MOG antibody is fused to the C-terminus of IgG of an anti-AVM antibody.

Using N5LG4PE_AVM as a template and using primer 33 (SEQ ID NO: 87) and primer 34 (SEQ ID NO: 88) and KOD plus DNA Polymerase (manufactured by Toyobo Co., Ltd.), a gene fragment of the AVM light chain region was amplified by PCR. In the PCR, 30 cycles of reaction of 30 seconds at 94° C., 30 seconds at 58° C. and 60 seconds at 68° C. were conducted.

Using N5LG4PE_AVM as a template and using primer 35 (SEQ ID NO: 89) and primer 32 (SEQ ID NO: 86) and KOD plus DNA Polymerase (manufactured by Toyobo Co., Ltd.), a gene fragment of the AVM VH region was amplified by PCR.

In the PCR, 30 cycles of reaction of 30 seconds at 94° C., 30 seconds at 58° C. and 45 seconds at 68° C. were conducted. The obtained gene fragment was inserted to pCI-hG4PE(R409K)_MOG01scFv produced above, and pCI-AVM-hLG4PE(R409K)_MOG01scFv was obtained.

(3) Production of Vector Expressing Antibody in which scFv of Anti-AVM Antibody is Fused to C-Terminus of IgG of Anti-AVM Antibody As a negative control antibody, a vector expressing an antibody in which scFv of an anti-AVM antibody is fused to the C-terminus of IgG of an anti-AVM antibody was named pCI-AVM-hLG4PE(R409K)_AVM scFv.

Using a synthetic gene of the heavy chain constant region as a template and using primer 36 (SEQ ID NO: 90) and primer 37 (SEQ ID NO: 91) and KOD plus DNA Polymerase (manufactured by Toyobo Co., Ltd.), a gene fragment of the CH1-Hinge-CH2-CH3-linker region was amplified by PCR.

In the PCR, 30 cycles of reaction of 30 seconds at 94° C., 30 seconds at 58° C. and two minutes at 68° C. were conducted. Using a synthetic gene of AVM scFv as a template and using primer 38 (SEQ ID NO: 92) and primer 39 (SEQ ID NO: 93) and KOD plus DNA Polymerase (manufactured by Toyobo Co., Ltd.), a gene fragment of the scFv region was amplified by PCR.

In the PCR, 30 cycles of reaction of 30 seconds at 94° C., 30 seconds at 58° C. and 90 seconds at 68° C. were conducted. Next, using the CH1-Hinge-CH2-CH3 region and the AVM scFv region as templates and using primer 36 (SEQ ID NO: 90) and primer 39 (SEQ ID NO: 93) and KOD plus DNA Polymerase (manufactured by Toyobo Co., Ltd.), CH1-Hinge-CH2-CH3-AVM scFv was amplified. In the PCR, 30 cycles of reaction of 30 seconds at 94° C., 30 seconds at 58° C. and two minutes at 68° C. were conducted.

The obtained gene fragment was inserted to the NheI-BamHI site of pCI-AVM-hLG4PE(R409K)_MOG01scFv, and pCI-AVM-hLG4PE(R409K)_AVM scFv was obtained.

Example 4

Production of Soluble MOG Antigen and Soluble HER2 Antigen (1) Production of Extracellular Domain Protein of Rat MOG to Which FLAG-Fc is Bound As a soluble antigen of rat MOG, an extracellular domain protein of MOG to which FLAG-Fc was added at the C-terminus was produced by the method described below. The nucleotide sequence encoding rMOG is shown in SEQ ID NO: 67, and the amino acid sequence deduced from the nucleotide sequence is shown in SEQ ID NO: 68.

A gene sequence of the extracellular domain of MOG was synthesized and inserted to the BglII-XbaI site of INPEP4 (manufactured by IDEC) vector to which FLAG-Fc had been inserted, and a plasmid vector INPEP4_rMOG-FLAG-Fc expressing the extracellular domain of MOG to which FLAG-Fc was added at the C-terminus was thus produced. The nucleotide sequence of rMOG-FLAG-Fc is shown in SEQ ID NO: 69, and the amino acid sequence deduced from the nucleotide sequence is shown in SEQ ID NO: 70.

INPEP4_rMOG-FLAG-Fc was introduced to suspension 293 cells using Expi293 (trademark) Expression System (manufactured by Thermo Fisher Scientific Inc.), and the cells were cultured to express the protein in a transient expression system. The culture supernatant was collected four days after the introduction of the vector and filtered through a membrane filter having a pore size of 0.22 μm (manufactured by Millipore Corporation.).

The MOG-FLAG-Fc protein in the culture supernatant was affinity-purified using Protein A resin (MabSelect SuRe, manufactured by GE Healthcare BioSciences). A phosphate buffer solution was used as a washing solution.

The protein adsorbed on the Protein A was eluted with 20 mM sodium citrate and 50 mM NaCl buffer solution (pH 3.4) and collected in a tube containing 1 M Tris-HCl Buffer Solution (pH 8.0).

Next, the solvent of the eluate was replaced with PBS by ultrafiltration using VIVASPIN (manufactured by Sartrius stealin) and a NAP column (manufactured by GE Healthcare BioSciences), and then filtration sterilization with a membrane filter having a pore size of 0.22 μm (Millex-GV, manufactured by Millipore Corporation) was conducted.

The concentration of the purified MOG-FLAG-Fc protein in the solution was measured from the absorbance at 280 nm.

(2) Production of Extracellular Domain Protein of MOG to Which GST is Bound

As a soluble antigen of rat MOG, an extracellular domain protein of MOG to which GST was added at the C-terminus was produced by the method described below.

A gene sequence of the extracellular domain of MOG was synthesized and inserted to the BglII-KpnI site of N5 vector (manufactured by IDEC) to which GST had been inserted, and a plasmid vector N5_rMOG-GST expressing the extracellular domain of MOG to which GST was added at the C-terminus was thus produced. The nucleotide sequence of rMOG-GST is shown in SEQ ID NO: 71, and the amino acid sequence deduced from the nucleotide sequence is shown in SEQ ID NO: 72.

As a soluble antigen of human HER2, an extracellular domain protein of HER2 to which GST was added at the C-terminus was produced by the method described below. A gene sequence of the extracellular domain of HER2 was synthesized and inserted to the BglII-KpnI site of N5 vector (manufactured by IDEC) to which GST had been inserted, and a plasmid vector N5_hHER2-GST expressing the extracellular domain of HER2 to which GST was added at the C-terminus was thus produced. The nucleotide sequence of hHER2-GST is shown in SEQ ID NO: 71, and the amino acid sequence deduced from the nucleotide sequence is shown in SEQ ID NO: 72.

N5_rMOG-GST and N5_hHER2-GST were introduced to suspension 293 cells using Expi293 (trademark) Expression System (manufactured by Thermo Fisher Scientific Inc.), and the cells were cultured to express the proteins in a transient expression system. The culture supernatants were collected four days after the introduction of the vectors and filtered through a membrane filter having a pore size of 0.22 μm (manufactured by Millipore Corporation).

The proteins in the culture supernatants were affinity-purified using Glutathione Sepharose 4B (manufactured by GE Healthcare BioSciences). A phosphate buffer solution was used as a washing solution. The proteins adsorbed on the Glutathione Sepharose 4B were eluted with 50 mM Tris-HCl and 10 mM reduced glutatione (pH 8.0).

Next, the solvents of the solutions were replaced with PBS by ultrafiltration using VIVASPIN (manufactured by Sartrius stealin) and a NAP column (manufactured by GE Healthcare BioSciences), and then filtration sterilization with a membrane filter having a pore size of 0.22 μm (Millex-GV, manufactured by Millipore Corporation) was conducted. The concentrations of the purified rMOG-GST protein and the hHER2-GST protein in the solutions were measured from the absorbances at 280 nm.

[Example 5] Production of Membrane MOG Antigen Expression Vectors

The entire gene sequences of rat MOG (rMOG), mouse MOG (mMOG), monkey MOG (cMOG) and human MOG (hMOG) were synthesized, and the gene sequences were each inserted to the BamHI-NotI site of pEF6/V5-His (manufactured by Thermo Fisher Scientific Inc.) vector. Plasmid vectors for expressing MOG in the membrane, pEF6_rMOG, pEF6_mMOG, pEF6_cMOG and pEF6_hMOG were thus produced.

The nucleotide sequence encoding mMOG is shown in SEQ ID NO: 73, and the amino acid sequence deduced from the nucleotide sequence is shown in SEQ ID NO: 74. The nucleotide sequence encoding cMOG is shown in SEQ ID NO: 75, and the amino acid sequence deduced from the nucleotide sequence is shown in SEQ ID NO: 76. The nucleotide sequence encoding hMOG is shown in SEQ ID NO: 77, and the amino acid sequence deduced from the nucleotide sequence is shown in SEQ ID NO: 78.

[Example 6] Preparation of Antibodies

The antibody expression plasmid vectors produced in Example 2 and Example 3 were introduced to suspension 293 cells using Expi293' Expression System (manufactured by Thermo Fisher Scientific Inc.), and the cells were cultured to express the antibodies in a transient expression system.

The culture supernatants were collected four days after the introduction of the vectors and filtered through a membrane filter having a pore size of 0.22 μm (manufactured by Millipore Corporation). The proteins in the culture supernatants were affinity-purified using Protein Aresin (MabSelect SuRe, manufactured by GE Healthcare BioSciences). A phosphate buffer solution was used as a washing solution. The antibodies adsorbed on the Protein A were eluted with 20 mM sodium citrate and 50 mM NaCl buffer solution (pH 3.4) and collected in tubes containing 1 M Tris-HCl Buffer Solution (pH 8.0).

Next, the solvents of the eluates were replaced with PBS by ultrafiltration using VIVASPIN (manufactured by Sartrius stealin) and a NAP column (manufactured by GE Healthcare BioSciences), and then filtration sterilization with a membrane filter having a pore size of 0.22 μm (Millex-GV, manufactured by Millipore Corporation) was conducted. The absorbances of the antibody solutions at 280 nm were measured, and the concentrations of the purified antibodies were calculated by converting the concentration 1 mg/mL to 1.40 Optimal density.

The anti-MOG human IgG antibodies expressed using the anti-MOG antibody expression vectors, N5LG4PE_MOG01, N5LG4PE_MOG09, N5KG4PE_MOG14 and N5G4PEFc_iMOG-3Rim1-S32 described in Example 2 are referred to as MOG01 antibody, MOG09 antibody, MOG14 antibody and iMOG-3Rim1-S32 antibody, respectively.

The antibodies obtained by expressing using the bispecific antibody expression vectors, pCI-AVM-hLG4PE(R409K)_AVM scFv, pCI-AVM-hLG4PE(R409K)_MOG01scFv and pCI-Trastuzumab-hKG4PE(R409K)_MOG01scFv produced in Example 3 were named AVM IgG4PE(R409K)_AVM dscFv antibody, AVM IgG4PE(R409K)_MOG01dscFv antibody and Trastuzumab IgG4PE(R409K)_MOG01scFv antibody, respectively.

[Example 7] Evaluation of Affinities of Anti-MOG Antibodies to MOG Using Flow Cytometer Binding of the anti-MOG antibodies, MOG01 antibody, MOG09 antibody, MOG14 antibody and iMOG-3Rim1-S32 antibody obtained in Example 6 to MOG were evaluated by the fluorescence activated cell sorting (FACS) method according to the following procedures.

The membrane MOG antigen expression vectors produced in Example 5 were introduced to suspension 293 cells using FreeStyle (trademark) 293 Expression System (manufactured by Thermo Fisher Scientific Inc.), and the cells were cultured to express the membrane antigens in a transient expression system. Using the cells, the reactivities of the anti-MOG antibodies were analyzed by the method described below.

rMOG/HEK293F, mMOG/HEK293F, cMOG/HEK293 and hMOG/HEK293 cells were suspended in a Staining Buffer (SB) of PBS containing 0.1% NaN$_3$ and 1% FBS each at a concentration of 5×10$^5$ cells/mL and dispensed to a round-bottom 96-well plate (manufactured by Becton Dickinson).

After centrifugation (2000 rpm, 4° C., two minutes), the supernatants were removed, and the antibodies obtained in Example 6 at 10 μg/mL were added to the pellets. After suspending the pellets, the plate was left to stand at ice temperature for 30 minutes. The supernatants were removed after further centrifugation (2000 rpm, 4° C., two minutes), and the pellets were washed with SB. Then, 1 μg/mL RPE fluorescently labeled goat anti-human antibody (manufactured by Southern Bioblot) was added, and the plate was incubated at ice temperature for 30 minutes.

Figure 2:
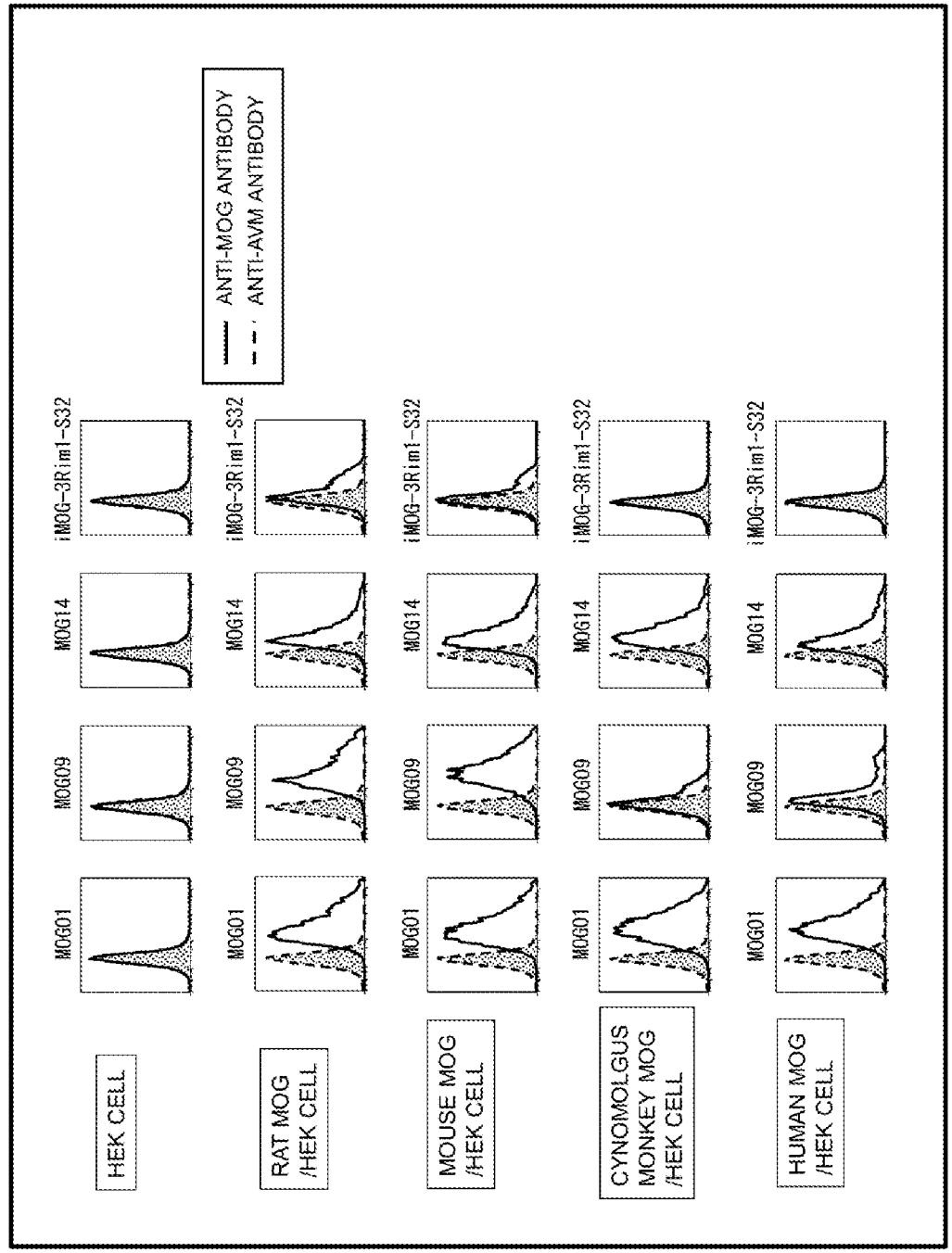
FIG. 2 shows the results of analysis using a flow cytometer of the affinities of anti-MOG antibodies to BEK cells, rat MOG/HEK cells, mouse MOG/HEK cells, cynomolgus monkey MOG/HEK cells or human MOG/HEK cells. The vertical axis shows the number of cells, and the horizontal axis shows the fluorescence intensity. A dotted line indicates a histogram of the affinity of an anti-AVM antibody used as a negative control, and a solid line indicates a histogram of the affinity of a MOG antibody.

After washing with SB, the cells were suspended in SB, and the fluorescence intensities of the cells were measured using a flow cytometer FACS CANTO II (manufactured by Becton Dickinson). The results obtained are shown in FIG. 2. As the negative control, an anti-AVM antibody was used.

As shown in FIG. 2, MOG01 antibody, MOG09 antibody, MOG14 antibody and iMOG-3Rim1-S32 antibody, which are anti-MOG antibodies, all showed binding activity to rMOG/HEK293F cells and mMOG/HEK293F cells. Moreover, MOG01 antibody and MOG14 antibody both showed binding activity also to cMOG/HEK293 cells and hMOG/HEK293 cells.

Accordingly, it was elucidated that anti-MOG human IgG antibodies, MOG01 and MOG14 recognize and bind to not only rat and mouse MOG but also cynomolgus monkey and human MOG.

[Example 8] Evaluation of Affinities of Anti-MOG Antibodies to MOG by Surface Plasmon Resonance Detection The affinities of the anti-MOG antibodies, MOG01 antibody, MOG09 antibody, MOG14 antibody and iMOG-3Rim1-S32 antibody obtained in Example 6 to rat MOG were measured using Biacore T-100 (GE Healthcare).

The antibodies were immobilized on CM5 sensor chips using a Human antibody Capture kit, and the binding abilities were evaluated using rMOG-GST produced in Example 4 as an analyte. The obtained sensorgrams were analyzed with BIA evaluation software, and the dissociation constants (KD values) were thus calculated. The results obtained are shown in Table 3.

TABLE 3

|  | ka (1/Ms) | kd (1/s) | KD (M) |
| --- | --- | --- | --- |
| MOG01 | 1.4E+05 | 9.5E−04 | 6.6E−09 |
| MOG09 | 9.0E+03 | 1.9E−07 | 2.1E−11 |
| MOG14 | 4.7E+03 | 1.9E−04 | 4.0E−08 |
| iMOG-3Rim1-S32 | 1.4E+06 | 8.4E−04 | 6.2E−10 |

As shown in Table 3, the dissociation constants (KD values) of the anti-MOG antibodies were $2.1 \times 10^{-11}$ (M) to $4.0 \times 10^{-8}$ (M), and it was elucidated that all the antibodies show excellent affinity. The dissociation rate constant kd of MOG09 antibody was outside the measurement range of the device, and the KD value could not be determined as a unique value.

[Example 9] Evaluation of Rat Brain Migration Properties of Anti-MOG Antibodies

An antibody was administered to the tail vein (i.v.) of a rat, and then blood was collected from the tail vein. On the same day of the blood collection, the brain tissues were collected after whole body perfusion under anesthesia with pentobarbital, and the weight was measured. A buffer solution was added to the collected brain tissues, and the brain tissues were homogenized. After centrifugation, the antibody solution eluted in the supernatant was collected. While the volume was measured, the antibody concentration was measured with AlphaLISA (manufactured by PerkinElmer, Inc.). The antibody amount per unit brain weight was calculated.

With respect to the anti-MOG antibodies, MOG01 antibody, MOG14 antibody and iMOG-3Rim1-S32 antibody and the anti-AVM antibody as a negative control, MOG01 antibody and MOG14 antibody were administered at an amount of 1 mg/kg body weight, and iMOG-3Rim1-S32 antibody was administered at an amount of 5 mg/kg body weight. The antibody concentrations in the serum and the antibody amounts per unit brain weight in the brain tissues four days after the administration of the antibodies are shown in FIGS. 3A and 3B.

Figure 3A:
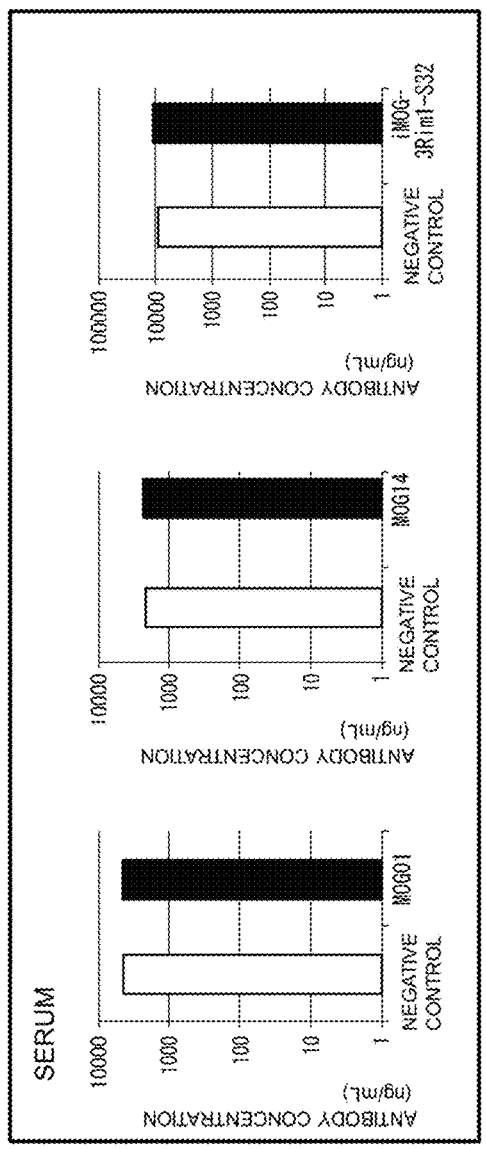
FIGS. 3A and 3B show the results of evaluation of the rat brain migration properties of anti-MOG antibodies.
Figure 3B:
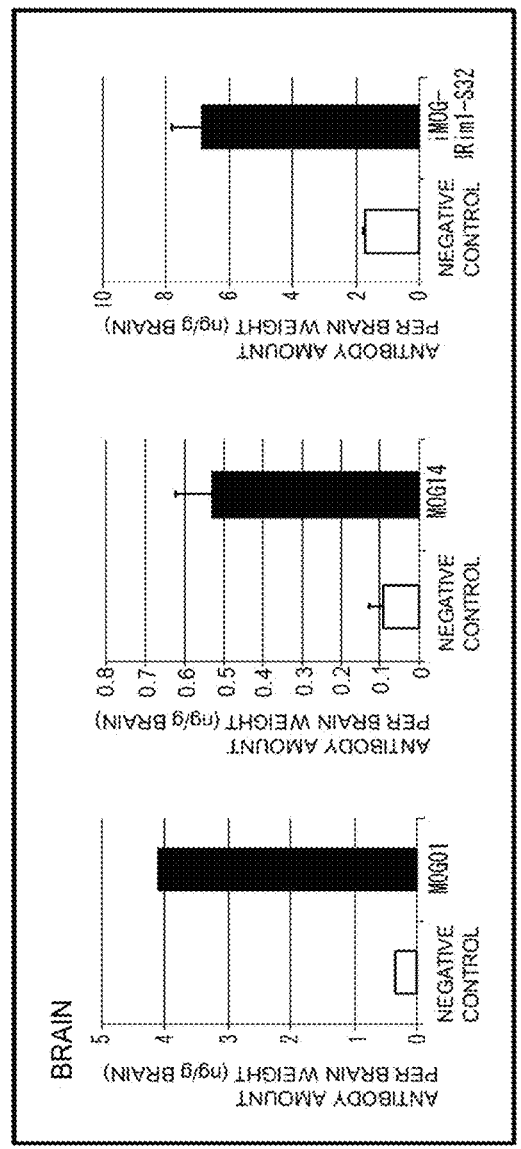

As shown in FIGS. 3A and 3B, it was shown that the antibody concentrations in the serum of all the anti-MOG antibodies did not change as compared to that of the negative control (AVM) but that the antibody amounts in the brain increased to 5-10 times.

With respect to the anti-MOG antibody, MOG01 antibody, the anti-transferrin receptor antibody, OX26 antibody and the anti-AVM antibody as a negative control, the antibody concentrations in the serum and the antibody amounts per unit brain weight in the brain tissues four days and 10 days after the administration of the antibodies at an amount of 5 mg/kg body weight are shown in FIGS. 4A and 4B.

As shown in FIG. 4A, the antibody concentration of OX26 antibody in the serum was the lowest of the evaluated antibodies after four days and was equal to or lower than the detection sensitivity after 10 days, and thus the dynamics of the antibody in the blood was poor. The antibody concentration in the serum of MOG01 antibody, which is an anti-MOG antibody, did not change largely four days and 10 days after the administration, and the antibody concentration was equivalent to that of the negative control. This suggests that the half-life of MOG01 antibody in the blood is equivalent to that of the negative control.

Moreover, as shown in FIG. 4B, with respect to the antibody amounts in the brain, the antibody amount of the negative control was the lowest of the evaluated antibodies four days after the administration, and the antibody amount further decreased after 10 days although it was a slight decrease.

The antibody amount of OX26 antibody rapidly decreased between four days and 10 days after the administration, and the antibody amount 10 days after the administration was not higher than that of the negative control. On the other hand, the antibody amount of MOG01 antibody increased between four days and 10 days after the administration. The antibody amount four days after the administration was about 2.5 times the amount of the negative control, and the antibody amount 10 days after the administration was about 10 times the amount of the negative control.

The above results show that, while the anti-MOG antibody, MOG01 antibody shows an antibody concentration equal to that of the negative control in the serum, MOG01 antibody can increase its amount in the brain to about 2.5 times the amount of the negative control four days after the administration and to about 10 times the amounts of the negative control and OX26 antibody 10 days after the administration.

[Example 10] Evaluation of Affinities of Bispecific Antibodies of MOG to MOG or HER2 Using Flow Cytometer Binding to MOG or HER2 of the bispecific antibody binding to MOG and Her2, Trastuzumab IgG4PE(R409K)_MOG01 dscFv antibody, the bispecific antibody binding to MOG and AVM, AVM IgG4PE(R409K)_MOG01 dscFv antibody and the antibody binding to AVM, AVM IgG4PE(R409K)_AVM dscFv antibody obtained in Example 6 was evaluated by the fluorescence activated cell sorting (FACS) method according to the following procedures.

The membrane MOG antigen expression vectors produced in Example 5 were introduced to suspension 293 cells using FreeStyle (trademark) 293Expression System (manufactured by Thermo Fisher Scientific Inc.), and the cells were cultured to express the membrane antigens in a transient expression system.

HEK293F cells, rMOG/HEK293F cells, hMOG/HEK293F cells and human breast cancer cell line SK-BR-3 cells were suspended in a Staining Buffer (SB) of PBS containing 0.1% NaN$_3$ and 1% FBS each at a concentration of 5×10$^5$ cells/mL and dispensed to a round-bottom 96-well plate (manufactured by Becton Dickinson).

After centrifugation (2000 rpm, 4° C., two minutes), the supernatants were removed, and the antibodies obtained in Example 6 at 10 μg/mL were added to the pellets. After suspending the pellets, the plate was left to stand at ice temperature for 30 minutes. The supernatants were removed after further centrifugation (2000 rpm, 4° C., two minutes), and the pellets were washed with SB. Then, 1 μg/mL RPE fluorescently labeled goat anti-human antibody (manufactured by Southern Bioblot) was added, and the plate was incubated at ice temperature for 30 minutes.

After washing with SB, the cells were suspended in SB, and the fluorescence intensities of the cells were measured with a flow cytometer FACS CANTO II (manufactured by Becton Dickinson). As the negative control, 10 μg/mL anti-AVM antibody was used. The results of the analysis of the affinities to HEK293F cells, rMOG/HEK293F cells and hMOG/HEK293 cells are shown in FIG. 5.

Figure 5:
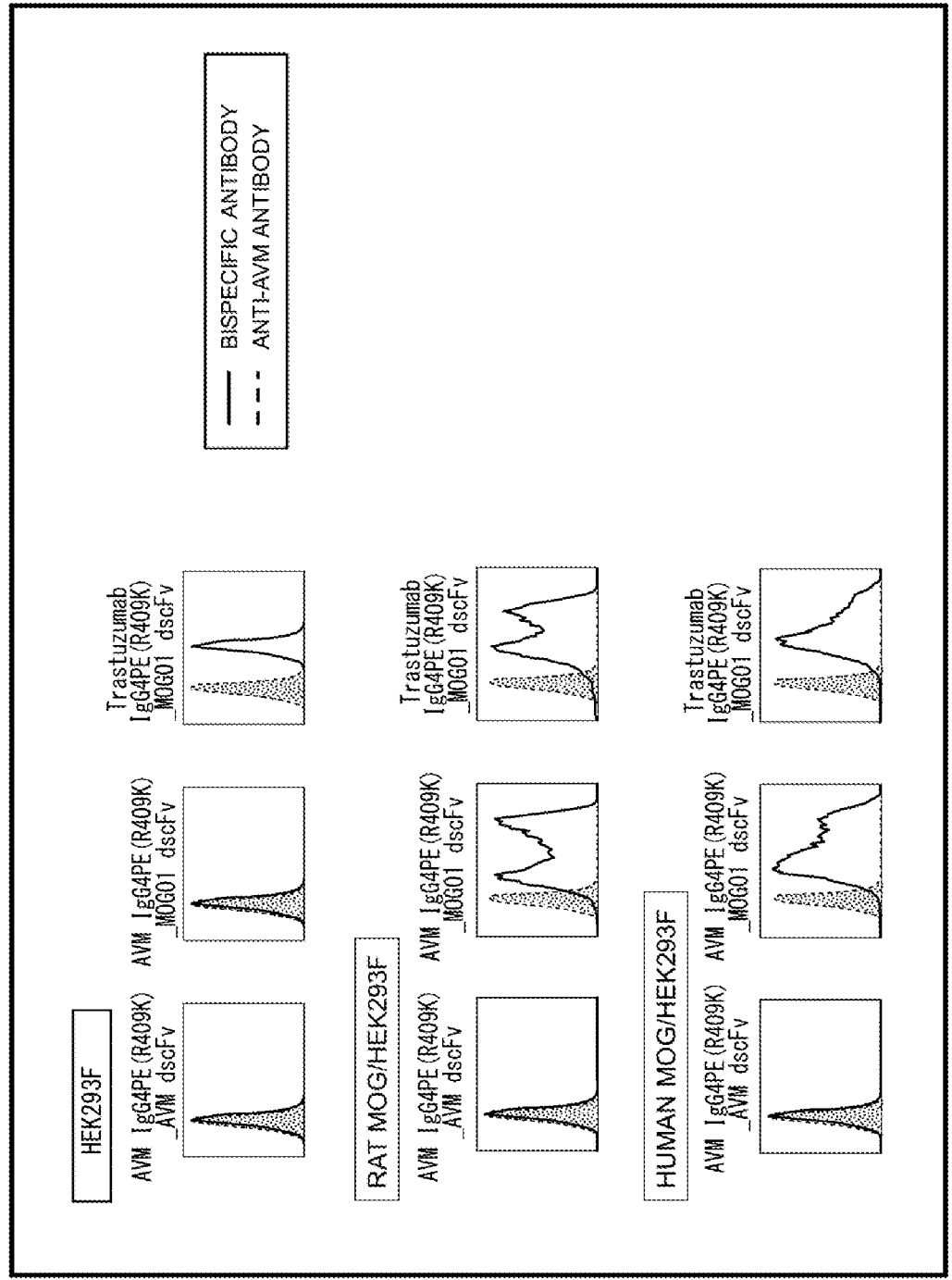
FIG. 5 shows the results of analysis using a flow cytometer of the affinities of bispecific antibodies to HEK293F cells, rat MOG/HEK293F cells or human MOG/HEK293F cells. The vertical axis shows the number of cells, and the horizontal axis shows the fluorescence intensity. A dotted line indicates a histogram of the affinity of an anti-AVM antibody used as a negative control, and a solid line indicates a histogram of the affinity of a bispecific antibody.

From FIG. 5, binding of AVM IgG4PE(R409K)_MOG01 dscFv antibody and Trastuzumab IgG4PE(R409K)_MOG01 dscFv antibody to rMOG/HEK293F cells and hMOG/HEK293 cells can be observed. Thus, it was shown that the antibodies maintain the affinities to rat MOG and human MOG also in the form of bispecific antibody.

Figure 6:
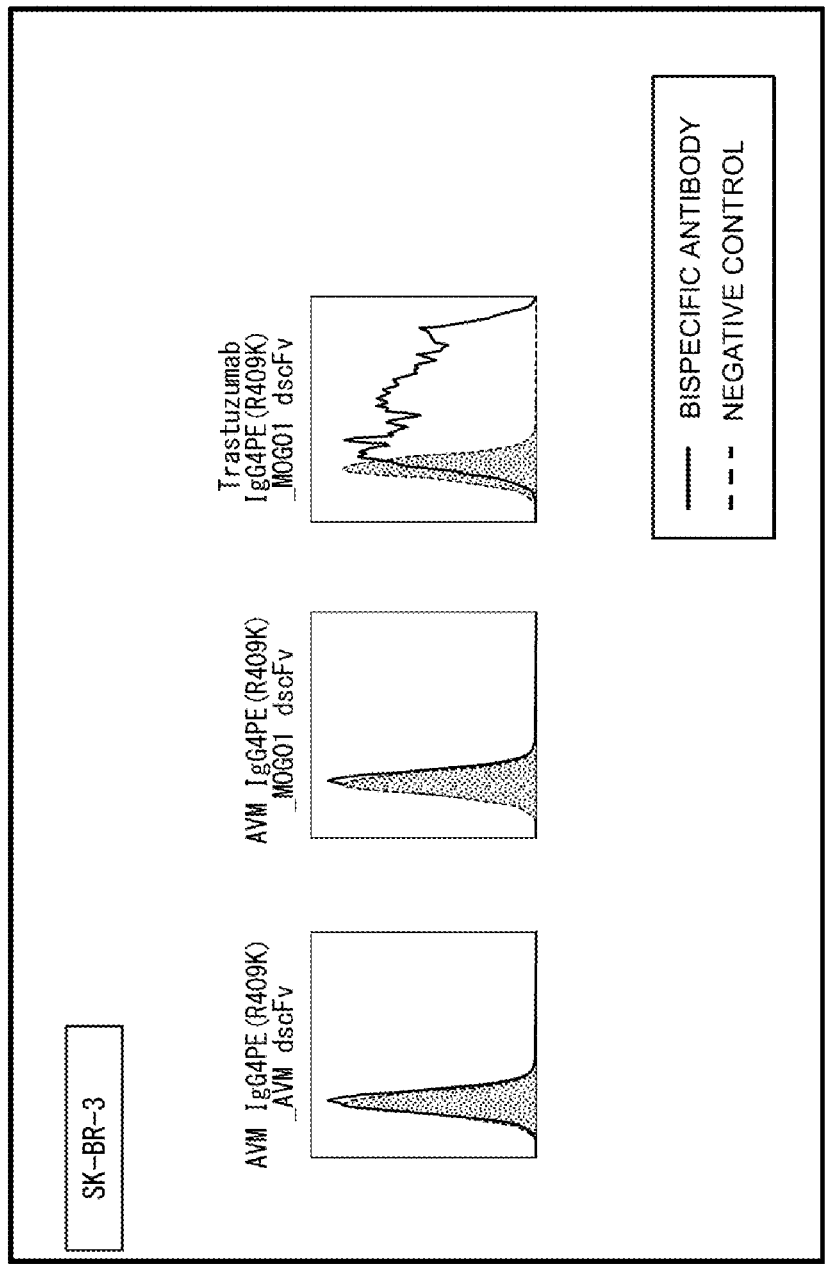
FIG. 6 shows the results of analysis using a flow cytometer of the affinities of bispecific antibodies to human breast cancer cell line, SK-BR-3. The vertical axis shows the number of cells, and the horizontal axis shows the fluorescence intensity. A dotted line indicates a histogram of the affinity of an anti-AVM antibody used as a negative control, and a solid line indicates a histogram of the affinity of a bispecific antibody.
Figure 13A:
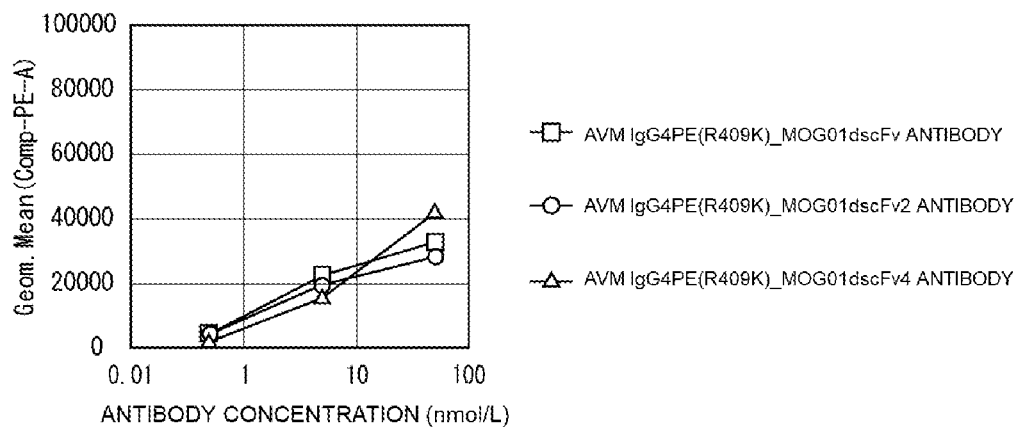
FIGS. 13A and 13B show the results of analysis using a flow cytometer of the affinities of bispecific antibodies to human MOG/L929 cells. The vertical axis shows the average fluorescence intensity, and the horizontal axis shows the antibody concentration.
Figure 13B:
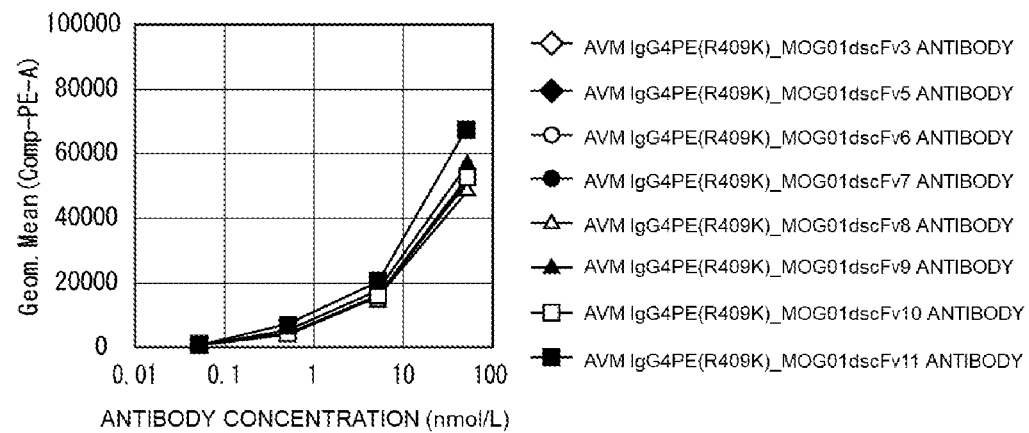

The results of the analysis of the affinities to human breast cancer cell line SK-BR-3 cells are shown in FIG. 6. It is known that HER2 is expressed in the cells.

From FIG. 6, it was shown that Trastuzumab IgG4PE(R409K)_MOG01 dscFv antibody maintains the affinity to HER2 also in the form of bispecific antibody.

[Example 11] Evaluation of Affinities of Bispecific Antibodies of MOG to MOG by Surface Plasmon Resonance Detection The affinities of the bispecific antibodies of MOG to MOG were measured by the same method as that of Example 8, and the results are shown in Table 4.

TABLE 4

| Antibody Name | ka (1/Ms) | kd (1/s) | KD (M) |
|---|---|---|---|
| AVM IgG4PE(R409K)_MOG01 dscFv | 2.3E+04 | 4.6E−03 | 2.0E−07 |
| Trastuzumab IgG4PE(R409K)_MOG01 dscFv | 2.4E+08 | 2.5E+01 | 1.0E−07 |

As shown in Table 4, the dissociation constant (KD value) of the bispecific antibody, AVM IgG4PE(R409K)_MOG01 dscFv antibody was $2.0 \times 10^{-7}$ (M), and that of Trastuzumab IgG4PE(R409K)_MOG01 dscFv antibody was $1.0 \times 10^{-7}$ (M). It was elucidated that both bispecific antibodies of MOG show excellent affinity.

The association rate constant ka and the dissociation rate constant kd of Trastuzumab IgG4PE(R409K)_MOG01 dscFv antibody were outside the measurement ranges of the device, and the KD value could not be determined as a unique value.

[Example 12] Evaluation of Affinity of Bispecific Antibody of MOG to HER2 by Surface Plasmon Resonance Detection The affinity of the bispecific antibody binding to MOG and HER2, Trastuzumab IgG4PE(R409K)_MOG01 dscFv antibody to HER2 was measured using Biacore T-100 (GE Healthcare).

The antibody was immobilized on a CM5 sensor chip using a Human antibody Capture kit, and the binding ability of the MOG-Her2 bispecific antibody was evaluated using HER2-GST produced in Example 4 as an analyte. The obtained sensorgram was analyzed with BIA evaluation software, and the dissociation constant (KD value) was thus calculated. The results are shown in Table 5.

TABLE 5

| Antibody Name | ka (1/Ms) | kd (1/s) | KD (M) |
|---|---|---|---|
| Trastuzumab IgG4PE(R409K)_MOG01 dscFv | 4.7E+04 | 1.8E−04 | 3.7E−09 |

As shown in Table 5, the dissociation constant (KD value) of Trastuzumab IgG4PE(R409K)_MOG01 dscFv antibody to HER2 was $3.7 \times 10^{-9}$ (M), and it was elucidated that this is an antibody showing excellent affinity.

[Example 13] Evaluation of Rat Brain Migration Properties of Bispecific Antibodies of MOG The rat brain migration properties of the bispecific antibodies, AVM IgG4PE(R409K)_MOG01 dscFv antibody, Trastuzumab IgG4PE(R409K)_MOG01 dscFv antibody and AVM IgG4PE(R409K)_AVM dscFv antibody was evaluated by the same method as that of Example 9. The antibody concentrations in the serum and the antibody amounts per unit brain weight in the brain tissues 10 days after the administration of the antibodies at an amount of 5 mg/kg body weight are shown in FIGS. 7A and 7B.

As shown in FIG. 7A, as compared to AVM IgG4PE (R409K)_AVM dscFv antibody, which is the negative control of the bispecific antibodies, the antibody concentrations in the serum of AVM IgG4PE(R409K)_MOG01 dscFv antibody and Trastuzumab IgG4PE(R409K)_MOG01 dscFv antibody were not different.

On the other hand, as shown in FIG. 7B, it was shown that, as compared to AVM IgG4PE(R409K)_AVM dscFv antibody, which is the negative control of the bispecific antibodies, the antibody amounts of AVM IgG4PE(R409K) MOG01 dscFv antibody and Trastuzumab IgG4PE (R409K)_ MOG01 dscFv antibody in the brain increased to about 10 times.

The above results show that while the bispecific antibodies which bind to MOG can increase the antibody amount in the brain to about 10 times the value of the bispecific antibody which does not bind to MOG, the half-lives in the blood do not change.

[Example 14] Evaluation of Mouse Brain Migration Property of Anti-MOG01 Antibody (1) Measurement of Antibody Amount Several days after administering the antibody to the tail vein (i.v.) of a mouse at 35 nmol/kg, blood was collected from the tail vein. On the same day of the blood collection, the brain tissues were collected after whole body perfusion under anesthesia with pentobarbital, and the weight was measured. A buffer solution was added to the collected brain tissues, and the brain tissues were homogenized. After centrifugation, the antibody solution eluted in the supernatant was collected. While the volume was measured, the antibody concentration was measured with AlphaLISA (manufactured by PerkinElmer, Inc.). The antibody amount per unit brain weight was calculated.

With respect to the anti-MOG01 human IgG antibody and an anti-AVM human IgG antibody as the negative control, the antibody concentrations in the serum and the antibody amounts per unit brain weight in the brain tissues 3, 6, 10, 14, 21 and 28 days after the administration of the antibodies are shown in FIGS. 8A and 8B, respectively.

As shown in FIG. 8A, the antibody concentrations of the anti-MOG01 human IgG antibody in the serum were not different from those of the negative control. On the other hand, as shown in FIG. 8B, it was shown that the antibody amount in the brain can be increased to several ten times over 28 days.

(2) Imaging Analysis

The anti-MOG01 human IgG antibody and the anti-AVM human IgG antibody as the negative control were labeled with Alexa FluorR 488 Protein Labeling Kit (manufactured by Molecular Probes). The labeled antibodies are referred to as AF488-MOG01 IgG4PE antibody and AF488-AVM IgG4PE antibody.

Several days after administering the labeled antibodies to the tail veins (i.v.) of mice at 10 mg/kg, Tomato lectin was administered, and the blood was collected from the cheeks of the mice. The brain tissues were collected after the blood collection and after whole body perfusion under anesthesia with pentobarbital, and the fluorescence intensities were measured with IVIS Spectrum (manufactured by PerkinElmer, Inc.). The brain images after six days are shown in FIG. 9A, and the brain images after 14 days are shown in FIG. 9B. The fluorescence amounts in the brain corrected with the fluorescence intensities of the administered antibodies are shown in FIG. 9C.

As shown in FIGS. 9A to 9C, it was shown that the anti-MOG01 antibody can increase the antibody amount to several ten times over the entire brain as compared to the negative control.

[Example 15] Construction of Bispecific Antibody Expression Vectors

Vectors expressing bispecific antibodies which have any of the structures described in FIGS. 10A to 10C and FIGS.

11A and 11B and which bind to AVM and MOG were produced by the following method. The names of the bispecific antibodies and the names of the antibody expression vectors are shown in Table 6, and the names of the antibody expression vectors, the nucleotide sequences of the antibodies and the amino acid sequences deduced from the nucleotide sequences are shown in Table 7.

a gene fragment of the MOG01 light chain region and a gene fragment of the MOG01 VH region were amplified by PCR using N5LG4PE_MOG01 as a template. The obtained gene fragments were inserted to pCI vector (manufactured by Promega Corporation), and pCI-MOG01-hLG4PE(R409K/Y349C/T366S/L368A/Y407V)-His tag vector was produced.

TABLE 6

| Name of Bispecific Antibody | Name of Antibody Expression Vector |
|---|---|
| AVM-MOG01 IgG4PE(R409K) antibody | pCI-AVM-hLG4PE(R409K/S354C/T366W)-FLAG tag<br>pCI-MOG01-hLG4PE(R409K/Y349C/T366S/L368A/Y407V)-His tag |
| AVM IgG4PE(R409K)_MOG01 Fab antibody | pCI-AVM-hLG4PE(R409K)-linker-MOG01VL-CL<br>pCI-MOG01VH-CH |
| AVM IgG4PE(R409K)_MOG01 sscFv antibody | pCI-AVM-hLG4PE(R409K/S354C/T366W)-linker-MOG01scFv-FLAG tag<br>pCI-AVM-hLG4PE(R409K/Y349C/T366S/L368A/Y407V)-His tag |
| AVM IgG4PE(R409K)_MOG01dscFv2 antibody | pCI-AVM-hLG4PE(R409K)_MOG01scFv2 |
| AVM IgG4PE(R409K)_MOG01dscFv3 antibody | pCI-AVM-hLG4PE(R409K)_MOG01scFv3 |
| AVM IgG4PE(R409K)_MOG01dscFv4 antibody | pCI-AVM-hLG4PE(R409K)_MOG01scFv4 |
| AVM IgG4PE(R409K)_MOG01dscFv5 antibody | pCI-AVM-hLG4PE(R409K)_MOG01scFv5 |
| AVM IgG4PE(R409K)_MOG01dscFv6 antibody | pCI-AVM-hLG4PE(R409K)_MOG01scFv6 |
| AVM IgG4PE(R409K)_MOG01dscFv7 antibody | pCI-AVM-hLG4PE(R409K)_MOG01scFv7 |
| AVM IgG4PE(R409K)_MOG01dscFv8 antibody | pCI-AVM-hLG4PE(R409K)_MOG01scFv8 |
| AVM IgG4PE(R409K)_MOG01dscFv9 antibody | pCI-AVM-hLG4PE(R409K)_MOG01scFv9 |
| AVM IgG4PE(R409K)_MOG01dscFv10 antibody | pCI-AVM-hLG4PE(R409K)_MOG01scFv10 |
| AVM IgG4PE(R409K)_MOG01dscFv11 antibody | pCI-AVM-hLG4PE(R409K)_MOG01scFv11 |

TABLE 7

| Name of Antibody Expression Vector | Light Chain Antibody Sequence | Nucleotide Sequence of Heavy Chain Antibody Sequence (excluding signal sequence) | Amino Acid Sequence of Heavy Chain Antibody Sequence (excluding signal sequence) |
|---|---|---|---|
| pCI-AVM-hLG4PE(R409K/S354C/T366W)-FLAG tag | AVM | SEQ ID NO: 108 | SEQ ID NO: 109 |
| pCI-MOG01-hLG4PE(R409K/Y349C/T366S/L368A/Y407V)-His tag | MOG01 | SEQ ID NO: 110 | SEQ ID NO: 111 |
| pCI-AVM-hLG4PE(R409K)-linker-MOG01VL-CL | AVM | SEQ ID NO: 112 | SEQ ID NO: 113 |
| pCI-MOG01VH-CH | None | SEQ ID NO: 114 | SEQ ID NO: 115 |
| pCI-AVM-hLG4PE(R409K/S354C/T366W)-linker-MOG01scFv-FLAG | AVM | SEQ ID NO: 116 | SEQ ID NO: 117 |
| pCI-AVM-hLG4PE(R409K/Y349C/T366S/L368A/Y407V)-His tag | AVM | SEQ ID NO: 118 | SEQ ID NO: 119 |
| pCI-AVM-hLG4PE(R409K)_MOG01scFv2 | AVM | SEQ ID NO: 120 | SEQ ID NO: 121 |
| pCI-AVM-hLG4PE(R409K)_MOG01scFv3 | AVM | SEQ ID NO: 122 | SEQ ID NO: 123 |
| pCI-AVM-hLG4PE(R409K)_MOG01scFv4 | AVM | SEQ ID NO: 124 | SEQ ID NO: 125 |
| pCI-AVM-hLG4PE(R409K)_MOG01scFv5 | AVM | SEQ ID NO: 126 | SEQ ID NO: 127 |
| pCI-AVM-hLG4PE(R409K)_MOG01scFv6 | AVM | SEQ ID NO: 128 | SEQ ID NO: 129 |
| pCI-AVM-hLG4PE(R409K)_MOG01scFv7 | AVM | SEQ ID NO: 130 | SEQ ID NO: 131 |
| pCI-AVM-hLG4PE(R409K)_MOG01scFv8 | AVM | SEQ ID NO: 132 | SEQ ID NO: 133 |
| pCI-AVM-hLG4PE(R409K)_MOG01scFv9 | AVM | SEQ ID NO: 134 | SEQ ID NO: 135 |
| pCI-AVM-hLG4PE(R409K)_MOG01scFv10 | AVM | SEQ ID NO: 136 | SEQ ID NO: 137 |
| pCI-AVM-hLG4PE(R409K)_MOG01scFv11 | AVM | SEQ ID NO: 138 | SEQ ID NO: 139 |

(1) Construction of Bispecific Antibody Expression Vectors Related to Structure in FIG. 10A (1-1) Construction of pCI-AVM-hLG4PE(R409K/S354C/T366W)-FLAG Tag Vector A gene fragment of the CH1-Hinge-CH2-CH3(R409K/S354C/T366W) region was amplified by PCR using a synthetic gene as a template and inserted to the NheI-BamHI site of pCI-AVM-hLG4PE(R409K)_AVMscFv, and pCI-AVM-hLG4PE(R409K/S354C/T366W)-FLAG tag vector was produced.

(1-2) Construction of pCI-MOG01-hLG4PE(R409K/Y349C/T366S/L368A/Y407V)-His Tag Vector A gene fragment of the CH1-Hinge-CH2-CH3(R409K/Y349C/T366S/L368A/Y407V)-His tag region was amplified by PCR using a synthetic gene as a template. Moreover, (2) Construction of Bispecific Antibody Expression Vectors Related to Structure in FIG. 10B (2-1) Construction of pCI-AVM-hLG4PE(R409K)-Linker-MOG01VL-CL Vector A gene fragment of the CH1-Hinge-CH2-CH3-linker-MOG01VL-CL region was amplified by PCR using a synthetic gene as a template and inserted to the NheI-BamHI site of pCI-AVM-hLG4PE(R409K)_AVMscFv, and pCI-AVM-hLG4PE(R409K)-linker-MOG01VL-CL vector was produced.

(2-2) CONSTRUCTION OF PCI-MOG01VH-CH VECTOR

A gene fragment of the MOG01VH-CH region was amplified by PCR using a synthetic gene as a template and inserted to pCI vector (manufactured by Promega Corporation), and pCI-MOG01VH-CH vector was produced.

(3) Construction of Bispecific Antibody Expression Vectors Related to Structure in FIG. 10C (3-1) Construction of pCI-AVM-hLG4PE(R409K/S354C/T366W)-Linker-MOG01scFv-FLAG Tag Vector A gene fragment of the CH1-Hinge-CH2-CH3(R409K/S354C/T366W)-linker region was amplified by PCR using a synthetic gene as a template. Moreover, a gene fragment of the linker-MOG01scFv region was amplified by PCR using MOG01scFv as a template. Furthermore, a gene fragment of the linker-MOG01scFv-FLAG tag region was amplified by PCR using the PCR product as a template. The gene fragments of the CH1-Hinge-CH2-CH3(R409K/S354C/T366W)-linker region and the linker-MOG01scFv-FLAG tag region were inserted to the NheI-BamHI site of pCI-AVM-hLG4PE(R409K)_AVM scFv, and pCI-AVM-hLG4PE(R409K/S354C/T366W)-linker-MOG01scFv-FLAG tag vector was produced.

(3-2) Construction of pCI-AVM-hLG4PE(R409K/Y349C/T366S/L368A/Y407V)-His tag Vector MOG01scFv5 vector, pCI-AVM-hLG4PE(R409K)_MOG01scFv6 vector, pCI-AVM-hLG4PE(R409K)_MOG01scFv7 vector, pCI-AVM-hLG4PE(R409K)_MOG01scFv8 vector, pCI-AVM-hLG4PE(R409K)_MOG01scFv9 vector, pCI-AVM-hLG4PE(R409K)_MOG01scFv10 vector and pCI-AVM-hLG4PE(R409K)_MOG01scFv11 vector were produced.

(5) Construction of Vectors Expressing Antibodies as Negative Controls

The antibodies as the negative controls were produced by the following method. The names of the antibodies and the names of the antibody expression vectors are shown in Table 8, and the names of the antibody expression vectors, the nucleotide sequences of the antibodies and the amino acid sequences deduced from the nucleotide sequences are shown in Table 9.

TABLE 8

| Name of Negative Control Antibody | Name of Antibody Expression Vector |
|---|---|
| AVM IgG4PE(R409K) antibody | pCI-AVM-hLG4PE(R409K) |
| AVM IgG4PE(R409K)_AVM Fab antibody | pCI-AVM-hLG4PE(R409K)-linker-AVMVL-CL<br>pCI-AVMVH-CH |
| AVM IgG4PE(R409K)_AVMsscFv antibody | pCI-AVM-hLG4PE(R409K/S354C/T366W)-linker-AVMscFv-FLAG tag<br>pCI-AVM-hLG4PE(R409K/Y349C/T366S/L368A/Y407V)-His tag |
| AVM IgG4PE(R409K)_AVMdscFv3 antibody | pCI-AVM-hLG4PE(R409K)_AVMscFv3 |
| AVM IgG4PE(R409K)_AVMdscFv5 antibody | pCI-AVM-hLG4PE(R409K)_AVMscFv5 |

TABLE 9

| Name of Antibody Expression Vector | Light Chain Antibody Sequence | Nucleotide Sequence of Heavy Chain Antibody Sequence (excluding signal sequence) | Amino Acid Sequence of Heavy Chain Antibody Sequence (excluding signal sequence) |
|---|---|---|---|
| pCI-AVM-hLG4PE(R409K)-linker-AVMVL-CL | AVM | SEQ ID NO: 140 | SEQ ID NO: 141 |
| pCI-AVMVH-CH | None | SEQ ID NO: 142 | SEQ ID NO: 143 |
| pCI-AVM-hLG4PE(R409K/S354C/T366W)-linker-AVMscFv-FLAG tag | AVM | SEQ ID NO: 144 | SEQ ID NO: 145 |
| pCI-AVM-hLG4PE(R409K)_AVMscFv3 | AVM | SEQ ID NO: 146 | SEQ ID NO: 147 |
| pCI-AVM-hLG4PE(R409K)_AVMscFv5 | AVM | SEQ ID NO: 148 | SEQ ID NO: 149 |

A gene fragment of the CH1-Hinge-CH2-CH3(R409K/Y349C/T366S/L368A/Y407V)-His tag region was amplified by PCR using a synthetic gene as a template and inserted to the NheI-BamHI site of pCI-AVM-hLG4PE(R409K)_AVMscFv, and pCI-AVM-hLG4PE(R409K/Y349C/T366S/L368A/Y407V)-His tag vector was produced.

(4) Construction of Vectors Expressing Bispecific Antibodies Having Structures in FIGS. 11A and 11B (4-1) Construction of pCI-AVM-hLG4PE(R409K)_MOG01scFv Vector A gene fragment of the CH1-Hinge-CH2-CH3-linker region was amplified by PCR using a synthetic gene as a template. Moreover, a gene fragment of the VH region and the VL region of MOG01 was amplified by PCR using MOG01scFv as a template. The gene fragment of the CH1-Hinge-CH2-CH3-linker region and the gene fragment of the VH region and the VL region of MOG01 were inserted to the NheI-BamHI site of pCI-AVM-hLG4PE(R409K)_AVMscFv, and pCI-AVM-hLG4PE(R409K)_MOG01scFv2 vector was produced.

In the same manner, pCI-AVM-hLG4PE(R409K)_MOG01scFv3 vector, pCI-AVM-hLG4PE(R409K)_MOG01scFv4 vector, pCI-AVM-hLG4PE(R409K)_

(2-1) Production of pCI-AVM-hLG4PE(R409K) Vector

A gene fragment of the VH region, the VL region and the antibody constant region of AVM was amplified by PCR using a synthetic gene as a template and inserted to pCI vector (manufactured by Promega Corporation), and pCI-AVM-hLG4PE(R409K) vector was produced.

(2-2) Production of pCI-AVM-hLG4PE(R409K)-linker-AVMVL-CL Vector

A gene fragment of the CH1-Hinge-CH2-CH3-linker-AVMVL-CL region was amplified by PCR using a synthetic gene as a template and inserted to the NheI-BamHI site of pCI-AVM-hLG4PE(R409K)_AVM scFv, and pCI-AVM-hLG4PE(R409K)-linker-AVMVL-CL vector was produced.

(2-3) Construction of pCI-AVMVH-CH Vector

A gene fragment of the AVMVH-CH region was amplified by PCR using a synthetic gene as a template and inserted to pCI vector (manufactured by Promega Corporation), and pCI-AVMVH-CH vector was produced.

(2-4) Construction of pCI-AVM-hLG4PE(R409K/S354C/T366W)-linker-AVMscFv-FLAG tag Vector A gene fragment of the CH1-Hinge-CH2-CH3(R409K/S354C/T366W)-linker region was amplified by PCR using a synthetic gene as a template. Moreover, a gene fragment of the linker-AVMscFv-FLAG tag region was amplified by PCR using N5LG4PE_AVM as a template. The gene fragments of the CH1-Hinge-CH2-CH3(R409K/S354C/T366W)-linker region and the linker-AVMscFv-FLAG tag region were inserted to the NheI-BamHI site of pCI-AVM-hLG4PE(R409K)_AVM scFv, and pCI-AVM-hLG4PE(R409K/S354C/T366W)-linker-AVMscFv-FLAG tag vector was produced.

(2-5) Construction of pCI-AVM-hLG4PE(R409K)_AVMscFv Vector

A gene fragment of the CH1-Hinge-CH2-CH3-linker region was amplified by PCR using a synthetic gene as a template. Moreover, a gene fragment of the VH region and the VL region of AVM was amplified by PCR using N5LG4PE_AVM as a template. The gene fragment of the CH1-Hinge-CH2-CH3-linker region and the gene fragment of the VH region and the VL region of AVM were inserted to the NheI-BamHI site of pCI-AVM-hLG4PE(R409K)_AVMscFv, and pCI-AVM-hLG4PE(R409K)_AVMscFv3 vector and pCI-AVM-hLG4PE(R409K)_AVMscFv5 vector were produced.

[Example 16] Preparation of Bispecific Antibodies

By the method described in Example 6, AVM IgG4PE(R409K)_MOG01 Fab antibody, AVM IgG4PE(R409K)_MOG01dscFv2 antibody, AVM IgG4PE(R409K)_MOG01dscFv3 antibody, AVM IgG4PE(R409K)_MOG01dscFv4 antibody, AVM IgG4PE(R409K)_MOG01dscFv5 antibody, AVM IgG4PE(R409K)_MOG01dscFv6 antibody, AVM IgG4PE(R409K)_MOG01dscFv7 antibody, AVM IgG4PE(R409K)_MOG01dscFv8 antibody, AVM IgG4PE(R409K)_MOG01dscFv9 antibody, AVM IgG4PE(R409K)_MOG01dscFv10 antibody, AVM IgG4PE(R409K)_MOG01dscFv11 antibody, AVM IgG4PE(R409K)_AVM Fab antibody, AVM IgG4PE(R409K)_AVMdscFv3 antibody and AVM IgG4PE(R409K)_AVMdscFv5 antibody were prepared.

AVM-MOG01 IgG4PE(R409K) antibody, AVM IgG4PE(R409K)_MOG01sscFv antibody and AVM IgG4PE(R409K)_AVMsscFv antibody were prepared by the method described below. The antibody expression plasmid vectors were introduced to suspension 293 cells using Expi293 (trademark) Expression System (manufactured by Thermo Fisher Scientific Inc.), and the cells were cultured to express the antibodies in a transient expression system.

The culture supernatants were collected four days after the introduction of the vectors and filtered through a membrane filter having a pore size of 0.22 µm (manufactured by Millipore Corporation). The proteins in the culture supernatants were affinity-purified with His tag using Ni Sepharose resin (manufactured by GE Healthcare BioSciences). A 20 mM Imidazole-phosphate buffer solution was used as a washing solution.

The antibodies adsorbed on the Ni Sepharose resin were eluted with a 500 mM Imidazole-phosphate buffer solution. Next, the solvents of the eluates were replaced with PBS by ultrafiltration using VIVASPIN (manufactured by Sartrius stealin) and a NAP column (manufactured by GE Healthcare BioSciences).

The proteins after the His tag purification were affinity-purified using FLAG antibody affinity gel (manufactured by Sigma-Aldrich Co. LLC.). A phosphate buffer solution was used as a washing solution. The antibodies adsorbed on the FLAG antibody affinity gel were eluted with 20 mM sodium citrate and 50 mM NaCl buffer solution (pH 3.4) and collected in tubes containing 1 M Tris-HCl Buffer Solution (pH 8.0).

Next, the solvents of the eluates were replaced with PBS by ultrafiltration using VIVASPIN (manufactured by Sartrius stealin) and a NAP column (manufactured by GE Healthcare BioSciences), and then filtration sterilization with a membrane filter having a pore size of 0.22 µm (Millex-GV, manufactured by Millipore Corporation) was conducted. The absorbances of the antibody solutions at 280 nm were measured, and the concentrations of the purified antibodies were calculated.

[Example 17] Evaluation of Affinities of Bispecific Antibodies to MOG Using Flow Cytometer Binding of the bispecific antibodies and the negative control antibodies obtained in Example 6 and Example 16 to MOG was evaluated by the fluorescence activated cell sorting (FACS) method according to the following procedures.

pEF6_hMOG obtained in Example 5 was introduced to mouse connective tissue-derived fibroblast L929 cells [American Type Culture Collection (ATCC) No.: CCL-1] using HilyMax (manufactured by Dojindo Laboratories). The gene-transfected cells were selected using an antibiotic substance, Blasticidin (manufactured by Invitrogen) and then cloned by the limiting dilution method. Using the L929 cells expressing hMOG on the cell surface (abbreviated as hMOG/L929 below), the reactivities of the bispecific antibodies were analyzed by the method described below.

The hMOG/L929 cells were suspended in a Staining Buffer (SB) of PBS containing 0.1% $NaN_3$ and 1% FBS and dispensed to a round-bottom 96-well plate (manufactured by Becton Dickinson). After centrifugation (2000 rpm, 4° C., two minutes), the supernatants were removed, and the MOG01 bispecific antibodies obtained in Example 6 and Example 16 were added to the pellets. After suspending the pellets, the plate was left to stand at ice temperature for 30 minutes. The supernatants were removed after further centrifugation (2000 rpm, 4° C., two minutes), and the pellets were washed with SB. Then, 1 µg/mL RPE fluorescently labeled goat anti-human antibody (manufactured by Southern Biotech) was added, and the plate was incubated at ice temperature for 30 minutes. After washing with SB, the cells were suspended in SB, and the fluorescence intensities of the cells were measured with a flow cytometer FACS CANTO II (manufactured by Becton Dickinson). The results are shown in FIGS. 12A to 12C and FIGS. 13A and 13B.

As shown in FIGS. 12A to 12C and FIGS. 13A and 13B, it was confirmed that all the bispecific antibodies have affinity to MOG. In particular, it was elucidated that the affinities of AVM IgG4PE(R409K)_MOG01Fab antibody [FIG. 10B and FIG. 12C], AVM IgG4PE(R409K)_MOG01dscFv3 antibody, AVM IgG4PE(R409K)_MOG01dscFv5 antibody, AVM IgG4PE(R409K)_MOG01dscFv6 antibody, AVM IgG4PE(R409K)_MOG01dscFv7 antibody, AVM IgG4PE(R409K)_MOG01dscFv8 antibody, AVM IgG4PE(R409K)_MOG01dscFv9 antibody, AVM IgG4PE(R409K)_MOG01dscFv10 antibody and AVM IgG4PE(R409K)_MOG01dscFv11 antibody [FIG. 11B and FIG. 13B] are high.

[Example 18] Evaluation of Affinities of Bispecific Antibodies to MOG by Surface Plasmon Resonance Detection Binding of the bispecific antibodies obtained in Example 6 and Example 16 to MOG was evaluated by the same method as that of Example 8. The results obtained are shown in Table 10 and Table 11.

TABLE 10

| Antibody Name | ka (1/Ms) | kd (1/s) | KD (M) |
| --- | --- | --- | --- |
| AVM-MOG01 IgG4PE(R409K) antibody | 1.3E+05 | 1.6E−03 | 1.2E−08 |
| AVM IgG4PE(R409K)_MOG01sscFv antibody | 5.1E+04 | 1.0E−02 | 2.0E−07 |
| AVM IgG4PE(R409K)_MOG01 Fab antibody | 1.0E+05 | 3.5E−03 | 3.4E−08 |

TABLE 11

| Antibody Name | ka (1/Ms) | kd (1/s) | KD (M) |
| --- | --- | --- | --- |
| AVM IgG4PE(R409K)_MOG01dscFv antibody | 2.4E+04 | 4.9E−03 | 2.0E−07 |
| AVM IgG4PE(R409K)_MOG01dscFv3 antibody | 1.7E+05 | 2.2E−03 | 1.3E−08 |
| AVM IgG4PE(R409K)_MOG01dscFv5 antibody | 2.0E+05 | 4.8E−03 | 2.4E−08 |

As shown in Table 10 and Table 11, the dissociation constants (KD values) of the bispecific antibodies of MOG were $1.2 \times 10^{-8}$ (M) to $2.0 \times 10^{-7}$ (M), and it was elucidated that all the antibodies show excellent affinity.

In particular, it was elucidated that the affinities of AVM-MOG01 IgG4PE(R409K) antibody [FIG. 10A], AVM IgG4PE(R409K)_MOG01Fab antibody [FIG. 10B], AVM IgG4PE(R409K)_MOG01dscFv3 antibody and AVM IgG4PE(R409K)_MOG01dscFv5 antibody [FIG. 11B] are high.

[Example 19] Evaluation of Mouse Brain Migration Properties of Bispecific Antibodies The mouse brain migration properties of the bispecific antibodies and the negative control antibodies obtained in Example 6 and Example 16 were evaluated by the method of Example 14.

AVM-MOG01 IgG4PE(R409K) antibody, AVM IgG4PE(R409K)_MOG01sscFv antibody and AVM IgG4PE(R409K)_MOG01 Fab antibody were administered at 5 mg/kg, and the antibody concentrations in the serum and the antibody amounts per unit brain weight in the brain tissues after 10 days are shown in FIG. 14A to FIG. 16B.

Figure 14A:
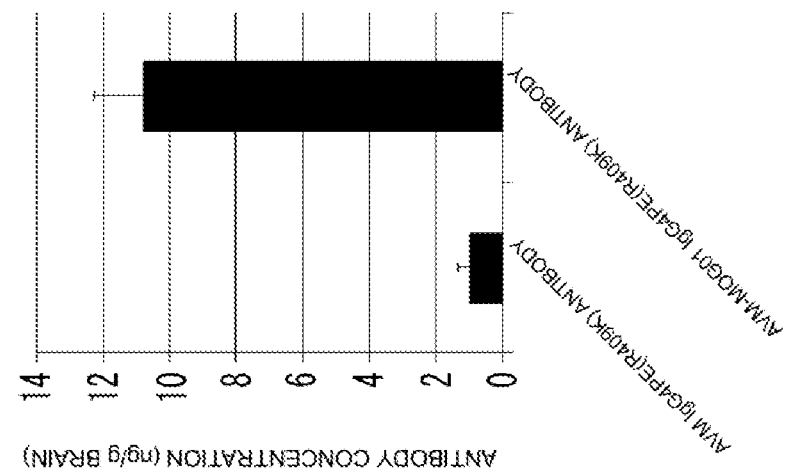
FIGS. 14A and 14B show the results of evaluation of the mouse brain migration properties of bispecific antibodies. The vertical axis shows the antibody concentration, and the horizontal axis shows the bispecific antibodies used.
Figure 14B:
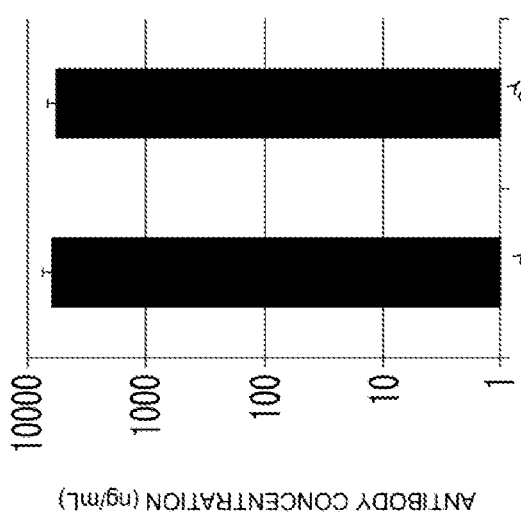

As shown in FIG. 14A, FIG. 15A and FIG. 16A, the antibody concentrations of all the MOG01 modified antibodies in the serum were not different from those of the negative controls. On the other hand, as shown in FIG. 14B, FIG. 15B and FIG. 16B, it was shown that the antibody amounts in the brain increase to about eight times in the case of AVM-MOG01 IgG4PE(R409K) antibody, about 12 times in the case of AVM IgG4PE(R409K)_MOG01sscFv antibody and about 30 times in the case of AVM IgG4PE(R409K)_MOG01 Fab antibody as compared to those of the negative controls.

The above results show that while the bispecific antibodies which bind to MOG can increase the antibody amount in the brain as compared to those of the negative control antibodies which do not bind to MOG, the half-lives in the blood do not change.

AVM IgG4PE(R409K) MOG01dscFv antibody, AVM IgG4PE(R409K)_MOG01dscFv3 antibody and AVM IgG4PE(R409K)_MOG01dscFv5 antibody were administered at 5 mg/kg, and the antibody concentrations in the serum and the antibody amounts per unit brain weight in the brain tissues after 10 days and after 28 days are shown in FIGS. 17A to 17D.

As shown in FIGS. 17A and 17C, the antibody concentrations of all the bispecific antibodies in the serum were not different from those of the negative controls. On the other hand, as shown in FIGS. 17B and 17D, it was shown that the antibody amounts in the brain of AVM IgG4PE(R409K)_MOG01dscFv antibody, AVM IgG4PE(R409K)_MOG01dscFv3 antibody and AVM IgG4PE(R409K)_MOG01dscFv5 antibody can be increased to several ten times over 28 days. Moreover, as shown in FIG. 17D, when the antibody amounts in the brain were high after 28 days, the affinities of the bispecific antibodies to MOG were also high (Table 11). It was elucidated that there is a correlation between the MOG binding activity and the antibody amount in the brain.

[Example 20] Acquisition of Novel MOG Antibodies Showing Higher Affinity to MOG than Anti-MOG01 Antibody (1) Production of Extracellular Domain Proteins of Soluble Human MOG Antigen and Soluble Mouse MOG Antigen to which FLAG-Fc is Bound Plasmid vectors, INPEP4_hMOG-FLAG-Fc and INPEP4_mMOG-FLAG-Fc, which each express an extracellular domain protein of MOG to which FLAG-Fc was added at the C-terminus, as soluble antigens of human MOG and mouse MOG were produced by the method described in Example 4. The nucleotide sequence of hMOG-FLAG-Fc is shown in SEQ ID NO: 100, and the amino acid sequence deduced from the nucleotide sequence is shown in SEQ ID NO: 101. The nucleotide sequence of mMOG-FLAG-Fc is shown in SEQ ID NO: 102, and the amino acid sequence deduced from the nucleotide sequence is shown in SEQ ID NO: 103. The extracellular domain proteins of MOG to which FLAG-Fc was bound were obtained by transiently expressing and purifying the proteins by the method described in Example 4.

(2) Production of Extracellular Domain Proteins of MOG to which GST is Bound

Plasmid vectors, N5_hMOG-GST and N5_mMOG-GST, which each express an extracellular domain protein of MOG to which GST was added at the C-terminus, as soluble antigens of human MOG and mouse MOG were produced by the method described in Example 4. The nucleotide sequence of hMOG-GST is shown in SEQ ID NO: 104, and the amino acid sequence deduced from the nucleotide sequence is shown in SEQ ID NO: 105. The nucleotide sequence of mMOG-GST is shown in SEQ ID NO: 106, and the amino acid sequence deduced from the nucleotide sequence is shown in SEQ ID NO: 107. The extracellular domain proteins of MOG to which GST was bound were obtained by transiently expressing and purifying the proteins by the method described in Example 4.

(3) Acquisition of Anti-MOG Antibodies from Human Antibody-Producing Mice hMOG-GST and mMOG-GST were mixed with pertussis vaccine and Alumgel and intraperitoneally or intradermally administered to human antibody-producing mice (Ishida & Lonberg, IBC's 11th Antibody Engineering, Abstract 2000; Ishida, I. et al., Cloning & Stem Cells 4, 85-96 (2002) and Ishida Isao (2002) Experimental Medicine 20, 6, 846-851).

After the first immunization, the mice were immunized with hMOG-GST and mMOG-GST three times. The individuals immunized by intraperitoneal administration were dissected four days after the final immunization, and the spleens were taken. After removing the red blood cells using a reagent for removing red blood cells (manufactured by Sigma Co. LLC.), the spleens were frozen with CELL-BANKER 1 (manufactured by Nippon Zenyaku Kogyo Co., Ltd.). The individuals immunized by intradermal administration were dissected, and the axillary lymph nodes were taken. After removing the red blood cells using a reagent for removing red blood cells, the axillary lymph nodes were frozen with CELLBANKER 1. RNAs were extracted from the obtained spleen cells and the cells of the axillary lymph nodes using an RNeasy Plus Mini kit (manufactured by QIAGEN), and cDNAs were synthesized with a SMARTer RACE cDNA amplification kit (manufactured by Clontech Laboratories, Inc.). Human antibody-producing mouse-derived phage libraries were produced using the synthesized cDNAs by the method described in Example 1.

Anti-human MOG monoclonal antibodies were obtained using the human antibody-producing mouse-derived phage libraries by the phage display method. The phage display method and cloning ELISA were conducted using hMOG-FLAG_Fc and mMOG-FLAG_Fc by the methods described in Example 1.

The sequences of the clones which bound to hMOG-FLAG_Fc, mMOG-FLAG_Fc and hMOG/Expi293F cells were analyzed, and anti-MOG antibody phagemid vectors, pCANTAB_MOG301, pCANTAB_MOG303, pCANTAB_MOG307, pCANTAB_MOG310, pCANTAB_MOG312, pCANTAB_MOG326, pCANTAB_MOG329, pCANTAB_MOG446, pCANTAB_MOG456 and pCANTAB_MOG473 were obtained.

In the following paragraphs, the names of the anti-MOG scFv antibodies displayed by the phages expressed using pCANTAB_MOG301, pCANTAB_MOG303, pCANTAB_MOG307, pCANTAB_MOG310, pCANTAB_MOG312, pCANTAB_MOG326, pCANTAB_MOG329, pCANTAB_MOG446, pCANTAB_MOG456 and pCANTAB_MOG473 are referred to as MOG301 antibody, MOG303 antibody, MOG307 antibody, MOG310 antibody, MOG312 antibody, MOG326 antibody, MOG329 antibody, MOG446 antibody, MOG456 antibody and MOG473 antibody, respectively.

The nucleotide sequences which encode VH or VL of the anti-MOG antibodies and the amino acid sequences deduced from the nucleotide sequences are shown in Table 12.

TABLE 12

| Clone Name | MOG301 | MOG303 | MOG307 | MOG310 | MOG312 | MOG326 | MOG329 | MOG446 | MOG456 | MOG473 |
|---|---|---|---|---|---|---|---|---|---|---|
| Nucleotide sequence encoding VH (excluding signal sequence) | SEQ ID NO: 151 | SEQ ID NO: 161 | SEQ ID NO: 171 | SEQ ID NO: 181 | SEQ ID NO: 191 | SEQ ID NO: 201 | SEQ ID NO: 211 | SEQ ID NO: 221 | SEQ ID NO: 231 | SEQ ID NO: 241 |
| Amino acid sequence of VH (excluding signal sequence) | SEQ ID NO: 152 | SEQ ID NO: 162 | SEQ ID NO: 172 | SEQ ID NO: 182 | SEQ ID NO: 192 | SEQ ID NO: 202 | SEQ ID NO: 212 | SEQ ID NO: 222 | SEQ ID NO: 232 | SEQ ID NO: 242 |
| Amino acid sequence of HCDR1 | SEQ ID NO: 153 | SEQ ID NO: 163 | SEQ ID NO: 173 | SEQ ID NO: 183 | SEQ ID NO: 193 | SEQ ID NO: 203 | SEQ ID NO: 213 | SEQ ID NO: 223 | SEQ ID NO: 233 | SEQ ID NO: 243 |
| Amino acid sequence of HCDR2 | SEQ ID NO: 154 | SEQ ID NO: 164 | SEQ ID NO: 174 | SEQ ID NO: 184 | SEQ ID NO: 194 | SEQ ID NO: 204 | SEQ ID NO: 214 | SEQ ID NO: 224 | SEQ ID NO: 234 | SEQ ID NO: 244 |
| Amino acid sequence of HCDR3 | SEQ ID NO: 155 | SEQ ID NO: 165 | SEQ ID NO: 175 | SEQ ID NO: 185 | SEQ ID NO: 195 | SEQ ID NO: 205 | SEQ ID NO: 215 | SEQ ID NO: 225 | SEQ ID NO: 235 | SEQ ID NO: 245 |
| Nucleotide sequence encoding VL (excluding signal sequence) | SEQ ID NO: 156 | SEQ ID NO: 166 | SEQ ID NO: 176 | SEQ ID NO: 186 | SEQ ID NO: 196 | SEQ ID NO: 206 | SEQ ID NO: 216 | SEQ ID NO: 226 | SEQ ID NO: 236 | SEQ ID NO: 246 |
| Amino acid sequence of VL (excluding signal sequence) | SEQ ID NO: 157 | SEQ ID NO: 167 | SEQ ID NO: 177 | SEQ ID NO: 187 | SEQ ID NO: 197 | SEQ ID NO: 207 | SEQ ID NO: 217 | SEQ ID NO: 227 | SEQ ID NO: 237 | SEQ ID NO: 247 |
| Amino acid sequence of LCDR1 | SEQ ID NO: 158 | SEQ ID NO: 168 | SEQ ID NO: 178 | SEQ ID NO: 188 | SEQ ID NO: 198 | SEQ ID NO: 208 | SEQ ID NO: 218 | SEQ ID NO: 228 | SEQ ID NO: 238 | SEQ ID NO: 248 |
| Amino acid sequence of LCDR2 | SEQ ID NO: 159 | SEQ ID NO: 169 | SEQ ID NO: 179 | SEQ ID NO: 189 | SEQ ID NO: 199 | SEQ ID NO: 209 | SEQ ID NO: 219 | SEQ ID NO: 229 | SEQ ID NO: 239 | SEQ ID NO: 249 |
| Amino acid sequence of LCDR3 | SEQ ID NO: 160 | SEQ ID NO: 170 | SEQ ID NO: 180 | SEQ ID NO: 190 | SEQ ID NO: 200 | SEQ ID NO: 210 | SEQ ID NO: 220 | SEQ ID NO: 230 | SEQ ID NO: 240 | SEQ ID NO: 250 |

Moreover, clones having similar sequences having homology of 91 to 93% to that of MOG301 antibody (MOG426 and MOG428), clones having similar sequences having homology of 85 to 95% to that of MOG303 antibody (MOG313, MOG314, MOG315, MOG331, MOG357 and MOG476), clones having similar sequences having homology of 97 to 99% to that of MOG307 antibody (MOG323, MOG341, MOG354 and MOG355), clones having similar sequences having homology of 85 to 98% to that of MOG310 antibody (MOG308, MOG316, MOG319, MOG320, MOG338, MOG352, MOG359 and MOG478), a clone having a similar sequence having homology of 85% to that of MOG329 antibody (MOG470) and a clone having a similar sequence having homology of 84% to that of MOG456 antibody (MOG418) were obtained by the phage display method using MOG affinity as an index. Because it was confirmed that these similar clones bind to hMOG-FLAG_Fc, mMOG-FLAG_Fc and hMOG/Expi293F cells, it was elucidated that antibody clones having high homology to the amino acid sequences of the antibody clones are also antibodies having MOG binding activity.

The nucleotide sequences which encode VH or VL of the similar clones and the amino acid sequences deduced from the nucleotide sequences are shown in Table 13, and comparisons of the amino acid sequences of the similar clones are shown in FIG. 18 to FIG. 22B.

hG4PE(R409K), pCI-MOG312 scFv-hG4PE(R409K), pCI-MOG326 scFv-hG4PE(R409K), pCI-MOG329 scFv-hG4PE(R409K), pCI-MOG446 scFv-hG4PE(R409K), pCI-MOG456 scFv-hG4PE(R409K) and pCI-MOG473 scFv-hG4PE(R409K).

The produced anti-MOG antibody expression vectors were prepared by the method described in Example 6. Antibodies were expressed using the anti-MOG antibody expression vectors, pCI-MOG301 scFv-hG4PE(R409K), pCI-MOG303 scFv-hG4PE(R409K), pCI-MOG307 scFv-hG4PE(R409K), pCI-MOG310 scFv-hG4PE(R409K), pCI-MOG312 scFv-hG4PE(R409K), pCI-MOG326 scFv-hG4PE(R409K), pCI-MOG329 scFv-hG4PE(R409K), pCI-MOG446 scFv-hG4PE(R409K), pCI-MOG456 scFv-hG4PE(R409K) and pCI-MOG473 scFv-hG4PE(R409K), and MOG301 scFv-hG4PE(R409K) antibody, MOG303 scFv-hG4PE(R409K) antibody, MOG307 scFv-hG4PE

TABLE 13

| Name of Representative Clone | Name of Similar Clone | Nucleotide sequence encoding VH (excluding signal sequence) | Amino acid sequence of VH (excluding signal sequence) | Nucleotide sequence encoding VL (excluding signal sequence) | Amino acid sequence of VL (excluding signal sequence) |
| --- | --- | --- | --- | --- | --- |
| MOG301 | MOG426 | SEQ ID NO: 251 | SEQ ID NO: 252 | SEQ ID NO: 253 | SEQ ID NO: 254 |
|  | MOG428 | SEQ ID NO: 255 | SEQ ID NO: 256 | SEQ ID NO: 257 | SEQ ID NO: 258 |
| MOG303 | MOG313 | SEQ ID NO: 259 | SEQ ID NO: 260 | SEQ ID NO: 261 | SEQ ID NO: 262 |
|  | MOG314 | SEQ ID NO: 263 | SEQ ID NO: 264 | SEQ ID NO: 265 | SEQ ID NO: 266 |
|  | MOG315 | SEQ ID NO: 267 | SEQ ID NO: 268 | SEQ ID NO: 269 | SEQ ID NO: 270 |
|  | MOG331 | SEQ ID NO: 271 | SEQ ID NO: 272 | SEQ ID NO: 273 | SEQ ID NO: 274 |
|  | MOG357 | SEQ ID NO: 275 | SEQ ID NO: 276 | SEQ ID NO: 277 | SEQ ID NO: 278 |
|  | MOG476 | SEQ ID NO: 279 | SEQ ID NO: 280 | SEQ ID NO: 281 | SEQ ID NO: 282 |
| MOG307 | MOG323 | SEQ ID NO: 283 | SEQ ID NO: 284 | SEQ ID NO: 285 | SEQ ID NO: 286 |
|  | MOG341 | SEQ ID NO: 287 | SEQ ID NO: 288 | SEQ ID NO: 289 | SEQ ID NO: 290 |
|  | MOG354 | SEQ ID NO: 291 | SEQ ID NO: 292 | SEQ ID NO: 293 | SEQ ID NO: 294 |
|  | MOG355 | SEQ ID NO: 295 | SEQ ID NO: 296 | SEQ ID NO: 297 | SEQ ID NO: 298 |
| MOG310 | MOG308 | SEQ ID NO: 299 | SEQ ID NO: 300 | SEQ ID NO: 301 | SEQ ID NO: 302 |
|  | MOG316 | SEQ ID NO: 303 | SEQ ID NO: 304 | SEQ ID NO: 305 | SEQ ID NO: 306 |
|  | MOG319 | SEQ ID NO: 307 | SEQ ID NO: 308 | SEQ ID NO: 309 | SEQ ID NO: 310 |
|  | MOG320 | SEQ ID NO: 311 | SEQ ID NO: 312 | SEQ ID NO: 313 | SEQ ID NO: 314 |
|  | MOG338 | SEQ ID NO: 315 | SEQ ID NO: 316 | SEQ ID NO: 317 | SEQ ID NO: 318 |
|  | MOG352 | SEQ ID NO: 319 | SEQ ID NO: 320 | SEQ ID NO: 321 | SEQ ID NO: 322 |
|  | MOG359 | SEQ ID NO: 323 | SEQ ID NO: 324 | SEQ ID NO: 325 | SEQ ID NO: 326 |
|  | MOG478 | SEQ ID NO: 327 | SEQ ID NO: 328 | SEQ ID NO: 329 | SEQ ID NO: 330 |
| MOG329 | MOG470 | SEQ ID NO: 331 | SEQ ID NO: 332 | SEQ ID NO: 333 | SEQ ID NO: 334 |
| MOG456 | MOG418 | SEQ ID NO: 335 | SEQ ID NO: 336 | SEQ ID NO: 337 | SEQ ID NO: 338 |

[Example 21] Production of Anti-MOG scFv-Fc Antibodies

A gene fragment of the scFv region was amplified by PCR using a phagemid vector pCANTAB_MOG01 as a template. A gene fragment of the Hinge-CH2-CH3 region was amplified by PCR using a synthetic gene of the heavy chain constant region as a template. The obtained gene fragments were inserted to N5KG4PE vector (described in International Publication No. 2002/088186), and N5-MOG01 scFv-hG4PE vector was produced.

A gene fragment of the scFv region was amplified by PCR using a phagemid vector pCANTAB_MOG301 as a template. A gene fragment of the Hinge-CH2-CH3 region was amplified by PCR using a synthetic gene of the heavy chain constant region as a template. The obtained gene fragments were inserted to pCI vector (manufactured by Promega Corporation), and pCI-MOG301 scFv-hG4PE(R409K) vector was produced.

By the same method, antibody expression vectors to which gene fragments of the scFv regions of the anti-MOG antibodies shown in Table 12 were inserted were produced and named pCI-MOG303 scFv-hG4PE(R409K), pCI-MOG307 scFv-hG4PE(R409K), pCI-MOG310 scFv- (R409K) antibody, MOG310 scFv-hG4PE(R409K) antibody, MOG312 scFv-hG4PE(R409K) antibody, MOG326 scFv-hG4PE(R409K) antibody, MOG329 scFv-hG4PE(R409K) antibody, MOG446 scFv-hG4PE(R409K) antibody, MOG456 scFv-hG4PE(R409K) antibody and MOG473 scFv-hG4PE(R409K) antibody were obtained, respectively.

[Example 22] Evaluation of Affinities of Anti-MOG Antibodies to MOG Using Flow Cytometer Binding of the anti-MOG antibodies obtained in Example 21 to MOG was evaluated by the same method as that of Example 7. The results are shown in FIGS. 23 to 25.

Figure 23:
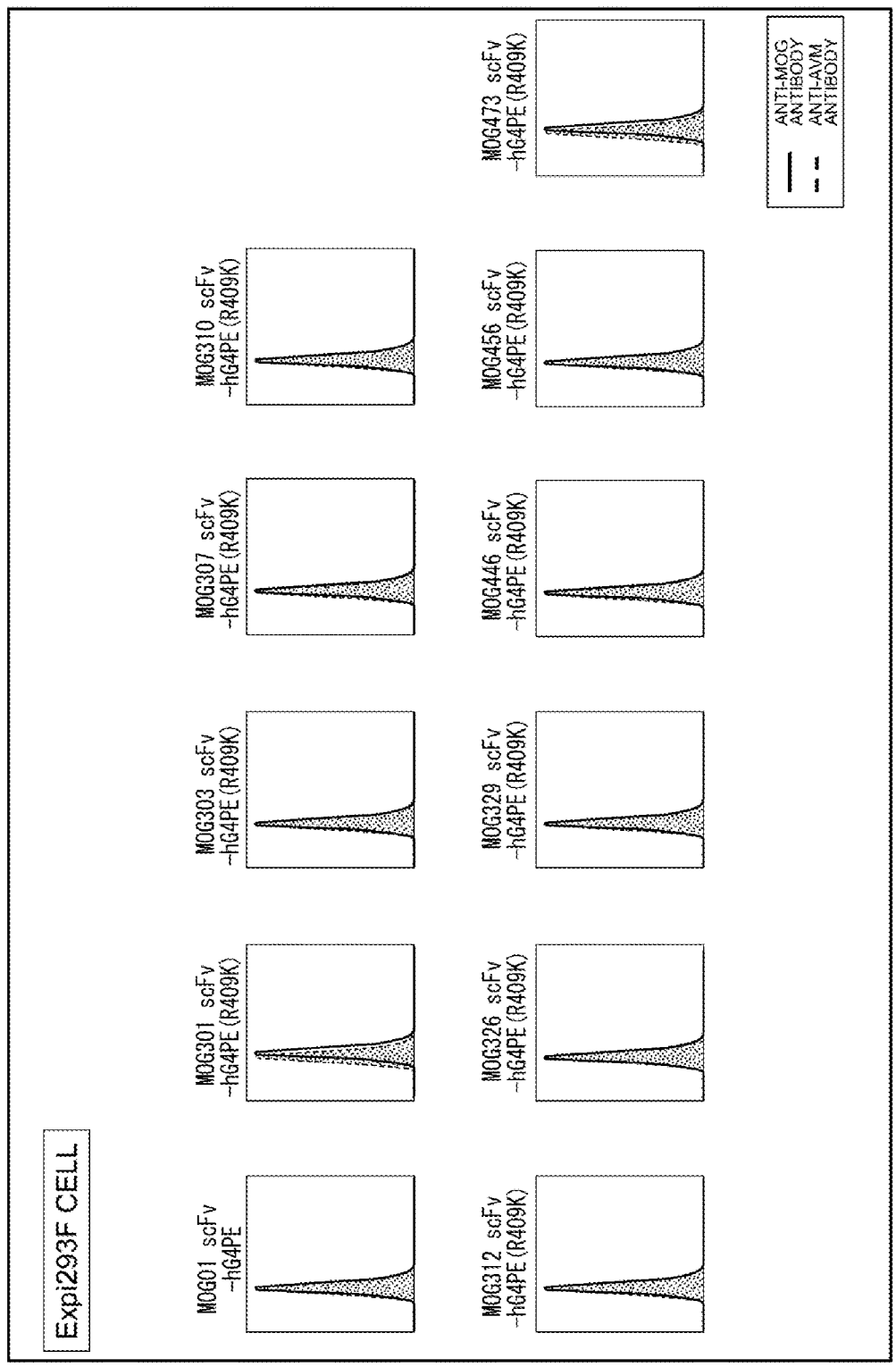
FIG. 23 shows the results of analysis using a flow cytometer of the affinities of anti-MOG antibodies to Expi293F cells. The vertical axis shows the number of cells, and the horizontal axis shows the fluorescence intensity. A dotted line indicates a histogram of the affinity of an anti-AVM antibody used as a negative control, and a solid line indicates a histogram of the affinity of a MOG antibody.
Figure 24:
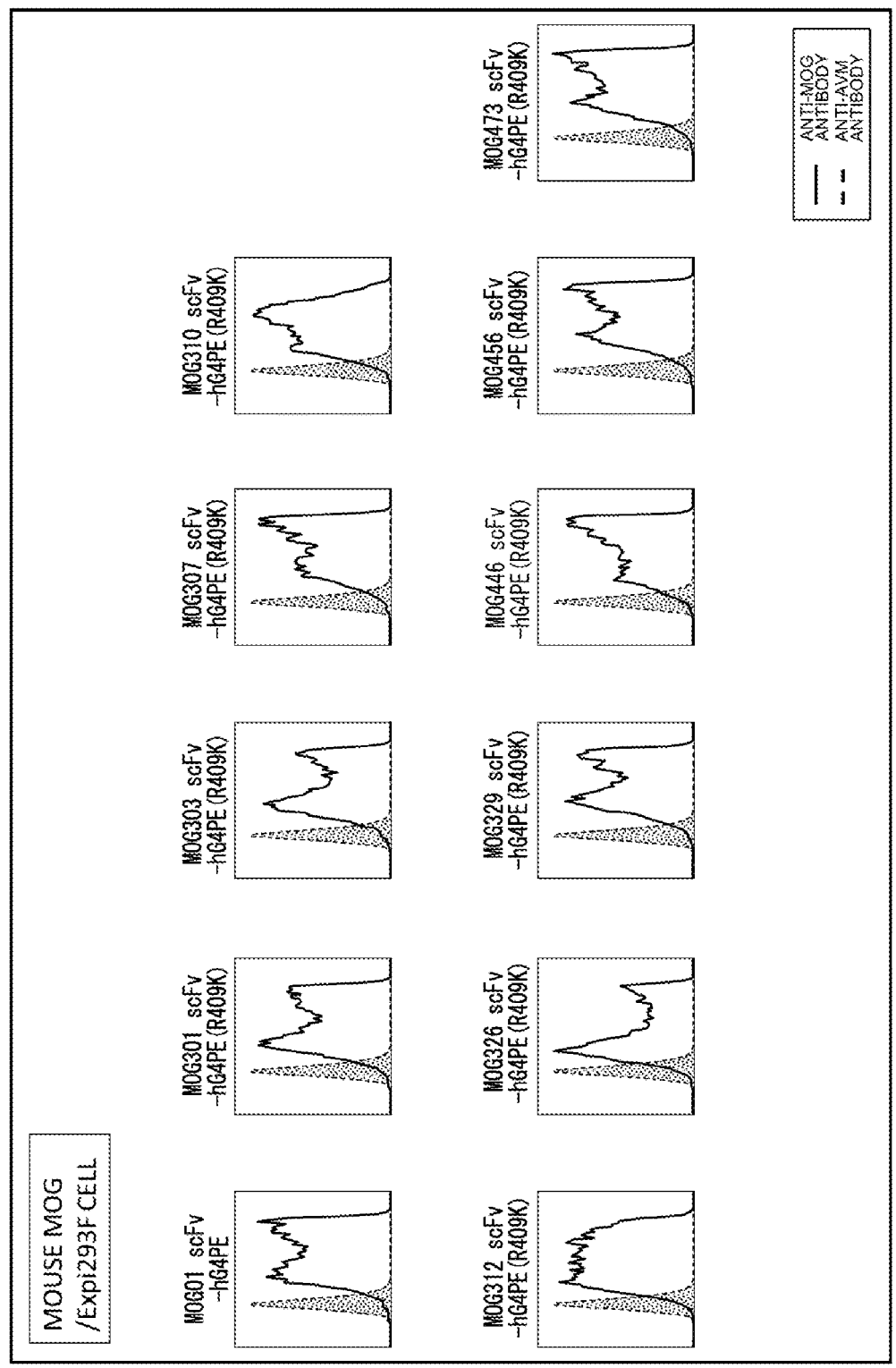
FIG. 24 shows the results of analysis using a flow cytometer of the affinities of anti-MOG antibodies to mouse MOG/Expi293F cells. The vertical axis shows the number of cells, and the horizontal axis shows the fluorescence intensity. A dotted line indicates a histogram of the affinity of an anti-AVM antibody used as a negative control, and a solid line indicates a histogram of the affinity of a MOG antibody.
Figure 25:
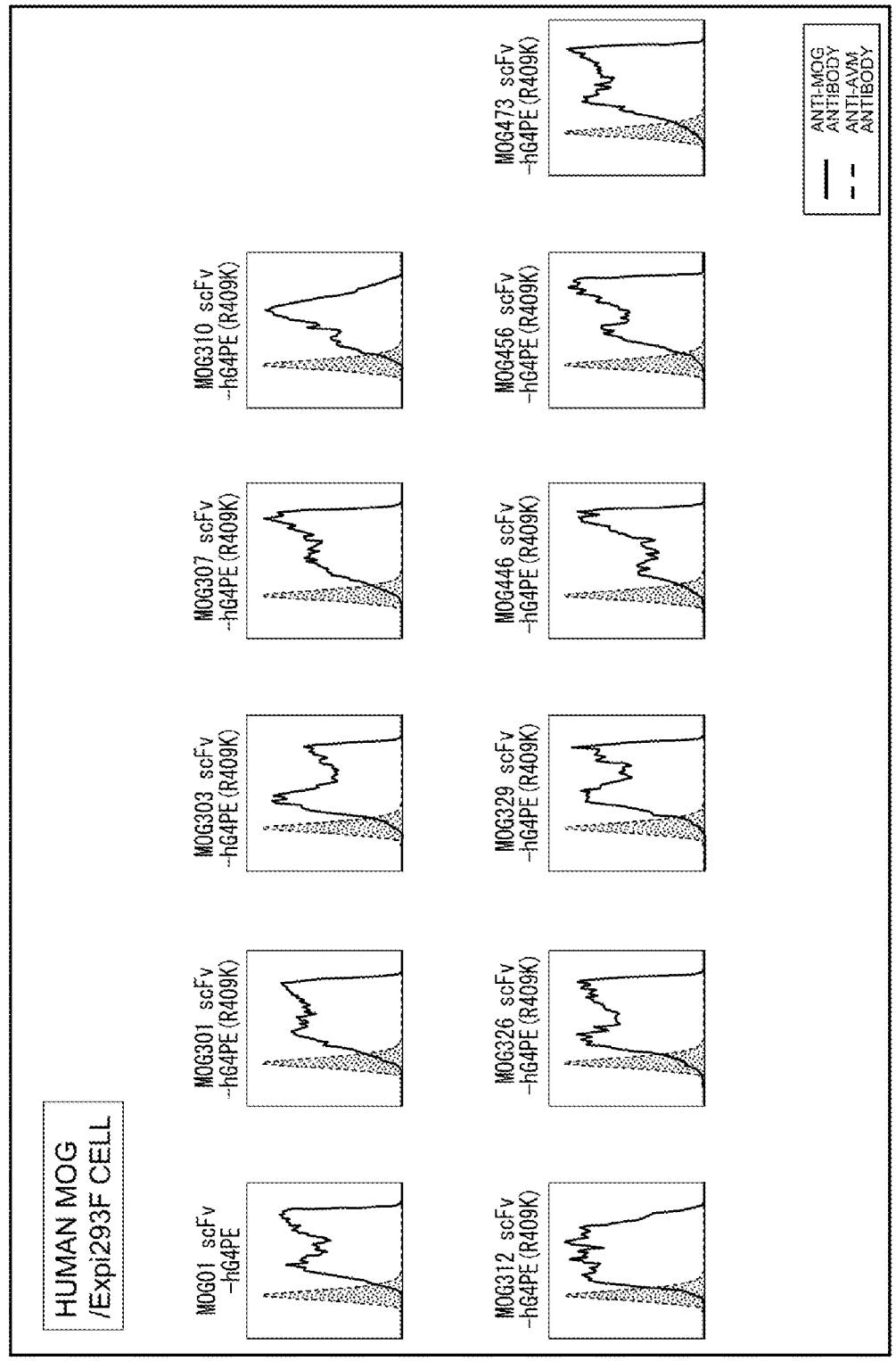
FIG. 25 shows the results of analysis using a flow cytometer of the affinities of anti-MOG antibodies to human MOG/Expi293F cells. The vertical axis shows the number of cells, and the horizontal axis shows the fluorescence intensity. A dotted line indicates a histogram of the affinity of an anti-AVM antibody used as a negative control, and a solid line indicates a histogram of the affinity of a MOG antibody.

As shown in FIGS. 23 to 25, MOG01 scFv-hG4PE, MOG301 scFv-hG4PE(R409K), MOG303 scFv-hG4PE(R409K), MOG307 scFv-hG4PE(R409K), MOG310 scFv-hG4PE(R409K), MOG312 scFv-hG4PE(R409K), MOG326 scFv-hG4PE(R409K), MOG329 scFv-hG4PE(R409K), MOG446 scFv-hG4PE(R409K), MOG456 scFv-hG4PE(R409K) and MOG473 scFv-hG4PE(R409K) all showed binding activity to hMOG/Expi293F cells and mMOG/Expi293F cells.

[Example 23] Evaluation of Affinities of Anti-MOG Antibodies to MOG by Surface Plasmon Resonance Detection Binding of MOG01 scFv-hG4PE, MOG301 scFv-hG4PE (R409K), MOG303 scFv-hG4PE(R409K), MOG307 scFv-hG4PE(R409K), MOG329 scFv-hG4PE(R409K), MOG446 scFv-hG4PE(R409K), MOG456 scFv-hG4PE(R409K) and MOG473 scFv-hG4PE(R409K) obtained in Example 21 to human MOG and mouse MOG was evaluated by the same method as that of Example 8. hMOG-GST and mMOG-GST were used as analytes. The results of evaluation of the affinities to human MOG are shown in Table 14, and the results of evaluation of the affinities to mouse MOG are shown in Table 15.

TABLE 14

Reactivity to human MOG

| Antibody Name | ka (1/Ms) | kd (1/s) | KD (M) |
| --- | --- | --- | --- |
| MOG01 scFv-hG4PE | 4.1E+06 | 1.5E−02 | 3.6E−09 |
| MOG301 scFv-hG4PE(R409K) | 1.1E+06 | 1.8E−04 | 1.8E−10 |
| MOG303 scFv-hG4PE(R409K) | 9.1E+05 | 1.6E−04 | 1.7E−10 |
| MOG307 scFv-hG4PE(R409K) | 1.6E+05 | 1.4E−04 | 8.9E−10 |
| MOG329 scFv-hG4PE(R409K) | 1.6E+06 | 2.1E−04 | 1.3E−10 |
| MOG446 scFv-hG4PE(R409K) | 1.9E+05 | 1.7E−04 | 8.7E−10 |
| MOG456 scFv-hG4PE(R409K) | 1.0E+06 | 2.6E−04 | 2.5E−10 |
| MOG473 scFv-hG4PE(R409K) | 1.5E+06 | 1.5E−04 | 1.0E−10 | ka of MOG01 was outside the measurement range.

TABLE 15

Reactivity to mouse MOG

| Antibody Name | ka (1/Ms) | kd (1/s) | KD (M) |
| --- | --- | --- | --- |
| MOG01 scFv-hG4PE | 5.9E+06 | 4.0E−02 | 6.9E−09 |
| MOG301 scFv-hG4PE(R409K) | 4.9E+05 | 2.1E−04 | 4.3E−10 |
| MOG303 scFv-hG4PE(R409K) | 1.1E+06 | 2.1E−04 | 1.9E−10 |
| MOG307 scFv-hG4PE(R409K) | 1.6E+05 | 1.5E−04 | 9.6E−10 |
| MOG329 scFv-hG4PE(R409K) | 1.1E+06 | 2.3E−04 | 2.2E−10 |
| MOG446 scFv-hG4PE(R409K) | 1.2E+05 | 3.7E−04 | 3.2E−09 |
| MOG456 scFv-hG4PE(R409K) | 7.6E+05 | 3.9E−04 | 5.2E−10 |
| MOG473 scFv-hG4PE(R409K) | 7.6E+05 | 3.7E−04 | 4.9E−10 |

As shown in Table 14 and Table 15, the dissociation constants (KD values) of the anti-MOG antibodies to human MOG were $1.0^{-10}$ (M) to $3.6 \times 10^{-9}$ (M), and the dissociation constants (KD values) to mouse MOG were $1.9 \times 10^{-10}$ (M) to $6.9 \times 10^{-9}$ (M). It was thus elucidated that all the antibodies show excellent affinity. The association rate constant ka of MOG01 scFv-hG4PE was outside the measurement range of the device, and the KD value could not be determined as a unique value.

[Example 24] Production of Enzyme-Fused Antibodies

Enzyme-fused antibodies in which acid sphingomyelinase (ASM) was fused to the C-terminus of anti-MOG01IgG antibody or anti-AVMIgG antibody were produced by the method described below. The vector expressing the antibody in which ASM was fused to the C-terminus of anti-MOG01IgG antibody was named pCI-MOG01-hLG4PE (R409K)_ASM, and the vector expressing the antibody in which ASM was fused to the C-terminus of anti-AVMIgG antibody was named pCI-AVM-hLG4PE(R409K)_ASM.

A gene fragment of the linker-ASM region was amplified by PCR using a synthetic gene of ASM shown in SEQ ID NO: 150 as a template. Moreover, a gene fragment of the CH1-Hinge-CH2-CH3(R409K) region was synthesized by PCR using a synthetic gene as a template. A gene fragment of the MOG01 light chain region and a gene fragment of the MOG01 VH region were amplified by PCR using N5LG4PE_MOG01 as a template.

The obtained gene fragments were inserted to pCI vector (manufactured by Promega Corporation), and pCI-MOG01-hLG4PE(R409K)_ASM vector was produced. A gene fragment of the CH2-CH3 region was amplified by PCR using a synthetic gene as a template. The gene fragments of the CH2-CH3 region and the linker-ASM region were inserted to the PmlI-BamHI site of pCI-AVM-hLG4PE(R409K) vector, and pCI-AVM-hLG4PE(R409K)_ASM was produced.

pCI-MOG01-hLG4PE(R409K)_ASM and pCI-AVM-hLG4PE(R409K)_ASM were expressed and purified by the method shown in Example 6. The antibody obtained by expression using pCI-MOG01-hLG4PE(R409K)_ASM was named MOG01 IgG4PE(R409K)-ASM, and the antibody obtained by expression using pCI-AVM-hLG4PE(R409K)_ASM was named AVM IgG4PE(R409K)-ASM.

[Example 25] Evaluation of Activities of Enzyme-Fused Antibodies

Figure 26:
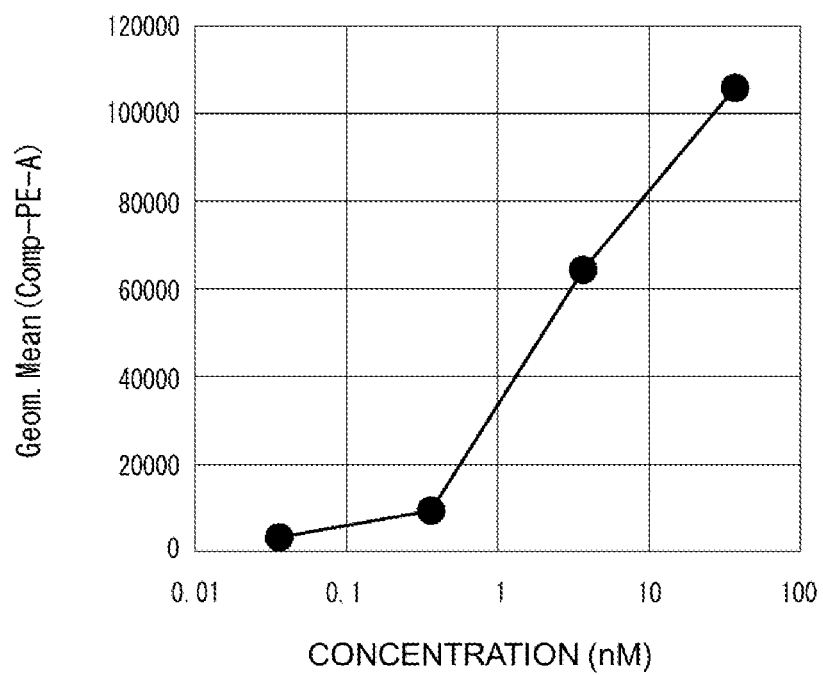
FIG. 26 shows the results of analysis using a flow cytometer of the affinity of an enzyme-fused antibody, MOG01 IgG4PE(R409K)-ASM to human MOG/L929 cells. The vertical axis shows the average fluorescence intensity, and the horizontal axis shows the antibody concentration.

The affinity of MOG01 IgG4PE(R409K)-ASM to MOG-expressing cells was examined by the same method as that of Example 23, and the results are shown in FIG. 26. Moreover, the affinity to MOG soluble antigen was examined by the same method as that of Example 8. As a result, the dissociation constant (KD value) of MOG01 IgG4PE (R409K)-ASM was $2.9 \times 10^{-9}$ (M), and excellent affinity was observed.

That an anti-ASM antibody (manufactured by LSBio) binds to produced MOG01 IgG4PE(R409K)-ASM and AVM IgG4PE(R409K)-ASM was confirmed by the ELISA method shown below.

In the ELISA, MOG01 IgG4PE(R409K)-ASM and AVM IgG4PE(R409K)-ASM were immobilized (100 ng/50 μL) on MAXISORP (manufactured by NUNC), and the sites to which MOG01 IgG4PE(R409K)-ASM and AVM IgG4PE (R409K)-ASM were not bound were blocked using Super-Block Blocking Buffer (manufactured by Thermo Fisher Scientific Inc.). As a negative control, a plate on which anti-MOG01IgG antibody and anti-AVMIgG antibody were immobilized (50 ng/50 μL) was also prepared. The anti-ASM antibody which was diluted to a concentration of 0.2, 1 or 5 μg/mL with PBS-T was added to the wells and reacted at room temperature for an hour, and then the wells were washed with PBS-T.

Next, a solution obtained by diluting horseradish peroxidase-labeled anti-Mouse Immunoglobulins antibody (manufactured by Dako) with PBS-T was added to the wells and reacted at room temperature for an hour. A TMB chromogenic substrate solution (manufactured by DAKO) was added, and the plates were incubated at room temperature. The chromogenic reaction was stopped by adding 2 M hydrochloric acid to the wells, and the absorbances at the wavelength of 450 nm (reference wavelength of 570 nm) were measured. The results obtained are shown in FIG. 27.

Figure 27:
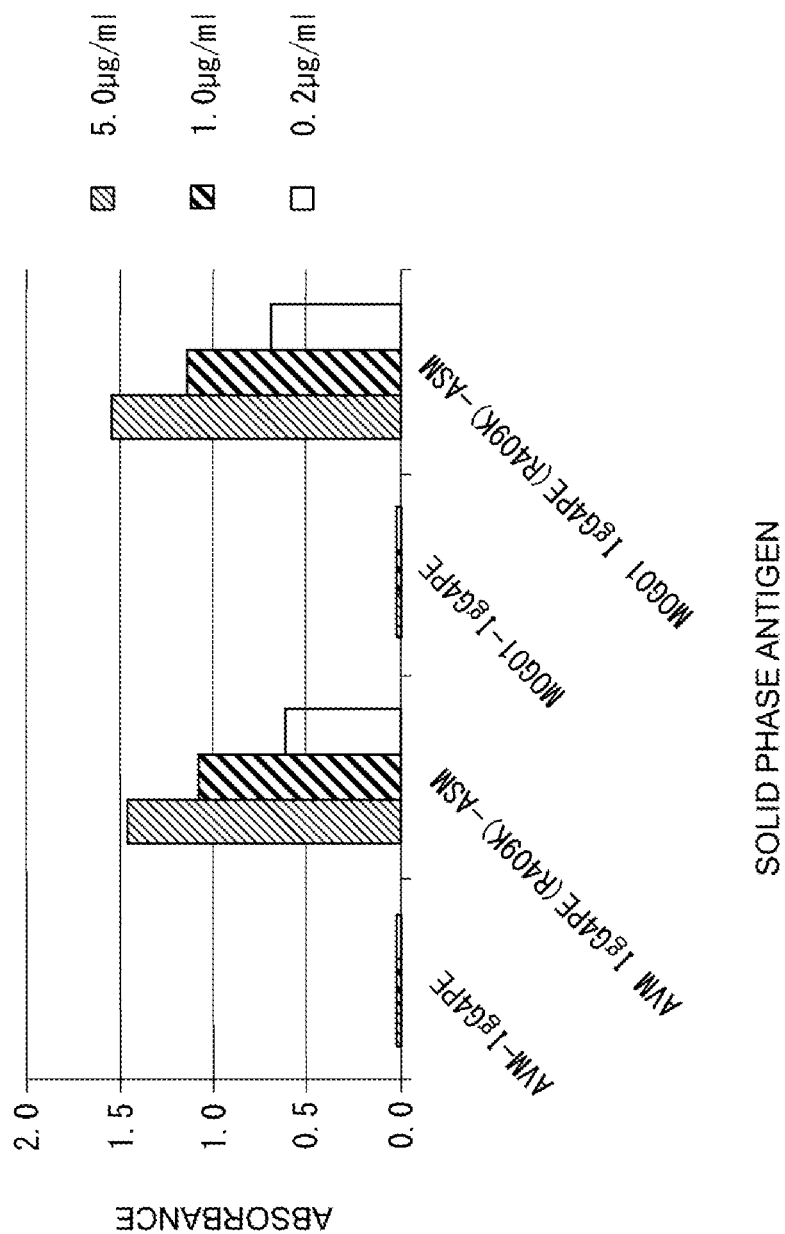
FIG. 27 shows the results of analysis by ELISA method of the affinities of anti-ASM antibodies (manufactured by LSBio) to MOG01 IgG4PE(R409K)-ASM and AVM IgG4PE(R409K)-ASM. The vertical axis shows the absorbance, and the horizontal axis shows the names of the immobilized antibodies. MOG01 IgG4PE and AVM IgG4PE were used as negative controls. The bars shaded with thin lines show the data of the anti-ASM antibodies at 5 μg/mL, and the bars shaded with thick lines show the data of the anti-ASM antibodies at 1 μg/mL. The white bars show the data of the anti-ASM antibodies at 0.2 μg/mL.

As shown in FIG. 27, it was shown that the anti-ASM antibody recognized and bound to the produced ASM-fused antibodies. Moreover, as a result of measurement of the sphingomyelinase activities of produced MOG01 IgG4PE (R409K)-ASM and AVM IgG4PE(R409K)-ASM using a sphingomyelinase activity measurement kit (manufactured by Echelon Biosciences), it was confirmed that the produced ASM-fused antibodies had enzymatic activities.

From the above results, it was confirmed that the enzyme-fused antibody obtained by fusing an enzyme to a MOG antibody maintains both the antigen binding activity and the enzymatic activity.

[Example 26] Evaluation of Mouse Brain Migration Properties of Enzyme-Fused Antibodies The mouse brain migration properties of the ASM-fused antibodies obtained in Example 24 were evaluated by the same method as that of Example 14. The antibody concentrations in the serum and the antibody amounts per unit brain weight in the brain tissues 10 days after administering the ASM-fused antibodies at 5 mg/kg are shown in FIGS. 28A and 28B.

As shown in FIGS. 28A and 28B, the antibody concentration of MOG01 IgG4PE(R409K)-ASM in the serum was not different from that of AVM IgG4PE(R409K)-ASM. On the other hand, it was shown that the antibody amount of MOG01 IgG4PE(R409K)-ASM in the brain increased to about 58 times the amount of AVM IgG4PE(R409K)-ASM.

The invention has been explained in detail using the specific aspects, but it is obvious for those skilled in the art that various changes and modifications can be made without departing from the spirit and scope of the invention. The present application is based on a Japanese patent application filed on Dec. 26, 2016 (patent application No. 2016-251106), which is incorporated by reference in its entirety.

SEQUENCE LISTING FREE TEXT

Definition of SEQ ID NO: 3-artificial sequence: amino acid sequence of VH of MOG01 excluding signal sequence
Definition of SEQ ID NO: 4-artificial sequence: amino acid sequence of HCDR1 of MOG01
Definition of SEQ ID NO: 5-artificial sequence: amino acid sequence of HCDR2 of MOG01
Definition of SEQ ID NO: 6-artificial sequence: amino acid sequence of HCDR3 of MOG01
Definition of SEQ ID NO: 9-artificial sequence: amino acid sequence of VL of MOG01 excluding signal sequence
Definition of SEQ ID NO: 10-artificial sequence: amino acid sequence of LCDR1 of MOG01
Definition of SEQ ID NO: 11-artificial sequence: amino acid sequence of LCDR2 of MOG01
Definition of SEQ ID NO: 12-artificial sequence: amino acid sequence of LCDR3 of MOG01
Definition of SEQ ID NO: 15-artificial sequence: amino acid sequence of VH of MOG09 excluding signal sequence
Definition of SEQ ID NO: 16-artificial sequence: amino acid sequence of HCDR1 of MOG09
Definition of SEQ ID NO: 17-artificial sequence: amino acid sequence of HCDR2 of MOG09
Definition of SEQ ID NO: 18-artificial sequence: amino acid sequence of HCDR3 of MOG09
Definition of SEQ ID NO: 21-artificial sequence: amino acid sequence of VL of MOG09 excluding signal sequence
Definition of SEQ ID NO: 22-artificial sequence: amino acid sequence of LCDR1 of MOG09
Definition of SEQ ID NO: 23-artificial sequence: amino acid sequence of LCDR2 of MOG09
Definition of SEQ ID NO: 24-artificial sequence: amino acid sequence of LCDR3 of MOG09
Definition of SEQ ID NO: 27-artificial sequence: amino acid sequence of VH of MOG14 excluding signal sequence
Definition of SEQ ID NO: 28-artificial sequence: amino acid sequence of HCDR1 of MOG14
Definition of SEQ ID NO: 29-artificial sequence: amino acid sequence of HCDR2 of MOG14
Definition of SEQ ID NO: 30-artificial sequence: amino acid sequence of HCDR3 of MOG14
Definition of SEQ ID NO: 33-artificial sequence: amino acid sequence of VL of MOG14 excluding signal sequence
Definition of SEQ ID NO: 34-artificial sequence: amino acid sequence of LCDR1 of MOG14
Definition of SEQ ID NO: 35-artificial sequence: amino acid sequence of LCDR2 of MOG14
Definition of SEQ ID NO: 36-artificial sequence: amino acid sequence of LCDR3 of MOG14
Definition of SEQ ID NO: 37-artificial sequence: nucleotide sequence of VHH of iMOG_3Rim1_S32 including signal sequence
Definition of SEQ ID NO: 38-artificial sequence: amino acid sequence of synthetic construct
Definition of SEQ ID NO: 39-artificial sequence: amino acid sequence of VHH of iMOG_3Rim1_S32 excluding signal sequence
Definition of SEQ ID NO: 40 (Thr Met Gly)-artificial sequence: amino acid sequence of CDR1 of iMOG_3Rim1_S32
Definition of SEQ ID NO: 41-artificial sequence: amino acid sequence of CDR2 of iMOG_3Rim1_S32
Definition of SEQ ID NO: 42-artificial sequence: amino acid sequence of CDR3 of iMOG 3Rim1 S32
Definition of SEQ ID NO: 43-artificial sequence: nucleotide sequence of primer 1
Definition of SEQ ID NO: 44-artificial sequence: nucleotide sequence of primer 2
Definition of SEQ ID NO: 45-artificial sequence: nucleotide sequence of primer 3
Definition of SEQ ID NO: 46-artificial sequence: nucleotide sequence of primer 4
Definition of SEQ ID NO: 47-artificial sequence: nucleotide sequence of primer 5
Definition of SEQ ID NO: 48-artificial sequence: nucleotide sequence of primer 6
Definition of SEQ ID NO: 49-artificial sequence: nucleotide sequence of primer 7
Definition of SEQ ID NO: 50-artificial sequence: nucleotide sequence of primer 8
Definition of SEQ ID NO: 51-artificial sequence: nucleotide sequence of primer 9
Definition of SEQ ID NO: 52-artificial sequence: nucleotide sequence of primer 10
Definition of SEQ ID NO: 53-artificial sequence: nucleotide sequence of primer 11
Definition of SEQ ID NO: 54-artificial sequence: nucleotide sequence of primer 12
Definition of SEQ ID NO: 55-artificial sequence: nucleotide sequence of primer 13
Definition of SEQ ID NO: 56-artificial sequence: nucleotide sequence of primer 14
Definition of SEQ ID NO: 57-artificial sequence: nucleotide sequence of primer 15

Definition of SEQ ID NO: 58-artificial sequence: nucleotide sequence of primer 16
Definition of SEQ ID NO: 59-artificial sequence: nucleotide sequence of primer 17
Definition of SEQ ID NO: 60-artificial sequence: nucleotide sequence of primer 18
Definition of SEQ ID NO: 61-artificial sequence: nucleotide sequence of primer 19
Definition of SEQ ID NO: 62-artificial sequence: nucleotide sequence of primer 20
Definition of SEQ ID NO: 63-artificial sequence: nucleotide sequence of primer 21
Definition of SEQ ID NO: 64-artificial sequence: nucleotide sequence of primer 22
Definition of SEQ ID NO: 65-artificial sequence: nucleotide sequence of primer 23
Definition of SEQ ID NO: 66-artificial sequence: nucleotide sequence of primer 24
Definition of SEQ ID NO: 69-artificial sequence: nucleotide sequence of rMOG-FLAG-Fc
Definition of SEQ ID NO: 70-artificial sequence: amino acid sequence of synthetic construct
Definition of SEQ ID NO: 71-artificial sequence: nucleotide sequence of rMOG-GST
Definition of SEQ ID NO: 72-artificial sequence: amino acid sequence of synthetic construct
Definition of SEQ ID NO: 79-artificial sequence: nucleotide sequence of primer 25
Definition of SEQ ID NO: 80-artificial sequence: nucleotide sequence of primer 26
Definition of SEQ ID NO: 81-artificial sequence: nucleotide sequence of primer 27
Definition of SEQ ID NO: 82-artificial sequence: nucleotide sequence of primer 28
Definition of SEQ ID NO: 83-artificial sequence: nucleotide sequence of primer 29
Definition of SEQ ID NO: 84-artificial sequence: nucleotide sequence of primer 30
Definition of SEQ ID NO: 85-artificial sequence: nucleotide sequence of primer 31
Definition of SEQ ID NO: 86-artificial sequence: nucleotide sequence of primer 32
Definition of SEQ ID NO: 87-artificial sequence: nucleotide sequence of primer 33
Definition of SEQ ID NO: 88-artificial sequence: nucleotide sequence of primer 34
Definition of SEQ ID NO: 89-artificial sequence: nucleotide sequence of primer 35
Definition of SEQ ID NO: 90-artificial sequence: nucleotide sequence of primer 36
Definition of SEQ ID NO: 91-artificial sequence: nucleotide sequence of primer 37
Definition of SEQ ID NO: 92-artificial sequence: nucleotide sequence of primer 38
Definition of SEQ ID NO: 93-artificial sequence: nucleotide sequence of primer 39
Definition of SEQ ID NO: 94-artificial sequence: nucleotide sequence of primer 40
Definition of SEQ ID NO: 95-artificial sequence: nucleotide sequence of primer 41
Definition of SEQ ID NO: 96-artificial sequence: nucleotide sequence of primer 42
Definition of SEQ ID NO: 97-artificial sequence: nucleotide sequence of primer 43
Definition of SEQ ID NO: 98-artificial sequence: nucleotide sequence of hHER2-GST
Definition of SEQ ID NO: 99-artificial sequence: amino acid sequence of synthetic construct
Definition of SEQ ID NO: 100-artificial sequence: nucleotide sequence of hMOG-FLAG-Fc (including signal sequence)
Definition of SEQ ID NO: 101-artificial sequence: amino acid sequence of hMOG-FLAG-Fc (including signal sequence)
Definition of SEQ ID NO: 102-artificial sequence: nucleotide sequence of mMOG-FLAG-Fc (including signal sequence)
Definition of SEQ ID NO: 103-artificial sequence: amino acid sequence of mMOG-FLAG-Fc (including signal sequence)
Definition of SEQ ID NO: 104-artificial sequence: nucleotide sequence of hMOG-GST (including signal sequence)
Definition of SEQ ID NO: 105-artificial sequence: amino acid sequence of hMOG-GST (including signal sequence)
Definition of SEQ ID NO: 106-artificial sequence: nucleotide sequence of mMOG-GST (including signal sequence)
Definition of SEQ ID NO: 107-artificial sequence: amino acid sequence of mMOG-GST (including signal sequence)
Definition of SEQ ID NO: 108-artificial sequence: nucleotide sequence of antibody sequence of pCI-AVM-hLG4PE(R409K/S354C/T366W)-FLAG tag (excluding signal sequence)
Definition of SEQ ID NO: 109-artificial sequence: amino acid sequence of antibody sequence of pCI-AVM-hLG4PE(R409K/S354C/T366W)-FLAG tag (excluding signal sequence)
Definition of SEQ ID NO: 110-artificial sequence: nucleotide sequence of antibody sequence of pCI-MOG01-hLG4PE(R409K/Y349C/T366S/L368A/Y407V)-His tag (excluding signal sequence)
Definition of SEQ ID NO: 111-artificial sequence: amino acid sequence of antibody sequence of pCI-MOG01-hLG4PE(R409K/Y349C/T366S/L368A/Y407V)-His tag (excluding signal sequence)
Definition of SEQ ID NO: 112-artificial sequence: nucleotide sequence of antibody sequence of pCI-AVM-hLG4PE(R409K)-linker-MOG01VL-CL (excluding signal sequence)
Definition of SEQ ID NO: 113-artificial sequence: amino acid sequence of antibody sequence of pCI-AVM-hLG4PE(R409K)-linker-MOG01VL-CL (excluding signal sequence)
Definition of SEQ ID NO: 114-artificial sequence: nucleotide sequence of antibody sequence of pCI-MOG01VH-CH (excluding signal sequence)
Definition of SEQ ID NO: 115-artificial sequence: amino acid sequence of antibody sequence of pCI-MOG01VH-CH (excluding signal sequence)
Definition of SEQ ID NO: 116-artificial sequence: nucleotide sequence of antibody sequence of pCI-AVM-hLG4PE(R409K/S354C/T366W)-linker-MOG01scFv-FLAG tag (excluding signal sequence)
Definition of SEQ ID NO: 117-artificial sequence: amino acid sequence of antibody sequence of pCI-AVM-hLG4PE(R409K/S354C/T366W)-linker-MOG01scFv-FLAG tag (excluding signal sequence)
Definition of SEQ ID NO: 118-artificial sequence: nucleotide sequence of antibody sequence of pCI- AVM-hLG4PE(R409K/Y349C/T366S/L368A/Y407V)-His tag (excluding signal sequence)

Definition of SEQ ID NO: 119-artificial sequence: amino acid sequence of antibody sequence of pCI-AVM-hLG4PE(R409K/Y349C/T366S/L368A/Y407V)-His tag (excluding signal sequence)

Definition of SEQ ID NO: 120-artificial sequence: nucleotide sequence of antibody sequence of pCI-AVM-hLG4PE(R409K)_MOG01scFv2 (excluding signal sequence)

Definition of SEQ ID NO: 121-artificial sequence: amino acid sequence of antibody sequence of pCI-AVM-hLG4PE(R409K)_MOG01scFv2 (excluding signal sequence)

Definition of SEQ ID NO: 122-artificial sequence: nucleotide sequence of antibody sequence of pCI-AVM-hLG4PE(R409K)_MOG01scFv3 (excluding signal sequence)

Definition of SEQ ID NO: 123-artificial sequence: amino acid sequence of antibody sequence of pCI-AVM-hLG4PE(R409K)_MOG01scFv3 (excluding signal sequence)

Definition of SEQ ID NO: 124-artificial sequence: nucleotide sequence of antibody sequence of pCI-AVM-hLG4PE(R409K)_MOG01scFv4 (excluding signal sequence)

Definition of SEQ ID NO: 125-artificial sequence: amino acid sequence of antibody sequence of pCI-AVM-hLG4PE(R409K)_MOG01scFv4 (excluding signal sequence)

Definition of SEQ ID NO: 126-artificial sequence: nucleotide sequence of antibody sequence of pCI-AVM-hLG4PE(R409K)_MOG01scFv5 (excluding signal sequence)

Definition of SEQ ID NO: 127-artificial sequence: amino acid sequence of antibody sequence of pCI-AVM-hLG4PE(R409K)_MOG01scFv5 (excluding signal sequence)

Definition of SEQ ID NO: 128-artificial sequence: nucleotide sequence of antibody sequence of pCI-AVM-hLG4PE(R409K)_MOG01scFv6 (excluding signal sequence)

Definition of SEQ ID NO: 129-artificial sequence: amino acid sequence of antibody sequence of pCI-AVM-hLG4PE(R409K)_MOG01scFv6 (excluding signal sequence)

Definition of SEQ ID NO: 130-artificial sequence: nucleotide sequence of antibody sequence of pCI-AVM-hLG4PE(R409K)_MOG01scFv7 (excluding signal sequence)

Definition of SEQ ID NO: 131-artificial sequence: amino acid sequence of antibody sequence of pCI-AVM-hLG4PE(R409K)_MOG01scFv7 (excluding signal sequence)

Definition of SEQ ID NO: 132-artificial sequence: nucleotide sequence of antibody sequence of pCI-AVM-hLG4PE(R409K)_MOG01scFv8 (excluding signal sequence)

Definition of SEQ ID NO: 133-artificial sequence: amino acid sequence of antibody sequence of pCI-AVM-hLG4PE(R409K)_MOG01scFv8 (excluding signal sequence)

Definition of SEQ ID NO: 134-artificial sequence: nucleotide sequence of antibody sequence of pCI-AVM-hLG4PE(R409K)_MOG01scFv9 (excluding signal sequence)

Definition of SEQ ID NO: 135-artificial sequence: amino acid sequence of antibody sequence of pCI-AVM-hLG4PE(R409K)_MOG01scFv9 (excluding signal sequence)

Definition of SEQ ID NO: 136-artificial sequence: nucleotide sequence of antibody sequence of pCI-AVM-hLG4PE(R409K)_MOG01scFv10 (excluding signal sequence)

Definition of SEQ ID NO: 137-artificial sequence: amino acid sequence of antibody sequence of pCI-AVM-hLG4PE(R409K)_MOG01scFv10 (excluding signal sequence)

Definition of SEQ ID NO: 138-artificial sequence: nucleotide sequence of antibody sequence of pCI-AVM-hLG4PE(R409K)_MOG01scFv11 (excluding signal sequence)

Definition of SEQ ID NO: 139-artificial sequence: amino acid sequence of antibody sequence of pCI-AVM-hLG4PE(R409K)_MOG01scFv11 (excluding signal sequence)

Definition of SEQ ID NO: 140-artificial sequence: nucleotide sequence of antibody sequence of pCI-AVM-hLG4PE(R409K)-linker-AVMVL-CL (excluding signal sequence)

Definition of SEQ ID NO: 141-artificial sequence: amino acid sequence of antibody sequence of pCI-AVM-hLG4PE(R409K)-linker-AVMVL-CL (excluding signal sequence)

Definition of SEQ ID NO: 142-artificial sequence: nucleotide sequence of antibody sequence of pCI-AVMVH-CH (excluding signal sequence)

Definition of SEQ ID NO: 143-artificial sequence: amino acid sequence of antibody sequence of pCI-AVMVH-CH (excluding signal sequence)

Definition of SEQ ID NO: 144-artificial sequence: nucleotide sequence of antibody sequence of pCI-AVM-hLG4PE(R409K/S354C/T366W)-linker-AVMscFv-FLAG tag (excluding signal sequence)

Definition of SEQ ID NO: 145-artificial sequence: amino acid sequence of antibody sequence of pCI-AVM-hLG4PE(R409K/S354C/T366W)-linker-AVMscFv-FLAG tag (excluding signal sequence)

Definition of SEQ ID NO: 146-artificial sequence: nucleotide sequence of antibody sequence of pCI-AVM-hLG4PE(R409K)_AVMscFv3 (excluding signal sequence)

Definition of SEQ ID NO: 147-artificial sequence: amino acid sequence of antibody sequence of pCI-AVM-hLG4PE(R409K)_AVMscFv3 (excluding signal sequence)

Definition of SEQ ID NO: 148-artificial sequence: nucleotide sequence of antibody sequence of pCI-AVM-hLG4PE(R409K)_AVMscFv5 (excluding signal sequence)

Definition of SEQ ID NO: 149-artificial sequence: amino acid sequence of antibody sequence of pCI-AVM-hLG4PE(R409K) AVMscFv5 (excluding signal sequence)

Definition of SEQ ID NO: 150-artificial sequence: nucleotide sequence of Acid Sphingomyelinase (ASM)

Definition of SEQ ID NO: 151-artificial sequence: nucleotide sequence encoding VH (excluding signal sequence) of MOG301

Definition of SEQ ID NO: 152-artificial sequence: amino acid sequence of VH (excluding signal sequence) of MOG301

Definition of SEQ ID NO: 153-artificial sequence: amino acid sequence of HCDR1 of MOG301
Definition of SEQ ID NO: 154-artificial sequence: amino acid sequence of HCDR2 of MOG301
Definition of SEQ ID NO: 155-artificial sequence: amino acid sequence of HCDR3 of MOG301
Definition of SEQ ID NO: 156-artificial sequence: nucleotide sequence encoding VL (excluding signal sequence) of MOG301
Definition of SEQ ID NO: 157-artificial sequence: amino acid sequence of VL (excluding signal sequence) of MOG301
Definition of SEQ ID NO: 158-artificial sequence: amino acid sequence of LCDR1 of MOG301
Definition of SEQ ID NO: 159-artificial sequence: amino acid sequence of LCDR2 of MOG301
Definition of SEQ ID NO: 160-artificial sequence: amino acid sequence of LCDR3 of MOG301
Definition of SEQ ID NO: 161-artificial sequence: nucleotide sequence encoding VH (excluding signal sequence) of MOG303
Definition of SEQ ID NO: 162-artificial sequence: amino acid sequence of VH (excluding signal sequence) of MOG303
Definition of SEQ ID NO: 163-artificial sequence: amino acid sequence of HCDR1 of MOG303
Definition of SEQ ID NO: 164-artificial sequence: amino acid sequence of HCDR2 of MOG303
Definition of SEQ ID NO: 165-artificial sequence: amino acid sequence of HCDR3 of MOG303
Definition of SEQ ID NO: 166-artificial sequence: nucleotide sequence encoding VL (excluding signal sequence) of MOG303
Definition of SEQ ID NO: 167-artificial sequence: amino acid sequence of VL (excluding signal sequence) of MOG303
Definition of SEQ ID NO: 168-artificial sequence: amino acid sequence of LCDR1 of MOG303
Definition of SEQ ID NO: 169-artificial sequence: amino acid sequence of LCDR2 of MOG303
Definition of SEQ ID NO: 170-artificial sequence: amino acid sequence of LCDR3 of MOG303
Definition of SEQ ID NO: 171-artificial sequence: nucleotide sequence encoding VH (excluding signal sequence) of MOG307
Definition of SEQ ID NO: 172-artificial sequence: amino acid sequence of VH (excluding signal sequence) of MOG307
Definition of SEQ ID NO: 173-artificial sequence: amino acid sequence of HCDR1 of MOG307
Definition of SEQ ID NO: 174-artificial sequence: amino acid sequence of HCDR2 of MOG307
Definition of SEQ ID NO: 175-artificial sequence: amino acid sequence of HCDR3 of MOG307
Definition of SEQ ID NO: 176-artificial sequence: nucleotide sequence encoding VL (excluding signal sequence) of MOG307
Definition of SEQ ID NO: 177-artificial sequence: amino acid sequence of VL (excluding signal sequence) of MOG307
Definition of SEQ ID NO: 178-artificial sequence: amino acid sequence of LCDR1 of MOG307
Definition of SEQ ID NO: 179-artificial sequence: amino acid sequence of LCDR2 of MOG307
Definition of SEQ ID NO: 180-artificial sequence: amino acid sequence of LCDR3 of MOG307
Definition of SEQ ID NO: 181-artificial sequence: nucleotide sequence encoding VH (excluding signal sequence) of MOG310
Definition of SEQ ID NO: 182-artificial sequence: amino acid sequence of VH (excluding signal sequence) of MOG310
Definition of SEQ ID NO: 183-artificial sequence: amino acid sequence of HCDR1 of MOG310
Definition of SEQ ID NO: 184-artificial sequence: amino acid sequence of HCDR2 of MOG310
Definition of SEQ ID NO: 185-artificial sequence: amino acid sequence of HCDR3 of MOG310
Definition of SEQ ID NO: 186-artificial sequence: nucleotide sequence encoding VL (excluding signal sequence) of MOG310
Definition of SEQ ID NO: 187-artificial sequence: amino acid sequence of VL (excluding signal sequence) of MOG310
Definition of SEQ ID NO: 188-artificial sequence: amino acid sequence of LCDR1 of MOG310
Definition of SEQ ID NO: 189-artificial sequence: amino acid sequence of LCDR2 of MOG310
Definition of SEQ ID NO: 190-artificial sequence: amino acid sequence of LCDR3 of MOG310
Definition of SEQ ID NO: 191-artificial sequence: nucleotide sequence encoding VH (excluding signal sequence) of MOG312
Definition of SEQ ID NO: 192-artificial sequence: amino acid sequence of VH (excluding signal sequence) of MOG312
Definition of SEQ ID NO: 193-artificial sequence: amino acid sequence of HCDR1 of MOG312
Definition of SEQ ID NO: 194-artificial sequence: amino acid sequence of HCDR2 of MOG312
Definition of SEQ ID NO: 195-artificial sequence: amino acid sequence of HCDR3 of MOG312
Definition of SEQ ID NO: 196-artificial sequence: nucleotide sequence encoding VL (excluding signal sequence) of MOG312
Definition of SEQ ID NO: 197-artificial sequence: amino acid sequence of VL (excluding signal sequence) of MOG312
Definition of SEQ ID NO: 198-artificial sequence: amino acid sequence of LCDR1 of MOG312
Definition of SEQ ID NO: 199-artificial sequence: amino acid sequence of LCDR2 of MOG312
Definition of SEQ ID NO: 200-artificial sequence: amino acid sequence of LCDR3 of MOG312
Definition of SEQ ID NO: 201-artificial sequence: nucleotide sequence encoding VH (excluding signal sequence) of MOG326
Definition of SEQ ID NO: 202-artificial sequence: amino acid sequence of VH (excluding signal sequence) of MOG326
Definition of SEQ ID NO: 203-artificial sequence: amino acid sequence of HCDR1 of MOG326
Definition of SEQ ID NO: 204-artificial sequence: amino acid sequence of HCDR2 of MOG326
Definition of SEQ ID NO: 205-artificial sequence: amino acid sequence of HCDR3 of MOG326
Definition of SEQ ID NO: 206-artificial sequence: nucleotide sequence encoding VL (excluding signal sequence) of MOG326
Definition of SEQ ID NO: 207-artificial sequence: amino acid sequence of VL (excluding signal sequence) of MOG326

Definition of SEQ ID NO: 208-artificial sequence: amino acid sequence of LCDR1 of MOG326
Definition of SEQ ID NO: 209-artificial sequence: amino acid sequence of LCDR2 of MOG326
Definition of SEQ ID NO: 210-artificial sequence: amino acid sequence of LCDR3 of MOG326
Definition of SEQ ID NO: 211-artificial sequence: nucleotide sequence encoding VH (excluding signal sequence) of MOG329
Definition of SEQ ID NO: 212-artificial sequence: amino acid sequence of VH (excluding signal sequence) of MOG329
Definition of SEQ ID NO: 213-artificial sequence: amino acid sequence of HCDR1 of MOG329
Definition of SEQ ID NO: 214-artificial sequence: amino acid sequence of HCDR2 of MOG329
Definition of SEQ ID NO: 215-artificial sequence: amino acid sequence of HCDR3 of MOG329
Definition of SEQ ID NO: 216-artificial sequence: nucleotide sequence encoding VL (excluding signal sequence) of MOG329
Definition of SEQ ID NO: 217-artificial sequence: amino acid sequence of VL (excluding signal sequence) of MOG329
Definition of SEQ ID NO: 218-artificial sequence: amino acid sequence of LCDR1 of MOG329
Definition of SEQ ID NO: 219-artificial sequence: amino acid sequence of LCDR2 of MOG329
Definition of SEQ ID NO: 220-artificial sequence: amino acid sequence of LCDR3 of MOG329
Definition of SEQ ID NO: 221-artificial sequence: nucleotide sequence encoding VH (excluding signal sequence) of MOG446
Definition of SEQ ID NO: 222-artificial sequence: amino acid sequence of VH (excluding signal sequence) of MOG446
Definition of SEQ ID NO: 223-artificial sequence: amino acid sequence of HCDR1 of MOG446
Definition of SEQ ID NO: 224-artificial sequence: amino acid sequence of HCDR2 of MOG446
Definition of SEQ ID NO: 225-artificial sequence: amino acid sequence of HCDR3 of MOG446
Definition of SEQ ID NO: 226-artificial sequence: nucleotide sequence encoding VL (excluding signal sequence) of MOG446
Definition of SEQ ID NO: 227-artificial sequence: amino acid sequence of VL (excluding signal sequence) of MOG446
Definition of SEQ ID NO: 228-artificial sequence: amino acid sequence of LCDR1 of MOG446
Definition of SEQ ID NO: 229-artificial sequence: amino acid sequence of LCDR2 of MOG446
Definition of SEQ ID NO: 230-artificial sequence: amino acid sequence of LCDR3 of MOG446
Definition of SEQ ID NO: 231-artificial sequence: nucleotide sequence encoding VH (excluding signal sequence) of MOG456
Definition of SEQ ID NO: 232-artificial sequence: amino acid sequence of VH (excluding signal sequence) of MOG456
Definition of SEQ ID NO: 233-artificial sequence: amino acid sequence of HCDR1 of MOG456
Definition of SEQ ID NO: 234-artificial sequence: amino acid sequence of HCDR2 of MOG456
Definition of SEQ ID NO: 235-artificial sequence: amino acid sequence of HCDR3 of MOG456
Definition of SEQ ID NO: 236-artificial sequence: nucleotide sequence encoding VL (excluding signal sequence) of MOG456
Definition of SEQ ID NO: 237-artificial sequence: amino acid sequence of VL (excluding signal sequence) of MOG456
Definition of SEQ ID NO: 238-artificial sequence: amino acid sequence of LCDR1 of MOG456
Definition of SEQ ID NO: 239-artificial sequence: amino acid sequence of LCDR2 of MOG456
Definition of SEQ ID NO: 240-artificial sequence: amino acid sequence of LCDR3 of MOG456
Definition of SEQ ID NO: 241-artificial sequence: nucleotide sequence encoding VH (excluding signal sequence) of MOG473
Definition of SEQ ID NO: 242-artificial sequence: amino acid sequence of VH (excluding signal sequence) of MOG473
Definition of SEQ ID NO: 243-artificial sequence: amino acid sequence of HCDR1 of MOG473
Definition of SEQ ID NO: 244-artificial sequence: amino acid sequence of HCDR2 of MOG473
Definition of SEQ ID NO: 245-artificial sequence: amino acid sequence of HCDR3 of MOG473
Definition of SEQ ID NO: 246-artificial sequence: nucleotide sequence encoding VL (excluding signal sequence) of MOG473
Definition of SEQ ID NO: 247-artificial sequence: amino acid sequence of VL (excluding signal sequence) of MOG473
Definition of SEQ ID NO: 248-artificial sequence: amino acid sequence of LCDR1 of MOG473
Definition of SEQ ID NO: 249-artificial sequence: amino acid sequence of LCDR2 of MOG473
Definition of SEQ ID NO: 250-artificial sequence: amino acid sequence of LCDR3 of MOG473
Definition of SEQ ID NO: 251-artificial sequence: nucleotide sequence encoding VH (excluding signal sequence) of MOG426
Definition of SEQ ID NO: 252-artificial sequence: amino acid sequence of VH (excluding signal sequence) of MOG426
Definition of SEQ ID NO: 253-artificial sequence: nucleotide sequence encoding VL (excluding signal sequence) of MOG426
Definition of SEQ ID NO: 254-artificial sequence: amino acid sequence of VL (excluding signal sequence) of MOG426
Definition of SEQ ID NO: 255-artificial sequence: nucleotide sequence encoding VH (excluding signal sequence) of MOG428
Definition of SEQ ID NO: 256-artificial sequence: amino acid sequence of VH (excluding signal sequence) of MOG428
Definition of SEQ ID NO: 257-artificial sequence: nucleotide sequence encoding VL (excluding signal sequence) of MOG428
Definition of SEQ ID NO: 258-artificial sequence: amino acid sequence of VL (excluding signal sequence) of MOG428
Definition of SEQ ID NO: 259-artificial sequence: nucleotide sequence encoding VH (excluding signal sequence) of MOG313
Definition of SEQ ID NO: 260-artificial sequence: amino acid sequence of VH (excluding signal sequence) of MOG313

Definition of SEQ ID NO: 261-artificial sequence: nucleotide sequence encoding VL (excluding signal sequence) of MOG313
Definition of SEQ ID NO: 262-artificial sequence: amino acid sequence of VL (excluding signal sequence) of MOG313
Definition of SEQ ID NO: 263-artificial sequence: nucleotide sequence encoding VH (excluding signal sequence) of MOG314
Definition of SEQ ID NO: 264-artificial sequence: amino acid sequence of VH (excluding signal sequence) of MOG314
Definition of SEQ ID NO: 265-artificial sequence: nucleotide sequence encoding VL (excluding signal sequence) of MOG314
Definition of SEQ ID NO: 266-artificial sequence: amino acid sequence of VL (excluding signal sequence) of MOG314
Definition of SEQ ID NO: 267-artificial sequence: nucleotide sequence encoding VH (excluding signal sequence) of MOG315
Definition of SEQ ID NO: 268-artificial sequence: amino acid sequence of VH (excluding signal sequence) of MOG315
Definition of SEQ ID NO: 269-artificial sequence: nucleotide sequence encoding VL (excluding signal sequence) of MOG315
Definition of SEQ ID NO: 270-artificial sequence: amino acid sequence of VL (excluding signal sequence) of MOG315
Definition of SEQ ID NO: 271-artificial sequence: nucleotide sequence encoding VH (excluding signal sequence) of MOG331
Definition of SEQ ID NO: 272-artificial sequence: amino acid sequence of VH (excluding signal sequence) of MOG331
Definition of SEQ ID NO: 273-artificial sequence: nucleotide sequence encoding VL (excluding signal sequence) of MOG331
Definition of SEQ ID NO: 274-artificial sequence: amino acid sequence of VL (excluding signal sequence) of MOG331
Definition of SEQ ID NO: 275-artificial sequence: nucleotide sequence encoding VH (excluding signal sequence) of MOG357
Definition of SEQ ID NO: 276-artificial sequence: amino acid sequence of VH (excluding signal sequence) of MOG357
Definition of SEQ ID NO: 277-artificial sequence: nucleotide sequence encoding VL (excluding signal sequence) of MOG357
Definition of SEQ ID NO: 278-artificial sequence: amino acid sequence of VL (excluding signal sequence) of MOG357
Definition of SEQ ID NO: 279-artificial sequence: nucleotide sequence encoding VH (excluding signal sequence) of MOG476
Definition of SEQ ID NO: 280-artificial sequence: amino acid sequence of VH (excluding signal sequence) of MOG476
Definition of SEQ ID NO: 281-artificial sequence: nucleotide sequence encoding VL (excluding signal sequence) of MOG476
Definition of SEQ ID NO: 282-artificial sequence: amino acid sequence of VL (excluding signal sequence) of MOG476
Definition of SEQ ID NO: 283-artificial sequence: nucleotide sequence encoding VH (excluding signal sequence) of MOG323
Definition of SEQ ID NO: 284-artificial sequence: amino acid sequence of VH (excluding signal sequence) of MOG323
Definition of SEQ ID NO: 285-artificial sequence: nucleotide sequence encoding VL (excluding signal sequence) of MOG323
Definition of SEQ ID NO: 286-artificial sequence: amino acid sequence of VL (excluding signal sequence) of MOG323
Definition of SEQ ID NO: 287-artificial sequence: nucleotide sequence encoding VH (excluding signal sequence) of MOG341
Definition of SEQ ID NO: 288-artificial sequence: amino acid sequence of VH (excluding signal sequence) of MOG341
Definition of SEQ ID NO: 289-artificial sequence: nucleotide sequence encoding VL (excluding signal sequence) of MOG341
Definition of SEQ ID NO: 290-artificial sequence: amino acid sequence of VL (excluding signal sequence) of MOG341
Definition of SEQ ID NO: 291-artificial sequence: nucleotide sequence encoding VH (excluding signal sequence) of MOG354
Definition of SEQ ID NO: 292-artificial sequence: amino acid sequence of VH (excluding signal sequence) of MOG354
Definition of SEQ ID NO: 293-artificial sequence: nucleotide sequence encoding VL (excluding signal sequence) of MOG354
Definition of SEQ ID NO: 294-artificial sequence: amino acid sequence of VL (excluding signal sequence) of MOG354
Definition of SEQ ID NO: 295-artificial sequence: nucleotide sequence encoding VH (excluding signal sequence) of MOG355
Definition of SEQ ID NO: 296-artificial sequence: amino acid sequence of VH (excluding signal sequence) of MOG355
Definition of SEQ ID NO: 297-artificial sequence: nucleotide sequence encoding VL (excluding signal sequence) of MOG355
Definition of SEQ ID NO: 298-artificial sequence: amino acid sequence of VL (excluding signal sequence) of MOG355
Definition of SEQ ID NO: 299-artificial sequence: nucleotide sequence encoding VH (excluding signal sequence) of MOG308
Definition of SEQ ID NO: 300-artificial sequence: amino acid sequence of VH (excluding signal sequence) of MOG308
Definition of SEQ ID NO: 301-artificial sequence: nucleotide sequence encoding VL (excluding signal sequence) of MOG308
Definition of SEQ ID NO: 302-artificial sequence: amino acid sequence of VL (excluding signal sequence) of MOG308
Definition of SEQ ID NO: 303-artificial sequence: nucleotide sequence encoding VH (excluding signal sequence) of MOG316
Definition of SEQ ID NO: 304-artificial sequence: amino acid sequence of VH (excluding signal sequence) of MOG316

Definition of SEQ ID NO: 305-artificial sequence: nucleotide sequence encoding VL (excluding signal sequence) of MOG316
Definition of SEQ ID NO: 306-artificial sequence: amino acid sequence of VL (excluding signal sequence) of MOG316
Definition of SEQ ID NO: 307-artificial sequence: nucleotide sequence encoding VH (excluding signal sequence) of MOG319
Definition of SEQ ID NO: 308-artificial sequence: amino acid sequence of VH (excluding signal sequence) of MOG319
Definition of SEQ ID NO: 309-artificial sequence: nucleotide sequence encoding VL (excluding signal sequence) of MOG319
Definition of SEQ ID NO: 310-artificial sequence: amino acid sequence of VL (excluding signal sequence) of MOG319
Definition of SEQ ID NO: 311-artificial sequence: nucleotide sequence encoding VH (excluding signal sequence) of MOG320
Definition of SEQ ID NO: 312-artificial sequence: amino acid sequence of VH (excluding signal sequence) of MOG320
Definition of SEQ ID NO: 313-artificial sequence: nucleotide sequence encoding VL (excluding signal sequence) of MOG320
Definition of SEQ ID NO: 314-artificial sequence: amino acid sequence of VL (excluding signal sequence) of MOG320
Definition of SEQ ID NO: 315-artificial sequence: nucleotide sequence encoding VH (excluding signal sequence) of MOG338
Definition of SEQ ID NO: 316-artificial sequence: amino acid sequence of VH (excluding signal sequence) of MOG338
Definition of SEQ ID NO: 317-artificial sequence: nucleotide sequence encoding VL (excluding signal sequence) of MOG338
Definition of SEQ ID NO: 318-artificial sequence: amino acid sequence of VL (excluding signal sequence) of MOG338
Definition of SEQ ID NO: 319-artificial sequence: nucleotide sequence encoding VH (excluding signal sequence) of MOG352
Definition of SEQ ID NO: 320-artificial sequence: amino acid sequence of VH (excluding signal sequence) of MOG352
Definition of SEQ ID NO: 321-artificial sequence: nucleotide sequence encoding VL (excluding signal sequence) of MOG352
Definition of SEQ ID NO: 322-artificial sequence: amino acid sequence of VL (excluding signal sequence) of MOG352
Definition of SEQ ID NO: 323-artificial sequence: nucleotide sequence encoding VH (excluding signal sequence) of MOG359
Definition of SEQ ID NO: 324-artificial sequence: amino acid sequence of VH (excluding signal sequence) of MOG359
Definition of SEQ ID NO: 325-artificial sequence: nucleotide sequence encoding VL (excluding signal sequence) of MOG359
Definition of SEQ ID NO: 326-artificial sequence: amino acid sequence of VL (excluding signal sequence) of MOG359
Definition of SEQ ID NO: 327-artificial sequence: nucleotide sequence encoding VH (excluding signal sequence) of MOG478
Definition of SEQ ID NO: 328-artificial sequence: amino acid sequence of VH (excluding signal sequence) of MOG478
Definition of SEQ ID NO: 329-artificial sequence: nucleotide sequence encoding VL (excluding signal sequence) of MOG478
Definition of SEQ ID NO: 330-artificial sequence: amino acid sequence of VL (excluding signal sequence) of MOG478
Definition of SEQ ID NO: 331-artificial sequence: nucleotide sequence encoding VH (excluding signal sequence) of MOG470
Definition of SEQ ID NO: 332-artificial sequence: amino acid sequence of VH (excluding signal sequence) of MOG470
Definition of SEQ ID NO: 333-artificial sequence: nucleotide sequence encoding VL (excluding signal sequence) of MOG470
Definition of SEQ ID NO: 334-artificial sequence: amino acid sequence of VL (excluding signal sequence) of MOG470
Definition of SEQ ID NO: 335-artificial sequence: nucleotide sequence encoding VH (excluding signal sequence) of MOG418
Definition of SEQ ID NO: 336-artificial sequence: amino acid sequence of VH (excluding signal sequence) of MOG418
Definition of SEQ ID NO: 337-artificial sequence: nucleotide sequence encoding VL (excluding signal sequence) of MOG418
Definition of SEQ ID NO: 338-artificial sequence: amino acid sequence of VL (excluding signal sequence) of MOG418

SEQUENCE LISTING

```
Sequence total quantity: 352
SEQ ID NO: 1            moltype = DNA  length = 438
FEATURE                 Location/Qualifiers
source                  1..438
                        mol_type = genomic DNA
                        organism = Homo sapiens
CDS                     1..438
                        protein_id = 339
                        translation = MNLGLSLIFLALILKGVQCQVQLQQSGAGLLKPSETLSLTCAVSGG
                        SFSGYYWTWIRQRPGKGLEWIGEINHRGSTDYNPSLKSRVTMSIDTSKSQFSLNLKSVT
                        AADTAVYYCARAAWGSCYDGTCYPAEYFQYWGQGTLVTVSS
SEQUENCE: 1
atgaacctcg ggctcagttt gattttcctt gccctcattt taaaaggtgt ccagtgtcag   60
```

```
gtacagctgc agcagtcagg cgcaggatta ttgaagcctt cggagaccct ttccctcacc   120
tgcgctgtgt ctggtgggtc cttcagtggt tactactgga cctggatccg ccagcgccca   180
gggaagggc tggagtggat tggagaaatc aatcatcgtg gaagcaccga ttacaacccg   240
tccctcaaga gtcgagtcac catgtcaata gacacgtcca agagccagtt ctccctgaat   300
ttgaaatctg tgaccgccgc ggacacggct gtgtattact gtgcgagagc cgcctggggg   360
tcttgttatg atgggacctg ctaccccgct gaatacttcc aatactgggg ccagggaacc   420
ctggtcaccg tctcctca                                                 438

SEQ ID NO: 2              moltype = AA  length = 146
FEATURE                   Location/Qualifiers
source                    1..146
                          mol_type = protein
                          organism = Homo sapiens
SEQUENCE: 2
MNLGLSLIFL ALILKGVQCQ VQLQQSGAGL LKPSETLSLT CAVSGGSFSG YYWTWIRQRP    60
GKGLEWIGEI NHRGSTDYNP SLKSRVTMSI DTSKSQFSLN LKSVTAADTA VYYCARAAWG   120
SCYDGTCYPA EYFQYWGQGT LVTVSS                                       146

SEQ ID NO: 3              moltype = AA  length = 127
FEATURE                   Location/Qualifiers
REGION                    1..127
                          note = Description of the artificial sequence: amino acid
                           sequence of VH of MOG01 excluding signal sequence
source                    1..127
                          mol_type = protein
                          organism = synthetic construct
SEQUENCE: 3
QVQLQQSGAG LLKPSETLSL TCAVSGGSFS GYYWTWIRQR PGKGLEWIGE INHRGSTDYN    60
PSLKSRVTMS IDTSKSQFSL NLKSVTAADT AVYYCARAAW GSCYDGTCYP AEYFQYWGQG   120
TLVTVSS                                                            127

SEQ ID NO: 4              moltype = AA  length = 5
FEATURE                   Location/Qualifiers
REGION                    1..5
                          note = Description of the artificial sequence: amino acid
                           sequence of HCDR1 of MOG01
source                    1..5
                          mol_type = protein
                          organism = synthetic construct
SEQUENCE: 4
GYYWT                                                                5

SEQ ID NO: 5              moltype = AA  length = 16
FEATURE                   Location/Qualifiers
REGION                    1..16
                          note = Description of the artificial sequence: amino acid
                           sequence of HCDR2 of MOG01
source                    1..16
                          mol_type = protein
                          organism = synthetic construct
SEQUENCE: 5
EINHRGSTDY NPSLKS                                                   16

SEQ ID NO: 6              moltype = AA  length = 19
FEATURE                   Location/Qualifiers
REGION                    1..19
                          note = Description of the artificial sequence: amino acid
                           sequence of HCDR3 of MOG01
source                    1..19
                          mol_type = protein
                          organism = synthetic construct
SEQUENCE: 6
AAWGSCYDGT CYPAEYFQY                                                19

SEQ ID NO: 7              moltype = DNA  length = 390
FEATURE                   Location/Qualifiers
source                    1..390
                          mol_type = genomic DNA
                          organism = Homo sapiens
CDS                       1..390
                          protein_id = 340
                          translation = MKLPVRLLVLMFWIPASSSQSALTQPASVSGSPGQSITISCTGTSR
                           DVGGYNYVSWYQQHPGKAPKLMIYDVNNRPSGVSNRFSGSKSGNTASLTISGLQAEDEA
                           DYFCSSYTSSSTPVVFGGGTKLTVL
SEQUENCE: 7
atgaagttgc ctgttaggct gttggtgctg atgttctgga ttcctgcttc agcagtcag    60
tctgccctga ctcagcctgc ctccgtgtct gggtctcctg gacagtcgat caccatctcc   120
tgcactggaa ccagccgtga cgttggtggt tataactatg tctcctggta ccaacaacac   180
ccaggcaaag ccccaaaact catgatttat gatgtcaata atcggccctc agggtgttct   240
```

```
aatcggttct ctggctccaa gtctggcaac acggcctccc tgaccatctc tgggctccag    300
gctgaggacg aggctgatta tttctgcagc tcatatacaa gcagtagcac ccctgtggta    360
ttcggcggtg ggaccaagct gaccgtccta                                      390
```

| SEQ ID NO: 8 | moltype = AA length = 130 |
|---|---|
| FEATURE | Location/Qualifiers |
| source | 1..130 |
| | mol_type = protein |
| | organism = Homo sapiens |

SEQUENCE: 8
```
MKLPVRLLVL MFWIPASSSQ SALTQPASVS GSPGQSITIS CTGTSRDVGG YNYVSWYQQH     60
PGKAPKLMIY DVNNRPSGVS NRFSGSKSGN TASLTISGLQ AEDEADYFCS SYTSSSTPVV    120
FGGGTKLTVL                                                           130
```

| SEQ ID NO: 9 | moltype = AA length = 111 |
|---|---|
| FEATURE | Location/Qualifiers |
| REGION | 1..111 |
| | note = Description of the artificial sequence: amino acid |
| | sequence of VL of MOG01 excluding signal sequence |
| source | 1..111 |
| | mol_type = protein |
| | organism = synthetic construct |

SEQUENCE: 9
```
QSALTQPASV SGSPGQSITI SCTGTSRDVG GYNYVSWYQQ HPGKAPKLMI YDVNNRPSGV     60
SNRFSGSKSG NTASLTISGL QAEDEADYFC SSYTSSSTPV VFGGGTKLTV L             111
```

| SEQ ID NO: 10 | moltype = AA length = 14 |
|---|---|
| FEATURE | Location/Qualifiers |
| REGION | 1..14 |
| | note = Description of the artificial sequence: amino acid |
| | sequence of LCDR1 of MOG01 |
| source | 1..14 |
| | mol_type = protein |
| | organism = synthetic construct |

SEQUENCE: 10
```
TGTSRDVGGY NYVS                                                       14
```

| SEQ ID NO: 11 | moltype = AA length = 7 |
|---|---|
| FEATURE | Location/Qualifiers |
| REGION | 1..7 |
| | note = Description of the artificial sequence: amino acid |
| | sequence of LCDR2 of MOG01 |
| source | 1..7 |
| | mol_type = protein |
| | organism = synthetic construct |

SEQUENCE: 11
```
DVNNRPS                                                                7
```

| SEQ ID NO: 12 | moltype = AA length = 11 |
|---|---|
| FEATURE | Location/Qualifiers |
| REGION | 1..11 |
| | note = Description of the artificial sequence: amino acid |
| | sequence of LCDR3 of MOG01 |
| source | 1..11 |
| | mol_type = protein |
| | organism = synthetic construct |

SEQUENCE: 12
```
SSYTSSSTPV V                                                          11
```

| SEQ ID NO: 13 | moltype = DNA length = 423 |
|---|---|
| FEATURE | Location/Qualifiers |
| source | 1..423 |
| | mol_type = genomic DNA |
| | organism = Homo sapiens |
| CDS | 1..423 |
| | protein_id = 341 |
| | translation = MNLGLSLIFLALILKGVQCQVQLQESGPGLVKSSETLSLTCAVSGH |
| | SISSAYYWGWIRQPPGKGLEWLGSIYHSGNTYYNPSLKSRVTISVDTSKNQFSLRLTSV |
| | TAADTAVYYCARGRGYSGYDSGMDVWGQGTTVTVSS |

SEQUENCE: 13
```
atgaacctcg ggctcagttt gatttccctt gccctcattt taaaaggtgt ccagtgtcag     60
gtgcagctgc aggagtcggg cccaggactg gtgaagtctt cggagaccct gtccctcacc    120
tgcgctgtct ctggtcactc catcagcagt gcttactact ggggctggat ccggcagccc    180
ccagggaagg ggctggagtg gcttgggagt atttatcata gtggaacac tactacaac     240
ccgtccctca agagtcgagt caccatatca gtagacacgt ccaagaacca gttctccctg    300
aggctgacct ctgtgaccgc cgcagacacg gccgtgtatt actgtgcgag agggcgtgga    360
tatagtggct acgatagcgg tatggacgtc tggggccaag ggaccacggt caccgtctcc    420
tca                                                                  423
```

```
SEQ ID NO: 14              moltype = AA   length = 141
FEATURE                    Location/Qualifiers
source                     1..141
                           mol_type = protein
                           organism = Homo sapiens
SEQUENCE: 14
MNLGLSLIFL ALILKGVQCQ VQLQESGPGL VKSSETLSLT CAVSGHSISS AYYWGWIRQP    60
PGKGLEWLGS IYHSGNTYYN PSLKSRVTIS VDTSKNQFSL RLTSVTAADT AVYYCARGRG   120
YSGYDSGMDV WGQGTTVTVS S                                             141

SEQ ID NO: 15              moltype = AA   length = 122
FEATURE                    Location/Qualifiers
REGION                     1..122
                           note = Description of the artificial sequence: amino acid
                            sequence of VH of MOG09 excluding signal sequence
source                     1..122
                           mol_type = protein
                           organism = synthetic construct
SEQUENCE: 15
QVQLQESGPG LVKSSETLSL TCAVSGHSIS SAYYWGWIRQ PPGKGLEWLG SIYHSGNTYY    60
NPSLKSRVTI SVDTSKNQFS LRLTSVTAAD TAVYYCARGR GYSGYDSGMD VWGQGTTVTV   120
SS                                                                  122

SEQ ID NO: 16              moltype = AA   length = 6
FEATURE                    Location/Qualifiers
REGION                     1..6
                           note = Description of the artificial sequence: amino acid
                            sequence of HCDR1 of MOG09
source                     1..6
                           mol_type = protein
                           organism = synthetic construct
SEQUENCE: 16
SAYYWG                                                                6

SEQ ID NO: 17              moltype = AA   length = 16
FEATURE                    Location/Qualifiers
REGION                     1..16
                           note = Description of the artificial sequence: amino acid
                            sequence of HCDR2 of MOG09
source                     1..16
                           mol_type = protein
                           organism = synthetic construct
SEQUENCE: 17
SIYHSGNTYY NPSLKS                                                    16

SEQ ID NO: 18              moltype = AA   length = 13
FEATURE                    Location/Qualifiers
REGION                     1..13
                           note = Description of the artificial sequence: amino acid
                            sequence of HCDR3 of MOG09
source                     1..13
                           mol_type = protein
                           organism = synthetic construct
SEQUENCE: 18
GRGYSGYDSG MDV                                                       13

SEQ ID NO: 19              moltype = DNA   length = 387
FEATURE                    Location/Qualifiers
source                     1..387
                           mol_type = genomic DNA
                           organism = Homo sapiens
CDS                        1..387
                           protein_id = 342
                           translation = MKLPVRLLVLMFWIPASSSSYVLTQPPSASGTPGQRVTISCSGTSS
                            NIGINSVNWYQQLPGMAPKLVIYSRDQRPSGVPDRFSGSQSGTSASLAINGLQSEDEAD
                            YWCSTWDDSLNGWVFGGGTKLTVL
SEQUENCE: 19
atgaagttgc ctgttaggct gttggtgctg atgttctgga ttcctgcttc cagcagttcc    60
tatgtgctga ctcagccacc ctcagcgtct gggacccccg ggcagagggt caccatctct   120
tgttctggaa gcagctccaa catcggaatc aatagtgtaa actggtatca acagctccca   180
ggaatggccc ccaaactcgt catctacagt agggatcagc ggccctcagg ggtccctgac   240
cgattctctg gctcccagtc tggcacctca gcctccctgg ccatcaatgg cctccagtct   300
gaggatgagg ctgattattg gtgttcaaca tgggatgaca gcctgaatgg ttgggtgttc   360
ggcggaggga ccaagctgac cgtccta                                       387

SEQ ID NO: 20              moltype = AA   length = 129
FEATURE                    Location/Qualifiers
source                     1..129
                           mol_type = protein
```

```
                            organism = Homo sapiens
SEQUENCE: 20
MKLPVRLLVL MFWIPASSSS YVLTQPPSAS GTPGQRVTIS CSGTSSNIGI NSVNWYQQLP    60
GMAPKLVIYS RDQRPSGVPD RFSGSQSGTS ASLAINGLQS EDEADYWCST WDDSLNGWVF   120
GGGTKLTVL                                                           129

SEQ ID NO: 21           moltype = AA  length = 110
FEATURE                 Location/Qualifiers
REGION                  1..110
                        note = Description of the artificial sequence: amino acid
                         sequence of VL of MOG09 excluding signal sequence
source                  1..110
                        mol_type = protein
                        organism = synthetic construct
SEQUENCE: 21
SYVLTQPPSA SGTPGQRVTI SCSGTSSNIG INSVNWYQQL PGMAPKLVIY SRDQRPSGVP    60
DRFSGSQSGT SASLAINGLQ SEDEADYWCS TWDDSLNGWV FGGGTKLTVL              110

SEQ ID NO: 22           moltype = AA  length = 13
FEATURE                 Location/Qualifiers
REGION                  1..13
                        note = Description of the artificial sequence: amino acid
                         sequence of LCDR1 of MOG09
source                  1..13
                        mol_type = protein
                        organism = synthetic construct
SEQUENCE: 22
SGTSSNIGIN SVN                                                       13

SEQ ID NO: 23           moltype = AA  length = 7
FEATURE                 Location/Qualifiers
REGION                  1..7
                        note = Description of the artificial sequence: amino acid
                         sequence of LCDR2 of MOG09
source                  1..7
                        mol_type = protein
                        organism = synthetic construct
SEQUENCE: 23
SRDQRPS                                                               7

SEQ ID NO: 24           moltype = AA  length = 11
FEATURE                 Location/Qualifiers
REGION                  1..11
                        note = Description of the artificial sequence: amino acid
                         sequence of LCDR3 of MOG09
source                  1..11
                        mol_type = protein
                        organism = synthetic construct
SEQUENCE: 24
STWDDSLNGW V                                                         11

SEQ ID NO: 25           moltype = DNA  length = 414
FEATURE                 Location/Qualifiers
source                  1..414
                        mol_type = genomic DNA
                        organism = Homo sapiens
CDS                     1..414
                        protein_id = 343
                        translation = MNLGLSLIFLALILKGVQCQVQLVQSGAEVKKPGASVKVSCQASGY
                         TFTGDYIHWVRQAPGQGLEYLGWINPDRGFTYYTQKFQGRVTMTRDTSSNTAYMELSSL
                         RSDDTAMYYCTRENPRAYFFDLWGQGTLVTVSS
SEQUENCE: 25
atgaacctcg ggctcagttt gattttcctt gccctcattt taaaaggtgt ccagtgtcag    60
gtgcagctgg tgcaatctgg ggctgaggtg aagaagcctg gggcctcagt gaaggtctcc   120
tgccaggctt ctggatacac gttcaccggc gactatattc actgggtgcg acaggcccct   180
ggacaagggc tggaatactt gggatggatc aaccctgaca ggggtttcac atactataca   240
cagaagtttc agggcagggt caccatgacc cgggacacgt ccagcaacac agcctacatg   300
gagctgagca gcctgagatc tgacgacacg gccatgtatt actgtacgag agaaaaccct   360
cgcgcgtact tcttcgacct ctggggccag ggaaccctgg tcaccgtctc ctca         414

SEQ ID NO: 26           moltype = AA  length = 138
FEATURE                 Location/Qualifiers
source                  1..138
                        mol_type = protein
                        organism = Homo sapiens
SEQUENCE: 26
MNLGLSLIFL ALILKGVQCQ VQLVQSGAEV KKPGASVKVS CQASGYTFTG DYIHWVRQAP    60
GQGLEYLGWI NPDRGFTYYT QKFQGRVTMT RDTSSNTAYM ELSSLRSDDT AMYYCTRENP   120
RAYFFDLWGQ GTLVTVSS                                                 138
```

```
SEQ ID NO: 27            moltype = AA   length = 119
FEATURE                  Location/Qualifiers
REGION                   1..119
                         note = Description of the artificial sequence: amino acid
                          sequence of VH of MOG14 excluding signal sequence
source                   1..119
                         mol_type = protein
                         organism = synthetic construct
SEQUENCE: 27
QVQLVQSGAE VKKPGASVKV SCQASGYTFT GDYIHWVRQA PGQGLEYLGW INPDRGFTYY    60
TQKFQGRVTM TRDTSSNTAY MELSSLRSDD TAMYYCTREN PRAYFFDLWG QGTLVTVSS    119

SEQ ID NO: 28            moltype = AA   length = 5
FEATURE                  Location/Qualifiers
REGION                   1..5
                         note = Description of the artificial sequence: amino acid
                          sequence of HCDR1 of MOG14
source                   1..5
                         mol_type = protein
                         organism = synthetic construct
SEQUENCE: 28
GDYIH                                                                 5

SEQ ID NO: 29            moltype = AA   length = 17
FEATURE                  Location/Qualifiers
REGION                   1..17
                         note = Description of the artificial sequence: amino acid
                          sequence of HCDR2 of MOG14
source                   1..17
                         mol_type = protein
                         organism = synthetic construct
SEQUENCE: 29
WINPDRGFTY YTQKFQG                                                   17

SEQ ID NO: 30            moltype = AA   length = 10
FEATURE                  Location/Qualifiers
REGION                   1..10
                         note = Description of the artificial sequence: amino acid
                          sequence of HCDR3 of MOG14
source                   1..10
                         mol_type = protein
                         organism = synthetic construct
SEQUENCE: 30
ENPRAYFFDL                                                           10

SEQ ID NO: 31            moltype = DNA   length = 381
FEATURE                  Location/Qualifiers
source                   1..381
                         mol_type = genomic DNA
                         organism = Homo sapiens
CDS                      1..381
                         protein_id = 344
                         translation = MKLPVRLLVLMFWIPASSSEIVLTQSPGTLSLSPGERATLSCRASQ
                          SISGSYVTWYQQKPGQAPRLLIYATSNRAIGIPDKFSGGGSGRDFTLTINRLEPEDFAV
                          YYCQQSVSSPYTFGQGTKVEIK
SEQUENCE: 31
atgaagttgc ctgttaggct gttggtgctg atgttctgga ttcctgcttc cagcagtgaa    60
atagtgttga cgcagtctcc aggcaccctg tctttgtctc cagggaaag agccactctc    120
tcctgcaggg ccagtcagag tattagcggc agctacgtga cctggtacca gcagaagcct   180
ggccaggctc ccaggctcct catctatgct acatccaata gggccattgg catcccagac   240
aagttcagtg gcggtgggtc tgggagagac ttcactctca ccatcaacag actggagcct   300
gaagattttg cagtgtatta ctgtcagcag agtgttagtt ctccgtacac ttttggccag   360
gggaccaagg tggaaatcaa a                                              381

SEQ ID NO: 32            moltype = AA   length = 127
FEATURE                  Location/Qualifiers
source                   1..127
                         mol_type = protein
                         organism = Homo sapiens
SEQUENCE: 32
MKLPVRLLVL MFWIPASSSE IVLTQSPGTL SLSPGERATL SCRASQSISG SYVTWYQQKP    60
GQAPRLLIYA TSNRAIGIPD KFSGGGSGRD FTLTINRLEP EDFAVYYCQQ SVSSPYTFGQ   120
GTKVEIK                                                             127

SEQ ID NO: 33            moltype = AA   length = 108
FEATURE                  Location/Qualifiers
REGION                   1..108
                         note = Description of the artificial sequence: amino acid
```

```
                              sequence of VL of MOG14 excluding signal sequence
source                        1..108
                              mol_type = protein
                              organism = synthetic construct
SEQUENCE: 33
EIVLTQSPGT LSLSPGERAT LSCRASQSIS GSYVTWYQQK PGQAPRLLIY ATSNRAIGIP    60
DKFSGGGSGR DFTLTINRLE PEDFAVYYCQ QSVSSPYTFG QGTKVEIK                108

SEQ ID NO: 34                 moltype = AA   length = 12
FEATURE                       Location/Qualifiers
REGION                        1..12
                              note = Description of the artificial sequence: amino acid
                                sequence of LCDR1 of MOG14
source                        1..12
                              mol_type = protein
                              organism = synthetic construct
SEQUENCE: 34
RASQSISGSY VT                                                        12

SEQ ID NO: 35                 moltype = AA   length = 7
FEATURE                       Location/Qualifiers
REGION                        1..7
                              note = Description of the artificial sequence: amino acid
                                sequence of LCDR2 of MOG14
source                        1..7
                              mol_type = protein
                              organism = synthetic construct
SEQUENCE: 35
ATSNRAI                                                               7

SEQ ID NO: 36                 moltype = AA   length = 9
FEATURE                       Location/Qualifiers
REGION                        1..9
                              note = Description of the artificial sequence: amino acid
                                sequence of LCDR3 of MOG14
source                        1..9
                              mol_type = protein
                              organism = synthetic construct
SEQUENCE: 36
QQSVSSPYT                                                             9

SEQ ID NO: 37                 moltype = DNA  length = 411
FEATURE                       Location/Qualifiers
misc_feature                  1..411
                              note = Description of the artificial sequence: sequence of
                                VHH of iMOG_3Rim1_S32 including signal sequence
source                        1..411
                              mol_type = other DNA
                              organism = synthetic construct
CDS                           1..411
                              protein_id = 345
                              translation = MYRMQLLSCIALSLALVTNSQVQLVESGGGLVQTGGSLRLSCAASG
                                SMFSTMGWFRQAPGNQRELVAIMSSGGTANYADSVKGRFTISGDNVKNTVTLQMNSLNP
                                EDTAVYYCRFTGWVKSSFSTYWGQGTQVTVSS
SEQUENCE: 37
atgtacagga tgcaactcct gtcttgcatt gcactaagtc ttgcacttgt cacgaattcg    60
caggtgcagc tcgtggagtc tgggggaggc ttggtgcaga ctgggggcgtc tctgagactc   120
tcctgtgcag cctctggaag catgttcagt accatgggct ggttccgcca ggctccaggg   180
aaccagcgcg agttggtcgc cattatgtca tccggtggta ccgcaaacta tgcagactct   240
gtgaagggcc gattcaccat ctccggagac aacgtcaaga cacggtgac tctccaaatg    300
aacagcctga atccagagga cacagccgtc tattattgta ggtttaccgg ttgggtcaag   360
agttcgttct ctacgtactg gggccagggg acccaggtca ccgtctcctc a            411

SEQ ID NO: 38                 moltype = AA   length = 137
FEATURE                       Location/Qualifiers
REGION                        1..137
                              note = Synthetic Construct
source                        1..137
                              mol_type = protein
                              organism = synthetic construct
SEQUENCE: 38
MYRMQLLSCI ALSLALVTNS QVQLVESGGG LVQTGGSLRL SCAASGSMFS TMGWFRQAPG    60
NQRELVAIMS SGGTANYADS VKGRFTISGD NVKNTVTLQM NSLNPEDTAV YYCRFTGWVK   120
SSFSTYWGQG TQVTVSS                                                  137

SEQ ID NO: 39                 moltype = AA   length = 117
FEATURE                       Location/Qualifiers
REGION                        1..117
                              note = Description of the artificial sequence: amino acid
```

```
                    sequence of VHH of iMOG_3Rim1_S32 excluding signal sequence
source              1..117
                    mol_type = protein
                    organism = synthetic construct
SEQUENCE: 39
QVQLVESGGG LVQTGGSLRL SCAASGSMFS TMGWFRQAPG NQRELVAIMS SGGTANYADS    60
VKGRFTISGD NVKNTVTLQM NSLNPEDTAV YYCRFTGWVK SSFSTYWGQG TQVTVSS      117

SEQ ID NO: 40       moltype =    length =
SEQUENCE: 40
000

SEQ ID NO: 41       moltype = AA   length = 16
FEATURE             Location/Qualifiers
REGION              1..16
                    note = Description of the artificial sequence: amino acid
                     sequence of CDR2 of iMOG_3Rim1_S32
source              1..16
                    mol_type = protein
                    organism = synthetic construct
SEQUENCE: 41
IMSSGGTANY ADSVKG                                                   16

SEQ ID NO: 42       moltype = AA   length = 11
FEATURE             Location/Qualifiers
REGION              1..11
                    note = Description of the artificial sequence: amino acid
                     sequence of CDR3 of iMOG_3Rim1_S32
source              1..11
                    mol_type = protein
                    organism = synthetic construct
SEQUENCE: 42
TGWVKSSFST Y                                                        11

SEQ ID NO: 43       moltype = DNA   length = 36
FEATURE             Location/Qualifiers
misc_feature        1..36
                    note = Description of the artificial sequence: primer1
source              1..36
                    mol_type = other DNA
                    organism = synthetic construct
SEQUENCE: 43
ggattcctgc ttccagcagt cagtctgccc tgactc                             36

SEQ ID NO: 44       moltype = DNA   length = 36
FEATURE             Location/Qualifiers
misc_feature        1..36
                    note = Description of the artificial sequence: primer2
source              1..36
                    mol_type = other DNA
                    organism = synthetic construct
SEQUENCE: 44
ggcggccttg ggctgaccta ggacggtcag cttggt                             36

SEQ ID NO: 45       moltype = DNA   length = 80
FEATURE             Location/Qualifiers
misc_feature        1..80
                    note = Description of the artificial sequence: primer3
source              1..80
                    mol_type = other DNA
                    organism = synthetic construct
SEQUENCE: 45
acgccatcac agatctgcct cttcaaaatg aagttgcctg ttaggctgtt ggtgctgatg    60
ttctggattc ctgcttccag                                               80

SEQ ID NO: 46       moltype = DNA   length = 36
FEATURE             Location/Qualifiers
misc_feature        1..36
                    note = Description of the artificial sequence: primer4
source              1..36
                    mol_type = other DNA
                    organism = synthetic construct
SEQUENCE: 46
aaaaggtgtc cagtgtcagg tacagctgca gcagtc                             36

SEQ ID NO: 47       moltype = DNA   length = 32
FEATURE             Location/Qualifiers
misc_feature        1..32
                    note = primer5
```

```
source                  1..32
                        mol_type = other DNA
                        organism = synthetic construct
SEQUENCE: 47
gcccctggt gctagctgag gagacggtga cc                                    32

SEQ ID NO: 48           moltype = DNA  length = 80
FEATURE                 Location/Qualifiers
misc_feature            1..80
                        note = Description of the artificial sequence: primer6
source                  1..80
                        mol_type = other DNA
                        organism = synthetic construct
SEQUENCE: 48
acacagaccc gtcgacccct caccatgaac ctcgggctca gtttgatttt ccttgccctc     60
attttaaaag gtgtccagtg                                                 80

SEQ ID NO: 49           moltype = DNA  length = 36
FEATURE                 Location/Qualifiers
misc_feature            1..36
                        note = Description of the artificial sequence: primer7
source                  1..36
                        mol_type = other DNA
                        organism = synthetic construct
SEQUENCE: 49
ggattcctgc ttccagcagt tcctatgtgc tgactc                               36

SEQ ID NO: 50           moltype = DNA  length = 36
FEATURE                 Location/Qualifiers
misc_feature            1..36
                        note = Description of the artificial sequence: primer8
source                  1..36
                        mol_type = other DNA
                        organism = synthetic construct
SEQUENCE: 50
ggcggccttg ggctgaccta ggacggtcag cttggt                               36

SEQ ID NO: 51           moltype = DNA  length = 36
FEATURE                 Location/Qualifiers
misc_feature            1..36
                        note = Description of the artificial sequence: primer9
source                  1..36
                        mol_type = other DNA
                        organism = synthetic construct
SEQUENCE: 51
aaaaggtgtc cagtgtcagg tgcagctgca ggagtc                               36

SEQ ID NO: 52           moltype = DNA  length = 32
FEATURE                 Location/Qualifiers
misc_feature            1..32
                        note = Description of the artificial sequence: primer10
source                  1..32
                        mol_type = other DNA
                        organism = synthetic construct
SEQUENCE: 52
gcccctggt gctagctgag gagacggtga cc                                    32

SEQ ID NO: 53           moltype = DNA  length = 40
FEATURE                 Location/Qualifiers
misc_feature            1..40
                        note = Description of the artificial sequence: primer11
source                  1..40
                        mol_type = other DNA
                        organism = synthetic construct
SEQUENCE: 53
ggattcctgc ttccagcagt gaaatagtgt tgacgcagtc                           40

SEQ ID NO: 54           moltype = DNA  length = 36
FEATURE                 Location/Qualifiers
misc_feature            1..36
                        note = Description of the artificial sequence: primer12
source                  1..36
                        mol_type = other DNA
                        organism = synthetic construct
SEQUENCE: 54
gtgcagccac cgtacgtttg atttccacct tggtcc                               36

SEQ ID NO: 55           moltype = DNA  length = 36
FEATURE                 Location/Qualifiers
```

```
misc_feature                1..36
                            note = Description of the artificial sequence: primer13
source                      1..36
                            mol_type = other DNA
                            organism = synthetic construct
SEQUENCE: 55
aaaaggtgtc cagtgtcagg tgcagctggt gcaatc                                      36

SEQ ID NO: 56               moltype = DNA   length = 32
FEATURE                     Location/Qualifiers
misc_feature                1..32
                            note = Description of the artificial sequence: primer14
source                      1..32
                            mol_type = other DNA
                            organism = synthetic construct
SEQUENCE: 56
gccccttggt gctagctgag gagacggtga cc                                          32

SEQ ID NO: 57               moltype = DNA   length = 40
FEATURE                     Location/Qualifiers
misc_feature                1..40
                            note = Description of the artificial sequence: primer15
source                      1..40
                            mol_type = other DNA
                            organism = synthetic construct
SEQUENCE: 57
tgcacttgtc acgaattcgc aggtgcagct cgtggagtct                                  40

SEQ ID NO: 58               moltype = DNA   length = 45
FEATURE                     Location/Qualifiers
misc_feature                1..45
                            note = Description of the artificial sequence: primer16
source                      1..45
                            mol_type = other DNA
                            organism = synthetic construct
SEQUENCE: 58
accatatttg gactcagatc tggccgctga ggagacggtg acctg                             45

SEQ ID NO: 59               moltype = DNA   length = 30
FEATURE                     Location/Qualifiers
misc_feature                1..30
                            note = Description of the artificial sequence: primer17
source                      1..30
                            mol_type = other DNA
                            organism = synthetic construct
SEQUENCE: 59
acagtctcct cagctagcac caaggggcca                                             30

SEQ ID NO: 60               moltype = DNA   length = 36
FEATURE                     Location/Qualifiers
misc_feature                1..36
                            note = Description of the artificial sequence: primer18
source                      1..36
                            mol_type = other DNA
                            organism = synthetic construct
SEQUENCE: 60
ctgctgcagc tgtacctggg accctcctcc tccgga                                      36

SEQ ID NO: 61               moltype = DNA   length = 33
FEATURE                     Location/Qualifiers
misc_feature                1..33
                            note = Description of the artificial sequence: primer19
source                      1..33
                            mol_type = other DNA
                            organism = synthetic construct
SEQUENCE: 61
ggaggaggag ggtcccaggt acagctgcag cag                                         33

SEQ ID NO: 62               moltype = DNA   length = 33
FEATURE                     Location/Qualifiers
misc_feature                1..33
                            note = Description of the artificial sequence: primer20
source                      1..33
                            mol_type = other DNA
                            organism = synthetic construct
SEQUENCE: 62
aagcggccgc ctggatcctc ataggacggt cag                                         33

SEQ ID NO: 63               moltype = DNA   length = 39
```

-continued

```
FEATURE                 Location/Qualifiers
misc_feature            1..39
                        note = Description of the artificial sequence: primer21
source                  1..39
                        mol_type = other DNA
                        organism = synthetic construct
SEQUENCE: 63
tcagtcataa tgtctagagg agacatccag atgacccag                              39

SEQ ID NO: 64           moltype = DNA  length = 37
FEATURE                 Location/Qualifiers
misc_feature            1..37
                        note = Description of the artificial sequence: primer22
source                  1..37
                        mol_type = other DNA
                        organism = synthetic construct
SEQUENCE: 64
gggcggcctt gggctgacct ttgatctcca ccttggt                                37

SEQ ID NO: 65           moltype = DNA  length = 41
FEATURE                 Location/Qualifiers
misc_feature            1..41
                        note = Description of the artificial sequence: primer23
source                  1..41
                        mol_type = other DNA
                        organism = synthetic construct
SEQUENCE: 65
cagcctttcc tggtatactt agtgaggtgc agttggtgga g                           41

SEQ ID NO: 66           moltype = DNA  length = 36
FEATURE                 Location/Qualifiers
misc_feature            1..36
                        note = Description of the artificial sequence: primer24
source                  1..36
                        mol_type = other DNA
                        organism = synthetic construct
SEQUENCE: 66
tggccccttg gtgctagccg aggagacggt gaccag                                 36

SEQ ID NO: 67           moltype = DNA  length = 738
FEATURE                 Location/Qualifiers
source                  1..738
                        mol_type = genomic DNA
                        organism = Rattus norvegicus
CDS                     1..738
                        protein_id = 346
                        translation = MAGVWSLSLPSCLLSLLLLLQLSRSYAGQFRVIGPGHPIRALVGDE
                        AELPCRISPGKNATGMEVGWYRSPFSRVVHLYRNGKDQDAEQAPEYRGRTELLKESIGE
                        GKVALRIQNVRFSDEGGYTCFFRDHSYQEEAAVELKVEDPFYWINPGVLALIALVPMLL
                        LQVSVGLVFLFLQHRLRGKLRAEVENLHRTFDPHFLRVPCWKITLFVIVPVLGPLVALI
                        ICYNWLHRRLAGQFLEELRNPF
SEQUENCE: 67
atggccggtg tgtggagcct ttctctgccc agctgcctcc tgtccctgct cctcctcctc     60
cagttgtcac gcagctacgc aggacagttc agagtgatag gccagggca tcccatccgg     120
gctttagttg gggatgaagc agaactgccg tgccgtatat ctcctgggaa gaatgccacg     180
ggcatggagg tggggtggta ccgttctccc ttttcaagag tggttcatct gtaccgaaat    240
ggcaaggacc aagacgcaga gcaagcgcct gaataccggg gacgcacaga gcttctgaaa     300
gagtctatcg gcgagggaaa ggttgccctc aggatccaga acgtgaggtt ctcggatgaa     360
ggaggctaca catgcttctt cagagaccac tcctaccaag aagaagccgc cgtggagttg    420
aaagtagaag atcccttcta ctggatcaac cctggcgtgc tggctctcat tgcccttgtg    480
cctatgctgc tcctgcaggt ctctgtaggc cttgtattcc tcttcctgca gcacagactg    540
agaggaaaac tccgtgcaga gtcgagaat ctccatcgga cttttgatcc tcacttcctg     600
agagtgcccc gctggaagat aacactgttt gttattgtcc ctgttcttgg acccctggtt    660
gctttgatca tctgctacaa ctggctgcac cgaagactgg caggacagtt tcttgaagag    720
ctaagaaacc cctttga                                                   738

SEQ ID NO: 68           moltype = AA  length = 245
FEATURE                 Location/Qualifiers
source                  1..245
                        mol_type = protein
                        organism = Rattus norvegicus
SEQUENCE: 68
MAGVWSLSLP SCLLSLLLLL QLSRSYAGQF RVIGPGHPIR ALVGDEAELP CRISPGKNAT      60
GMEVGWYRSP FSRVVHLYRN GKDQDAEQAP EYRGRTELLK ESIGEGKVAL RIQNVRFSDE     120
GGYTCFFRDH SYQEEAAVEL KVEDPFYWIN PGVLALIALV PMLLLQVSVG LVFLFLQHRL     180
RGKLRAEVEN LHRTFDPHFL RVPCWKITLF VIVPVLGPLV ALIICYNWLH RRLAGQFLEE     240
LRNPF                                                                245

SEQ ID NO: 69           moltype = DNA  length = 1167
```

```
FEATURE               Location/Qualifiers
misc_feature          1..1167
                      note = Description of the artificial sequence: sequence of
                      rMOG-FLAG-Fc
source                1..1167
                      mol_type = other DNA
                      organism = synthetic construct
CDS                   1..1167
                      protein_id = 347
                      translation = MAGVWSLSLPSCLLSLLLLLQLSRSYAGQFRVIGPGHPIRALVGDE
                      AELPCRISPGKNATGMEVGWYRSPFSRVVHLYRNGKDQDAEQAPEYRGRTELLKESIGE
                      GKVALRIQNVRFSDEGGYTCFFRDHSYQEEAAVELKVEDPFYWSRADYKDDDDKTSDKT
                      HTCPPCPAPELLGGPSVFLFPPKPKDTLMISRTPEVTCVVVDVSHEDPEVKFNWYVDGV
                      EVHNAKTKPREEQYNSTYRVVSVLTVLHQDWLNGKEYKCKVSNKALPAPIEKTISKAKG
                      QPREPQVYTLPPSRDELTKNQVSLTCLVKGFYPSDIAVEWESNGQPENNYKTTPPVLDS
                      DGSFFLYSKLTVDKSRWQQGNVFSCSVMHEALHNHYTQKSLSLSPGK
SEQUENCE: 69
atggccggtg tgtggagcct ttctctgccc agctgcctcc tgtccctgct cctcctcctc   60
cagttgtcac gcagctacgc aggacagttc agagtgatag gcccagggca tcccatccgg  120
gctttagttg gggatgaagc agaactgccg tgccgtatat ctcctgggaa gaatgccacg  180
ggcatggagg tgggGtggta ccgttctccc ttttcaagag tggttcatct gtaccgaaat  240
ggcaaggacc aagacgcaga gcaagcgcct gaataccggg acgcacagag cttctgaaa   300
gagtctatcg gcgagggaaa ggttgccctc aggatccaga acgtgaggtt ctcggatgaa  360
ggaggctaca catgcttctt cagagaccac tcctaccaag aagaagccgc cgtggagttg  420
aaagtagaag atccccttcta ctggtctaga gcagactaca aggacgacga tgacaagact  480
agtgacaaaa ctcacacatg cccaccgtgc ccagcacctg aactcctggg gggaccgtca  540
gtcttcctct tcccccccaaa acccaaggac accctcatga tctcccggac ccctgaggtc  600
acatgcgtgg tggtggacgt gagccacgaa gaccctgagg tcaagttcaa ctggtacgtg  660
gacggcgtgg aggtgcataa tgccaagaca aagccgcggg aggagcagta caacagcacg  720
taccgtgtgg tcagcgtcct caccgtcctg caccaggact ggctgaatgg caaggagtac  780
aagtgcaagg tctccaacaa agccctccca gcccccatcg agaaaaccat ctccaaagcc  840
aaagggcagc cccgagaacc acaggtgtac accctgcccc catcccggga tgagctgacc  900
aagaaccagg tcagcctgac ctgcctggtc aaaggcttct atcccagcga catcgccgtg  960
gagtgggaga gcaatgggca gccggagaac aactacaaga ccacgcctcc cgtgctggac 1020
tccgacggct ccttcttcct ctacagcaag ctcaccgtgg acaagagcag gtggcagcag 1080
gggaacgtct tctcatgctc cgtgatgcat gaggctctgc acaaccacta cacgcagaag 1140
agcctctccc tgtctccggg taaatga                                     1167

SEQ ID NO: 70         moltype = AA  length = 388
FEATURE               Location/Qualifiers
REGION                1..388
                      note = Synthetic Construct
source                1..388
                      mol_type = protein
                      organism = synthetic construct
SEQUENCE: 70
MAGVWSLSLP SCLLSLLLLL QLSRSYAGQF RVIGPGHPIR ALVGDEAELP CRISPGKNAT    60
GMEVGWYRSP FSRVVHLYRN GKDQDAEQAP EYRGRTELLK ESIGEGKVAL RIQNVRFSDE   120
GGYTCFFRDH SYQEEAAVEL KVEDPFYWSR ADYKDDDDKT SDKTHTCPPC PAPELLGGPS   180
VFLFPPKPKD TLMISRTPEV TCVVVDVSHE DPEVKFNWYV DGVEVHNAKT KPREEQYNST   240
YRVVSVLTVL HQDWLNGKEY KCKVSNKALP APIEKTISKA KGQPREPQVY TLPPSRDELT   300
KNQVSLTCLV KGFYPSDIAV EWESNGQPEN NYKTTPPVLD SDGSFFLYSK LTVDKSRWQQ   360
GNVFSCSVMH EALHNHYTQK SLSLSPGK                                     388

SEQ ID NO: 71         moltype = DNA  length = 1137
FEATURE               Location/Qualifiers
misc_feature          1..1137
                      note = Description of the artificial sequence: sequence of
                      rMOG-GST
source                1..1137
                      mol_type = other DNA
                      organism = synthetic construct
CDS                   1..1137
                      protein_id = 348
                      translation = MAGVWSLSLPSCLLSLLLLLQLSRSYAGQFRVIGPGHPIRALVGDE
                      AELPCRISPGKNATGMEVGWYRSPFSRVVHLYRNGKDQDAEQAPEYRGRTELLKESIGE
                      GKVALRIQNVRFSDEGGYTCFFRDHSYQEEAAVELKVEDPFYWGTLEVLFQGPMSPILG
                      YWKIKGLVQPTRLLLEYLEEKYEEHLYERDEGDKWRNKKFELGLEFPNLPYYIDGDVKL
                      TQSMAIIRYIADKHNMLGGCPKERAEISMLEGAVLDIRYGVSRIAYSKDFETLKVDFLS
                      KLPEMLKMFEDRLCHKTYLNGDHVTHPDFMLYDALDVVLYMDPMCLDAFPKLVCFKKRI
                      EAIPQIDYLKSSKYIAWPLQGWQATFGGGDHPPKSD
SEQUENCE: 71
atggccggtg tgtggagcct ttctctgccc agctgcctcc tgtccctgct cctcctcctc   60
cagttgtcac gcagctacgc aggacagttc agagtgatag gcccagggca tcccatccgg  120
gctttagttg gggatgaagc agaactgccg tgccgtatat ctcctgggaa gaatgccacg  180
ggcatggagg tgggGtggta ccgttctccc ttttcaagag tggttcatct gtaccgaaat  240
ggcaaggacc aagacgcaga gcaagcgcct gaataccggg acgcacagag cttctgaaa   300
gagtctatcg gcgagggaaa ggttgccctc aggatccaga acgtgaggtt ctcggatgaa  360
ggaggctaca catgcttctt cagagaccac tcctaccaag aagaagccgc cgtggagttg  420
```

```
aaagtagaag atcccttcta ctggggtacc ctggaagttc tgttccaggg gcccatgtcc    480
cctatactag gttattggaa aattaagggc cttgtgcaac ccactcgact tctttttggaa    540
tatcttgaag aaaaatatga agagcatttg tatgagcgcg atgaaggtga taaatggcga    600
aacaaaaagt ttgaattggg tttggagttt cccaatcttc cttattatat tgatggtgat    660
gttaaattaa cacagtctat ggccatcata cgttatatcg ctgacaagca caacatgttg    720
ggtggttgtc caaagagcg tgcagagatt tcaatgcttg aaggagcggt tttggatatt    780
agatacggtg tttcgagaat tgcatatagt aaagactttg aaactctcaa agttgatttt    840
cttagcaagc tacctgaaat gctgaaaatg ttcgaagatc gtttatgtca taaaacatat    900
ttaaatggtg atcatgtaac ccatcctgac ttcatgtttt atgacgctct tgatgttgtt    960
ttatacatgg acccaatgtg cctggatgcg ttcccaaaat tagtttgttt taaaaaacgt   1020
attgaagcta tcccacaaat tgataagtac ttgaaatcca gcaagtatat agcatggcct   1080
ttgcagggct ggcaagccac gtttggtggt ggcgaccatc ctccaaaatc ggattga      1137

SEQ ID NO: 72           moltype = AA   length = 378
FEATURE                 Location/Qualifiers
REGION                  1..378
                        note = Synthetic Construct
source                  1..378
                        mol_type = protein
                        organism = synthetic construct
SEQUENCE: 72
MAGVWSLSLP SCLLSLLLLL QLSRSYAGQF RVIGPGHPIR ALVGDEAELP CRISPGKNAT    60
GMEVGWYRSP FSRVVHLYRN GKDQDAEQAP EYRGRTELLK ESIGEGKVAL RIQNVRFSDE   120
GGYTCFFRDH SYQEEAAVEL KVEDPFYWGT LEVLFQGPMS PILGYWKIKG LVQPTRLLLE   180
YLEEKYEEHL YERDEGDKWR NKKFELGLEF PNLPYYIDGD VKLTQSMAII RYIADKHNML   240
GGCPKERAEI SMLEGAVLDI RYGVSRIAYS KDFETLKVDF LSKLPEMLKM FEDRLCHKTY   300
LNGDHVTHPD FMLYDALDVV LYMDPMCLDA FPKLVCFKKR IEAIPQIDKY LKSSKYIAWP   360
LQGWQATFGG GDHPPKSD                                                 378

SEQ ID NO: 73           moltype = DNA   length = 744
FEATURE                 Location/Qualifiers
source                  1..744
                        mol_type = genomic DNA
                        organism = Mus musculus
CDS                     1..744
                        protein_id = 349
                        translation = MACLWSFSWPSCFLSLLLLLLQLSCSYAGQFRVIGPGYPIRALVG
                        DEAELPCRISPGKNATGMEVGWYRSPFSRVVHLYRNGKDQDAEQAPEYRGRTELLKETI
                        SEGKVTLRIQNVRFSDEGGYTCFFRDHSYQEEAAMELKVEDPFYWVNPGVLTLIALVPT
                        ILLQVSVGLVFLFLQHRLRGKLRAEVENLHRTFDPHFLRVPCWKITLFVIVPVLGPLVA
                        LIICYNWLHRRLAGQFLEELRNPF
SEQUENCE: 73
atggcctgtt tgtggagctt ctcttggccc agctgcttcc tctccttct cctcctcctt     60
ctcctccagt tgtcatgcag ctatgcagga caattcagag tgataggacc agggtatccc   120
atccgggctt tagttgggga tgaagcagag ctgccgtgcc gcatctctcc tgggaaaaat   180
gccacgggca tggaggtggg ttggtaccgt tctcccttct caagagtggt tcacctctac   240
cgaaatgcag aggaccaaga tgcagagcaa gcacctgcat accggggacg cacagagctt   300
ctgaaagaga ctatcagtga gggaaaggtt acccttagga ttcagaacgt gagattctca   360
gatgaaggag gctacacctg cttcttcaga gaccactctt accaagaaga ggcagcaatg   420
gagttgaaag tggaagatcc cttctattgg gtcaaccccg gtgtgctgac tctcatcgca   480
cttgtgccta cgatcctcct gcaggtctct gtaggccttg tattcctctt cctgcagcag   540
agactgagag gaaaacttcg tgcagaagta gagaatctcc atcggacttt tgatcctcac   600
ttcctgaggg tgccctgctg gaagataaca ctgtttgtta ttgtgcctgt tcttggaccc   660
ctggttgcct tgatcatctg ctacaactgg ctgcaccgaa gactggcagg acagtttctt   720
gaaagagcta gaaaccccct ttga                                           744

SEQ ID NO: 74           moltype = AA   length = 247
FEATURE                 Location/Qualifiers
source                  1..247
                        mol_type = protein
                        organism = Mus musculus
SEQUENCE: 74
MACLWSFSWP SCFLSLLLLL LLQLSCSYAG QFRVIGPGYP IRALVGDEAE LPCRISPGKN    60
ATGMEVGWYR SPFSRVVHLY RNGKDQDAEQ APEYRGRTEL LKETISEGKV TLRIQNVRFS   120
DEGGYTCFFR DHSYQEEAAM ELKVEDPFYW VNPGVLTLIA LVPTILLQVS VGLVFLFLQH   180
RLRGKLRAEV ENLHRTFDPH FLRVPCWKIT LFVIVPVLGP LVALIICYNW LHRRLAGQFL   240
EELRNPF                                                             247

SEQ ID NO: 75           moltype = DNA   length = 744
FEATURE                 Location/Qualifiers
source                  1..744
                        mol_type = genomic DNA
                        organism = Macaca fascicularis
CDS                     1..744
                        protein_id = 350
                        translation = MASLSRPSLPSCLCSFLLLLLLQVSSSYAGQFRVIGPRQPIRALVG
                        DEVELPCRISPGKNATGMEVGWYRPPFSRVVHLYRNGRDQDGEQAPEYRGRTELLKDAI
                        GEGKVTLRIRNVRFSDEGGFTCFFRDHSYQEEAAIELKVEDPFYWVSPAVLVLLAVLPV
                        LLLQITVGLVFLCLQYRLRGKLRAEIENLHRTFDPHFLRVPCWKITLFVIVPVLGPLVA
```

```
                         LIICYNWLHRRLAGQFLEELRNPF
SEQUENCE: 75
atggcaagct tatcaagacc ctctctgccc agctgcctct gctccttcct cctcctcctg    60
ctcctccaag tgtcttccag ctacgcagga cagttcagag tgataggacc aagacaacct   120
atccgggctc tggtcggtga tgaagtggaa ttgccatgtc gcatatctcc tgggaagaac   180
gctacaggca tggaagtggg atggtaccgg ccccccttct ctagggtggt tcatctctac   240
agaaatggca gggaccaaga tggagagcaa gcacctgaat atcggggccg gacagagctg   300
ctgaaagacg ctattggtga gggaaaggtg actctcagga tccggaatgt aaggttctca   360
gatgaggag gtttcacctg cttcttccga gatcattctt accaagagga ggcagcaata   420
gaattgaaag tggaagatcc cttctactgg gtcagccctg cagtgctggt tctcctcgcg   480
gtgctgcctg tgctccttct gcagatcact gtcggcctcg tcttcctctg cctgcagtat   540
agactgagag aaaacttcg agcagagata gagaatctcc accggacttt tgatccccac   600
tttctgaggg tgccctgctg gaagataacc ctgtttgtaa ttgtgccggt tcttggaccc   660
ctggttgcct tgatcatctg ctacaactgg ctacatcgaa gactagcagg gcaattcctt   720
gaagagctaa gaaaccctt ctga                                           744

SEQ ID NO: 76              moltype = AA   length = 247
FEATURE                    Location/Qualifiers
source                     1..247
                           mol_type = protein
                           organism = Macaca fascicularis
SEQUENCE: 76
MASLSRPSLP SCLCSFLLLL LLQVSSSYAG QFRVIGPRQP IRALVGDEVE LPCRISPGKN    60
ATGMEVGWYR PPFSRVVHLY RNGRDQDGEQ APEYRGRTEL LKDAIGEGKV TLRIRNVRFS   120
DEGGFTCFFR DHSYQEEAAI ELKVEDPFYW VSPAVLVLLA VLPVLLLQIT VGLVFLCLQY   180
RLRGKLRAEI ENLHRTFDPH FLRVPCWKIT LFVIVPVLGP LVALIICYNW LHRRLAGQFL   240
EELRNPF                                                             247

SEQ ID NO: 77              moltype = DNA   length = 744
FEATURE                    Location/Qualifiers
source                     1..744
                           mol_type = genomic DNA
                           organism = Homo sapiens
CDS                        1..744
                           protein_id = 351
                           translation = MASLSRPSLPSCLCSFLLLLLLQVSSSYAGQFRVIGPRHPIRALVG
                           DEVELPCRISPGKNATGMEVGWYRPPFSRVVHLYRNGKDQDGDQAPEYRGRTELLKDAI
                           GEGKVTLRIRNVRFSDEGGFTCFFRDHSYQEEAAMELKVEDPFYWVSPGVLVLLAVLPV
                           LLLQITVGLVFLCLQYRLRGKLRAEIENLHRTFDPHFLRVPCWKITLFVIVPVLGPLVA
                           LIICYNWLHRRLAGQFLEELRNPF
SEQUENCE: 77
atggcaagct tatcaagacc ctctctgccc agctgcctct gctccttcct cctcctcctc    60
ctcctccaag tgtcttccag ctatgcaggg cagttcagag tgataggacc aagacacct   120
atccgggctc tggtcgggga tgaagtggaa ttgccatgtc gcatatctcc tgggaagaac   180
gctacaggca tggaggtggg gtggtaccgc ccccccttct ctagggtggt tcatctctac   240
agaaatggca aggaccaaga tggagaccag gcacctgaat atcggggccg gacagagctg   300
ctgaaagacg ctattggtga gggaaaggtg actctcagga tccggaatgt aaggttctca   360
gatgaaggag gtttcacctg cttcttccga gatcattctt accaagagga ggcagcaatg   420
gaattgaaag tagaagatcc tttctactgg gtgagccctg gagtgctggt tctcctcgcg   480
gtgctgcctg tgctcctcct gcagatcact gttggcctcg tcttcctctg cctgcagtac   540
agactgagag aaaacttcg agcagagata gagaatctcc accggacttt tgatccccac   600
tttctgaggg tgccctgctg gaagataacc ctgtttgtaa ttgtgccggt tcttggaccc   660
ttggttgcct tgatcatctg ctacaactgg ctacatcgaa gactagcagg gcaattcctt   720
gaagagctac gaaatccctt ctga                                          744

SEQ ID NO: 78              moltype = AA   length = 247
FEATURE                    Location/Qualifiers
source                     1..247
                           mol_type = protein
                           organism = Homo sapiens
SEQUENCE: 78
MASLSRPSLP SCLCSFLLLL LLQVSSSYAG QFRVIGPRHP IRALVGDEVE LPCRISPGKN    60
ATGMEVGWYR PPFSRVVHLY RNGKDQDGDQ APEYRGRTEL LKDAIGEGKV TLRIRNVRFS   120
DEGGFTCFFR DHSYQEEAAM ELKVEDPFYW VSPGVLVLLA VLPVLLLQIT VGLVFLCLQY   180
RLRGKLRAEI ENLHRTFDPH FLRVPCWKIT LFVIVPVLGP LVALIICYNW LHRRLAGQFL   240
EELRNPF                                                             247

SEQ ID NO: 79              moltype = DNA   length = 33
FEATURE                    Location/Qualifiers
misc_feature               1..33
                           note = Description of the artificial sequence: primer25
source                     1..33
                           mol_type = other DNA
                           organism = synthetic construct
SEQUENCE: 79
gagacgccat cacagatcat cccaccatgt aca                                 33

SEQ ID NO: 80              moltype = DNA   length = 33
FEATURE                    Location/Qualifiers
```

```
misc_feature            1..33
                        note = Description of the artificial sequence: primer26
source                  1..33
                        mol_type = other DNA
                        organism = synthetic construct
SEQUENCE: 80
gtaaccgtta acggatcctc atttacccag aga                                    33

SEQ ID NO: 81           moltype = DNA  length = 36
FEATURE                 Location/Qualifiers
misc_feature            1..36
                        note = Description of the artificial sequence: primer27
source                  1..36
                        mol_type = other DNA
                        organism = synthetic construct
SEQUENCE: 81
accaaggtgg agatcaaacg tacggtggct gcacca                                 36

SEQ ID NO: 82           moltype = DNA  length = 36
FEATURE                 Location/Qualifiers
misc_feature            1..36
                        note = Description of the artificial sequence: primer28
source                  1..36
                        mol_type = other DNA
                        organism = synthetic construct
SEQUENCE: 82
cggccacacg ttgaattctc aacactctcc cctgtt                                 36

SEQ ID NO: 83           moltype = DNA  length = 36
FEATURE                 Location/Qualifiers
misc_feature            1..36
                        note = Description of the artificial sequence: primer29
source                  1..36
                        mol_type = other DNA
                        organism = synthetic construct
SEQUENCE: 83
gattcctgct tccagcagtc agtttgtgct ttctca                                 36

SEQ ID NO: 84           moltype = DNA  length = 36
FEATURE                 Location/Qualifiers
misc_feature            1..36
                        note = Description of the artificial sequence: primer30
source                  1..36
                        mol_type = other DNA
                        organism = synthetic construct
SEQUENCE: 84
ggcggccttg ggctgaccta ggacagtgag cttggt                                 36

SEQ ID NO: 85           moltype = DNA  length = 36
FEATURE                 Location/Qualifiers
misc_feature            1..36
                        note = Description of the artificial sequence: primer31
source                  1..36
                        mol_type = other DNA
                        organism = synthetic construct
SEQUENCE: 85
ttaaaaggtg tccagtgtga ggtgcagctg gtggaa                                 36

SEQ ID NO: 86           moltype = DNA  length = 36
FEATURE                 Location/Qualifiers
misc_feature            1..36
                        note = Description of the artificial sequence: primer32
source                  1..36
                        mol_type = other DNA
                        organism = synthetic construct
SEQUENCE: 86
tggccccttg gtgctagctg aggagactgt gaccat                                 36

SEQ ID NO: 87           moltype = DNA  length = 38
FEATURE                 Location/Qualifiers
misc_feature            1..38
                        note = Description of the artificial sequence: primer33
source                  1..38
                        mol_type = other DNA
                        organism = synthetic construct
SEQUENCE: 87
tcagtcataa tgtctagagg acagtttgtg ctttctca                               38

SEQ ID NO: 88           moltype = DNA  length = 36
```

```
FEATURE                 Location/Qualifiers
misc_feature            1..36
                        note = Description of the artificial sequence: primer34
source                  1..36
                        mol_type = other DNA
                        organism = synthetic construct
SEQUENCE: 88
cggccacacg ttgaattctc atgaacattc tgtagg                                   36

SEQ ID NO: 89           moltype = DNA  length = 41
FEATURE                 Location/Qualifiers
misc_feature            1..41
                        note = Description of the artificial sequence: primer35
source                  1..41
                        mol_type = other DNA
                        organism = synthetic construct
SEQUENCE: 89
cagcctttcc tggtatactt agtgaggtgc agctggtgga a                             41

SEQ ID NO: 90           moltype = DNA  length = 30
FEATURE                 Location/Qualifiers
misc_feature            1..30
                        note = Description of the artificial sequence: primer36
source                  1..30
                        mol_type = other DNA
                        organism = synthetic construct
SEQUENCE: 90
acagtctcct cagctagcac caaggggcca                                          30

SEQ ID NO: 91           moltype = DNA  length = 35
FEATURE                 Location/Qualifiers
misc_feature            1..35
                        note = Description of the artificial sequence: primer37
source                  1..35
                        mol_type = other DNA
                        organism = synthetic construct
SEQUENCE: 91
tccaccagct gcacctcgga ccctcctcct ccgga                                    35

SEQ ID NO: 92           moltype = DNA  length = 33
FEATURE                 Location/Qualifiers
misc_feature            1..33
                        note = Description of the artificial sequence: primer38
source                  1..33
                        mol_type = other DNA
                        organism = synthetic construct
SEQUENCE: 92
ggaggaggag ggtccgaggt gcagctggtg gaa                                      33

SEQ ID NO: 93           moltype = DNA  length = 36
FEATURE                 Location/Qualifiers
misc_feature            1..36
                        note = Description of the artificial sequence: primer39
source                  1..36
                        mol_type = other DNA
                        organism = synthetic construct
SEQUENCE: 93
aagcggccgc ctggatcctc ataggacagt gagctt                                   36

SEQ ID NO: 94           moltype = DNA  length = 33
FEATURE                 Location/Qualifiers
misc_feature            1..33
                        note = Description of the artificial sequence: primer40
source                  1..33
                        mol_type = other DNA
                        organism = synthetic construct
SEQUENCE: 94
agacgccatc acagatctgc ctcttcaaaa tga                                      33

SEQ ID NO: 95           moltype = DNA  length = 36
FEATURE                 Location/Qualifiers
misc_feature            1..36
                        note = Description of the artificial sequence: primer41
source                  1..36
                        mol_type = other DNA
                        organism = synthetic construct
SEQUENCE: 95
tggtgcagcc accgtacgtt tgatttccag cttggt                                   36
```

```
SEQ ID NO: 96              moltype = DNA   length = 33
FEATURE                    Location/Qualifiers
misc_feature               1..33
                           note = Description of the artificial sequence: primer42
source                     1..33
                           mol_type = other DNA
                           organism = synthetic construct
SEQUENCE: 96
gaacacagac ccgtcgaccc ctcaccatga acc                                  33

SEQ ID NO: 97              moltype = DNA   length = 36
FEATURE                    Location/Qualifiers
misc_feature               1..36
                           note = Description of the artificial sequence: primer43
source                     1..36
                           mol_type = other DNA
                           organism = synthetic construct
SEQUENCE: 97
tggcccttg gtgctagcgg aggagactgt gagagt                                36

SEQ ID NO: 98              moltype = DNA   length = 2640
FEATURE                    Location/Qualifiers
misc_feature               1..2640
                           note = Description of the artificial sequence: sequence of
                           hHER2-GST
source                     1..2640
                           mol_type = other DNA
                           organism = synthetic construct
CDS                        1..2640
                           protein_id = 352
                           translation = MELAALCRWGLLLALLPPGAASTQVCTGTDMKLRLPASPETHLDML
                           RHLYQGCQVVQGNLELTYLPTNASLSFLQDIQEVQGYVLIAHNQVRQVPLQRLRIVRGT
                           QLFEDNYALAVLDNGDPLNNTTPVTGASPGGLRELQLRSLTEILKGGVLIQRNPQLCYQ
                           DTILWKDIFHKNNQLALTLIDTNRSRACHPCSPMCKGSRCWGESSEDCQSLTRTVCAGG
                           CARCKGPLPTDCCHEQCAAGCTGPKHSDCLACLHFNHSGICELHCPALVTYNTDTFESM
                           PNPEGRYTFGASCVTACPYNYLSTDVGSCTLVCPLHNQEVTAEDGTQRCEKCSKPCARV
                           CYGLGMEHLREVRAVTSANIQEFAGCKKIFGSLAFLPESFDGDPASNTAPLQPEQLQVF
                           ETLEEITGYLYISAWPDSLPDLSVFQNLQVIRGRILHNGAYSLTLQGLGISWLGLRSLR
                           ELGSGLALIHHNTHLCFVHTVPWDQLFRNPHQALLHTANRPEDECVGEGLACHQLCARG
                           HCWGPGPTQCVNCSQFLRGQECVEECRVLQGLPREYVNARHCLPCHPECQPQNGSVTCF
                           GPEADQCVACAHYKDPPFCVARCPSGVKPDLSYMPIWKFPDEEGACQPCPINCTHSCVD
                           LDDKGCPAEQRASGTLEVLFQGPMSPILGYWKIKGLVQPTRLLLEYLEEKYEEHLYERD
                           EGDKWRNKKFELGLEFPNLPYYIDGDVKLTQSMAIIRYIADKHNMLGGCPKERAEISML
                           EGAVLDIRYGVSRIAYSKDFETLKVDFLSKLPEMLKMFEDRLCHKTYLNGDHVTHPDFM
                           LYDALDVVLYMDPMCLDAFPKLVCFKKRIEAIPQIDKYLKSSKYIAWPLQGWQATFGGG
                           DHPPKSD
SEQUENCE: 98
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag     120
acccacctgg acatgctccg ccacctctac cagggctgcc aggtggtgca gggaaacctg     180
gaactcacct acctgcccac caatgccagc ctgtccttct gcaggatat ccaggaggtg      240
cagggctacg tgctcatcgc tcacaaccaa gtgaggcagg tcccactgca gaggctgcgg     300
attgtgcgag gcacccagct ctttgaggac aactatgccc tggccgtgct agacaatgga     360
gacccgctga caataccac ccctgtcaca ggggcctccc caggaggcct gcgggagctg      420
cagcttcgaa gcctcacaga gatcttgaaa ggagggggtct tgatccagcg gaaccccag    480
ctctgctacc aggacacgat tttgtggaag gacatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gctgacgcg cactgtctgt     660
gccggtggct gtgcccgctg caaggggcca ctgccccactg actgctgctg tgagcagtgt    720
gctgccggct gcacgggccc caagcactct gactgcctgg cctgtctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgccccct gcacaaccaa    960
gaggtgacag cagaggatgg aacacagcgg tgtgagaagt gcagcaagcc ctgtgccga    1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catgcccgga cagcctgcct   1260
gacctcagcg tcttccagaa cctgcaagta atccgggaca gaattctgca caatggcgcc   1320
tactcgctga ccctgcaagg gctgggcatc agctggctgg gctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc aaccggcca    1500
gaggacagt gtgtgggcga gggcctggcc tgccaccagc tgtgcgcccg agggcactgc    1560
tggggtccag gccaccca gtgtgtcaac tgcagccagt tcctccggga ccaggagtgc    1620
gtggaggaat gccgagtact gcaggggctc cccagggagt atgtgaatgc caggcactgt    1680
ttgccgtgcc accctgagtg tcagcccag aatggctcag tgacctgttt tggaccggag    1740
gctgaccagt gtgtggcctg tgcccactat aaggaccctc ccttctgcgt ggcccgctgc    1800
cccagcggtg tgaaacctga cctctcctac atgcccatct ggaagtttcc agatgaggag    1860
ggcgcatgcc agccttgccc catcaactgc acccactcct gtgtggacct ggatgacaag    1920
```

```
ggctgcccccg ccgagcagag agccagcggt accctggaag ttctgttcca ggggcccatg 1980
tccctatac taggttattg gaaaattaag ggccttgtgc aacccactcg acttcttttg 2040
gaatatcttg aagaaaaata tgaagagcat ttgtatgagc gcgatgaagg tgataaatgg 2100
cgaaacaaaa agtttgaatt gggtttggag tttcccaatc ttccttatta tattgatggt 2160
gatgttaaat taacacagtc tatgccatc atacgttata tagctgacaa gcacaacatg 2220
ttgggtggtt gtccaaaaga gcgtgcagag atttcaatgc ttgaaggagc ggttttggat 2280
attagatacg gtgtttcgag aattgcatat agtaaagact ttgaaactct caaagttgat 2340
tttcttagca agctacctga aatgctgaaa atgttcgaag atcgtttatg tcataaaaca 2400
tatttaaatg gtgatcatgt aacccatcct gacttcatgc tgtatgacgc tcttgatgtt 2460
gttttataca tggacccaat gtgcctggat gcgttcccaa aattagtttg ttttaaaaaa 2520
cgtattgaag ctatcccaca aattgataag tacttgaaat ccagcaagta tatagcatgg 2580
cctttgcagg gctggcaagc cacgtttggt ggtggcgacc atcctccaaa atcggattga 2640
```

SEQ ID NO: 99        moltype = AA  length = 879
FEATURE               Location/Qualifiers
REGION                1..879
                        note = Synthetic Construct
source                1..879
                        mol_type = protein
                        organism = synthetic construct

```
SEQUENCE: 99
MELAALCRWG LLLALLPPGA ASTQVCTGTD MKLRLPASPE THLDMLRHLY QGCQVVQGNL  60
ELTYLPTNAS LSFLQDIQEV QGYVLIAHNQ VRQVPLQRLR IVRGTQLFED NYALAVLDNG 120
DPLNNTTPVT GASPGGLREL QLRSLTEILK GGVLIQRNPQ LCYQDTILWK DIFHKNNQLA 180
LTLIDTNRSR ACHPCSPMCK GSRCWGESSE DCQSLTRTVC AGGCARCKGP LPTDCCHEQC 240
AAGCTGPKHS DCLACLHFNH SGICELHCPA LVTYNTDTFE SMPNPEGRYT FGASCVTACP 300
YNYLSTDVGS CTLVCPLHNQ EVTAEDGTQR CEKCSKPCAR VCYGLGMEHL REVRAVTSAN 360
IQEFAGCKKI FGSLAFLPES FDGDPASNTA PLQPEQLQVF ETLEEITGYL YISAWPDSLP 420
DLSVFQNLQV IRGRILHNGA YSLTLQGLGI SWLGLRSLRE LGSGLALIHH NTHLCFVHTV 480
PWDQLFRNPH QALLHTANRP EDECVGEGLA CHQLCARGHC WGPGPTQCVN CSQFLRGQEC 540
VEECRVLQGL PREYVNARHC LPCHPECQPQ NGSVTCFGPE ADQCVACAHY KDPPFCVARC 600
PSGVKPDLSY MPIWKFPDEE GACQPCPINC THSCVDLDDK GCPAEQRASG TLEVLFQGPM 660
SPILGYWKIK GLVQPTRLLL EYLEEKYEEH LYERDEGDKW RNKKFELGLE FPNLPYYIDG 720
DVKLTQSMAI IRYIADKHNM LGGCPKERAE ISMLEGAVLD IRYGVSRIAY SKDFETLKVD 780
FLSKLPEMLK MFEDRLCHKT YLNGDHVTHP DFMLYDALDV VLYMDPMCLD AFPKLVCFKK 840
RIEAIPQIDK YLKSSKYIAW PLQGWQATFG GGDHPPKSD                       879
```

SEQ ID NO: 100       moltype = DNA  length = 1182
FEATURE               Location/Qualifiers
misc_feature      1..1182
                        note = Description of the artificial sequence: base
                        sequence of hMOG-FLAG-Fc including signal sequence
source                1..1182
                        mol_type = other DNA
                        organism = synthetic construct

```
SEQUENCE: 100
atggcaagct tatcaagacc ctctctgccc agctgcctct gtccttcct cctcctcctc   60
ctcctccaag tgtcttccag ctatgcaggg cagttcagag tgataggacc aagacaccct  120
atccgggctc tggtcgggga tgaagtggaa ttgccatgtc gcatatctcc tgggaagaac  180
gctacaggca tggaggtggg gtggtaccgc ccccccttct ctagggtggt tcatctctac  240
agaaatgggc aggaccaaga tggagaccag gcacctgaat atcggggccg gacagagcta  300
ctgaaagatg ctattggtga gggaaaggtg actctcagga tccggaatgt aaggttctca  360
gatgaaggag gtttcacctg cttcttccga gatcattctt accaagagga ggcagcaatg  420
gaattgaaag tagaagatcc tttctactgg gtgagccctg gatctagagc agactacaag  480
gacgacgatg acaagactag tgacaaaact cacacatgcc caccgtgccc agcacctgaa  540
ctcctggggg gaccgtcagt cttcctcttc ccccccaaaac ccaaggacac cctcatgatc  600
tcccggaccc ctgaggtcac atgcgtggtg gtggacgtga gccacgaaga ccctgaggtc  660
aagttcaact ggtacgtgga cggcgtggag gtgcataatg ccaagacaaa gccgcgggag  720
gagcagtaca acagcacgta ccgtgtggtc agcgtcctca ccgtcctgca ccaggactgg  780
ctgaatggca aggagtacaa gtgcaaggtc tccaacaaag cccttcccagc ccccatcgag  840
aaaaccatct ccaaagccaa agggcagccc cgagaaccac aggtgtacac cctgcccca   900
tcccgggatg agctgaccaa gaaccaggtc agcctgacct gcctggtcaa aggcttctat  960
cccagcgaca tcgccgtgga gtgggagagc aatgggcagc cggagaacaa ctacaagacc 1020
acgcctcccg tgctggactc cgacggctcc ttcttcctct acagcaagct caccgtggac 1080
aagagcaggt ggcagcaggg gaacgtcttc tcatgctccg tgatgcatga ggctctgcac 1140
aaccactaca cgcagaagag cctctccctg tctccgggta aa                    1182
```

SEQ ID NO: 101       moltype = AA  length = 394
FEATURE               Location/Qualifiers
REGION                1..394
                        note = Description of the artificial sequence: amino acid
                        sequence of hMOG-FLAG-Fc including signal sequence
source                1..394
                        mol_type = protein
                        organism = synthetic construct

```
SEQUENCE: 101
MASLSRPSLP SCLCSFLLLL LLQVSSSYAG QFRVIGPRHP IRALVGDEVE LPCRISPGKN  60
ATGMEVGWYR PPFSRVVHLY RNGKDQDGDQ APEYRGRTEL LKDAIGEGKV TLRIRNVRFS 120
DEGGFTCFFR DHSYQEEAAM ELKVEDPFYW VSPGSRADYK DDDDKTSDKT HTCPPCPAPE 180
```

```
LLGGPSVFLF PPKPKDTLMI SRTPEVTCVV VDVSHEDPEV KFNWYVDGVE VHNAKTKPRE  240
EQYNSTYRVV SVLTVLHQDW LNGKEYKCKV SNKALPAPIE KTISKAKGQP REPQVYTLPP  300
SRDELTKNQV SLTCLVKGFY PSDIAVEWES NGQPENNYKT TPPVLDSDGS FFLYSKLTVD  360
KSRWQQGNVF SCSVMHEALH NHYTQKSLSL SPGK                              394

SEQ ID NO: 102          moltype = DNA   length = 1182
FEATURE                 Location/Qualifiers
misc_feature            1..1182
                        note = The Description of the artificial sequence: base
                          sequence of mMOG-FLAG-Fc including signal sequence
source                  1..1182
                        mol_type = other DNA
                        organism = synthetic construct
SEQUENCE: 102
atggcctgtt tgtggagctt ctcttggccc agctgcttcc tctcccttct cctcctcctt   60
ctcctccagt tgtcatgcag ctatgcagga caattcagag tgataggacc agggtatccc  120
atccgggctt tagttgggga tgaagcagag ctgccgtgcc gcatctctcc tgggaaaaat  180
gccacgggca tggaggtggg ttggtaccgt tctcccttct caagagtggt tcacctctac  240
cgaaatggca aggaccaaga tgcagagcaa gcacctgaat accggggacg cacagagctt  300
ctgaaagaga ctatcagtga gggaaaggtt acccttagga ttcagaacgt gagattctca  360
gatgaaggag gctacacctg cttcttcaga gaccactctt accaagaaga ggcagcaatg  420
gagttgaaag tggaagatcc cttctattgg gtcaacccg ttctagagc agactacaag  480
gacgacgatg acaagactag tgacaaaact cacacatgcc caccgtgccc agcacctgaa  540
ctcctggggg gaccgtcagt cttcctcttc cccccaaaac ccaaggacac cctcatgatc  600
tcccggaccc ctgaggtcac atgcgtggtg gtggacgtga gccacgaaga ccctgaggtc  660
aagttcaact ggtacgtgga cggcgtggag gtgcataatg ccaagacaaa gccgcgggag  720
gagcagtaca acagcacgta ccgtgtggtc agcgtcctca ccgtcctgca ccaggactgg  780
ctgaatggca aggagtacaa gtgcaaggtc tccaacaaag cccttccagc ccccatcgag  840
aaaaccatct ccaaagccaa agggcagccc cgagaaccac aggtgtacac cctgccccca  900
tcccgggatg agctgaccaa gaaccaggtc agcctgacct gcctggtcaa aggcttctat  960
cccagcgaca tcgccgtgga gtgggagagc aatgggcagc cggagaacaa ctacaagacc 1020
acgcctcccg tgctggactc cgacggctcc ttcttcctct acagcaagct caccgtggac 1080
aagagcaggt ggcagcaggg gaacgtcttc tcatgctccg tgatgcatga ggctctgcac 1140
aaccactaca cgcagaagag cctctccctg tctccgggta aa                   1182

SEQ ID NO: 103          moltype = AA   length = 394
FEATURE                 Location/Qualifiers
REGION                  1..394
                        note = Description of the artificial sequence: amino acid
                          sequence of mMOG-FLAG-Fc including signal sequence
source                  1..394
                        mol_type = protein
                        organism = synthetic construct
SEQUENCE: 103
MACLWSFSWP SCFLSLLLLL LLQLSCSYAG QFRVIGPGYP IRALVGDEAE LPCRISPGKN   60
ATGMEVGWYR SPFSRVVHLY RNGKDQDAEQ APEYRGRTEL LKETISEGKV TLRIQNVRFS  120
DEGGYTCFFR DHSYQEEAAM ELKVEDPFYW VNPGSRADYK DDDDKTHTCP PCPAPE      180
LLGGPSVFLF PPKPKDTLMI SRTPEVTCVV VDVSHEDPEV KFNWYVDGVE VHNAKTKPRE  240
EQYNSTYRVV SVLTVLHQDW LNGKEYKCKV SNKALPAPIE KTISKAKGQP REPQVYTLPP  300
SRDELTKNQV SLTCLVKGFY PSDIAVEWES NGQPENNYKT TPPVLDSDGS FFLYSKLTVD  360
KSRWQQGNVF SCSVMHEALH NHYTQKSLSL SPGK                              394

SEQ ID NO: 104          moltype = DNA   length = 1152
FEATURE                 Location/Qualifiers
misc_feature            1..1152
                        note = Description of the artificial sequence: base
                          sequence of hMOG-GST including signal sequence
source                  1..1152
                        mol_type = other DNA
                        organism = synthetic construct
SEQUENCE: 104
atggcaagct tatcaagacc ctctctgccc agctgcctct gctccttcct cctcctcctc   60
ctcctccaag tgtcttccag ctatgcaggg cagttcagag tgataggacc aagacaccct  120
atccgggctc tggtcgggga tgaagtggaa ttgccatgtc gcatatctcc tgggaagaac  180
gctacaggca tggaggtggg gtggtaccgc ccccccttct ctagggtggt tcatctctac  240
agaaatggca aggaccaaga tgagaccag gcacctgaat atcggggccg acagagctg  300
ctgaaagatg ctattggtga gggaaaggtg actctcagga tccggaatgt aaggttctca  360
gatgaaggag gtttcacctg cttcttccga gatcattctt accaagagga ggcagcaatg  420
gaattgaaag tagaagatcc tttctactgg gtgagccctg gaggtacctg ggaagttctg  480
ttccagggc ccatgtcccc tatactaggt tattggaaaa ttaagggcct tgtgcaaccc  540
actcgacttc ttttggaata tcttgaagaa aaatatgaag agcatttgta tgagcgcgat  600
gaaggtgata aatggcgaaa caaaaagttt gaattgggtt tggagtttcc aatcttcct  660
tattatattg atggtgatgt taaattaaca cagtctatgg ccatcatacg ttatatagct  720
gacaagcaca acatgttggg tggttgtcca aagagcgtg aggagattg aatgcttgaa  780
ggagcggttt tggatattag atacggtgtt tcgagaattg catatagtaa agactttgaa  840
actctcaaag ttgatttct tagcaagcta cctgaaatgc tgaaaatgtt cgaagatcgt  900
ttatgtcata aaacatattt aaatggtgat catgtaaccc atcctgactt catgttgtat  960
gacgtcttg atgttgtttt atacatggac caatgtgcc tggatgcgtt cccaaaatta 1020
gtttgtttta aaaaacgtat tgaagctatc ccacaaattg ataagtactt gaaatccagc 1080
```

```
aagtatatag catggccttt gcagggctgg caagccacgt ttggtggtgg cgaccatcct    1140
ccaaaatcgg at                                                        1152

SEQ ID NO: 105          moltype = AA  length = 384
FEATURE                 Location/Qualifiers
REGION                  1..384
                        note = Description of the artificial sequence: amino acid
                        sequence of hMOG-GST including signal sequence
source                  1..384
                        mol_type = protein
                        organism = synthetic construct
SEQUENCE: 105
MASLSRPSLP SCLCSFLLLL LLQVSSSYAG QFRVIGPRHP IRALVGDEVE LPCRISPGKN    60
ATGMEVGWYR PPFSRVVHLY RNGKDQDGDQ APEYRGRTEL LKDAIGEGKV TLRIRNVRFS    120
DEGGFTCFFR DHSYQEEAAM ELKVEDPFYW VSPGGTLEVL FQGPMSPILG YWKIKGLVQP    180
TRLLLEYLEE KYEEHLYERD EGDKWRNKKF ELGLEFPNLP YYIDGDVKLT QSMAIIRYIA    240
DKHNMLGGCP KERAEISMLE GAVLDIRYGV SRIAYSKDFE TLKVDFLSKL PEMLKMFEDR    300
LCHKTYLNGD HVTHPDFMLY DALDVVLYMD PMCLDAFPKL VCFKKRIEAI PQIDKYLKSS    360
KYIAWPLQGW QATFGGGDHP PKSD                                           384

SEQ ID NO: 106          moltype = DNA  length = 1152
FEATURE                 Location/Qualifiers
misc_feature            1..1152
                        note = Description of the artificial sequence: base
                        sequence of mMOG-GST including signal sequence
source                  1..1152
                        mol_type = other DNA
                        organism = synthetic construct
SEQUENCE: 106
atggcctgtt tgtggagctt ctcttggccc agctgcttcc tctcccttct cctcctcctt    60
ctcctccagt tgtcatgcag ctatgcagga caattcagag tgataggacc agggtatccc    120
atccgggctt tagttgggga tgaagcagag ctgccgtgcc gcatctctcc tgggaaaaat    180
gccacgggca tggaggtggg ttggtaccgt tctcccttct caagagtggt tcacctctac    240
cgaaatggca aggaccaaga tgcagagcaa gcacctgagt accggggacg cacagagctt    300
ctgaaagaca ctatcagtga gggaaaggtt acccttagga ttcagaacgt gagattctca    360
gatgaaggag ctacacctg cttcttcaga gaccactctt accaagaaga ggcagcaatg    420
gagttgaaag tggaagatcc cttctattgg gtcaaccccg gtggtaccct ggaagttctg    480
ttccagggc ccatgtcccc tatactaggt tattggaaaa ttaagggcct tgtgcaaccc    540
actcgacttc ttttggaata tcttgaagaa aaatatgaag agcatttgta tgagcgcgat    600
gaaggtgata aatggcgaaa caaaaagttt gaattgggtt tggagtttcc caatcttcct    660
tattatattg atggtgatgt taaattaaca cagtctatgg ccatcatacg ttatatagct    720
gacaagcaca acatgttggg tggttgtcca aaagagcgtg cagagatttc aatgcttgaa    780
ggagcggttt tggatattag atacggtgtt tcgagaattg catatagtaa agactttgaa    840
actctcaaag ttgattttct tagcaagcta cctgaaatgc tgaaaatgtt cgaagatcgt    900
ttatgtcata aacatatttt aaatggtgat catgtaaccc atcctgactt catgttgtat    960
gacgctcttg atgttgtttt atacatggac ccaatgtgcc tggatgcgtt cccaaaatta    1020
gtttgtttta aaaaacgtat tgaagctatc ccacaaattg ataagtactt gaaatccagc    1080
aagtatatag catggccttt gcagggctgg caagccacgt ttggtggtgg cgaccatcct    1140
ccaaaatcgg at                                                        1152

SEQ ID NO: 107          moltype = AA  length = 384
FEATURE                 Location/Qualifiers
REGION                  1..384
                        note = Description of the artificial sequence: amino acid
                        sequence of mMOG-GST including signal sequence
source                  1..384
                        mol_type = protein
                        organism = synthetic construct
SEQUENCE: 107
MACLWSFSWP SCFLSLLLLL LLQLSCSYAG QFRVIGPYP IRALVGDEAE LPCRISPGKN    60
ATGMEVGWYR SPFSRVVHLY RNGKDQDAEQ APEYRGRTEL LKETISEGKV TLRIQNVRFS    120
DEGGYTCFFR DHSYQEEAAM ELKVEDPFYW VNPGGTLEVL FQGPMSPILG YWKIKGLVQP    180
TRLLLEYLEE KYEEHLYERD EGDKWRNKKF ELGLEFPNLP YYIDGDVKLT QSMAIIRYIA    240
DKHNMLGGCP KERAEISMLE GAVLDIRYGV SRIAYSKDFE TLKVDFLSKL PEMLKMFEDR    300
LCHKTYLNGD HVTHPDFMLY DALDVVLYMD PMCLDAFPKL VCFKKRIEAI PQIDKYLKSS    360
KYIAWPLQGW QATFGGGDHP PKSD                                           384

SEQ ID NO: 108          moltype = DNA  length = 1371
FEATURE                 Location/Qualifiers
misc_feature            1..1371
                        note = Description of the artificial sequence: base
                        sequence of the antibody sequence of pCI-AVM-hLG4PE (R409K
                        / S354C / T366W) -FLAG tag excluding signal sequence
source                  1..1371
                        mol_type = other DNA
                        organism = synthetic construct
SEQUENCE: 108
gaggtgcagc tggtggaatc tggggggaggc ttagtgcagc ctggaagatc cctgaaactc    60
tcctgtgcag cctcaggatt cactttcagt aactatgcca tggcttgggt ccgccgggct    120
```

```
ccaacgaagg gtctggagtg ggtcgcatcc attagtaatg gtggtggtaa cacttactat   180
cgcgactccg tgaagggccg attcactatc tccagagatg atgcaaaaaa cacccctatac  240
ctgcaaatgg acagtctgag gtctgaggac acggccactt attactgtgc aagacacggg   300
aattatatat attatgggtc cttctttgat tactggggcc aaggagtcat ggtcacagtc   360
tcctcagcta gcaccaaggg gccatccgtc ttccccctgg cgccctgctc caggagcacc   420
tccgagagca cagccgccct gggctgcctg gtcaaggact acttccccga accggtgacg   480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacg   600
aagacctaca cctgcaacgt agatcacaag cccagcaaca ccaaggtgga caagagagtt   660
gagtccaaat atggtccccc atgcccacca tgcccagcac ctgagttcga gggggggacca  720
tcagtcttcc tgttcccccc aaaacccaag gacactctca tgatctcccg gacccctgag   780
gtcacgtgcg tggtggtgga cgtgagccag gaagacccccg aggtccagtt caactggtac   840
gtggatggcg tggaggtgca taatgccaag acaaagccgc gggaggagca gttcaacagc   900
acgtaccgtg tggtcagcgt cctcaccgtc ctgcaccagg actggctgaa cggcaaggag   960
tacaagtgca aggtctccaa caaaggcctc ccgtcctcca tcgagaaaac catctccaaa   1020
gccaaagggc agccccgaga gccacaggtg tacaccctgc ccccatgcca ggaggagatg   1080
accaagaacc aggtcagcct gtggtgcctg gtcaaaggct tctacccag cgacatcgcc    1140
gtggagtggg agagcaatgg gcagccggag aacaactaca agaccacgcc tcccgtgctg   1200
gactccgacg gctccttctt cctctacagc aagctaaccg tggacaagag caggtggcag   1260
gaggggaatg tcttctcatg ctccgtgatg catgaggctc tgcacaacca ctacacacag   1320
aagagcctct ccctgtctct gggtaaagac tacaaggacg acgatgacaa g             1371

SEQ ID NO: 109             moltype = AA   length = 457
FEATURE                    Location/Qualifiers
REGION                     1..457
                           note = Description of the artificial sequence: amino acid
                             sequence of the antibody sequence of pCI-AVM-hLG4PE (R409K
                             / S354C / T366W) -FLAG tag excluding signal sequence
source                     1..457
                           mol_type = protein
                           organism = synthetic construct
SEQUENCE: 109
EVQLVESGGG LVQPGRSLKL SCAASGFTFS NYAMAWVRRA PTKGLEWVAS ISNGGGNTYY   60
RDSVKGRFTI SRDDAKNTLY LQMDSLRSED TATYYCARHG NYIYYGSPFD YWGQGVMVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFEGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPCQEEM   360
TKNQVSLWCL VKGFYPSDIA VEWESNGQPE NNYKTTPPVL DSDGSFFLYS KLTVDKSRWQ   420
EGNVFSCSVM HEALHNHYTQ KSLSLSLGKD YKDDDDK                             457

SEQ ID NO: 110             moltype = DNA   length = 1380
FEATURE                    Location/Qualifiers
misc_feature               1..1380
                           note = Description of the artificial sequence: base
                             sequence of the antibody sequence of pCI-MOG01-hLG4PE
                             (R409K / Y349C / T366S / L368A / Y407V) -His tag excluding
                             signal sequence
source                     1..1380
                           mol_type = other DNA
                           organism = synthetic construct
SEQUENCE: 110
caggtacagc tgcagcagtc aggcgcagga ttattgaagc cttcggagac cctttccctc   60
acctgcgctg tgtctggtgg gtccttcagt ggttactact ggacctggat ccgccagcgc   120
ccagggaagg ggctggagtg gattggagaa atcaatcatc gtggaagcac cgattacaac   180
ccgtccctca agagtcgagt caccatgtca atagacacgt ccaagagcca gttctccctg   240
aatttgaaat ctgtgaccgc cgcggacacg gctgtgtatt actgtgcgag agccgcctgg   300
gggtcttgtt atgatgggac ctgctacccc gctgaatact ccaatactg gggccaggga   360
accctggtca ccgtctcctc agctagcacc aaggggccat ccgtcttccc cctggcgccc   420
tgctccagga gcacctccga gagcacagcc gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
agcagcttgg gcacgaagac ctacacctgc aactagatc acaagcccag caacaccaag   660
gtggacaaga gagttgagtc caaatatggt cccccatgcc cagcacctga gcacctaag   720
ttcgaggggg gaccatcagt cttcctgttc cccccaaaac ccaaggacac tctcatgatc   780
tcccggaccc ctgaggtcac gtgcgtggtg gtggacgtga gccaggaaga cccccgaggtc   840
cagttcaact ggtacgtgga tggcgtggag gtgcataatg ccaagacaaa gccgcgggag   900
gagcagttca acagcacacg tacacgta ccgtgtggtc agcgtcctca ccgtcctgca ccaggactgg   960
ctgaacggca aggagtacaa gtgcaaggtc tccaacaaag gcctcccgtc ctccatcgag   1020
aaaaccatct ccaaagccaa agggcagccc cgagagccac aggtgtgcac cctgccccca   1080
tcccaggagg agatgaccaa gaaccagtc agcctgtcct gcgcgtcaa aggcttctac    1140
cccagcgaca tcgccgtgga gtgggagagc aatgggcagc cggagaacaa ctacaagacc   1200
acgcctcccg tgctggactc cgacggctcc ttcttcctcg tcagcaagct aaccgtggac   1260
aagagcaggt ggcaggaggg gaatgtcttc tcatgctccg tgatgcatga ggctctgcac   1320
aaccactaca cacagaagag cctctccctg tctctgggta aacaccacca ccaccaccac   1380

SEQ ID NO: 111             moltype = AA   length = 460
FEATURE                    Location/Qualifiers
REGION                     1..460
```

```
                        note = Description of the artificial sequence: amino acid
                            sequence of the antibody sequence of pCI-MOG01-hLG4PE
                            (R409K / Y349C / T366S / L368A / Y407V)-His tag excluding
                            signal sequence
source                  1..460
                        mol_type = protein
                        organism = synthetic construct
SEQUENCE: 111
QVQLQQSGAG LLKPSETLSL TCAVSGGSFS GYYWTWIRQR PGKGLEWIGE INHRGSTDYN   60
PSLKSRVTMS IDTSKSQFSL NLKSVTAADT AVYYCARAAW GSCYDGTCYP AEYFQYWGQG  120
TLVTVSSAST KGPSVFPLAP CSRSTSESTA ALGCLVKDYF PEPVTVSWNS GALTSGVHTF  180
PAVLQSSGLY SLSSVVTVPS SSLGTKTYTC NVDHKPSNTK VDKRVESKYG PPCPPCPAPE  240
FEGGPSVFLF PPKPKDTLMI SRTPEVTCVV VDVSQEDPEV QFNWYVDGVE VHNAKTKPRE  300
EQFNSTYRVV SVLTVLHQDW LNGKEYKCKV SNKGLPSSIE KTISKAKGQP REPQVCTLPP  360
SQEEMTKNQV SLSCAVKGFY PSDIAVEWES NGQPENNYKT TPPVLDSDGS FFLVSKLTVD  420
KSRWQEGNVF SCSVMHEALH NHYTQKSLSL SLGKHHHHHH                        460

SEQ ID NO: 112          moltype = DNA  length = 2043
FEATURE                 Location/Qualifiers
misc_feature            1..2043
                        note = Description of the artificial sequence: base
                            sequence of the antibody sequence of pCI-AVM-hLG4PE
                            (R409K)-linker-MOG01 VL-CL excluding signal sequence
source                  1..2043
                        mol_type = other DNA
                        organism = synthetic construct
SEQUENCE: 112
gaggtgcagc tggtggaatc tgggggaggc ttagtgcagc ctggaagatc cctgaaactc    60
tcctgtgcag cctcaggatt cactttcagt aactatgcca tggcttgggt ccgccgggct   120
ccaacgaagg gtctggaagtg ggtcgcatcc attagtaatg gtggtggtaa cacttactat   180
cgcgactccg tgaagggccg attcactatc tccagagatg atgcaaaaaa caccctatac   240
ctgcaaatgg acagtctgag gtctgaggac acggccactt attactgtgc aagacacggg   300
aattatatat attatgggtc ttcttttgat tactggggcc aaggagtcat ggtcacagtc   360
tcctcagcta gcaccaaggg gccatccgtc ttccccctgg cgccctgctc caggagcacc   420
tccgagagca cagccgcccct gggctgcctg gtcaaggact acttccccga accggtgacg   480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacg   600
aagacctaca cctgcaacgt agatcacaag cccagcaaca ccaaggtgga caagagagtt   660
gagtccaaat atggtccccc atgcccacca tgcccagttc ctgagttgca gggggggacca   720
tcagtcttcc tgttcccccc aaaacccaag gacactctca tgatctcccg gacccctgag   780
gtcacgtgcg tggtggtgga cgtgagccag gaagaccccg aggtccagtt caactggtac   840
gtggatggcg tggaggtgca taatgccaag acaaagccgc gggaggagca gttcaacagc   900
acgtaccgtg tggtcagcgt cctcaccgtc ctgcaccagg actggctgaa cggcaaggag   960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctacccag cgacatcgcc  1140
gtggagtggg agagcaatgg gcagccggag aacaactaca agaccacgcc tcccgtgctg  1200
gactccgacg gctccttctt cctctacagc aagctaaccg tggacaagag caggtggcag  1260
gaggggaatg tcttctcatg ctccgtgatg catgaggctc tgcacaacca ctacacacag  1320
aagagcctct ccctgtctct gggtaaagga ggaggagggt ccggaggagg aggtccggga  1380
ggaggaggt cccagtctgc cctgactcag cctgcctccg tgtctgggtc tcctggacag  1440
tcgatcacca tctcctgcac tggaaccagc cgtgacgttg gtggttataa ctatgtctcc  1500
tggtaccaac aacacccagg caaagccccc aaactcatga tttatgatgt caataatcgg  1560
ccctcagggg tttctaatcg gttctctggc tccaagtctg gcaacacggc ctccctgacc  1620
atctctgggc tccaggctga ggacgaggct gattatttct gcagctcata tacaagcagt  1680
agcacccctg tggtattcgg cggtgggacc aagctgaccg tcctaggtca gcccaaggcc  1740
gccccctcgg tcactctgtt cccgccctcc tctgaggagc ttcaagccaa caaggccaca  1800
ctggtgtgtc tcataagtga cttctacccg ggagccgtga cagtggcctg aaggcagat  1860
agcagccccg tcaaggcggg agtggagacc accacaccc ccaaacaaag caacaacaag  1920
tacgcggcca gcagctacct gagcctgacg cctgagcagt ggaagtcccc cagaagctac  1980
agctgccagg tcacgcatga agggagcacc gtggagaaga cagtggcccc tacagaatgt  2040
tca                                                                 2043

SEQ ID NO: 113          moltype = AA  length = 681
FEATURE                 Location/Qualifiers
REGION                  1..681
                        note = Description of the artificial sequence: amino acid
                            sequence of the antibody sequence of pCI-AVM-hLG4PE
                            (R409K)-linker-MOG01 VL-CL excluding signal sequence
source                  1..681
                        mol_type = protein
                        organism = synthetic construct
SEQUENCE: 113
EVQLVESGGG LVQPGRSLKL SCAASGFTFS NYAMAWVRRA PTKGLEWVAS ISNGGGNTYY   60
RDSVKGRFTI SRDDAKNTLY LQMDSLRSED TATYYCARHG NYIYYGSFFD YWGQGVMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFEGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
```

```
TKNQVSLTCL VKGFYPSDIA VEWESNGQPE NNYKTTPPVL DSDGSFFLYS KLTVDKSRWQ    420
EGNVFSCSVM HEALHNHYTQ KSLSLSLGKG GGGSGGGGSG GGGSQSALTQ PASVSGSPGQ    480
SITISCTGTS RDVGGYNYVS WYQQHPGKAP KLMIYDVNNR PSGVSNRFSG SKSGNTASLT    540
ISGLQAEDEA DYFCSSYTSS STPVVFGGGT KLTVLGQPKA APSVTLFPPS SEELQANKAT    600
LVCLISDFYP GAVTVAWKAD SSPVKAGVET TTPSKQSNNK YAASSYLSLT PEQWKSHRSY    660
SCQVTHEGST VEKTVAPTEC S                                             681

SEQ ID NO: 114          moltype = DNA   length = 675
FEATURE                 Location/Qualifiers
misc_feature            1..675
                        note = Description of the artificial sequence: base
                          sequence of antibody sequence of pCI-MOG01 VH-CH excluding
                          signal sequence
source                  1..675
                        mol_type = other DNA
                        organism = synthetic construct
SEQUENCE: 114
caggtacagc tgcagcagtc aggcgcagga ttattgaagc cttcggagac cctttccctc    60
acctgcgctg tgtctggtgg gtccttcagt ggttactact ggacctggat ccgccagcgc    120
ccagggaagg ggctggagtg gattggagaa atcaatcatc gtggaagcac cgattacaac    180
ccgtccctca gagtcgagt caccatgtca atagacacgt ccaagagcca gttctccctg    240
aatttgaaat ctgtgaccgc cgcggacacg gctgtgtatt actgtgcgag accgcctgg    300
gggtcttgtt atgatgggac ctgctacccc gctaatact tccaatactg gggccaggga    360
accctggtca ccgtctcctc agctagcacc aaggggccat ccgtcttccc cctggcgccc    420
tgctccagga gcacctccga gagcacagcc gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacgaagac ctacacctgc aacgtagatc acaagcccag caacaccaag    660
gtggacaaga gagtt                                                    675

SEQ ID NO: 115          moltype = AA   length = 225
FEATURE                 Location/Qualifiers
REGION                  1..225
                        note = Description of the artificial sequence: amino acid
                          sequence of antibody sequence of pCI-MOG01 VH-CH excluding
                          signal sequence
source                  1..225
                        mol_type = protein
                        organism = synthetic construct
SEQUENCE: 115
QVQLQQSGAG LLKPSETLSL TCAVSGGSFS GYYWTWIRQR PGKGLEWIGE INHRGSTDYN    60
PSLKSRVTMS IDTSKSQFSL NLKSVTAADT AVYYCARAAW GSCYDGTCYP AEYFQYWGQG    120
TLVTVSSAST KGPSVFPLAP CSRSTSESTA ALGCLVKDYF PEPVTVSWNS GALTSGVHTF    180
PAVLQSSGLY SLSSVVTVPS SSLGTKTYTC NVDHKPSNTK VDKRV                    225

SEQ ID NO: 116          moltype = DNA   length = 2181
FEATURE                 Location/Qualifiers
misc_feature            1..2181
                        note = Description of the artificial sequence: base
                          sequence of antibody sequence of pCI-AVM-hLG4PE (R409K /
                          S354C / T366W)-linker-MOG01 scFv-FLAG tag excluding
                          signal sequence
source                  1..2181
                        mol_type = other DNA
                        organism = synthetic construct
SEQUENCE: 116
gaggtgcagc tggtggaatc tgggggaggc ttagtgcagc ctggaagatc cctgaaactc    60
tcctgtgcag cctcaggatt cacttcagt aactatgcca tggcttgggt ccgccgggct    120
ccaacgaagg gtctggagtg ggtcgcatcc attagtaatg gtggtggtaa cacttactat    180
cgcgactccg tgaagggccg attcactatc tccagagatg atgcaaaaa caccctatac    240
ctgcaaatgg acagtctgag gtctgaggac acggccactt attactgtgc aagacacggg    300
aattatata attatgggtc ctttctttgat tactggggcc aaggagtcat ggtcacagtc    360
tcctcagcta gcaccaaggg gccatccgtc ttccccctgg cgcctgctc caggagcacc    420
tccgagagca gcgccct gggctgcctg gtcaaggact acttccccga accggtgtca    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtcccaaat atggtccccc atgcccacca tgcccagcac ctgatctcga gggggaccca    720
tcagtcttcc tgttcccccc aaaacccaag gacactctca tgatctcccg gaccccctga    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa    1020
gccaaaggg cagccccgag gccacagtta tacaccctgc ccccatgcca ggagagatg    1080
accaagaacc aggtcagcct gtggtgcctg gtcaaaggct tctacccag cgacatcgcc    1140
gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtggagga agcggaggag gagggtccgg aggaggaggg    1380
```

-continued

```
tccggaggag gagggtccca ggtacagctg cagcagtcag gcgcaggatt attgaagcct    1440
tcggagaccc tttccctcac ctgcgctgtg tctggtgggt ccttcagtgg ttactactgg    1500
acctggatcc gccagcgccc agggaagggg ctggagtgga ttggagaaat caatcatcgt    1560
ggaagcaccg attacaaccc gtccctcaag agtcgagtca ccatgtcaat agacacgtcc    1620
aagagccagt tctccctgaa tttgaaatct gtgaccgccg cggacacggc tgtgtattac    1680
tgtgcgagag ccgcctgggg gtcttgttat gatgggaccc gctacccgc tgaatacttc     1740
caatactggg gccagggaac cctggtcacc gtctcctcag gaggcggtgg cagcggtggg    1800
cgcgcctcgg gcggaggtgg ttcacagtct gccctgactc agcctgcctc cgtgtctggg    1860
tctcctggac agtcgatcac catctcctgc actggaacca gccgtgacgt tggtggttat    1920
aactatgtct cctggtacca acaacaccca ggcaaagccc ccaaactcat gatttatgat    1980
gtcaataatc ggccctcagg ggtttctaat cggttctctg gctccaagtc tggcaacacg    2040
gcctccctga ccatctctgg gctccaggct gaggacgagg ctgattattt ctgcagctca    2100
tatacaagca gtagcacccc tgtggtattc ggcggtggga ccaagctgac cgtcctagac    2160
tacaaggacg acgatgacaa g                                              2181
```

| SEQ ID NO: 117 | moltype = AA   length = 727 |
|---|---|
| FEATURE | Location/Qualifiers |
| REGION | 1..727 |
|  | note = Description of the artificial sequence: amino acid sequence of the antibody sequence of pCI-AVM-hLG4PE (R409K / S354C / T366W) -linker-MOG01 scFv-FLAG tag excluding signal sequence |
| source | 1..727 |
|  | mol_type = protein |
|  | organism = synthetic construct |

SEQUENCE: 117
```
EVQLVESGGG LVQPGRSLKL SCAASGFTFS NYAMAWVRRA PTKGLEWVAS ISNGGGNTYY     60
RDSVKGRFTI SRDDAKNTLY LQMDSLRSED TATYYCARHG NYIYYGSFFD YWGQGVMVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFEGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPCQEEM    360
TKNQVSLWCL VKGFYPSDIA VEWESNGQPE NNYKTTPPVL DSDGSFFLYS KLTVDKSRWQ    420
EGNVFSCSVM HEALHNHYTQ KSLSLSLGGG SGGGGSGGGG SGGGGSQVQL QQSGAGLLKP    480
SETLSLTCAV SGGSFSGYYW TWIRQRPGKG LEWIGEINHR GSTDYNPSLK SRVTMSIDTS    540
KSQFSLNLKS VTAADTAVYY CARAAWGSCY DGTCYPAEYF QYWGQGTLVT VSSGGGGSGG    600
RASGGGGSQS ALTQPASVSG SPGQSITISC TGTSRDVGGY NYVSWYQQHP GKAPKLMIYD    660
VNNRPSGVSN RFSGSKSGNT ASLTISGLQA EDEADYFCSS YTSSSTPVVF GGGTKLTVLD    720
YKDDDDK                                                              727
```

| SEQ ID NO: 118 | moltype = DNA   length = 1365 |
|---|---|
| FEATURE | Location/Qualifiers |
| misc_feature | 1..1365 |
|  | note = Description of the artificial sequence: base sequence of the antibody sequence of pCI-AVM-hLG4PE (R409K / Y349C / T366S / L368A / Y407V) -His tag excluding signal sequence |
| source | 1..1365 |
|  | mol_type = other DNA |
|  | organism = synthetic construct |

SEQUENCE: 118
```
gaggtgcagc tggtggaatc tgggggaggc ttagtgcagc ctggaagatc cctgaaactc     60
tcctgtgcag cctcaggatt cactttcagt aactatgcca tggcttgggt ccgccgggct    120
ccaacgaagg gtctggagtg ggtcgcatcc attagtaatg gtggtggtaa cacttactat    180
cgcgactccg tgaagggccg attcactatc tccagagatg acgcaaaaaa cacccctatc    240
ctgcaaatgg acagtctgag gtctgaggac acggccactt attactgtgc aagcacggga    300
aattatatat attatgggtc cttctttgat tactggggcc aaggagtcat ggtcacagtc    360
tcctcagcta gcaccaaggg gccatccgtc ttccccctgg cgccctgctc caggagcacc    420
tccgagagca cagccgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccacca tgcccagcac ctgagttcga gggggggacca    720
tcagtcttcc tgttcccccc aaaacccaag gacactctca tgatctcccg gacccctgag    780
gtcacgtgcg tggtggtgga cgtgagccag gaagacccg aggtccagtt caactggtac     840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa    1020
gccaaagggc agccccgaga gccacaggtg tgcaccctgc ccccatccca ggagatgatg   1080
accaagaacc aggtcagcct gtcctgcgcg gtcaaaggct tctacccag cgacatcgcc    1140
gtggagtggg agagcaatgg gcagccggag aacaactaca agaccacgcc tcccgtgctg    1200
gactccgacg gctccttctt cctcgtcagc aagctaaccg tggacaagag caggtggcag    1260
gaggggaatg tcttctcatg ctccgtgatg catgaggctc tgcacaacca ctacacacag    1320
aagagcctct ccctgtctct gggtaaaaac caccaccacc accac                    1365
```

| SEQ ID NO: 119 | moltype = AA   length = 455 |
|---|---|
| FEATURE | Location/Qualifiers |
| REGION | 1..455 |
|  | note = Description of the artificial sequence: amino acid |

```
                        sequence of the antibody sequence of pCI-AVM-hLG4PE (R409K
                        / Y349C / T366S / L368A / Y407V) -His tag excluding signal
                        sequence
source                  1..455
                        mol_type = protein
                        organism = synthetic construct
SEQUENCE: 119
EVQLVESGGG LVQPGRSLKL SCAASGFTFS NYAMAWVRRA PTKGLEWVAS ISNGGGNTYY   60
RDSVKGRFTI SRDDAKNTLY LQMDSLRSED TATYYCARHG NYIYYGSFFD YWGQGVMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFEGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV CTLPPSQEEM  360
TKNQVSLSCA VKGFYPSDIA VEWESNGQPE NNYKTTPPVL DSDGSFFLVS KLTVDKSRWQ  420
EGNVFSCSVM HEALHNHYTQ KSLSLSLGKH HHHH                              455

SEQ ID NO: 120          moltype = DNA  length = 2151
FEATURE                 Location/Qualifiers
misc_feature            1..2151
                        note = Description of the artificial sequence: base
                         sequence of the antibody sequence of pCI-AVM-hLG4PE
                         (R409K) _MOG01 scFv2 excluding signal sequence
source                  1..2151
                        mol_type = other DNA
                        organism = synthetic construct
SEQUENCE: 120
gaggtgcagc tggtggaatc tgggggaggc ttagtgcagc ctggaagatc cctgaaactc    60
tcctgtgcag cctcaggatt cactttcagt aactatgcca tggcttgggt ccgcgggct   120
ccaacgaagg gtctggagtg ggtcgcatcc attagtaatg gtggtggtaa cacttactat   180
cgcgactccg tgaagggccg attcactatc tccagagatg atgcaaaaaa cacccctacc   240
ctgcaaatgg acagtctgag gtctgaggac acggccactt attactgtgc aagcacggag   300
aattatatat attatgggtc cttctttgat tactggggcc aaggagtcat ggtcacagtc   360
tcctcagcta gcaccaaggg gccatccgtc ttccccctgg cgccctgctc caggagcacc   420
tccgagagca gccgcccct gggctgcctg gtcaaggact acttcccga accggtgacg   480
gtgtcgtgga actcaggcgc cctgaccagc ggcgtgcaca ccttccccggc tgtcctacag   540
tcctcaggac tctactccct cagcagcgtg gtgaccgtgc cctccagcag cttgggcacg   600
aagacctaca cctgcaacgt agatcacaag cccagcaaca ccaaggtgga caagagagtt   660
gagtccaaat atggtccccc atgcccacca tgcccagcac ctgagttcga gggggaccca   720
tcagtcttcc tgttcccccc aaaacccaag gacactctca tgatctcccg gacccctgag   780
gtcacgtgcg tggtggtgga cgtgagccag gaagaccccg aggtccagtt caactggtac   840
gtggatggcg tggaggtgca taatgccaag acaaagccgc gggaggagca gttcaacagc   900
acgtaccgtg tggtcagcgt cctcaccgtc ctgcaccagg actggctgaa cggcaaggag   960
tacaagtgca aggtctccaa caaagggctc cgtcctccca tcgagaaaaa catctccaaa  1020
gccaaaggg agccccgaga gccacaggtg tacaccctgc cccatccca ggaggagatg  1080
accaagaacc aggtcagcct gacctgcctg gtcaaaggct tctacccag cgacatcgcc  1140
gtggagtggg agagcaatgg gcagccggag aacaactaca agaccacgcc tcccgtgctg  1200
gactccgacg gctccttctt cctctacagc aagctaaccg tggacaagag caggtggcag  1260
gaggggaatg tcttctcatg ctccgtgatg catgaggctc tgcacaacca ctacacacag  1320
aagagcctct ccctgtctct gggtaaagga ggagagggt ccggaggagg agggtccgga  1380
ggaggaggt cccaggtaca gctgcagcag tcaggcgcag gattattgaa gccttcggag  1440
acccttttccc tcacctgcgc tgtgtctggt gggtccttca gtggttacta ctggacctgg  1500
atccgccagc cccagggaa ggggctggag tggattggaa aaatcaatca tcgtggaagc  1560
accgattaca acccgtccct caagagtcga gtcaccatgt caatagacac gtccaagagc  1620
cagttctccc tgaatttgaa atctgtgacc gccgcggaca cggctgtgta ttactgtgcg  1680
agagccgcct gggggtcttg ttatgatggg acctgctacc ccgctgaata cttccaatac  1740
tggggccagg gaaccctggt caccgtctcc tcaggaggcg gtggcagcgg tgggcgcgcc  1800
tcgggcggag gtggttcaca gtctgccctg actcagcctg cctccgtgtc tgggtctcct  1860
ggacagtcga tcaccatctc ctgcactgga accagccgtg acgttggtgg ttataactat  1920
gtctcctggt accaacaaca cccaggcaaa gcccccaaac tcatgattta tgatgtcaat  1980
aatcggccct caggggtttc taatcggttc tctggctcca agtctggcaa cacgcctcc  2040
ctgaccatct ctgggctcca ggctgaggac gaggctgatt atttctgcag ctcatataca  2100
agcagtagca cccctgtggt attcggcggt gggaccaagc tgaccgtcct a          2151

SEQ ID NO: 121          moltype = AA  length = 717
FEATURE                 Location/Qualifiers
REGION                  1..717
                        note = Description of the artificial sequence: amino acid
                         sequence of antibody sequence of pCI-AVM-hLG4PE (R409K)
                         _MOG 01 scFv 2 excluding signal sequence
source                  1..717
                        mol_type = protein
                        organism = synthetic construct
SEQUENCE: 121
EVQLVESGGG LVQPGRSLKL SCAASGFTFS NYAMAWVRRA PTKGLEWVAS ISNGGGNTYY   60
RDSVKGRFTI SRDDAKNTLY LQMDSLRSED TATYYCARHG NYIYYGSFFD YWGQGVMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFEGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
```

```
TKNQVSLTCL VKGFYPSDIA VEWESNGQPE NNYKTTPPVL DSDGSFFLYS KLTVDKSRWQ  420
EGNVFSCSVM HEALHNHYTQ KSLSLSLGKG GGGSGGGGSG GGGSQVQLQQ SGAGLLKPSE  480
TLSLTCAVSG GSFSGYYWTW IRQRPGKGLE WIGEINHRGS TDYNPSLKSR VTMSIDTSKS  540
QFSLNLKSVT AADTAVYYCA RAAWGSCYDG TCYPAEYFQY WGQGTLVTVS SGGGGSGGRA  600
SGGGGSQSAL TQPASVSGSP GQSITISCTG TSRDVGGYNY VSWYQQHPGK APKLMIYDVN  660
NRPSGVSNRF SGSKSGNTAS LTISGLQAED EADYFCSSYT SSSTPVVFGG GTKLTVL    717
```

```
SEQ ID NO: 122          moltype = DNA   length = 2157
FEATURE                 Location/Qualifiers
misc_feature            1..2157
                        note = Description of the artificial sequence: base
                         sequence of antibody sequence of pCI-AVM-hLG4PE (R409K)
                         _MOG01 scFv3 excluding signal sequence
source                  1..2157
                        mol_type = other DNA
                        organism = synthetic construct
SEQUENCE: 122
gaggtgcagc tggtggaatc tgggggaggc ttagtgcagc ctggaagatc cctgaaactc   60
tcctgtgcag cctcaggatt cactttcagt aactatgcca tggcttgggt ccgccgggct  120
ccaacgaagg gtctggagtg gtcgcatcc attagtaatg gtggtggtaa cacttactat  180
cgcgactccg tgaagggccg attcactatc tccagagatg atgcaaaaaa caccctatac  240
ctgcaaatgg acagtctgag gtctgaggac acggccactt attactgtgc aagacacggg  300
aattatatat attatgggtc cttctttgat tactgggggcc aaggagtcat ggtcacagtc  360
tcctcagcta gcaccaaggg gccatccgtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca cctttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccacca tgcccagcac ctgagttcga gggggaccca  720
tcagtcttcc tgttcccccc aaaacccaag gacactctca tgatctcccg gacccctgag  780
gtcacgtgcg tggtggtgga cgtgagccag gaagacccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctccca tcgagaaaac catctccaaa 1020
gccaaaggc agccccgaga gccacaggtg tacaccctgc ccccatccca ggaggagatg 1080
accaagaacc aggtcagcct gacctgcctg gtcaaaggct tctacccag cgacatcgcc 1140
gtggagtggg agagcaatgg gcagccggag aacaactaca agaccacgcc tcccgtgctg 1200
gactccgacg gctccttctt cctctacagc aagctaaccg tggacaagag caggtggcag 1260
gaggggaatg tcttctcatg ctccgtgatg catgaggctc tgcacaacca ctacacaca  1320
aagagcctct ccctgtctct gggtggagga gcggaggag gagggtccgg aggaggaggg 1380
tccggaggag gagggtccca gtctgccctg actcagcctg cctccgtgtc tgggtctcct 1440
ggacagtcga tcaccatctc ctgcactgga accagccgtg acgttggtgg ttataactat 1500
gtctcctggt accaacaaca cccaggcaaa gcccccaaac tcatgattta tgatgtcaat 1560
aatcggccct caggggtttc taatcggttc tctggctcca agtctggcaa cacggcctcc 1620
ctgaccatct ctgggctcca ggctgaggac gaggctgatt attctgcag ctcatataca 1680
agcagtagca ccccctgtggt attcggcggt gggaccaagc tgaccgtcct aggaggcggt 1740
ggcagcggtg gcgcgcctc gggcgagggt ggttcacagt acagcctgga gcagtcaggc 1800
gcaggattat tgaagccttc ggagaccctt tccctcacct gcgctgtgtc tggtgggtcc 1860
ttcagtggtt actactggac ctggatccgc cagcgcccag gaaggggct ggagtggatt 1920
ggagaaatca atcatcgtgg aagcaccgat acaacccgt ccctcaagag tcgagtcacc 1980
atgtcaatag acacgtccaa gagccagttc tccctgaatt tgaaatctgt gaccgccgcg 2040
gacacggctg tgtattactg tgcgagagcc gcctgggggt cttgttatga tgggacctgc 2100
taccccgctg aatacttcca atactggggc cagggaaccc tggtcaccgt ctcctca    2157
```

```
SEQ ID NO: 123          moltype = AA    length = 719
FEATURE                 Location/Qualifiers
REGION                  1..719
                        note = Description of the artificial sequence: amino acid
                         sequence of the antibody sequence of pCI-AVM-hLG4PE
                         (R409K) _MOG 01 scFv 3 excluding signal sequence
source                  1..719
                        mol_type = protein
                        organism = synthetic construct
SEQUENCE: 123
EVQLVESGGG LVQPGRSLKL SCAASGFTFS NYAMAWVRRA PTKGLEWVAS ISNGGGNTYY   60
RDSVKGRFTI SRDDAKNTLY LQMDSLRSED TATYYCARHG NYIYYGSFFD YWGQGVMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFEGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS KLTVDKSRWQ  420
EGNVFSCSVM HEALHNHYTQ KSLSLSLGGG SGGGGSGGGG SGGGSQSAL TQPASVSGSP  480
GQSITISCTG TSRDVGGYNY VSWYQQHPGK APKLMIYDVN NRPSGVSNRF SGSKSGNTAS  540
LTISGLQAED EADYFCSSYT SSSTPVVFGG GTKLTVLGGG GSGGGRASGG GSQVQLQQSG  600
AGLLKPSETL SLTCAVSGGS FSGYYWTWIR QRPGKGLEWI GEINHRGSTD YNPSLKSRVT  660
MSIDTSKSQF SLNLKSVTAA DTAVYYCARA AWGSCYDGTC YPAEYFQYWG QGTLVTVSS   719
```

```
SEQ ID NO: 124          moltype = DNA   length = 2175
FEATURE                 Location/Qualifiers
```

```
misc_feature            1..2175
                        note = Description of the artificial sequence: base
                          sequence of the antibody sequence of pCI-AVM-hLG4PE
                          (R409K) _MOG 01 scFv 4 excluding signal sequence
source                  1..2175
                        mol_type = other DNA
                        organism = synthetic construct
SEQUENCE: 124
gaggtgcagc tggtggaatc tgggggaggc ttagtgcagc ctggaagatc cctgaaactc   60
tcctgtgcag cctcaggatt cactttcagt aactatgcca tggcttgggt ccgccgggct  120
ccaacgaagg gtctggagtg ggtcgcatcc attagtaatg gtggtggtaa cacttactat  180
cgcgactccg tgaagggccg attcactatc tccagagatg atgcaaaaaa cacccctatac 240
ctgcaaatgg acagtctgag gtctgaggac acggccactt attactgtgc aagacacggg  300
aattatatat attatgggtc cttctttgat tactggggcc aaggagtcat ggtcacagtc  360
tcctcagcta gcaccaaggg gccatccgtc ttccccctgg cgccctgctc caggagcacc  420
tccgagagca gcccgccct gggctgcctg gtcaaggact acttcccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccacca tgcccagcac ctgagttcga gggggaccca  720
tcagtcttcc tgttcccccc aaaacccaag gacactctca tgatctcccg gacccctgag  780
gtcacgtgcg tggtggtgga cgtgagccag gaagacccg aggtccagtt caactggtac  840
gtggatggcg tggaggtgca taatgccaag acaaagccgc gggaggagca gttcaacagc  900
acgtaccgtg tggtcagcgt cctcaccgtc ctgaccagg actggctgaa cggcaaggag  960
tacaagtgca aggtctccaa caaaggcctc ccgtcctcca tcgagaaaac catctccaaa 1020
gccaaaggc agccccgaga gccacaggtg tacaccctgc ccccatccca ggaggagatg 1080
accaagaacc aggtcagcct gacctgcctg gtcaaaggct tctacccag cgacatcgcc 1140
gtggagtggg agagcaatgg gcagccggag aacaactaca agaccacgcc tcccgtgctg 1200
gactccgacg gctccttctt cctctacagc aagctaaccg tggacaagag caggtggcag 1260
gagggaaatg tcttctcatg ctccgtgatg catgaggctc tgcacaacca ctacacacag 1320
aagagcctct ccctgtctct gggtggagga ggagggtccg gaggaggagg gtccggtgga 1380
ggtgggtccc aggtacagct gcagcagtca ggcgcaggat tattgaagcc ttcggagacc 1440
ctttccctca cctgcgctgt gtctggtggg tccttcagtg gttactactg gacctggatc 1500
cgccagcgcc cagggaaggg gctggagtgg attggagaaa tcaatcatcg tggaagcacc 1560
gattacaacc cgtccctcaa gagtcgagtc accatgtcaa tagacacgtc caagagccag 1620
ttctccctga atttgaaatc tgtgaccgcc gcggacacgg ctgtgtatta ctgtgcgaga 1680
gccgcctggg ggtcttgtta tgatgggacc tgctacccg ctgaatactt ccaatactgg 1740
ggccagggaa ccctggtcac cgtctcctca gctagcaccg gaggcggtgg cagcggagga 1800
ggagggtccg gtgggggcgg ctcgggcgga ggtggttcac agtctgccct gactcagcct 1860
gcctccgtgt ctgggtctcc tggacagtcg atcaccatct cctgcactgg aaccagccgt 1920
gacgttggtg gttataacta tgtctcctcg taccaacaac cccaggcaa agcccccaaa 1980
ctcatgattt atgatgtcaa taatcggccc tcaggggttt ctaatcggtt ctctggctcc 2040
aagtctggca acacggcctc cctgaccatc tctgggctcc aggctgagga cgaggctgat 2100
tatttctgca gctcatatac aagcagtagc acccctgtgg tattcggcgg tgggaccaag 2160
ctgaccgtcc taggt                                                  2175

SEQ ID NO: 125          moltype = AA   length = 725
FEATURE                 Location/Qualifiers
REGION                  1..725
                        note = Description of the artificial sequence: amino acid
                          sequence of the antibody sequence of pCI-AVM-hLG4PE
                          (R409K) _MOG 01 scFv 4 excluding signal sequence
source                  1..725
                        mol_type = protein
                        organism = synthetic construct
SEQUENCE: 125
EVQLVESGGG LVQPGRSLKL SCAASGFTFS NYAMAWVRRA PTKGLEWVAS ISNGGGNTYY   60
RDSVKGRFTI SRDDAKNTLY LQMDSLRSED TATYYCARHG NYIYYGSFFD YWGQGVMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFEGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS KLTVDKSRWQ  420
EGNVFSCSVM HEALHNHYTQ KSLSLSLGGG GGSGGGGSGG GGSQVQLQQS GAGLLKPSET  480
LSLTCAVSGG SFSGYYWTWI RQRPGKGLEW IGEINHRGST DYNPSLKSRV TMSIDTSKSQ  540
FSLNLKSVTA ADTAVYYCAR AAWGSCYDGT CYPAEYFQYW GQGTLVTVSS ASTGGGGSGG  600
GGSGGGGSGG GGSQSALTQP ASVSGSPGQS ITISCTGTSR DVGGYNYVSW YQQHPGKAPK  660
LMIYDVNNRP SGVSNRFSGS KSGNTASLTI SGLQAEDEAD YFCSSYTSSS TPVVFGGGTK  720
LTVLG                                                              725

SEQ ID NO: 126          moltype = DNA   length = 2175
FEATURE                 Location/Qualifiers
misc_feature            1..2175
                        note = Description of the artificial sequence: base
                          sequence of antibody sequence of pCI-AVM-hLG4PE (R409K)
                          _MOG 01 scFv 5 excluding signal sequence
source                  1..2175
                        mol_type = other DNA
                        organism = synthetic construct
```

-continued

```
SEQUENCE: 126
gaggtgcagc tggtggaatc tggggagggc ttagtgcagc ctggaagatc cctgaaactc    60
tcctgtgcag cctcaggatt cactttcagt aactatgcca tggcttgggt ccgccgggct   120
ccaacgaagg gtctggagtg ggtcgcatcc attagtaatg gtggtggtaa cacttactat   180
cgcgactccg tgaagggccg attcactatc tccagagatg atgcaaaaaa caccctatac   240
ctgcaaatgg acagtctgag gtctgaggac acggccactt attactgtgc aagacacggg   300
aattatatat attatgggtc cttctttgat tactggggcc aaggagtcat ggtcacagtc   360
tcctcagcta gcaccaaggg gccatccgtc ttccccctgg cgccctgctc caggagcacc   420
tccgagagca cagccgccct gggctgcctg gtcaaggact acttccccga accggtgacg   480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacg   600
aagacctaca cctgcaacgt agatcacaag cccagcaaca ccaaggtgga caagagagtt   660
gagtccaaat atggtccccc atgcccacca tgcccagcac ctgagttcga gggggaccca   720
tcagtcttcc tgttccccc aaaacccaag gacactctca tgatctcccg gacccctgag   780
gtcacgtgcg tggtggtgga cgtgagccag gaagaccccg aggtccagtt caactggtac   840
gtggatggcg tggaggtgca taatgccaag acaaagccgc gggaggagca gttcaacagc   900
acgtaccgtg tggtcagcgt cctcaccgtc ctgcaccagg actggctgaa cggcaaggag   960
tacaagtgca aggtctccaa caaaggcctc ccgtcctcca tcgagaaaac catctccaaa  1020
gccaaagggc agccccgaga gccacaggtg tacaccctgc cccatcccaa ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aagctaaccg tggacaagag caggtggcag  1260
gaggggaatg tcttctcatg ctccgtgatg catgaggctc tgcacaacca ctacacacag  1320
aagagcctct ccctgtctct gggtggagga ggagggtccg gaggaggagg gtccggtgga  1380
ggtgggtccc agtctgccct gactcagcct gcctccgtgt ctgggtctcc tggacagtcg  1440
atcaccatct cctgcactgg aaccaccgt gacgttggtg gttataacta tgtctcctgg  1500
taccaacaac acccaggcaa agcccccaaa ctcatgattt atgatgtcaa taatcggccc  1560
tcagggggttt ctaatcggtt ctctggctcc aagtctggca acacggcctc cctgaccatc  1620
tctgggctcc aggctgagga cgaggctgat tatttctgca gctcatatac aagcagtagc  1680
accctgtgg tattcggcgg tgggaccaag ctgaccgtcc taggtggagg cggttggcagc  1740
ggaggaggag ggtccggtgg gggcggctcg gcggaggtg gttcacaggt acagctgcag  1800
cagtcaggcg caggattatt gaagccttcg gagacccttt ccctcacctg cgctgtgtct  1860
ggtgggtcct tcagtggtta ctactggacc tggatccgcc agcgcccagg gaaggggctg  1920
gagtggattg gagaaatcaa tcatcgtgga agcaccgatt acaacccgtc cctcaagagt  1980
cgagtcacca tgtcaataga cacgtccaag agccagttct ccctgaattt gaatctctgg  2040
accgccgcgg acacggctgt gtattactgt gcgagagccg cctgggggtc ttgttatgat  2100
gggacctgct accccgctga atacttccaa tactggggcc agggaaccct ggtcaccgtc  2160
tcctcagcta gcacc                                                   2175
```

SEQ ID NO: 127 moltype = AA length = 725
FEATURE Location/Qualifiers
REGION 1..725
  note = Description of the artificial sequence: amino acid
  sequence of the antibody sequence of pCI-AVM-hLG4PE
  (R409K)_MOG01 scFv5 excluding signal sequence
source 1..725
  mol_type = protein
  organism = synthetic construct

```
SEQUENCE: 127
EVQLVESGGG LVQPGRSLKL SCAASGFTFS NYAMAWVRRA PTKGLEWVAS ISNGGGNTYY    60
RDSVKGRFTI SRDDAKNTLY LQMDSLRSED TATYYCARHG NYIYYGSFFD YWGQGVMVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFEGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS KLTVDKSRWQ   420
EGNVFSCSVM HEALHNHYTQ KSLSLSLGGG GSGGGGSGG GGSQSALTQP ASVSGSPGQS   480
ITISCTGTSR DVGGYNYVSW YQQHPGKAPK LMIYDVNNRP SGVSNRFSGS KSGNTASLTI   540
SGLQAEDEAD YFCSSYTSSS TPVVFGGGTK LTVLGGGGGS GGGGGGGGS GGGSQVQLQ   600
QSGAGLLKPS ETLSLTCAVS GGSFSGYYWT WIRQRPGKGL EWIGEINHRG STDYNPSLKS   660
RVTMSIDTSK SQFSLNLKSV TAADTAVYYC ARAAWGSCYD GTCYPAEYFQ YWGQGTLVTV   720
SSAST                                                              725
```

SEQ ID NO: 128 moltype = DNA length = 2148
FEATURE Location/Qualifiers
misc_feature 1..2148
  note = Description of the artificial sequence: base
  sequence of the antibody sequence of pCI-AVM-hLG4PE
  (R409K)_MOG01 scFv6 excluding signal sequence
source 1..2148
  mol_type = other DNA
  organism = synthetic construct

```
SEQUENCE: 128
gaggtgcagc tggtggaatc tggggagggc ttagtgcagc ctggaagatc cctgaaactc    60
tcctgtgcag cctcaggatt cactttcagt aactatgcca tggcttgggt ccgccgggct   120
ccaacgaagg gtctggagtg ggtcgcatcc attagtaatg gtggtggtaa cacttactat   180
cgcgactccg tgaagggccg attcactatc tccagagatg atgcaaaaaa caccctatac   240
ctgcaaatgg acagtctgag gtctgaggac acggccactt attactgtgc aagacacggg   300
aattatatat attatgggtc cttctttgat tactggggcc aaggagtcat ggtcacagtc   360
```

-continued

```
tcctcagcta gcaccaaggg gccatccgtc ttccccctgg cgccctgctc caggagcacc    420
tccgagagca cagccgccct gggctgcctg tcaaggact  acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccacca tgcccagcac ctgagttcga gggggggacca   720
tcagtcttcc tgttcccccc aaaacccaag gacactctca tgatctcccg gacccctgag    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtacctgt ggtcagcgt  cctcaccgtc ctgcaccagg actggctgaa cggcaaggag    960
tacaagtgca aggtctccaa caaaggcctc ccgtcctcca tcgagaaaac catctccaaa   1020
gccaaagggc agcccgaga  gccacaggtg tacaccctgc cccatccca  ggaggagatg   1080
accaagaacc aggtcagcct gacctgcctg gtcaaaggct tctaccccag cgacatcgcc   1140
gtggagtggg agagcaatgg gcagccggag aacaactaca agaccacgcc tcccgtgctg   1200
gactccgacg gctccttctt cctctacagc aagctaaccg tggacaagag caggtggcag   1260
gaggggaatg tcttctcatg ctccgtgatg catgaggctc tgcacaacca ctacacacag   1320
aagagcctct ccctgtctct gggtggagga ggagggtccg gaggaggagg gtccggtgga   1380
ggtggggtccc agtctgccct gactcagcct gcctccgtgt ctgggtctcc tggacagtcg   1440
atcaccatct cctgcactgg aaccagccgt gacgttggtg gttataacta tgtctcctgg   1500
taccaacaac acccaggcaa agcccccaaa ctcatgattt atgatgtcaa taatcggccc   1560
tcaggggttt ctaatcggtt ctctggctcc aagtctggca acacgccctc cctgaccatc   1620
tctgggctcc aggctgagga cgaggctgat tatttctgca gctcatatac aagcagtagc   1680
accctgtgg  tattcggcgg tgggaccaag ctgaccgtcc taggaggcgg tggcagcggg   1740
gggcgcgcct cggggcggagg tggttcacag gtacagctgc agcagtcagg cgcaggatta   1800
ttgaagcctt cggagaccct ttccctcacc tgcgctgtgt ctggtgggtc cttcagtggt   1860
tactactgga cctggatccg ccagcgccca gggaagggcc tggagtggat tggagaaatc   1920
aatcatcgtg gaagcaccga ttacaacccg tccctcaaga gtcgagtcac catgtcaata   1980
gacacgtcca agagccagtt ctccctgaat ttgaaatctg tgaccgccgc ggacacggct   2040
gtgtattact gtgcgagagc cgcctggggg tcttgttatg atgggacctg ctaccccgct   2100
gaatacttcc aatactgggg ccagggaacc ctggtcaccg tctcctca               2148
```

```
SEQ ID NO: 129          moltype = AA  length = 716
FEATURE                 Location/Qualifiers
REGION                  1..716
                        note = Description of the artificial sequence: amino acid
                          sequence of the antibody sequence of pCI-AVM-hLG4PE
                          (R409K) _MOG 01 scFv 6 excluding signal sequence
source                  1..716
                        mol_type = protein
                        organism = synthetic construct
SEQUENCE: 129
EVQLVESGGG LVQPGRSLKL SCAASGFTFS NYAMAWVRRA PTKGLEWVAS ISNGGGNTYY     60
RDSVKGRFTI SRDDAKNTLY LQMDSLRSED TATYYCARHG NYIYYGSFFD YWGQGVMVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFEGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS KLTVDKSRWQ    420
EGNVFSCSVM HEALHNHYTQ KSLSLSLGGG GSGGGGSGG  GGSQSALTQP ASVSGSPGQS    480
ITISCTGTSR DVGGYNYVSW YQQHPGKAPK LMIYDVNNRP SGVSNRFSGS KSGNTASLTI    540
SGLQAEDEAD YFCSSYTSSS TPVVFGGGTK LTVLGGGGSG GRASGGGGSQ VQLQQSGAGL    600
LKPSETLSLT CAVSGGSFSG YYWTWIRQRP GKGLEWIGEI NHRGSTDYNP SLKSRVTMSI    660
DTSKSQFSLN LKSVTAADTA VYYCARAAWG SCYDGTCYPA EYFQYWGQGT LVTVSS        716
```

```
SEQ ID NO: 130          moltype = DNA  length = 2172
FEATURE                 Location/Qualifiers
misc_feature            1..2172
                        note = Description of the artificial sequence: base
                          sequence of the antibody sequence of pCI-AVM-hLG4PE
                          (R409K) _MOG01 scFv7 excluding signal sequence
source                  1..2172
                        mol_type = other DNA
                        organism = synthetic construct
SEQUENCE: 130
gaggtgcagc tggtggaatc tggggaggc  ttagtgcagc ctggaagatc cctgaaactc     60
tcctgtgcag cctcaggatt cactttcagt aactatgcca tggcttgggt ccgccgggct    120
ccaacgaagg gtctggagtg ggtcgcatcc attagtaatg gtggtggtaa cacttactat    180
cgcgactccg tgaagggccg attcactatc tccagagatg atgcaaaaaa cacctatac    240
ctgcaaatgg acagtctgag actgaggact acggccactt attactgtgc aagacacgg    300
aattatat   attatgggtc cttctttgat tactggggcc aaggagtcat ggtcacagtc    360
tcctcagcta gcaccaaggg gccatccgtc ttccccctgg cgccctgctc caggagcacc    420
tccgagagca cagccgccct gggctgcctg tcaaggact  acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccacca tgcccagcac ctgagttcga gggggggacca   720
tcagtcttcc tgttcccccc aaaacccaag gacactctca tgatctcccg gacccctgag    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
```

```
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag cgacatcgcc    1140
gtggagtggg agagcaatgg gcagccggag aacaactaca agaccacgcc tcccgtgctg   1200
gactccgacg gctccttctt cctctacagc aagctaaccg tggacaagag caggtggcag   1260
gaggggaatg tcttctcatg ctccgtgatg catgaggctc tgcacaacca ctacacacag   1320
aagagcctct ccctgtctct gggtggagga gcggaggag gagggtccgg aggaggaggg    1380
tccggaggag gagggtccca gtctgccctg actcagcgtc cctccgtgtc tgggtctcct   1440
ggacagtcga tcaccatctc ctgcactgga accagccgtg acgttggtgg ttataactat   1500
gtctcctggt accaacaaca cccaggcaaa gcccccaaac tcatgattta tgatgtcaat   1560
aatcggccct caggggtttc taatcggttc tctggctcca agtctggcaa cacggcctcc   1620
ctgaccatct ctgggctcca ggctgaggac gaggctgatt atttctgcag ctcatataca   1680
agcagtagca cccctgtggt attcggcggt gggaccaagc tgaccgtcct aggaggcggt   1740
ggcagcggag gaggagggtc cggtgggggc ggctcgggcg gaggtggttc acaggtacag   1800
ctgcagcagt caggcgcagg attattgaag ccttcggaga ccctttccct cacctgcgct   1860
gtgtctggtg gtccttcag tggttactac tggacctgga tccgcagcg cccagggaag    1920
gggctggagt ggattggaga aatcaatcat cgtggaagca ccgattacaa ccctccctc    1980
aagagtcgag tcaccatgtc aatagacacg tccaagagcc agttctccct gaatttgaaa   2040
tctgtgaccg ccgcggacac ggctgtgtat tactgtgcga gagccgcctg ggggtcttgt   2100
tatgatggga cctgctaccc cgctgaatac ttccaatact ggggccaggg aaccctggtc   2160
accgtctcct ca                                                      2172

SEQ ID NO: 131        moltype = AA   length = 724
FEATURE               Location/Qualifiers
REGION                1..724
                      note = Description of the artificial sequence: amino acid
                        sequence of the antibody sequence of pCI-AVM-hLG4PE
                        (R409K) _MOG01 scFv7 excluding signal sequence
source                1..724
                      mol_type = protein
                      organism = synthetic construct
SEQUENCE: 131
EVQLVESGGG LVQPGRSLKL SCAASGFTFS NYAMAWVRRA PTKGLEWVAS ISNGGGNTYY     60
RDSVKGRFTI SRDDAKNTLY LQMDSLRSED TATYYCARHG NYIYYGSFFD YWGQGVMVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFEGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS KLTVDKSRWQ    420
EGNVFSCSVM HEALHNHYTQ KSLSLSLGGG SGGGGSGGGG SGGGGSQSAL TQPASVSGSP    480
GQSITISCTG TSRDVGGYNY VSWYQQHPGK APKLMIYDVN NRPSGVSNRF SGSKSGNTAS    540
LTISGLQAED EADYFCSSYT SSSTPVVFGG GTKLTVLGGG SGGGGSGGGG GSGGGGSGGG    600
LQQSGAGLLK PSETLSLTCA VSGGSFSGYY WTWIRQRPGK GLEWIGEINH RGSTDYNPSL    660
KSRVTMSIDT SKSQFSLNLK SVTAADTAVY YCARAAWGSC YDGTCYPAEY FQYWGQGTLV    720
TVSS                                                                 724

SEQ ID NO: 132        moltype = DNA   length = 2169
FEATURE               Location/Qualifiers
misc_feature          1..2169
                      note = Description of the artificial sequence: base
                        sequence of the antibody sequence of pCI-AVM-hLG4PE
                        (R409K) _MOG 01 scFv 8 excluding signal sequence
source                1..2169
                      mol_type = other DNA
                      organism = synthetic construct
SEQUENCE: 132
gaggtgcagc tggtggaatc tggggggaggc ttagtgcagc ctggaagatc cctgaaactc     60
tcctgtgcag cctcaggatt cactttcagt aactatgcca tggcttgggt ccgccgggct    120
ccaacgaagg gtctggagtg ggtcgcatcc attagtaatg gtggtggtaa cacttactat    180
cgcgactccg tgaagggccg attcactatc tccagagatg atgcaaaaaa caccctatac    240
ctgcaaatgg acagtctgag gtctgaggac acggccactt attactgtgc aagacacggg    300
aattatatat attatgggtc cttctttgat tactggggcc aaggagtcat ggtcacagtc    360
tcctcagcta gcaccaaggg gccatccgtc ttccccctgg cccctgctc caggagcacc    420
tccgagagca cagccgccct gggctgcctg gtcaaggact acttcccga accggtgacg    480
gtgtcgtgga actcaggcgc cctgaccagc ggcgtgcaca cctttccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccagca cctgagttgg gggggaccac    720
tcagtcttcc tgttccccccc aaaacccaag gacactctca tgatctcccg gacccctgag    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag cgacatcgcc    1140
gtggagtggg agagcaatgg gcagccggag aacaactaca agaccacgcc tcccgtgctg   1200
gactccgacg gctccttctt cctctacagc aagctaaccg tggacaagag caggtggcag   1260
gaggggaatg tcttctcatg ctccgtgatg catgaggctc tgcacaacca ctacacacag   1320
```

```
                                      -continued
aagagcctct ccctgtctct gggtggagga agcggaggag gagggtccgg aggaggaggg 1380
tccggaggag gagggtccca gtctgccctg actcagcctg cctccgtgtc tgggtctcct 1440
ggacagtcga tcaccatctc ctgcactgga accagccgtg acgttggtgg ttataactat 1500
gtctcctggt accaacaaca cccaggcaaa gcccccaaac tcatgattta tgatgtcaat 1560
aatcggccct caggggtttc taatcggttc tctggctcca agtctggcaa cacggcctcc 1620
ctgaccatct ctgggctcca ggctgaggac gaggctgatt atttctgcag ctcatataca 1680
agcagtagca cccctgtggt attcggcggt gggaccaagc tgaccgtcct aggtggaggc 1740
ggtggcagcg gtgggcgcgc tcgggcggg ggtggttcac aggtacagct gcagcagtca 1800
ggcgcaggat tattgaagcc ttcggagacc ctttccctca cctgcgctgt gtctggtggg 1860
tccttcagtg gttactactg gacctggatc cgccagcgcc cagggaaggg gctggagtgg 1920
attggagaaa tcaatcatcg tggaagcacc gattacaacc cgtccctcaa gagtcgagtc 1980
accatgtcaa tagacacgtc caagagccag ttctccctga atttgaaatc tgtgaccgcc 2040
gcggacacgg ctgtgtatta ctgtgcgaga gccgcctggg ggtcttgtta tgatgggacc 2100
tgctaccccg ctgaatactt ccaatactgg ggccaggaa ccctggtcac cgtctcctca 2160
gctagcacc                                                         2169

SEQ ID NO: 133           moltype = AA  length = 723
FEATURE                  Location/Qualifiers
REGION                   1..723
                         note = Description of the artificial sequence: amino acid
                          sequence of the antibody sequence of pCI-AVM-hLG4PE
                          (R409K) _MOG 01 scFv 8 excluding signal sequence
source                   1..723
                         mol_type = protein
                         organism = synthetic construct
SEQUENCE: 133
EVQLVESGGG LVQPGRSLKL SCAASGFTFS NYAMAWVRRA PTKGLEWVAS ISNGGGNTYY  60
RDSVKGRFTI SRDDAKNTLY LQMDSLRSED TATYYCARHG NYIYYGSFFD YWGQGVMVTV 120
SSASTKGPSV FPLAPCSRST SESTAALGCL VKDYFPEPVT VSWNSGALTS GVHTFPAVLQ 180
SSGLYSLSSV VTVPSSSLGT KTYTCNVDHK PSNTKVDKRV ESKYGPPCPP CPAPEFEGGP 240
SVFLFPPKPK DTLMISRTPE VTCVVVDVSQ EDPEVQFNWY VDGVEVHNAK TKPREEQFNS 300
TYRVVSVLTV LHQDWLNGKE YKCKVSNKGL PSSIEKTISK AKGQPREPQV YTLPPSQEEM 360
TKNQVSLTCL VKGFYPSDIA VEWESNGQPE NNYKTTPPVL DSDGSFFLYS KLTVDKSRWQ 420
EGNVFSCSVM HEALHNHYTQ KSLSLSLGGG SGGGGSGGGS SGGGGSQSAL TQPASVSGSP 480
GQSITISCTG TSRDVGGYNY VSWYQQHPGK APKLMIYDVN NRPSGVSNRF SGSKSGNTAS 540
LTISGLQAED EADYFCSSYT SSSTPVVFGG GTKLTVLGGG GGSGGRASGG GGSQVQLQQS 600
GAGLLKPSET LSLTCAVSGG SFSGYYWTWI RQRPGKGLEW IGEINHRGST DYNPSLKSRV 660
TMSIDTSKSQ FSLNLKSVTA ADTAVYYCAR AAWGSCYDGT CYPAEYFQYW GQGTLVTVSS 720
AST                                                                723

SEQ ID NO: 134           moltype = DNA  length = 2163
FEATURE                  Location/Qualifiers
misc_feature             1..2163
                         note = Description of the artificial sequence: base
                          sequence of antibody sequence of pCI-AVM-hLG4PE (R409K)
                          _MOG01 scFv9 excluding signal sequence
source                   1..2163
                         mol_type = other DNA
                         organism = synthetic construct
SEQUENCE: 134
gaggtgcagc tggtggaatc tgggggaggc ttagtgcagc ctggaagatc cctgaaactc  60
tcctgtgcag cctcaggatt cacttttcagt aactatgcca tggcttgggt ccgccgggct 120
ccaacgaagg gtctggagtg ggtcgcatcc attagtaatg gtggtggtaa cacttactat 180
cgcgactccg tgaagggccg attcactatc tccagagatg atgcaaaaaa caccctatac 240
ctgcaaatgg acagtctgag gtctgaggac acggccactt attactgtgc aagacacggg 300
aattatatat attatgggtc cttctttgat tactggggcc aaggagtcat ggtcacagtc 360
tcctcagcta gcaccaaggg gccatccgtc ttccccctgg cgccctgctc caggagcacc 420
tccgagagca gccgccctg ggctgcctg gtcaaggact acttcccga accggtgacg 480
gtgtcgtgga actcaggcgc cctgaccagc ggcgtgcaca cctttcccggc tgtcctacag 540
tcctcaggac tctactcccct cagcagcgtg gtgaccgtgc cctccagcag cttgggcacg 600
aagacctaca cctgcaacgt agatcacaag cccagcaaca ccaaggtgga caagagagtt 660
gagtccaaat atggtccccc atgcccacca tgcccagcac ctgagttcga gggggaccca 720
tcagtcttcc tgttcccccc aaaacccaag gacactctca tgatctcccg gacccctgag 780
gtcacgtgcg tggtggtgga cgtgagccag gaagacccc aggtccagtt caactggtac 840
gtggatggcg tggaggtgca taatgccaag acaaagccgc gggaggagca gttcaacagc 900
acgtaccgtg tggtcagcgt cctcaccgtc ctgcaccagg actggctgaa cggcaaggag 960
tacaagtgca aggtctccaa caaaggcctc ccgtcctcca tcgagaaaac catctccaaa 1020
gccaaagggc agccccgaga gccacaggtg tacaccctgc cccatccca ggaggagatg 1080
accaagaacc aggtcagcct gacctgcctg gtcaaaggct tctaccccag cgacatcgtg 1140
gtggagtggg agagcaatgg gcagccggag aacaactaca agaccacgcc tcccgtgctg 1200
gactccgacg gctccttctt cctctacagc aagctaaccg tggacaagag caggtggcag 1260
gaggggaatg tcttctcatg ctccgtgatg catgaggctc tgcacaacca ctacacacag 1320
aagagcctct ccctgtctct gggtggagga ggagggtccg gaggaggagg gtccggtgga 1380
tccggggtcc agtctgccct gactcagcct cctccgtgtc tgggtctcct ggacagtcg 1440
atcaccatct cctgcactgg aaccagccgt gacgttggtg gttataacta tgtctcctgg 1500
taccaacaac acccaggcaa agcccccaaa ctcatgattt atgatgtcaa taatcggccc 1560
tcaggggttt ctaatcggtt ctctggctcc agtctggca acacggcctc cctgaccatc 1620
tctgggctcc aggctgagga cgaggctgat tatttctgca gctcatatac aagcagtagc 1680
acccctgtgg tattcggcgg tgggaccaag ctgaccgtcc taggaggcgg tggcagcgga 1740
```

```
ggaggagggt ccggtggggg cggctcgggc ggaggtggtt cacaggtaca gctgcagcag 1800
tcaggcgcag gattattgaa gccttcggag accctttccc tcacctgcgc tgtgtctggt 1860
gggtccttca gtggttacta ctggacctgg atccgccagc gcccaggaa ggggctggag 1920
tggattggag aaatcaatca tcgtggaagc accgattaca acccgtccct caagagtcga 1980
gtcaccatgt caatagacac gtccaagagc cagttctccc tgaatttgaa atctgtgacc 2040
gccgcggaca cggctgtgta ttactgtgcg agagccgcct gggggtcttg ttatgatggg 2100
acctgctacc ccgctgaata cttccaatac tggggccagg gaaccctggt caccgtctcc 2160
tca                                                               2163

SEQ ID NO: 135         moltype = AA  length = 721
FEATURE                Location/Qualifiers
REGION                 1..721
                       note = Description of the artificial sequence: amino acid
                        sequence of the antibody sequence of pCI-AVM-hLG4PE
                        (R409K) _MOG01 scFv9 excluding signal sequence
source                 1..721
                       mol_type = protein
                       organism = synthetic construct
SEQUENCE: 135
EVQLVESGGG LVQPGRSLKL SCAASGFTFS NYAMAWVRRA PTKGLEWVAS ISNGGGNTYY  60
RDSVKGRFTI SRDDAKNTLY LQMDSLRSED TATYYCARHG NYIYYGSFFD YWGQGVMVTV 120
SSASTKGPSV FPLAPCSRST SESTAALGCL VKDYFPEPVT VSWNSGALTS GVHTFPAVLQ 180
SSGLYSLSSV VTVPSSSLGT KTYTCNVDHK PSNTKVDKRV ESKYGPPCPP CPAPEFEGGP 240
SVFLFPPKPK DTLMISRTPE VTCVVVDVSQ EDPEVQFNWY VDGVEVHNAK TKPREEQFNS 300
TYRVVSVLTV LHQDWLNGKE YKCKVSNKGL PSSIEKTISK AKGQPREPQV YTLPPSQEEM 360
TKNQVSLTCL VKGFYPSDIA VEWESNGQPE NNYKTTPPVL DSDGSFFLYS KLTVDKSRWQ 420
EGNVFSCSVM HEALHNHYTQ KSLSLSLGGG GGSGGGGSGG GGSQSALTQP ASVSGSPGQS 480
ITISCTGTSR DVGGYNYVSW YQQHPGKAPK LMIYDVNNRP SGVSNRFSGS KSGNTASLTI 540
SGLQAEDEAD YFCSSYTSSS TPVVFGGGTK LTVLGGGGSG GGGSGGGGSG GGGSQVQLQQ 600
SGAGLLKPSE TLSLTCAVSG GSFSGYYWTW IRQRPGKGLE WIGEINHRGS TDYNPSLKSR 660
VTMSIDTSKS QFSLNLKSVT AADTAVYYCA RAAWGSCYDG TCYPAEYFQY WGQGTLVTVS 720
S                                                                721

SEQ ID NO: 136         moltype = DNA  length = 2160
FEATURE                Location/Qualifiers
misc_feature           1..2160
                       note = Description of the artificial sequence: base
                        sequence of antibody sequence of pCI-AVM-hLG4PE (R409K)
                        _MOG 01 scFv 10 excluding signal sequence
source                 1..2160
                       mol_type = other DNA
                       organism = synthetic construct
SEQUENCE: 136
gaggtgcagc tggtggaatc tgggggaggc ttagtgcagc ctggaagatc cctgaaactc   60
tcctgtgcag cctcaggatt cactttcagt aactatgcca tggcttgggt ccgccgggct  120
ccaacgaagg gtctggagtg ggtcgcatcc attagtaatg gtggtggtaa cacttactat  180
cgcgactccg tgaaggatcg attcactatc tccagagatg acgcaaaaaa caccctatac  240
ctgcaaatgg acagtctgag gtctgaggac acgccactt attactgtgc aagacacggg  300
aattatatat attatgggtc ctttttttga tactggggcc aaggagtcat ggtcacagtc  360
tcctcagcta gcaccaaggg gccatccgtc ttccccctgg cgccctgctc caggagcacc  420
tccgagagca gcgccctg ggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtcccaaa tatgtcccc catgcccacca tgcccagcac ctgagttgac ggggggacca  720
tcagtcttcc tgttccccc aaaacccaag gacactctca tgatctcccg gacccctgag  780
gtcacgtgcg tggtggtgga cgtgagccag gaagaccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa 1020
gccaaagggc agccccgaga gccacaggtg tacaccctgc cccatccca ggaggagatg 1080
accaagaacc aggtcagcct gacctgcctg gtcaaaggct tctacccag cgacatcgcc 1140
gtggagtggg agagcaatgg gcagccggag aacaactaca agaccacgcc tcccgtgctg 1200
gactccgacg gctccttctt cctctacagc aagctaaccg tggacaagag caggtggcag 1260
gaggggaatg tcttctcatg ctccgtgatg catgaggctc tgcacaacca ctacacacag 1320
aagagcctct ccctgtctct gggtggagga ggagggtccg gaggaggagg gtccggtgga 1380
ggtgggtccc agtctgccct gactcagcct gcctccgtgt ctgggtctcc tggacagtcg 1440
atcaccatct cctgcactgg aaccagccgt gacgttggtg gttataacta tgtctcctgg 1500
taccaacaac acccaggcaa agcccccaaa ctcatgattt atgatgtcaa taatcggccc 1560
tcaggggttt ctaatcggtt ctctggctcc aagtctggca acacggcctc cctgaccatc 1620
tctgggctcc aggctgagga cgaggctgat tatttctgca gctcatatac aagcagtagc 1680
accccctgtg tattcggcgg tgggaccaag ctgaccgtcc taggtggagg cggtggcagc 1740
ggtgggcgcg cctcggcgg aggtggtca caggtacagc tgcagcagtc aggcgcagga 1800
ttattgaagc cttcggagac cctttcctc acctgcgctg tgtctggtgg ttcttcagt 1860
ggttactact ggacctggat ccgccagcgc ccagggaagg gctggagtg gattggagaa 1920
atcaatcatc gtggaagcac cgattacaac ccgtccctca gagtcgagt caccatgtca 1980
atagacacgt ccaagagcca gttctccctg aatttgaaat ctgtgaccgc cgcggacacg 2040
gctgtgtatt actgtgcgag agccgcctgg gggtcttgtt atgatgggac tgctaccccg 2100
ctgaatactt ccaatactgg ggccaggga accctggtca ccgtctcctc agctagcacc 2160
```

```
SEQ ID NO: 137          moltype = AA  length = 720
FEATURE                 Location/Qualifiers
REGION                  1..720
                        note = Description of the artificial sequence: amino acid
                         sequence of the antibody sequence of pCI-AVM-hLG4PE
                         (R409K) _MOG 01 scFv 10 excluding signal sequence
source                  1..720
                        mol_type = protein
                        organism = synthetic construct
SEQUENCE: 137
EVQLVESGGG LVQPGRSLKL SCAASGFTFS NYAMAWVRRA PTKGLEWVAS ISNGGGNTYY    60
RDSVKGRFTI SRDDAKNTLY LQMDSLRSED TATYYCARHG NYIYYGSFFD YWGQGVMVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFEGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS KLTVDKSRWQ   420
EGNVFSCSVM HEALHNHYTQ KSLSLSLGGG GGSGGGGSGG GGSQSALTQP ASVSGSPGQS   480
ITISCTGTSR DVGGYNYVSW YQQHPGKAPK LMIYDVNNRP SGVSNRFSGS KSGNTASLTI   540
SGLQAEDEAD YFCSSYTSSS TPVVFGGGTK LTVLGGGGS GGRASGGGGS QVQLQQSGAG   600
LLKPSETLSL TCAVSGGSFS GYYWTWIRQR PGKGLEWIGE INHRGSTDYN PSLKSRVTMS   660
IDTSKSQFSL NLKSVTAADT AVYYCARAAW GSCYDGTCYP AEYFQYWGQG TLVTVSSAST   720

SEQ ID NO: 138          moltype = DNA  length = 2184
FEATURE                 Location/Qualifiers
misc_feature            1..2184
                        note = Description of the artificial sequence: base
                         sequence of the antibody sequence of pCI-AVM-hLG4PE
                         (R409K) _MOG01 scFv11 excluding signal sequence
source                  1..2184
                        mol_type = other DNA
                        organism = synthetic construct
SEQUENCE: 138
gaggtgcagc tggtggaatc tgggggaggc ttagtgcagc ctggaagatc cctgaaactc    60
tcctgtgcag cctcaggatt cactttcagt aactatgcca tggcttgggt ccgccgggct   120
ccaacgaagg gtctggagtg gtcgcatcc attagtaatg gtggtggtaa cacttactat   180
cgcgactccg tgaagggccg attcactatc tccagagatg atgcaaaaaa cccctatac   240
ctgcaaatgg acagtctgag gtctgaggac acggccactt attactgtgc aagacacggg   300
aattatatat attatgggtc cttctttgat tactggggcc aaggagtcat ggtcacagtc   360
tcctcagcta gcaccaaggg gccatccgtc ttccccctgg cgccctgctc caggagcacc   420
tccgagagca cagccgccct gggctgcctg gtcaaggact acttcccga accggtgacg   480
gtgtcgtgga actcaggcgc cctgaccagc ggcgtgcaca cctteccggc tgtcctacag   540
tcctcaggac tctactccct cagcagcgtg gtgaccgtgc cctccagcag cttgggcacg   600
aagacctaca cctgcaacgt agatcacaag cccagcaaca ccaaggtgga caagagagtt   660
gagtccaaat atggtccccc atgcccacca tgcccagcac ctgagttcga ggggggacca   720
tcagtcttcc tgttcccccc aaaacccaag gacactctca tgatctcccg gacccctgag   780
gtcacgtgcg tggtggtgga cgtgagccag gaagacccg aggtccagtt caactgctac   840
gtggatggcg tggaggtgca taatgccaag acaaagccgc gggaggagca gttcaacagc   900
acgtaccgtg tggtcagcgt cctcaccgtc ctgcaccagg actggctgaa cggcaaggag   960
tacaagtgca aggtctccaa caaaggcctc ccgtcctccc tcgagaaaac catctccaaa  1020
gccaaaggc agccccgaga gccacaggtg tacaccctgc ccccatccca ggaggagatg  1080
accaagaacc aggtcagcct gacctgcctg gtcaaaggct tctacccag cgacatcgcc  1140
gtggagtggg agagcaatgg gcagccggag aacaactaca agaccacgcc tcccgtgctg  1200
gactccgacg gctccttctt cctctacagc aagctaaccg tggacaagag caggtggcag  1260
gagggganatg tcttctcatg ctccgtgatg catgaggctc tgcacaacca ctacacacag  1320
aagagcctct ccctgtctct gggtggagga agcggaggag gagggtccgg aggaggaggg  1380
tccggaggag gagggtccca gtctgccctg actcagcctg cctccgtgtc tgggtctcct  1440
ggacagtcga tcaccatctc ctgcactgga accagcgtg acgttggtgg ttataactat  1500
gtctcctggt accaacaaca cccaggcaaa gcccccaaac tcatgattta tgatgtcaat  1560
aatcggccct cagggggtttc taatcggttc tctggctcca agtctggcaa cacggcctcc  1620
ctgaccatct ctgggctcca ggctgaggac gaggctgatt attttctgcag ctcatatata  1680
agcagtagca cccctgtggt attcggcggt gggaccaagc tgaccgtcct aggtggaggc  1740
ggttggcagcg gaggaggagg gtccggtggg ggcggctcgg gcggaggtgg ttcacaggta  1800
cagctgcagc agtcaggcgc aggattattg aagccttcgg agaccctttc cctcacctgc  1860
gctgtgtctg gtgggtcctt cagtggttac tactggacct ggatccgcca gcgcccaggg  1920
aagggctga gtggattgg agaaatcaat catcgtggaa gcaccgatta caacccgtcc  1980
ctcaagagtc gagtcaccat gtcaatagac acgtccaaga gccagttctc cctgaatttg  2040
aaatctgtga ccgccgcgga cacggctgtg tattactgtg cgagagccgc ctgggggtct  2100
tgttatgatg ggacctgcta ccccgctgaa tacttccaat actgggccca gggaaccctg  2160
gtcaccgtct cctcagctag cacc                                         2184

SEQ ID NO: 139          moltype = AA  length = 728
FEATURE                 Location/Qualifiers
REGION                  1..728
                        note = Description of the artificial sequence: amino acid
                         sequence of the antibody sequence of pCI-AVM-hLG4PE
                         (R409K) _MOG 01 scFv 11 excluding signal sequence
source                  1..728
```

```
                        mol_type = protein
                        organism = synthetic construct
SEQUENCE: 139
EVQLVESGGG LVQPGRSLKL SCAASGFTFS NYAMAWVRRA PTKGLEWVAS ISNGGGNTYY    60
RDSVKGRFTI SRDDAKNTLY LQMDSLRSED TATYYCARHG NYIYYGSFFD YWGQGVMVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFEGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS KLTVDKSRWQ   420
EGNVFSCSVM HEALHNHYTQ KSLSLSLGGG SGGGGSGGGG SGGGGSQSAL TQPASVSGSP   480
GQSITISCTG TSRDVGGYNY VSWYQQHPGK APKLMIYDVN NRPSGVSNRF SGSKSGNTAS   540
LTISGLQAED EADYFCSSYT SSSTPVVFGG GTKLTVLGGG GSGGGGSGG  GGSGGGGSQV   600
QLQQSGAGLL KPSETLSLTC AVSGGSFSGY YWTWIRQRPG KGLEWIGEIN HRGSTDYNPS   660
LKSRVTMSID TSKSQFSLNL KSVTAADTAV YYCARAAWGS CYDGTCYPAE YFQYWGQGTL   720
VTVSSAST                                                            728

SEQ ID NO: 140         moltype = DNA  length = 2040
FEATURE                Location/Qualifiers
misc_feature           1..2040
                       note = Description of the artificial sequence: base
                        sequence of the antibody sequence of pCI-AVM-hLG4PE
                        (R409K)-linker-AVMVL-CL excluding signal sequence
source                 1..2040
                       mol_type = other DNA
                       organism = synthetic construct
SEQUENCE: 140
gaggtgcagc tggtggaatc tgggggaggc ttagtgcagc ctggaagatc cctgaaactc      60
tcctgtgcag cctcaggatt cactttcagt aactatgcca tggcttgggt ccgccgggct    120
ccaacgaagg gtctggaagt ggtcgcatcc attagtaatg gtgtggtaa cacttactat     180
cgcgactccg tgaagggccg attcactatc tccagagatg atgcaaaaaa caccctatac    240
ctgcaaatgg acagtctgag gtctgaggac acggccactt attactgtgc aagacacggg    300
aattatatat attatgggtc cttctttgat tactggggcc aaggagtcat ggtcacagtc    360
tcctcagcta gcaccaaggg gccatccgtc ttcccctgg cgcctgctc caggagcacc      420
tccgagagca gccgccct gggctgcctg gtcaaggact acttcccga accggtgacg       480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccacca tgcccagttcga ggggggacca              720
tcagtcttcc tgttcccccc aaaacccaag gacactctca tgatctcccg gacccctgag    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag cgacatcgcc    1140
gtggagtggg agagcaatgg gcagccggag aacaactaca agaccacgcc tcccgtgctg   1200
gactccgacg gctccttctt cctctacagc aagctaaccg tggacaagag caggtggcag   1260
gaggggaatg tcttctcatg ctccgtgatg catgaggctc tgcacaacca ctacacacag   1320
aagagcctct ccctgtctct gggtaaagga ggagggggt ccggaggagg agggtccgga    1380
ggaggagggt cccagtttgt gctttctcag ccaaactctg tgtctacgaa tctcggaagc   1440
acagtcaaac tgtcttgcaa gcgcagcact ggtaacattg gaagcaatta tgtgagctgg   1500
taccagcagc atgagggaag atctcccacc actatgattt atagggatga taagagacca   1560
gatggagttc ctgacaggtt ctctggctcc attgacagat cttccgactc agccctcctg   1620
acaatcaata atgtgcagac tgaagatgaa gctgactact tctgtcagtc ttacagtagt   1680
ggtattaata ttttcggcgg tggaaccaag ctcactgtcc taggtcagcc caaggccgcc   1740
ccctcggtca ctctgttccc gccctcctct gaggagcttc aagccaacaa ggccacactg   1800
gtgtgtctca taagtgactt ctacccggga gccgtgacag tggcctggaa ggcagatagc   1860
agccccgtca aggcgggagt ggagaccacc acaccctcca aacaaagcaa caacaagtac   1920
gcggccagca gctacctgag cctgactcct gagcagtgga agtcccacag aagctacagc   1980
tgccaggtca cgcatgaagg gagcaccgtg gagaagacag tggcccctac agaatgttca   2040

SEQ ID NO: 141          moltype = AA  length = 680
FEATURE                 Location/Qualifiers
REGION                  1..680
                        note = Description of the artificial sequence: amino acid
                         sequence of the antibody sequence of pCI-AVM-hLG4PE
                         (R409K)-linker-AVMVL-CL excluding signal sequence
source                  1..680
                        mol_type = protein
                        organism = synthetic construct
SEQUENCE: 141
EVQLVESGGG LVQPGRSLKL SCAASGFTFS NYAMAWVRRA PTKGLEWVAS ISNGGGNTYY    60
RDSVKGRFTI SRDDAKNTLY LQMDSLRSED TATYYCARHG NYIYYGSFFD YWGQGVMVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFEGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS KLTVDKSRWQ   420
```

```
EGNVFSCSVM HEALHNHYTQ KSLSLSLGKG GGGSGGGGSG GGGSQFVLSQ PNSVSTNLGS    480
TVKLSCKRST GNIGSNYVSW YQQHEGRSPT TMIYRDDKRP DGVPDRFSGS IDRSSDSALL    540
TINNVQTEDE ADYFCQSYSS GINIFGGGTK LTVLGQPKAA PSVTLFPPSS EELQANKATL    600
VCLISDFYPG AVTVAWKADS SPVKAGVETT TPSKQSNNKY AASSYLSLTP EQWKSHRSYS    660
CQVTHEGSTV EKTVAPTECS                                                680

SEQ ID NO: 142          moltype = DNA   length = 660
FEATURE                 Location/Qualifiers
misc_feature            1..660
                        note = Description of the artificial sequence: base
                         sequence of antibody sequence of pCI-AVMVH-CH excluding
                         signal sequence
source                  1..660
                        mol_type = other DNA
                        organism = synthetic construct
SEQUENCE: 142
gaggtgcagc tggtggaatc tgggggaggc ttagtgcagc ctggaagatc cctgaaactc     60
tcctgtgcag cctcaggatt cactttcagt aactatgcca tggcttgggt ccgccgggct    120
ccaacgaagg gtctggagtg ggtcgcatcc attagtaatg gtggtggtaa cacttactat    180
cgcgactccg tgaagggccg attcactatc tccagagata tgcaaaaaa caccctatac    240
ctgcaaatgg acagtctgag gtctgaggac acggccactt attactgtgc aagacacggg    300
aattatatat attatgggtc cttctttgat tactgggggc aaggagtcat ggtcacagtc    360
tcctcagcta gcaccaaggg gccatccgtc ttccccctgg cgccctgctc caggagcacc    420
tccgagagca cagccgccct gggctgcctg gtcaaggact acttcccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660

SEQ ID NO: 143          moltype = AA   length = 220
FEATURE                 Location/Qualifiers
REGION                  1..220
                        note = Description of the artificial sequence: amino acid
                         sequence of antibody sequence of pCI-AVMVH-CH excluding
                         signal sequence
source                  1..220
                        mol_type = protein
                        organism = synthetic construct
SEQUENCE: 143
EVQLVESGGG LVQPGRSLKL SCAASGFTFS NYAMAWVRRA PTKGLEWVAS ISNGGGNTYY     60
RDSVKGRFTI SRDDAKNTLY LQMDSLRSED TATYYCARHG NYIYYGSFFD YWGQGVMVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV                          220

SEQ ID NO: 144          moltype = DNA   length = 2163
FEATURE                 Location/Qualifiers
misc_feature            1..2163
                        note = Description of the artificial sequence: base
                         sequence of the antibody sequence of pCI-AVM-hLG4PE (R409K
                         / S354C / T366W) -linker-AVMscFv-FLAG tag excluding signal
                         sequence
source                  1..2163
                        mol_type = other DNA
                        organism = synthetic construct
SEQUENCE: 144
gaggtgcagc tggtggaatc tgggggaggc ttagtgcagc ctggaagatc cctgaaactc     60
tcctgtgcag cctcaggatt cactttcagt aactatgcca tggcttgggt ccgccgggct    120
ccaacgaagg gtctggagtg ggtcgcatcc attagtaatg gtggtggtaa cacttactat    180
cgcgactccg tgaagggccg attcactatc tccagagata tgcaaaaaa caccctatac    240
ctgcaaatgg acagtctgag gtctgaggac acggccactt attactgtgc aagacacggg    300
aattatatat attatgggtc cttctttgat tactggggcc aaggagtcat ggtcacagtc    360
tcctcagcta gcaccaaggg gccatccgtc ttccccctgg cgccctgctc caggagcacc    420
tccgagagca cagccgccct gggctgcctg gtcaaggact acttcccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccacca tgcccagcac ctgagttcga gggggaccca    720
tcagtcttcc tgttcccccc aaaacccaag gacactctca tgatctcccg gacccctgag    780
gtcacgtgcg tggtggtgga cgtgagccag gaagacccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatgcca ggaggagatg   1080
accaagaacc aggtcagcct gtggtgcctg gtcaaaggct tctaccccag cgacatcgcc   1140
gtggagtggg agagcaatgg gcagccggag aacaactaca agaccacgcc tcccgtgctg   1200
gactccgacg gctccttctt cctctacagc aagctaaccg tggacaagag caggtggcag   1260
gaggggaatg tcttctcatg ctccgtgatg catgaggctc tgcacaacca ctacacacag   1320
aagagcctct ccctgtctct gggtggagga agcggaggag gagggtccgg aggagggggg   1380
tccggaggag agggtccga ggtgcagctg gtggaatctg ggggaggctt agtgcagcct   1440
ggaagatccc tgaaactctc ctgtgcagcc tcaggattca ctttcagtaa ctatgccatg   1500
```

-continued

```
gcttgggtcc gccgggctcc aacgaagggg ctggagtggg tcgcatccat tagtaatggt  1560
ggtggtaaca cttactatcg cgactccgtg aagggccgat tcactatctc cagagatgat  1620
gcaaaaaaca ccctatacct gcaaatggac agtctgaggt ctgaggacac ggccacttat  1680
tactgtgcaa gacacgggaa ttatatatat tatgggtcct tctttgatta ctggggccaa  1740
ggagtcatgg tcacagtctc ctcaggaggc ggtggcagcg gtgggcgcgc ctcgggcgga  1800
ggtggttcac agtttgtgct ttctcagcca aactctgtgt ctacgaatct cggaagcaca  1860
gtcaaactgt cttgcaagcg cagcactggt aacattggaa gcaattatgt gagctggtac  1920
cagcagcatg agggaagatc tcccaccact atgatttata gggatgataa agaccagat  1980
ggagttcctg acaggttctc tggctccatt gacagatctt ccgactcagc cctcctgaca  2040
atcaataatg tgcagactga agatgaagct gactacttct gtcagtctta cagtagtggt  2100
attaatattt tcggcggtgg aaccaagctc actgtcctag actacaagga cgacgatgac  2160
aag                                                                2163

SEQ ID NO: 145         moltype = AA  length = 721
FEATURE                Location/Qualifiers
REGION                 1..721
                       note = Description of the artificial sequence: amino acid
                         sequence of the antibody sequence of pCI-AVM-hLG4PE (R409K
                         / S354C / T366W) -linker-AVMscFv-FLAG tag excluding signal
                         sequence
source                 1..721
                       mol_type = protein
                       organism = synthetic construct
SEQUENCE: 145
EVQLVESGGG LVQPGRSLKL SCAASGFTFS NYAMAWVRRA PTKGLEWVAS ISNGGGNTYY  60
RDSVKGRFTI SRDDAKNTLY LQMDSLRSED TATYYCARHG NYIYYGSFFD YWGQGVMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFEGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPCQEEM  360
TKNQVSLWCL VKGFYPSDIA VEWESNGQPE NNYKTTPPVL DSDGSFFLYS KLTVDKSRWQ  420
EGNVFSCSVM HEALHNHYTQ KSLSLSLGGG SGGGGSGGGG SGGGGSEVQL VESGGGLVQP  480
GRSLKLSCAA SGFTFSNYAM AWVRRAPTKG LEWVASISNG GGNTYYRDSV KGRFTISRDD  540
AKNTLYLQMD SLRSEDTATY YCARHGNYIY YGSFFDYWGQ GVMVTVSSGG GGSGGRASGG  600
GGSQFVLSQP NSVSTNLGST VKLSCKRSTG NIGSNYVSWY QQHEGRSPTT MIYRDDKRPD  660
GVPDRFSGSI DRSSDSALLT INNVQTEDEA DYFCQSYSSG INIFGGGTKL TVLDYKDDDD  720
K                                                                  721

SEQ ID NO: 146         moltype = DNA  length = 2139
FEATURE                Location/Qualifiers
misc_feature           1..2139
                       note = Description of the artificial sequence: base
                         sequence of the antibody sequence of pCI-AVM-hLG4PE
                         (R409K) _AVMscFv3 excluding signal sequence
source                 1..2139
                       mol_type = other DNA
                       organism = synthetic construct
SEQUENCE: 146
gaggtgcagc tggtggaatc tgggggaggc ttagtgcagc ctggaagatc cctgaaactc  60
tcctgtgcag cctcaggatt cactttcagt aactatgcca tggcttgggt ccgccgggct  120
ccaacgaagg gtctgaagtg ggtcgcatcc attagtaatg gtggtggtaa cacttactat  180
cgcgactccg tgaagggccg attcactatc tccagagatg atgcaaaaaa cacccctatac  240
ctgcaaatgg acagtctgag gtctgaggac acggccactt attactgtgc aagacacggg  300
aattatatat attatgggtc cttctttgat tactggggcc aaggagtcat ggtcacagtc  360
tcctcagcta gcaccaaggg gccatccgtc ttccccctgg cgccctgctc caggagcacc  420
tccgagagca gccgccct gggctgcctg tcaaggact acttcccga accggtgacg  480
gtgtcgtgga actcaggcgc cctgaccagc ggcgtgcaca cctttcccgg cgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccacca tgcccagcac ctgagttgca gggggacca  720
tcagtcttcc tgttcccccc aaaacccaag gacactctca tgatctcccg gacccctgag  780
gtcacgtgcg tggtggtgga cgtgagccag gaagaccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aagctaaccg tggacaagag caggtggcag  1260
gaggggaatg tcttctcatg ctccgtgatg catgaggctc tgcacaacca ctacacacag  1320
aagagcctct ccctgtctct gggtggagga gcggaggag gagggtccgg aggaggaggg  1380
tccgaggag gagggtccca gtttgtgctt tctcagccaa actctgtgtc tacgaatctc  1440
ggaagcacag tcaaactgtc ttgcaagcgc agcactggta acattggaag caattatgtg  1500
agctggtacc agcagcacta gggaagatct cccaccacta tgatttatag ggatgataag  1560
agaccagatg gagttcctga caggttctct ggctccattg acagatcttc cgactcagcc  1620
ctcctgacaa tcaataatgt gcagactgaa gatgaagctg actacttctg tcagtcttac  1680
agtagtggta ttaatatttt cggcggtgga accaagctca ctgtcctagg aggcggtggc  1740
agcggtgggc gcgcctcggg cggaggtggt tcagaggtgc agctggtgga atctggggga  1800
ggcttagtgc agcctggaag atccctgaaa ctctcctgtg cagcctcagg attcactttc  1860
```

```
agtaactatg ccatggcttg ggtccgccgg gctccaacga agggtctgga gtgggtcgca   1920
tccattagta atggtggtgg taacacttac tatcgcgact ccgtgaaggg ccgattcact   1980
atctccagag atgatgcaaa aaacacccta tacctgcaaa tggacagtct gaggtctgag   2040
gacacggcca cttattactg tgcaagacac gggaattata tatattatgg gtccttcttt   2100
gattactggg gccaaggagt catggtcaca gtctcctca                          2139

SEQ ID NO: 147           moltype = AA   length = 713
FEATURE                  Location/Qualifiers
REGION                   1..713
                         note = Description of the artificial sequence: amino acid
                          sequence of the antibody sequence of pCI-AVM-hLG4PE
                          (R409K) _AVMscFv3 excluding signal sequence
source                   1..713
                         mol_type = protein
                         organism = synthetic construct
SEQUENCE: 147
EVQLVESGGG LVQPGRSLKL SCAASGFTFS NYAMAWVRRA PTKGLEWVAS ISNGGGNTYY    60
RDSVKGRFTI SRDDAKNTLY LQMDSLRSED TATYYCARHG NYIYYGSFFD YWGQGVMVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFEGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS KLTVDKSRWQ   420
EGNVFSCSVM HEALHNHYTQ KSLSLSLGGG SGGGGSGGGG SGGGGSQFVL SQPNSVSTNL   480
GSTVKLSCKR STGNIGSNYV SWYQQHEGRS PTTMIYRDDK RPDGVPDRFS GSIDRSSDSA   540
LLTINNVQTE DEADYFCQSY SSGINIFGGG TKLTVLGGGS SGGRASGGGS SEVQLVESGG   600
GLVQPGRSLK LSCAASGFTF SNYAMAWVRR APTKGLEWVA SISNGGGNTY YRDSVKGRFT   660
ISRDDAKNTL YLQMDSLRSE DTATYYCARH GNYIYYGSFF DYWGQGVMVT VSS           713

SEQ ID NO: 148           moltype = DNA   length = 2157
FEATURE                  Location/Qualifiers
misc_feature             1..2157
                         note = Description of the artificial sequence: base
                          sequence of the antibody sequence of pCI-AVM-hLG4PE
                          (R409K) _AVMscFv5 excluding signal sequence
source                   1..2157
                         mol_type = other DNA
                         organism = synthetic construct
SEQUENCE: 148
gaggtgcagc tggtggaatc tgggggaggc ttagtgcagc ctggaagatc cctgaaactc     60
tcctgtgcag cctcaggatt cactttcagt aactatgcca tggcttgggt ccgccgggct   120
ccaacgaagg gtctggagtg ggtcgcatcc attagtaatg gtggtggtaa cacttactat   180
cgcgactccg tgaagggccg attcactatc tccagagatg atgcaaaaaa ccctatac    240
ctgcaaatgg acagtctgag gtctgaggac acgccactt attactgtgc aagacacggg   300
aattatatat attatgggtc cttctttgat tactggggcc aaggagtcat ggtcacagtc   360
tcctcagcta gcaccaaggg gccatccgtc ttccccctgg cgccctgctc caggagcacc   420
tccgagagca cagccgccct gggctgcctg gtcaaggact acttccccga accggtgacg   480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacg   600
aagacctaca cctgcaacgt agatcacaag cccagcaaca caaggtgga caagagagtt   660
gagtccaaat atggtccccc atgcccacca tgcccagctg agttgaa gggggaccca   720
tcagtcttcc tgttcccccc aaaacccaag gacactctca tgatctcccg gacccctgag   780
gtcacgtgcg tggtggtgga cgtgagccag gaagaccccg aggtccagtt caactggtac   840
gtggatggcg tggaggtgca taatgccaag acaaagccgc gggaggagca gttcaacagc   900
acgtaccgtg tggtcagcgt cctcaccgtc ctgcaccagg actggctgaa cggcaaggag   960
tacaagtgca aggtctccaa caaaggcctc ccgtcctcca tcgagaaaac catctccaaa  1020
gccaaagggc agccccgaga gccacaggtg tacaccctgc cccatccca ggaggagatg  1080
accaagaacc aggtcagcct gacctgcctg gtcaaaggct tctacccag cgacatcgcc  1140
gtggagtggg agagcaatgg gcagccggag aacaactaca agaccacgcc tcccgtgctg  1200
gactccgacg gctccttctt cctctacagc aagctaaccg tggacaagag caggtggcag  1260
gaggggaatg tcttctcatg ctccgtgatg catgaggctc tgcacaacca ctacacacag  1320
aagagcctct ccctgtctct gggtggagga ggagggtccg gaggaggagg gtccggtgga  1380
ggtgggtccc agtttgtgct ttctcagcca actctgtgt ctacgaatct cggaagcaca  1440
gtcaaactgt cttgcaagcg cagcactggt aacattgat gcaattatgt gagctggtac  1500
cagcagcatg agggaagatc tcccaccact atgatttata gggatgataa agaccagat  1560
ggagttcctg acaggttctc tggctccatt gacagatctt ccgactcagc cctcctgaca  1620
atcaataatg tgcagactga agatgaagct gactacttct gtcagtctta cagtagtggt  1680
attatatttt tcggcggtgg aaccaagctc actgtcctag gtggaggcgg tggcagcgga  1740
ggaggagggt ccggtgggggg cggtcgggc ggagtggt cagaggtgca gctggtggaa  1800
tctgggggag gcttagtgca gcctggaaga tccctgaaac tctcctgtgc agcctcagga  1860
ttcactttca gtaactatgc catggcttgg gtccgccggg ctccaacgaa gggtctggag  1920
tgggtcgcat ccattagtaa tggtggtggt aacacttact atcgcgactc cgtgaagggc  1980
cgattcacta tctccagaga tgatgcaaaa aacaccctat acctgcaaat ggacagtctg  2040
aggtctgagg acacgccac ttattactgt gcaagacacg ggaattata tattatggg    2100
tccttctttg attactgggg ccaaggagtc atggtcacag tctcctcagc tagcacc      2157

SEQ ID NO: 149           moltype = AA   length = 719
FEATURE                  Location/Qualifiers
REGION                   1..719
```

```
                        note = Description of the artificial sequence: amino acid
                           sequence of the antibody sequence of pCI-AVM-hLG4PE
                           (R409K) _AVMscFv5 excluding signal sequence
source                  1..719
                        mol_type = protein
                        organism = synthetic construct
SEQUENCE: 149
EVQLVESGGG LVQPGRSLKL SCAASGFTFS NYAMAWVRRA PTKGLEWVAS ISNGGGNTYY  60
RDSVKGRFTI SRDDAKNTLY LQMDSLRSED TATYYCARHG NYIYYGSFFD YWGQGVMVTV 120
SSASTKGPSV FPLAPCSRST SESTAALGCL VKDYFPEPVT VSWNSGALTS GVHTFPAVLQ 180
SSGLYSLSSV VTVPSSSLGT KTYTCNVDHK PSNTKVDKRV ESKYGPPCPP CPAPEFEGGP 240
SVFLFPPKPK DTLMISRTPE VTCVVVDVSQ EDPEVQFNWY VDGVEVHNAK TKPREEQFNS 300
TYRVVSVLTV LHQDWLNGKE YKCKVSNKGL PSSIEKTISK AKGQPREPQV YTLPPSQEEM 360
TKNQVSLTCL VKGFYPSDIA VEWESNGQPE NNYKTTPPVL DSDGSFFLYS KLTVDKSRWQ 420
EGNVFSCSVM HEALHNHYTQ KSLSLSLGGG GGSGGGGSGG GGSQFVLSQP NSVSTNLGST 480
VKLSCKRSTG NIGSNYVSWY QQHEGRSPTT MIYRDDKRPD GVPDRFSGSI DRSSDSALLT 540
INNVQTEDEA DYFCQSYSSG INIFGGGTKL TVLGGGGSGG GGSGGGGSG GGGSEVQLVE 600
SGGGLVQPGR SLKLSCAASG FTFSNYAMAW VRRAPTKGLE WVASISNGGG NTYYRDSVKG 660
RFTISRDDAK NTLYLQMDSL RSEDTATYYC ARHGNYIYYG SFFDYWGQGV MVTVSSAST  719

SEQ ID NO: 150          moltype = DNA  length = 1887
FEATURE                 Location/Qualifiers
misc_feature            1..1887
                        note = Description of the artificial sequence: base
                           sequence of Acid Sphingomyelinase (ASM)
source                  1..1887
                        mol_type = other DNA
                        organism = synthetic construct
SEQUENCE: 150
atgccccgct acggagcgtc actccgccag agctgcccca ggtccggccg ggagcaggga   60
caagacggga ccgccggagc ccccggactc ctttggatgg gcctggtgct ggcgctggcg  120
ctggcgctgg cgctggctct gtctgactct cgggttctct gggctccggc agaggctcac  180
cctctttctc cccaaggcca tcctgccagg ttacatcgca tagtgccccg gctccgagat  240
gtctttgggt gggggaacct cacctgccca atctgcaaag gtctattcac cgccatcaac  300
ctcgggctga agaaggaacc caatgtggct cgcgtgggct ccgtggccat caagctgtgc  360
aatctgctga agatagcacc acctgccgtg tgccaatcca ttgtccacct cttttgaggat  420
gacatggtgg aggtgtggag acgctcagtg ctgagcccat ctgaggcctg tggcctgctc  480
ctgggctcca cctgtgggca ctgggacatt ttctcatctt ggaacatctc tttgcctact  540
gtgccgaagc cgccccccaa accccctagc ccccagaccc caggtgcccc tgtcagccgc  600
atcctcttcc tcactgacct gcactgggat catgactacc tggagggcac ggaccctgac  660
tgtgcagacc cactgtgctg ccgccggggt tctggcctgc cgcccgcatc ccggccaggt  720
gccggatact ggggcgaata cagcaagtgt gacctgcccc tgaggaccct ggagagcctg  780
ttgagtgggc tggccagc cggccttttt gatatgtggt actgacaggg agacatcccc  840
gcacatgatg tctggcacca gactcgtcag gaccaactgc gggccctgac accgtcaca  900
gcacttgtga ggaagttcct ggggccagtg ccagtgtacc ctgctgtggg taaccatgaa  960
agcatacctg tcaatagctt ccctccccc ttcattgagg caaccactc ctcccgctgg 1020
ctctatgaag cgatggccaa ggcttgggag ccctggctgg cctgaagc cctgcgcacc 1080
ctcagaattg gggggttcta tgctcttttc ccatacccg gtctccgcct catctctctc 1140
aatatgaatt tttgttcccg tgagaacttc tggctcttga tcaactccac ggatcccgca 1200
ggacagctcc agtggctggt gggggagctt caggctgctg aggatcgagg agacaaagtg 1260
catataattg gccacattcc cccagggcac tgtctggagc gtggagctg gaattattac 1320
cgaattgtag ccaggtatga gaacaccctg gctgctcagt tctttggcca cactcatgtg 1380
gatgaatttg aggtcttcta tgatgaagag actctgagcc ggccgctggc tgtagccttc 1440
ctggcaccca gtgcaactac ctacatcggc cttaatcctg gtaccgtgt gtaccaaata 1500
gatggaaact actccaggag ctctcacgtg tccctgacc atgagaccta catcctgaat 1560
ctgacccagg caaacatacc gggagccata ccgcactggc agcttctcta cagggctcga 1620
gaaacctatg gctgcccaa cacactgcct accgcctggc acaacctggt atatcgcatg 1680
cggggcgaca tgcaactttt ccagaccttc tggtttctct accataaggg ccacccaccc 1740
tcggagccct gtggcacgcc ctgccgtctg gctactcttt gtgcccagct ctctgcccgt 1800
gctgacagcc ctgctctgtg ccgccacctg atgcagatgg gagcctccc agaggccag 1860
agcctgtggc caaggccact gttttgc                                    1887

SEQ ID NO: 151          moltype = DNA  length = 369
FEATURE                 Location/Qualifiers
misc_feature            1..369
                        note = Description of the artificial sequence: base
                           sequence encoding VH excluding signal sequence of MOG 301
source                  1..369
                        mol_type = other DNA
                        organism = synthetic construct
SEQUENCE: 151
caggtgcagc tggtgcagtc tggagctgag gtgaagaagc ctgggcctc agtgaaggtc  60
tcctgcaagg cttctggtta cagctttacc agctatggta tcaactgggt gcgacaggcc 120
cccaggacaa ggcttgagtg gatgggatgg atcagcgctt acaatggtta cacaaactat 180
gcacagaagc tccagggcag agtcaccatg accagagaca catccacgcg cacagcctac 240
atggagctga ggagcctgag atctgacgac acggccgtgt attactgtgc gagagagtac 300
gatatttga ctggttattc cgatgctttt gatatctggg gccaagggac cctggtcact 360
gtctcctca                                                         369
```

| | |
|---|---|
| SEQ ID NO: 152 | moltype = AA   length = 123 |
| FEATURE | Location/Qualifiers |
| REGION | 1..123 |
| | note = The Description of the artificial sequence: amino acid sequence of VH excluding signal sequence of MOG 301 |
| source | 1..123 |
| | mol_type = protein |
| | organism = synthetic construct |

SEQUENCE: 152
```
QVQLVQSGAE VKKPGASVKV SCKASGYSFT SYGINWVRQA PGQGLEWMGW ISAYNGYTNY   60
AQKLQGRVTM TRDTSTRTAY MELRSLRSDD TAVYYCAREY DILTGYSDAF DIWGQGTLVT  120
VSS                                                               123
```

| | |
|---|---|
| SEQ ID NO: 153 | moltype = AA   length = 5 |
| FEATURE | Location/Qualifiers |
| REGION | 1..5 |
| | note = The Description of the artificial sequence: amino acid sequence of HCDR1 of MOG 301 |
| source | 1..5 |
| | mol_type = protein |
| | organism = synthetic construct |

SEQUENCE: 153
```
SYGIN                                                               5
```

| | |
|---|---|
| SEQ ID NO: 154 | moltype = AA   length = 17 |
| FEATURE | Location/Qualifiers |
| REGION | 1..17 |
| | note = The Description of the artificial sequence: amino acid sequence of HCDR2 of MOG 301 |
| source | 1..17 |
| | mol_type = protein |
| | organism = synthetic construct |

SEQUENCE: 154
```
WISAYNGYTN YAQKLQG                                                  17
```

| | |
|---|---|
| SEQ ID NO: 155 | moltype = AA   length = 14 |
| FEATURE | Location/Qualifiers |
| REGION | 1..14 |
| | note = The Description of the artificial sequence: amino acid sequence of HCDR3 of MOG 301 |
| source | 1..14 |
| | mol_type = protein |
| | organism = synthetic construct |

SEQUENCE: 155
```
EYDILTGYSD AFDI                                                     14
```

| | |
|---|---|
| SEQ ID NO: 156 | moltype = DNA   length = 324 |
| FEATURE | Location/Qualifiers |
| misc_feature | 1..324 |
| | note = Description of the artificial sequence: base sequence encoding VL excluding signal sequence of MOG 301 |
| source | 1..324 |
| | mol_type = other DNA |
| | organism = synthetic construct |

SEQUENCE: 156
```
gaaatagtga tgacacagtc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccgct cactttcggc  300
ggagggacca aggtggaaat caaa                                         324
```

| | |
|---|---|
| SEQ ID NO: 157 | moltype = AA   length = 108 |
| FEATURE | Location/Qualifiers |
| REGION | 1..108 |
| | note = Description of the artificial sequence: amino acid sequence of VL excluding signal sequence of MOG 301 |
| source | 1..108 |
| | mol_type = protein |
| | organism = synthetic construct |

SEQUENCE: 157
```
EIVMTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPLTFG GGTKVEIK               108
```

| | |
|---|---|
| SEQ ID NO: 158 | moltype = AA   length = 12 |
| FEATURE | Location/Qualifiers |
| REGION | 1..12 |
| | note = The Description of the artificial sequence: amino acid sequence of LCDR 1 of MOG 301 |

```
source                  1..12
                        mol_type = protein
                        organism = synthetic construct
SEQUENCE: 158
RASQSVSSSY LA                                                            12

SEQ ID NO: 159          moltype = AA   length = 7
FEATURE                 Location/Qualifiers
REGION                  1..7
                        note = The Description of the artificial sequence: amino
                         acid sequence of LCDR 2 of MOG 301
source                  1..7
                        mol_type = protein
                        organism = synthetic construct
SEQUENCE: 159
GASSRAT                                                                  7

SEQ ID NO: 160          moltype = AA   length = 9
FEATURE                 Location/Qualifiers
REGION                  1..9
                        note = The Description of the artificial sequence: amino
                         acid sequence of LCDR 3 of MOG 301
source                  1..9
                        mol_type = protein
                        organism = synthetic construct
SEQUENCE: 160
QQYGSSPLT                                                                9

SEQ ID NO: 161          moltype = DNA   length = 366
FEATURE                 Location/Qualifiers
misc_feature            1..366
                        note = The Description of the artificial sequence: base
                         sequence encoding VH excluding signal sequence of MOG 303
source                  1..366
                        mol_type = other DNA
                        organism = synthetic construct
SEQUENCE: 161
gaggtgcagc tggtggagtc tgggggaggc ttggtacagc ctggggggtc cctgagactc         60
tcctgtgcag cctctggatt cacctttagc agctatgcca tgggctgggt ccgccaggct        120
ccagggaagg ggctggaatg ggtctcagct gttagtggta gtggtggtag cacatactac        180
gcagactccg tgaagggccg gttcaccatc tccagagaca attccaagaa cacgctgtat        240
ctgcaaatga acagcctgag agccgaggac acggccgtat attactgtgc gaaaggagga        300
tacgatattt tgactggtta cttctttgac tactggggcc agggaaccac ggtcactgtc        360
tcctca                                                                  366

SEQ ID NO: 162          moltype = AA   length = 122
FEATURE                 Location/Qualifiers
REGION                  1..122
                        note = The Description of the artificial sequence: amino
                         acid sequence of VH excluding signal sequence of MOG303
source                  1..122
                        mol_type = protein
                        organism = synthetic construct
SEQUENCE: 162
EVQLVESGGG LVQPGGSLRL SCAASGFTFS SYAMGWVRQA PGKGLEWVSA VSGSGGSTYY         60
ADSVKGRFTI SRDNSKNTLY LQMNSLRAED TAVYYCAKGG YDILTGYFFD YWGQGTTVTV        120
SS                                                                      122

SEQ ID NO: 163          moltype = AA   length = 5
FEATURE                 Location/Qualifiers
REGION                  1..5
                        note = The Description of the artificial sequence: amino
                         acid sequence of HCDR1 of MOG303
source                  1..5
                        mol_type = protein
                        organism = synthetic construct
SEQUENCE: 163
SYAMG                                                                    5

SEQ ID NO: 164          moltype = AA   length = 17
FEATURE                 Location/Qualifiers
REGION                  1..17
                        note = The Description of the artificial sequence: amino
                         acid sequence of HCDR2 of MOG303
source                  1..17
                        mol_type = protein
                        organism = synthetic construct
SEQUENCE: 164
AVSGSGGSTY YADSVKG                                                       17
```

```
SEQ ID NO: 165         moltype = AA  length = 13
FEATURE                Location/Qualifiers
REGION                 1..13
                       note = The Description of the artificial sequence: amino
                        acid sequence of HCDR3 of MOG303
source                 1..13
                       mol_type = protein
                       organism = synthetic construct
SEQUENCE: 165
GGYDILTGYF FDY                                                           13

SEQ ID NO: 166         moltype = DNA  length = 321
FEATURE                Location/Qualifiers
misc_feature           1..321
                       note = The Description of the artificial sequence: base
                        sequence encoding VL excluding signal sequence of MOG 303
source                 1..321
                       mol_type = other DNA
                       organism = synthetic construct
SEQUENCE: 166
gccatccaga tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt acccattcac tttcggccct   300
gggacacgac tggagattaa a                                              321

SEQ ID NO: 167         moltype = AA  length = 107
FEATURE                Location/Qualifiers
REGION                 1..107
                       note = The Description of the artificial sequence: amino
                        acid sequence of VL excluding signal sequence of MOG 303
source                 1..107
                       mol_type = protein
                       organism = synthetic construct
SEQUENCE: 167
AIQMTQSPSS LSASVGDRVT ITCRASQGIS SALAWYQQKP GKAPKLLIYD ASSLESGVPS    60
RFSGSGSGTD FTLTISSLQP EDFATYYCQQ FNSYPFTFGP GTRLEIK                 107

SEQ ID NO: 168         moltype = AA  length = 11
FEATURE                Location/Qualifiers
REGION                 1..11
                       note = The Description of the artificial sequence: amino
                        acid sequence of LCDR 1 of MOG 303
source                 1..11
                       mol_type = protein
                       organism = synthetic construct
SEQUENCE: 168
RASQGISSAL A                                                             11

SEQ ID NO: 169         moltype = AA  length = 7
FEATURE                Location/Qualifiers
REGION                 1..7
                       note = The Description of the artificial sequence: amino
                        acid sequence of LCDR 2 of MOG 303
source                 1..7
                       mol_type = protein
                       organism = synthetic construct
SEQUENCE: 169
DASSLES                                                                   7

SEQ ID NO: 170         moltype = AA  length = 9
FEATURE                Location/Qualifiers
REGION                 1..9
                       note = The Description of the artificial sequence: amino
                        acid sequence of LCDR 3 of MOG 303
source                 1..9
                       mol_type = protein
                       organism = synthetic construct
SEQUENCE: 170
QQFNSYPFT                                                                 9

SEQ ID NO: 171         moltype = DNA  length = 381
FEATURE                Location/Qualifiers
misc_feature           1..381
                       note = The Description of the artificial sequence: base
                        sequence encoding VH (excluding signal sequence) of MOG 307
source                 1..381
```

```
                      mol_type = other DNA
                      organism = synthetic construct
SEQUENCE: 171
cgggtcacct tgagggagtc tggtcctacg ctggtgaaac ccacacagac cctcacgctg    60
acctgcacct tctctgggtt ctcactcagc actagtggag tgggtgtggg ctggatccgt   120
cagcccccag gaaaggccct ggagtggctt gcactcattt tttgggatga tgatagtcac   180
tacagcccat ctctgaagag caggtcacc atcaccaagg acacctccaa aaaccaggtg    240
gtccttacaa tgaccaacat ggaccctgtg gacacagcca catattactg tgcacggtat   300
tactttggtt cggggagtta tttccctagc tactggtact cgatctctg gggccgtggc   360
accctggtca ctgtctcctc a                                             381

SEQ ID NO: 172           moltype = AA  length = 127
FEATURE                  Location/Qualifiers
REGION                   1..127
                         note = The Description of the artificial sequence: amino
                           acid sequence of VH excluding signal sequence of MOG 307
source                   1..127
                         mol_type = protein
                         organism = synthetic construct
SEQUENCE: 172
RVTLRESGPT LVKPTQTLTL TCTFSGFSLS TSGVGVGWIR QPPGKALEWL ALIFWDDDSH    60
YSPSLKSRLT ITKDTSKNQV VLTMTNMDPV DTATYYCARY YFGSGSYFPS YWYFDLWGRG   120
TLVTVSS                                                             127

SEQ ID NO: 173           moltype = AA  length = 7
FEATURE                  Location/Qualifiers
REGION                   1..7
                         note = The Description of the artificial sequence: amino
                           acid sequence of HCDR1 of MOG 307
source                   1..7
                         mol_type = protein
                         organism = synthetic construct
SEQUENCE: 173
TSGVGVG                                                               7

SEQ ID NO: 174           moltype = AA  length = 16
FEATURE                  Location/Qualifiers
REGION                   1..16
                         note = The Description of the artificial sequence: amino
                           acid sequence of HCDR2 of MOG 307
source                   1..16
                         mol_type = protein
                         organism = synthetic construct
SEQUENCE: 174
LIFWDDDSHY SPSLKS                                                    16

SEQ ID NO: 175           moltype = AA  length = 17
FEATURE                  Location/Qualifiers
REGION                   1..17
                         note = The Description of the artificial sequence: amino
                           acid sequence of HCDR3 of MOG 307
source                   1..17
                         mol_type = protein
                         organism = synthetic construct
SEQUENCE: 175
YYFGSGSYFP SYWYFDL                                                   17

SEQ ID NO: 176           moltype = DNA  length = 321
FEATURE                  Location/Qualifiers
misc_feature             1..321
                         note = The Description of the artificial sequence: base
                           sequence encoding VL excluding signal sequence of MOG 307
source                   1..321
                         mol_type = other DNA
                         organism = synthetic construct
SEQUENCE: 176
gaaatagtga tgacacagtc tccagccacc ctgtctttgt ctccagggga agagccacc     60
ctctcctgca gggccagtca gagtgttagc agctactag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccgac gttcggccaa   300
gggaccaagg tggagatcaa a                                             321

SEQ ID NO: 177           moltype = AA  length = 107
FEATURE                  Location/Qualifiers
REGION                   1..107
                         note = The Description of the artificial sequence: amino
                           acid sequence of VL excluding signal sequence of MOG 307
source                   1..107
```

```
                            mol_type = protein
                            organism = synthetic construct
SEQUENCE: 177
EIVMTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPPTFGQ GTKVEIK                 107

SEQ ID NO: 178              moltype = AA   length = 11
FEATURE                     Location/Qualifiers
REGION                      1..11
                            note = The Description of the artificial sequence: amino
                             acid sequence of LCDR 1 of MOG 307
source                      1..11
                            mol_type = protein
                            organism = synthetic construct
SEQUENCE: 178
RASQSVSSYL A                                                         11

SEQ ID NO: 179              moltype = AA   length = 7
FEATURE                     Location/Qualifiers
REGION                      1..7
                            note = The Description of the artificial sequence: amino
                             acid sequence of LCDR 2 of MOG 307
source                      1..7
                            mol_type = protein
                            organism = synthetic construct
SEQUENCE: 179
DASNRAT                                                               7

SEQ ID NO: 180              moltype = AA   length = 9
FEATURE                     Location/Qualifiers
REGION                      1..9
                            note = The Description of the artificial sequence: amino
                             acid sequence of LCDR 3 of MOG 307
source                      1..9
                            mol_type = protein
                            organism = synthetic construct
SEQUENCE: 180
QQRSNWPPT                                                             9

SEQ ID NO: 181              moltype = DNA   length = 360
FEATURE                     Location/Qualifiers
misc_feature                1..360
                            note = The Description of the artificial sequence: base
                             sequence encoding VH excluding signal sequence of MOG 310
source                      1..360
                            mol_type = other DNA
                            organism = synthetic construct
SEQUENCE: 181
caggtgcagc tggtgcaatc tggggctgag gtgaagaagc ctgggtcctc ggtgaaggtc    60
tcctgcaagg cttctggagg cacctttcagc agatatgcta tcagctgggt gcgacaggcc   120
cctggacaag ggcttgagtg gatgggaggg atcatcccta tgtttagtac agcaaactac   180
gcacagaagt tccagggcag agtcacgatt accgcggacg aatccacgag cacagcctac   240
atggagctga gcagcctgag atctgaggac acggccgtgt attactgtgc gagagattgg   300
gcagtggctg gtatgggctt taactactgg ggccagggaa ccctggtcac tgtctcctca   360

SEQ ID NO: 182              moltype = AA   length = 120
FEATURE                     Location/Qualifiers
REGION                      1..120
                            note = The Description of the artificial sequence: amino
                             acid sequence of VH excluding signal sequence of MOG 310
source                      1..120
                            mol_type = protein
                            organism = synthetic construct
SEQUENCE: 182
QVQLVQSGAE VKKPGSSVKV SCKASGGTFS RYAISWVRQA PGQGLEWMGG IIPMFSTANY    60
AQKFQGRVTI TADESTSTAY MELSSLRSED TAVYYCARDW AVAGMGFNYW GQGTLVTVSS   120

SEQ ID NO: 183              moltype = AA   length = 5
FEATURE                     Location/Qualifiers
REGION                      1..5
                            note = The Description of the artificial sequence: amino
                             acid sequence of HCDR1 of MOG 310
source                      1..5
                            mol_type = protein
                            organism = synthetic construct
SEQUENCE: 183
RYAIS                                                                 5

SEQ ID NO: 184              moltype = AA   length = 17
```

```
FEATURE                    Location/Qualifiers
REGION                     1..17
                           note = The Description of the artificial sequence: amino
                             acid sequence of HCDR2 of MOG 310
source                     1..17
                           mol_type = protein
                           organism = synthetic construct
SEQUENCE: 184
GIIPMFSTAN YAQKFQG                                                          17

SEQ ID NO: 185             moltype = AA  length = 11
FEATURE                    Location/Qualifiers
REGION                     1..11
                           note = The Description of the artificial sequence: amino
                             acid sequence of HCDR3 of MOG 310
source                     1..11
                           mol_type = protein
                           organism = synthetic construct
SEQUENCE: 185
DWAVAGMGFN Y                                                                11

SEQ ID NO: 186             moltype = DNA  length = 324
FEATURE                    Location/Qualifiers
misc_feature               1..324
                           note = The Description of the artificial sequence: base
                             sequence encoding VL excluding signal sequence of MOG 310
source                     1..324
                           mol_type = other DNA
                           organism = synthetic construct
SEQUENCE: 186
gaaattgtgt tgacacagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgta cacttttggc   300
caggggacca agtggatat caaa                                           324

SEQ ID NO: 187             moltype = AA  length = 108
FEATURE                    Location/Qualifiers
REGION                     1..108
                           note = The Description of the artificial sequence: amino
                             acid sequence of VL excluding signal sequence of MOG 310
source                     1..108
                           mol_type = protein
                           organism = synthetic construct
SEQUENCE: 187
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPYTFG QGTKVDIK               108

SEQ ID NO: 188             moltype = AA  length = 12
FEATURE                    Location/Qualifiers
REGION                     1..12
                           note = The Description of the artificial sequence: amino
                             acid sequence of LCDR1 of MOG 310
source                     1..12
                           mol_type = protein
                           organism = synthetic construct
SEQUENCE: 188
RASQSVSSSY LA                                                               12

SEQ ID NO: 189             moltype = AA  length = 7
FEATURE                    Location/Qualifiers
REGION                     1..7
                           note = The Description of the artificial sequence: amino
                             acid sequence of LCDR 2 of MOG 310
source                     1..7
                           mol_type = protein
                           organism = synthetic construct
SEQUENCE: 189
GASSRAT                                                                      7

SEQ ID NO: 190             moltype = AA  length = 9
FEATURE                    Location/Qualifiers
REGION                     1..9
                           note = The Description of the artificial sequence: amino
                             acid sequence of LCDR3 of MOG 310
source                     1..9
                           mol_type = protein
                           organism = synthetic construct
```

```
SEQUENCE: 190
QQYGSSPYT                                                                            9

SEQ ID NO: 191           moltype = DNA  length = 354
FEATURE                  Location/Qualifiers
misc_feature             1..354
                         note = The Description of the artificial sequence: base
                          sequence encoding VH excluding signal sequence of MOG 312
source                   1..354
                         mol_type = other DNA
                         organism = synthetic construct
SEQUENCE: 191
caggtgcagc tacagcagtg gggcgcagga ctgttgaagc cttcggagac cctgtccctc   60
acctgcgctg tctatggtgg gtccttaagt ggttactact ggagctggat ccgccagccc  120
ccagggaagg ggctggagtg gattggggat atcactcata gtggaagcac caactacaac  180
ccgtccctca agagtcgagt caccatgtca gttgacacgt ccaaaaacca gttctccctg  240
aacctgaact ctgtgaccgc cgcggacacg gctgtgtatt actgtgcgag aagggggata  300
ggagctgctg tctttgacct ctggggccag ggaaccctgg tcactgtctc ctca        354

SEQ ID NO: 192           moltype = AA  length = 118
FEATURE                  Location/Qualifiers
REGION                   1..118
                         note = The Description of the artificial sequence: amino
                          acid sequence of VH excluding signal sequence of MOG 312
source                   1..118
                         mol_type = protein
                         organism = synthetic construct
SEQUENCE: 192
QVQLQQWGAG LLKPSETLSL TCAVYGGSLS GYYWSWIRQP PGKGLEWIGD ITHSGSTNYN   60
PSLKSRVTMS VDTSKNQFSL NLNSVTAADT AVYYCARRGI GAAVFDLWGQ GTLVTVSS    118

SEQ ID NO: 193           moltype = AA  length = 5
FEATURE                  Location/Qualifiers
REGION                   1..5
                         note = The Description of the artificial sequence: amino
                          acid sequence of HCDR1 of MOG 312
source                   1..5
                         mol_type = protein
                         organism = synthetic construct
SEQUENCE: 193
GYYWS                                                                                5

SEQ ID NO: 194           moltype = AA  length = 16
FEATURE                  Location/Qualifiers
REGION                   1..16
                         note = The Description of the artificial sequence: amino
                          acid sequence of HCDR2 of MOG 312
source                   1..16
                         mol_type = protein
                         organism = synthetic construct
SEQUENCE: 194
DITHSGSTNY NPSLKS                                                                   16

SEQ ID NO: 195           moltype = AA  length = 10
FEATURE                  Location/Qualifiers
REGION                   1..10
                         note = The Description of the artificial sequence: amino
                          acid sequence of HCDR3 of MOG 312
source                   1..10
                         mol_type = protein
                         organism = synthetic construct
SEQUENCE: 195
RGIGAAVFDL                                                                          10

SEQ ID NO: 196           moltype = DNA  length = 324
FEATURE                  Location/Qualifiers
misc_feature             1..324
                         note = The Description of the artificial sequence: base
                          sequence encoding VL excluding signal sequence of MOG 312
source                   1..324
                         mol_type = other DNA
                         organism = synthetic construct
SEQUENCE: 196
gaaatagtgt tgacgcagtc tccagccacc ctgtctttgt ctccagggga aagagccacc   60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagcgtagca ctggcctct cactttcggc   300
ggagggacca aggtggagat caaa                                          324
```

```
SEQ ID NO: 197         moltype = AA  length = 108
FEATURE                Location/Qualifiers
REGION                 1..108
                       note = The Description of the artificial sequence: amino
                        acid sequence of VL excluding signal sequence of MOG 312
source                 1..108
                       mol_type = protein
                       organism = synthetic construct
SEQUENCE: 197
EIVLTQSPAT LSLSPGERAT LSCRASQSVS SSYLAWYQQK PGQAPRLLIY GASSRATGIP    60
DRFSGSGSGT DFTLTISRLE PEDFAVYYCQ QRSNWPLTFG GGTKVEIK                108

SEQ ID NO: 198         moltype = AA  length = 12
FEATURE                Location/Qualifiers
REGION                 1..12
                       note = The Description of the artificial sequence: amino
                        acid sequence of LCDR 1 of MOG 312
source                 1..12
                       mol_type = protein
                       organism = synthetic construct
SEQUENCE: 198
RASQSVSSSY LA                                                        12

SEQ ID NO: 199         moltype = AA  length = 7
FEATURE                Location/Qualifiers
REGION                 1..7
                       note = The Description of the artificial sequence: amino
                        acid sequence of LCDR 2 of MOG 312
source                 1..7
                       mol_type = protein
                       organism = synthetic construct
SEQUENCE: 199
GASSRAT                                                              7

SEQ ID NO: 200         moltype = AA  length = 9
FEATURE                Location/Qualifiers
REGION                 1..9
                       note = The Description of the artificial sequence: amino
                        acid sequence of LCDR 3 of MOG 312
source                 1..9
                       mol_type = protein
                       organism = synthetic construct
SEQUENCE: 200
QQRSNWPLT                                                            9

SEQ ID NO: 201         moltype = DNA  length = 366
FEATURE                Location/Qualifiers
misc_feature           1..366
                       note = The Description of the artificial sequence: base
                        sequence encoding VH excluding signal sequence of MOG 326
source                 1..366
                       mol_type = other DNA
                       organism = synthetic construct
SEQUENCE: 201
gaggtccagc tggtacagtc tggggctgag gtgaagaagc ctggggcctc agtgaaggtt    60
tcctgcaagg catctggata cacccttcacc agctactata tgcactgggt gcgacaggcc  120
cctggacaag gccttgagtg gatgggaata atcaacccta gtggtggtag cacaagctac   180
gcacagaagt tccagggcag agtcaccatg accagggaca cgtccacgag cacagtctac   240
atggagctga gcagcctgag atctgaggac acggccgtgt attactgtgc gagagggtat   300
tacgatattt tgactggttc cttctttgac tactggggcc agggaaccct ggtcactgtc   360
tcctca                                                              366

SEQ ID NO: 202         moltype = AA  length = 122
FEATURE                Location/Qualifiers
REGION                 1..122
                       note = The Description of the artificial sequence: amino
                        acid sequence of VH excluding signal sequence of MOG 326
source                 1..122
                       mol_type = protein
                       organism = synthetic construct
SEQUENCE: 202
EVQLVQSGAE VKKPGASVKV SCKASGYTFT SYYMHWVRQA PGQGLEWMGI INPSGGSTSY    60
AQKFQGRVTM TRDTSTSTVY MELSSLRSED TAVYYCARGY YDILTGSFFD YWGQGTLVTV   120
SS                                                                  122

SEQ ID NO: 203         moltype = AA  length = 5
FEATURE                Location/Qualifiers
REGION                 1..5
```

```
                        note = The Description of the artificial sequence: amino
                        acid sequence of HCDR1 of MOG 326
source                  1..5
                        mol_type = protein
                        organism = synthetic construct
SEQUENCE: 203
SYYMH                                                                        5

SEQ ID NO: 204          moltype = AA  length = 17
FEATURE                 Location/Qualifiers
REGION                  1..17
                        note = The Description of the artificial sequence: amino
                        acid sequence of HCDR2 of MOG 326
source                  1..17
                        mol_type = protein
                        organism = synthetic construct
SEQUENCE: 204
IINPSGGSTS YAQKFQG                                                          17

SEQ ID NO: 205          moltype = AA  length = 13
FEATURE                 Location/Qualifiers
REGION                  1..13
                        note = The Description of the artificial sequence: amino
                        acid sequence of HCDR3 of MOG 326
source                  1..13
                        mol_type = protein
                        organism = synthetic construct
SEQUENCE: 205
GYYDILTGSF FDY                                                              13

SEQ ID NO: 206          moltype = DNA  length = 321
FEATURE                 Location/Qualifiers
misc_feature            1..321
                        note = The Description of the artificial sequence: base
                        sequence encoding VL excluding signal sequence of MOG 326
source                  1..321
                        mol_type = other DNA
                        organism = synthetic construct
SEQUENCE: 206
gacatcgtga tgacccagtc tccatcctcc ctgtctgcat ctgtaggaga cagagtcacc            60
atcacttgcc gggcaagtca gggcattagc agtgctttag tctggtatca gcagaaacca          120
gggaaagctc ctaagctcct gatctatgat gcctccagtt tggaaagtgg ggtcccatca          180
aggttcagcg gcagtggatc tgggacagat ttcactctca ccatcagcag cctgcagcct          240
gaagattttg caacttatta ctgtcaacag tttaatagtt accctctcac tttcggcgga          300
gggaccaaag tggatatcaa a                                                    321

SEQ ID NO: 207          moltype = AA  length = 107
FEATURE                 Location/Qualifiers
REGION                  1..107
                        note = The Description of the artificial sequence: amino
                        acid sequence of VL excluding signal sequence of MOG 326
source                  1..107
                        mol_type = protein
                        organism = synthetic construct
SEQUENCE: 207
DIVMTQSPSS LSASVGDRVT ITCRASQGIS SALVWYQQKP GKAPKLLIYD ASSLESGVPS            60
RFSGSGSGTD FTLTISSLQP EDFATYYCQQ FNSYPLTFGG GTKVDIK                         107

SEQ ID NO: 208          moltype = AA  length = 11
FEATURE                 Location/Qualifiers
REGION                  1..11
                        note = The Description of the artificial sequence: amino
                        acid sequence of LCDR 1 of MOG 326
source                  1..11
                        mol_type = protein
                        organism = synthetic construct
SEQUENCE: 208
RASQGISSAL V                                                                11

SEQ ID NO: 209          moltype = AA  length = 7
FEATURE                 Location/Qualifiers
REGION                  1..7
                        note = The Description of the artificial sequence: amino
                        acid sequence of LCDR 2 of MOG 326
source                  1..7
                        mol_type = protein
                        organism = synthetic construct
SEQUENCE: 209
DASSLES                                                                      7
```

```
SEQ ID NO: 210          moltype = AA  length = 9
FEATURE                 Location/Qualifiers
REGION                  1..9
                        note = The Description of the artificial sequence: amino
                         acid sequence of LCDR 3 of MOG 326
source                  1..9
                        mol_type = protein
                        organism = synthetic construct
SEQUENCE: 210
QQFNSYPLT                                                                    9

SEQ ID NO: 211          moltype = DNA  length = 357
FEATURE                 Location/Qualifiers
misc_feature            1..357
                        note = The Description of the artificial sequence: base
                         sequence encoding VH excluding signal sequence of MOG 329
source                  1..357
                        mol_type = other DNA
                        organism = synthetic construct
SEQUENCE: 211
caggtgcagc tggtggagtc tgggggaggc ttggtacagc ctggggggtc cctgagactc    60
tcctgtgcag cctctggatt cgcctttcgc aactatgcca tgaactgggt ccgccaggct   120
ccagggaagg gctggagtg gtctcagct attagtggta gtggtggtag cacatactac    180
gcagactccg tgaagggccg gttcaccatc tccagagaca attccaagaa cacgctgtat   240
ctgcaaatga acagcctgag agccgaggac acggccgttt attactgtgc gagagactac   300
ggtggtatct ccccctttga ctactggggc cagggaaccc tggtcactgt ctcctca     357

SEQ ID NO: 212          moltype = AA  length = 119
FEATURE                 Location/Qualifiers
REGION                  1..119
                        note = The Description of the artificial sequence: amino
                         acid sequence of VH excluding signal sequence of MOG 329
source                  1..119
                        mol_type = protein
                        organism = synthetic construct
SEQUENCE: 212
QVQLVESGGG LVQPGGSLRL SCAASGFAFR NYAMNWVRQA PGKGLEWVSA ISGSGGSTYY    60
ADSVKGRFTI SRDNSKNTLY LQMNSLRAED TAVYYCARDY GGISPFDYWG QGTLVTVSS   119

SEQ ID NO: 213          moltype = AA  length = 5
FEATURE                 Location/Qualifiers
REGION                  1..5
                        note = The Description of the artificial sequence: amino
                         acid sequence of HCDR1 of MOG 329
source                  1..5
                        mol_type = protein
                        organism = synthetic construct
SEQUENCE: 213
NYAMN                                                                        5

SEQ ID NO: 214          moltype = AA  length = 17
FEATURE                 Location/Qualifiers
REGION                  1..17
                        note = The Description of the artificial sequence: amino
                         acid sequence of HCDR2 of MOG 329
source                  1..17
                        mol_type = protein
                        organism = synthetic construct
SEQUENCE: 214
AISGSGGSTY YADSVKG                                                          17

SEQ ID NO: 215          moltype = AA  length = 10
FEATURE                 Location/Qualifiers
REGION                  1..10
                        note = The Description of the artificial sequence: amino
                         acid sequence of HCDR3 of MOG 329
source                  1..10
                        mol_type = protein
                        organism = synthetic construct
SEQUENCE: 215
DYGGISPFDY                                                                  10

SEQ ID NO: 216          moltype = DNA  length = 321
FEATURE                 Location/Qualifiers
misc_feature            1..321
                        note = The Description of the artificial sequence: base
                         sequence encoding VL excluding signal sequence of MOG 329
source                  1..321
```

```
                            mol_type = other DNA
                            organism = synthetic construct
SEQUENCE: 216
gacatccagt tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt acccagtcac ttttggccag   300
gggaccaaag tggatatcaa a                                              321

SEQ ID NO: 217          moltype = AA  length = 107
FEATURE                 Location/Qualifiers
REGION                  1..107
                        note = The Description of the artificial sequence: amino
                          acid sequence of VL excluding signal sequence of MOG 329
source                  1..107
                        mol_type = protein
                        organism = synthetic construct
SEQUENCE: 217
DIQLTQSPSS LSASVGDRVT ITCRASQGIS SALAWYQQKP GKAPKLLIYD ASSLESGVPS    60
RFSGSGSGTD FTLTISSLQP EDFATYYCQQ FNSYPHTFGQ GTKVDIK                 107

SEQ ID NO: 218          moltype = AA  length = 11
FEATURE                 Location/Qualifiers
REGION                  1..11
                        note = The Description of the artificial sequence: amino
                          acid sequence of LCDR 1 of MOG 329
source                  1..11
                        mol_type = protein
                        organism = synthetic construct
SEQUENCE: 218
RASQGISSAL A                                                          11

SEQ ID NO: 219          moltype = AA  length = 7
FEATURE                 Location/Qualifiers
REGION                  1..7
                        note = The Description of the artificial sequence: amino
                          acid sequence of LCDR 2 of MOG 329
source                  1..7
                        mol_type = protein
                        organism = synthetic construct
SEQUENCE: 219
DASSLES                                                                7

SEQ ID NO: 220          moltype = AA  length = 9
FEATURE                 Location/Qualifiers
REGION                  1..9
                        note = The Description of the artificial sequence: amino
                          acid sequence of LCDR 3 of MOG 329
source                  1..9
                        mol_type = protein
                        organism = synthetic construct
SEQUENCE: 220
QQFNSYPHT                                                              9

SEQ ID NO: 221          moltype = DNA  length = 372
FEATURE                 Location/Qualifiers
misc_feature            1..372
                        note = The Description of the artificial sequence: base
                          sequence encoding VH excluding signal sequence of MOG446
source                  1..372
                        mol_type = other DNA
                        organism = synthetic construct
SEQUENCE: 221
caggtgcagc tggtggagtc tgggggaggt gtggtacggc cggggggtc cctgagactc     60
tcctgtgcag cctctggatt cacctttgat gattatggca tgagctgggt ccgccaagct   120
ccagggaagg ggctggagtg ggtctctaat attaattgga atggtgatag cacaggttat   180
gtagactctg tgaagggccg attcaccatc tccagagaca acgccaagaa ctccctgtat   240
ctgcaaatga acagtctgag agccgaggac acggccttgt attactgtgc gagagcgagg   300
acctattact atgtttcggg gaggtactac tttgactact ggggccaggg aaccctggtc   360
actgtctcct ca                                                        372

SEQ ID NO: 222          moltype = AA  length = 124
FEATURE                 Location/Qualifiers
REGION                  1..124
                        note = The Description of the artificial sequence: amino
                          acid sequence of VH excluding signal sequence of MOG446
source                  1..124
                        mol_type = protein
```

```
                        organism = synthetic construct
SEQUENCE: 222
QVQLVESGGG VVRPGGSLRL SCAASGFTFD DYGMSWVRQA PGKGLEWVSN INWNGDSTGY   60
VDSVKGRFTI SRDNAKNSLY LQMNSLRAED TALYYCARAR TYYYVSGRYY FDYWGQGTLV  120
TVSS                                                               124

SEQ ID NO: 223          moltype = AA  length = 5
FEATURE                 Location/Qualifiers
REGION                  1..5
                        note = The Description of the artificial sequence: amino
                         acid sequence of HCDR1 of MOG446
source                  1..5
                        mol_type = protein
                        organism = synthetic construct
SEQUENCE: 223
DYGMS                                                                5

SEQ ID NO: 224          moltype = AA  length = 17
FEATURE                 Location/Qualifiers
REGION                  1..17
                        note = The Description of the artificial sequence: amino
                         acid sequence of HCDR2 of MOG446
source                  1..17
                        mol_type = protein
                        organism = synthetic construct
SEQUENCE: 224
NINWNGDSTG YVDSVKG                                                  17

SEQ ID NO: 225          moltype = AA  length = 15
FEATURE                 Location/Qualifiers
REGION                  1..15
                        note = The Description of the artificial sequence: amino
                         acid sequence of HCDR3 of MOG446
source                  1..15
                        mol_type = protein
                        organism = synthetic construct
SEQUENCE: 225
ARTYYYVSGR YYFDY                                                    15

SEQ ID NO: 226          moltype = DNA  length = 321
FEATURE                 Location/Qualifiers
misc_feature            1..321
                        note = The Description of the artificial sequence: base
                         sequence encoding VL excluding signal sequence of MOG446
source                  1..321
                        mol_type = other DNA
                        organism = synthetic construct
SEQUENCE: 226
gacatccaga tgacccagtc tccatcctcc ctgtctgcat ctgtaggaga cagagtcacc   60
atcacttgcc gggcaagtca gggcattagc agtgctttag cctggtatca gcagaaacca  120
gggaaagctc ctaagctcct gatctatgat gcctccagtt tggaaagtgg ggtcccatca  180
aggttcagcg gcagtggatc tgggacagat ttcactctca ccatcagcag cctgcagcct  240
gaagattttg caacttatta ctgtcaacag tttaatagtt acccgctcac tttcggcgga  300
gggaccaagg tggaaatcaa a                                            321

SEQ ID NO: 227          moltype = AA  length = 107
FEATURE                 Location/Qualifiers
REGION                  1..107
                        note = The Description of the artificial sequence: amino
                         acid sequence of VL excluding signal sequence of MOG446
source                  1..107
                        mol_type = protein
                        organism = synthetic construct
SEQUENCE: 227
DIQMTQSPSS LSASVGDRVT ITCRASQGIS SALAWYQQKP GKAPKLLIYD ASSLESGVPS   60
RFSGSGSGTD FTLTISSLQP EDFATYYCQQ FNSYPLTFGG GTKVEIK                107

SEQ ID NO: 228          moltype = AA  length = 11
FEATURE                 Location/Qualifiers
REGION                  1..11
                        note = The Description of the artificial sequence: amino
                         acid sequence of LCDR1 of MOG446
source                  1..11
                        mol_type = protein
                        organism = synthetic construct
SEQUENCE: 228
RASQGISSAL A                                                        11

SEQ ID NO: 229          moltype = AA  length = 7
```

```
FEATURE                 Location/Qualifiers
REGION                  1..7
                        note = The Description of the artificial sequence: amino
                        acid sequence of LCDR2 of MOG446
source                  1..7
                        mol_type = protein
                        organism = synthetic construct
SEQUENCE: 229
DASSLES                                                                     7

SEQ ID NO: 230          moltype = AA   length = 9
FEATURE                 Location/Qualifiers
REGION                  1..9
                        note = The Description of the artificial sequence: amino
                        acid sequence of LCDR3 of MOG446
source                  1..9
                        mol_type = protein
                        organism = synthetic construct
SEQUENCE: 230
QQFNSYPLT                                                                   9

SEQ ID NO: 231          moltype = DNA   length = 366
FEATURE                 Location/Qualifiers
misc_feature            1..366
                        note = The Description of the artificial sequence: base
                        sequence encoding VH excluding signal sequence of MOG456
source                  1..366
                        mol_type = other DNA
                        organism = synthetic construct
SEQUENCE: 231
gaggtgcagc tggtggagtc tgggggaggc ctggtcaagc ctggggggtc cctgagactc            60
tcctgtgcag cctctggatt caccttcagt agctatagca tgcactgggt ccgccaggct           120
ccagggaagg gctggagtg gtctcatcc attggtagta ggagtcgtta catatactac            180
gcagactcag tgaagggccg attcaccatc tccagagaca acgccaagaa ctcactgtat           240
ctgcaaatga acagcctgag agccgaggac acggctgtgt attactgcgc gaaagggtat           300
tacgatattt tgactggttc tctctttgac tactggggcc agggaaccct ggtcactgtc           360
tcctca                                                                    366

SEQ ID NO: 232          moltype = AA   length = 122
FEATURE                 Location/Qualifiers
REGION                  1..122
                        note = The Description of the artificial sequence: amino
                        acid sequence of VH excluding signal sequence of MOG 456
source                  1..122
                        mol_type = protein
                        organism = synthetic construct
SEQUENCE: 232
EVQLVESGGG LVKPGGSLRL SCAASGFTFS SYSMHWVRQA PGKGLEWVSS IGSRSRYIYY            60
ADSVKGRFTI SRDNAKNSLY LQMNSLRAED TAVYYCAKGY YDILTGSLFD YWGQGTLVTV           120
SS                                                                        122

SEQ ID NO: 233          moltype = AA   length = 5
FEATURE                 Location/Qualifiers
REGION                  1..5
                        note = The Description of the artificial sequence: amino
                        acid sequence of HCDR1 of MOG456
source                  1..5
                        mol_type = protein
                        organism = synthetic construct
SEQUENCE: 233
SYSMH                                                                       5

SEQ ID NO: 234          moltype = AA   length = 17
FEATURE                 Location/Qualifiers
REGION                  1..17
                        note = The Description of the artificial sequence: amino
                        acid sequence of HCDR2 of MOG456
source                  1..17
                        mol_type = protein
                        organism = synthetic construct
SEQUENCE: 234
SIGSRSRYIY YADSVKG                                                         17

SEQ ID NO: 235          moltype = AA   length = 13
FEATURE                 Location/Qualifiers
REGION                  1..13
                        note = The Description of the artificial sequence: amino
                        acid sequence of HCDR3 of MOG 456
source                  1..13
```

```
                        mol_type = protein
                        organism = synthetic construct
SEQUENCE: 235
GYYDILTGSL FDY                                                    13

SEQ ID NO: 236          moltype = DNA  length = 321
FEATURE                 Location/Qualifiers
misc_feature            1..321
                        note = The Description of the artificial sequence: base
                         sequence encoding VL excluding signal sequence of MOG456
source                  1..321
                        mol_type = other DNA
                        organism = synthetic construct
SEQUENCE: 236
gacatcgtga tgacccagtc tccatcctca ctgtctgcat ctgtaggaga cagagtcacc  60
atcacttgtc gggcgagtca gggtattagc agtgctttag cctggtatca gcagaaacca  120
gggaaagctc ctaagctcct gatctatgat gcctccagtt tggaaagtgg ggtcccatca  180
aggttcagcg gcagtggatc tgggacagat ttcactctca ccatcagcag cctgcagcct  240
gaagattttg caacttatta ctgtcaacag tttaatagtt acccgtggac gttcggccaa  300
gggaccaagg tggagatcaa a                                           321

SEQ ID NO: 237          moltype = AA  length = 107
FEATURE                 Location/Qualifiers
REGION                  1..107
                        note = The Description of the artificial sequence: amino
                         acid sequence of VL excluding signal sequence of MOG456
source                  1..107
                        mol_type = protein
                        organism = synthetic construct
SEQUENCE: 237
DIVMTQSPSS LSASVGDRVT ITCRASQGIS SALAWYQQKP GKAPKLLIYD ASSLESGVPS  60
RFSGSGSGTD FTLTISSLQP EDFATYYCQQ FNSYPWTFGQ GTKVEIK               107

SEQ ID NO: 238          moltype = AA  length = 11
FEATURE                 Location/Qualifiers
REGION                  1..11
                        note = The Description of the artificial sequence: amino
                         acid sequence of LCDR 1 of MOG 456
source                  1..11
                        mol_type = protein
                        organism = synthetic construct
SEQUENCE: 238
RASQGISSAL A                                                      11

SEQ ID NO: 239          moltype = AA  length = 7
FEATURE                 Location/Qualifiers
REGION                  1..7
                        note = The Description of the artificial sequence: amino
                         acid sequence of LCDR 2 of MOG 456
source                  1..7
                        mol_type = protein
                        organism = synthetic construct
SEQUENCE: 239
DASSLES                                                           7

SEQ ID NO: 240          moltype = AA  length = 9
FEATURE                 Location/Qualifiers
REGION                  1..9
                        note = The Description of the artificial sequence: amino
                         acid sequence of LCDR 3 of MOG 456
source                  1..9
                        mol_type = protein
                        organism = synthetic construct
SEQUENCE: 240
QQFNSYPWT                                                         9

SEQ ID NO: 241          moltype = DNA  length = 357
FEATURE                 Location/Qualifiers
misc_feature            1..357
                        note = The Description of the artificial sequence: base
                         sequence encoding VH excluding signal sequence of MOG 473
source                  1..357
                        mol_type = other DNA
                        organism = synthetic construct
SEQUENCE: 241
caggtgcagc tggtggagtc tgggggaggc ctggtcaagc ctggggggtc cctgagactc  60
tcctgtgcag cctctggatt caccttcagt agctatagca tgcactgggt ccgccaggct  120
ccagggaagg ggctggagtg ggtttcggac attagtacta atagtagaac cagaaactat  180
gcagactctg tgaagggccg attcaccatc tccagagaca tgccaagaa ctcagtgtat  240
```

-continued

```
ctgcaaatgc acagcctgag ggacgaggac acggctgtgt actactgtgc gagagactac    300
ggtggtatct attactttga ctattggggc cagggaaccc tggtcactgt ctcctca       357
```

| SEQ ID NO: 242 | moltype = AA  length = 119 |
|---|---|
| FEATURE | Location/Qualifiers |
| REGION | 1..119 |
| | note = The Description of the artificial sequence: amino acid sequence of VH excluding signal sequence of MOG 473 |
| source | 1..119 |
| | mol_type = protein |
| | organism = synthetic construct |

SEQUENCE: 242
```
QVQLVESGGG LVKPGGSLRL SCAASGFTFS SYSMHWVRQA PGKGLEWVSD ISTNSRTRNY    60
ADSVKGRFTI SRDNAKNSVY LQMHSLRDED TAVYYCARDY GGIYYFDYWG QGTLVTVSS    119
```

| SEQ ID NO: 243 | moltype = AA  length = 5 |
|---|---|
| FEATURE | Location/Qualifiers |
| REGION | 1..5 |
| | note = The Description of the artificial sequence: amino acid sequence of HCDR1 of MOG 473 |
| source | 1..5 |
| | mol_type = protein |
| | organism = synthetic construct |

SEQUENCE: 243
```
SYSMH                                                                  5
```

| SEQ ID NO: 244 | moltype = AA  length = 17 |
|---|---|
| FEATURE | Location/Qualifiers |
| REGION | 1..17 |
| | note = The Description of the artificial sequence: amino acid sequence of HCDR2 of MOG 473 |
| source | 1..17 |
| | mol_type = protein |
| | organism = synthetic construct |

SEQUENCE: 244
```
DISTNSRTRN YADSVKG                                                    17
```

| SEQ ID NO: 245 | moltype = AA  length = 10 |
|---|---|
| FEATURE | Location/Qualifiers |
| REGION | 1..10 |
| | note = The Description of the artificial sequence: amino acid sequence of HCDR3 of MOG 473 |
| source | 1..10 |
| | mol_type = protein |
| | organism = synthetic construct |

SEQUENCE: 245
```
DYGGIYYFDY                                                            10
```

| SEQ ID NO: 246 | moltype = DNA  length = 324 |
|---|---|
| FEATURE | Location/Qualifiers |
| misc_feature | 1..324 |
| | note = The Description of the artificial sequence: base sequence encoding VL excluding signal sequence of MOG 473 |
| source | 1..324 |
| | mol_type = other DNA |
| | organism = synthetic construct |

SEQUENCE: 246
```
gaaatagtga tgacacagtc tccagccacc ctgtctttgt ctccagggga aagagccacc    60
ctctcctgca gggccagtca gagtgttagc agctacttag actggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccgta cacttttggc   300
caggggacca agctggagat caaa                                           324
```

| SEQ ID NO: 247 | moltype = AA  length = 108 |
|---|---|
| FEATURE | Location/Qualifiers |
| REGION | 1..108 |
| | note = The Description of the artificial sequence: amino acid sequence of VL excluding signal sequence of MOG 473 |
| source | 1..108 |
| | mol_type = protein |
| | organism = synthetic construct |

SEQUENCE: 247
```
EIVMTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPPYTFG QGTKLEIK                108
```

| SEQ ID NO: 248 | moltype = AA  length = 11 |
|---|---|
| FEATURE | Location/Qualifiers |
| REGION | 1..11 |

```
                        note = The Description of the artificial sequence: amino
                         acid sequence of LCDR1 of MOG 473
source                  1..11
                        mol_type = protein
                        organism = synthetic construct
SEQUENCE: 248
RASQSVSSYL A                                                             11

SEQ ID NO: 249          moltype = AA   length = 7
FEATURE                 Location/Qualifiers
REGION                  1..7
                        note = The Description of the artificial sequence: amino
                         acid sequence of LCDR 2 of MOG 473
source                  1..7
                        mol_type = protein
                        organism = synthetic construct
SEQUENCE: 249
DASNRAT                                                                   7

SEQ ID NO: 250          moltype = AA   length = 10
FEATURE                 Location/Qualifiers
REGION                  1..10
                        note = The Description of the artificial sequence: amino
                         acid sequence of LCDR 3 of MOG 473
source                  1..10
                        mol_type = protein
                        organism = synthetic construct
SEQUENCE: 250
QQRSNWPPYT                                                               10

SEQ ID NO: 251          moltype = DNA   length = 369
FEATURE                 Location/Qualifiers
misc_feature            1..369
                        note = The Description of the artificial sequence: base
                         sequence encoding VH excluding signal sequence of MOG426
source                  1..369
                        mol_type = other DNA
                        organism = synthetic construct
SEQUENCE: 251
caggtccagc tggtacagtc tggagctgag gtgaagaagc ctggggcctc agtgaaggtc       60
tcctgcaagg cttctggtta cagctttaac agctatggta tcaactgggt gcgacaggcc      120
cctggacaag ggcttgagtg gatgggatgg atcagcgctt acactggtaa aacaagttat      180
gcacagaagg tccagggcag agtcaccatg accacagaca gatccacgag cacagcctac      240
atggagctga ggagcctgag atctgacgac acggccatgt attactgtgc gagagagtac      300
gatattttga ctggttattc cgatgctttt gatacctggg gccaagggac aatggtcacc      360
gtctcttca                                                              369

SEQ ID NO: 252          moltype = AA   length = 123
FEATURE                 Location/Qualifiers
REGION                  1..123
                        note = The Description of the artificial sequence: amino
                         acid sequence of VH excluding signal sequence of MOG426
source                  1..123
                        mol_type = protein
                        organism = synthetic construct
SEQUENCE: 252
QVQLVQSGAE VKKPGASVKV SCKASGYSFN SYGINWVRQA PGQGLEWMGW ISAYTGKTSY        60
AQKVQGRVTM TTDRSTSTAY MELRSLRSDD TAMYYCAREY DILTGYSDAF DTWGQGTMVT       120
VSS                                                                    123

SEQ ID NO: 253          moltype = DNA   length = 321
FEATURE                 Location/Qualifiers
misc_feature            1..321
                        note = The Description of the artificial sequence: base
                         sequence encoding VL excluding signal sequence of MOG426
source                  1..321
                        mol_type = other DNA
                        organism = synthetic construct
SEQUENCE: 253
gaaattgtgt tgacgcagtc tccagccacc ctgtctttgt ctccagggga aagagccacc        60
ctctcctgca gggccagtca gagtgttagc agctacttag cctggtacca acagaaacct      120
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg cagtttatta ctgtcagcag cgtggcaact ggccgctcac tttcggcgga      300
gggaccaagc tggagatcaa a                                                321

SEQ ID NO: 254          moltype = AA   length = 107
FEATURE                 Location/Qualifiers
REGION                  1..107
```

```
                        note = The Description of the artificial sequence: amino
                           acid sequence of VL excluding signal sequence of MOG426
source                  1..107
                        mol_type = protein
                        organism = synthetic construct
SEQUENCE: 254
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RGNWPLTFGG GTKLEIK                 107

SEQ ID NO: 255          moltype = DNA   length = 369
FEATURE                 Location/Qualifiers
misc_feature            1..369
                        note = The Description of the artificial sequence: base
                           sequence encoding VH excluding signal sequence of MOG428
source                  1..369
                        mol_type = other DNA
                        organism = synthetic construct
SEQUENCE: 255
gaggtccagc tggtacagtc tggagctgag gtgaagaagc ctggggcctc agtgaaggtc    60
tcctgcaagg cttctggtta cagctttaac agctatggta tcaactgggt gcgacaggcc   120
cctggacaag gcttgagtg gatgggatgg atcagcgctt acactggtaa aacaagttat    180
gcacagaagg tccagggcag agtcaccatg accacagacc gatccactag cacagcctac   240
atggagctga ggagcctgag atctgacgac acggccatgt attactgtgc gagagagtac   300
gatattttga ctggttattc cgatgctttt gatacctggg gccaagggac aatggtcacc   360
gtctcttca                                                           369

SEQ ID NO: 256          moltype = AA    length = 123
FEATURE                 Location/Qualifiers
REGION                  1..123
                        note = The Description of the artificial sequence: amino
                           acid sequence of VH excluding signal sequence of MOG428
source                  1..123
                        mol_type = protein
                        organism = synthetic construct
SEQUENCE: 256
EVQLVQSGAE VKKPGASVKV SCKASGYSFN SYGINWVRQA PGQGLEWMGW ISAYTGKTSY    60
AQKVQGRVTM TTDRSTSTAY MELRSLRSDD TAMYYCAREY DILTGYSDAF DTWGQGTMVT   120
VSS                                                                 123

SEQ ID NO: 257          moltype = DNA   length = 324
FEATURE                 Location/Qualifiers
misc_feature            1..324
                        note = The Description of the artificial sequence: base
                           sequence encoding VL excluding signal sequence of MOG428
source                  1..324
                        mol_type = other DNA
                        organism = synthetic construct
SEQUENCE: 257
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctcg gacgttcggc   300
caagggacca gctggagat caaa                                           324

SEQ ID NO: 258          moltype = AA    length = 108
FEATURE                 Location/Qualifiers
REGION                  1..108
                        note = The Description of the artificial sequence: amino
                           acid sequence of VL excluding signal sequence of MOG428
source                  1..108
                        mol_type = protein
                        organism = synthetic construct
SEQUENCE: 258
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPRTFG QGTKLEIK                108

SEQ ID NO: 259          moltype = DNA   length = 366
FEATURE                 Location/Qualifiers
misc_feature            1..366
                        note = The Description of the artificial sequence: base
                           sequence encoding VH excluding signal sequence of MOG 313
source                  1..366
                        mol_type = other DNA
                        organism = synthetic construct
SEQUENCE: 259
caggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg gctggagtg ggtctcagtt attagtggta gtggtggtag cacatactac   180
```

```
gcagactccg tgaagggccg gttcaccatc tccagagaca attccaagaa cacgctgtat    240
ctgcaaatga acagcctgag agccgaggac acggccgtat attactgtgc gaaagcatat    300
tacgatattt tgactggttc cctctttgac tcctggggcc agggaaccct ggtcactgtc    360
tcctca                                                               366

SEQ ID NO: 260          moltype = AA  length = 122
FEATURE                 Location/Qualifiers
REGION                  1..122
                        note = The Description of the artificial sequence: amino
                         acid sequence of VH excluding signal sequence of MOG 313
source                  1..122
                        mol_type = protein
                        organism = synthetic construct
SEQUENCE: 260
QVQLVESGGG LVQPGGSLRL SCAASGFTFS SYAMSWVRQA PGKGLEWVSV ISGSGGSTYY    60
ADSVKGRFTI SRDNSKNTLY LQMNSLRAED TAVYYCAKAY YDILTGSLFD SWGQGTLVTV    120
SS                                                                   122

SEQ ID NO: 261          moltype = DNA  length = 321
FEATURE                 Location/Qualifiers
misc_feature            1..321
                        note = The Description of the artificial sequence: base
                         sequence encoding VL excluding signal sequence of MOG 313
source                  1..321
                        mol_type = other DNA
                        organism = synthetic construct
SEQUENCE: 261
gacatcgtga tgacccagtc tccatcctcc ctgtctgcat ctgtaggaga cagagtcacc    60
atcacttgcc gggcaagtca gggcattagc agtgctttag cctggtatca gcagaaacca    120
gggaaagctc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt accctctcac tttcggcgga    300
gggaccaagg tggaaatcaa a                                              321

SEQ ID NO: 262          moltype = AA  length = 107
FEATURE                 Location/Qualifiers
REGION                  1..107
                        note = The Description of the artificial sequence: amino
                         acid sequence of VL excluding signal sequence of MOG
source                  1..107
                        mol_type = protein
                        organism = synthetic construct
SEQUENCE: 262
DIVMTQSPSS LSASVGDRVT ITCRASQGIS SALAWYQQKP GKAPKLLIYD ASSLESGVPS    60
RFSGSGSGTD FTLTISSLQP EDFATYYCQQ FNSYPLTFGG GTKVEIK                  107

SEQ ID NO: 263          moltype = DNA  length = 366
FEATURE                 Location/Qualifiers
misc_feature            1..366
                        note = The Description of the artificial sequence: base
                         sequence encoding VH excluding signal sequence of MOG 314
source                  1..366
                        mol_type = other DNA
                        organism = synthetic construct
SEQUENCE: 263
caggtgcagc tggtggagtc tgggggaggc ttggtacagc ctgggggggtc cctgagactc    60
tcctgtgcag cctctggatt cacctttagc agctatgcca tgagctgggt ccgccaggct    120
ccagggaagg ggctggagtg ggtctcagct attagtggta gaggtagtag cacatactac    180
gcagactccg tgaagggccg gttcaccatc tccagagaca attccaagaa cacgctgtat    240
ctgcaaatga acagcctgag agccgaggac acggccgtat attactgtgc gaaaggctat    300
tacgatattt tgactggttc cttctttgac tactggggcc agggaaccct ggtcaccgtc    360
tcctca                                                               366

SEQ ID NO: 264          moltype = AA  length = 122
FEATURE                 Location/Qualifiers
REGION                  1..122
                        note = The Description of the artificial sequence: amino
                         acid sequence of VH excluding signal sequence of MOG 314
source                  1..122
                        mol_type = protein
                        organism = synthetic construct
SEQUENCE: 264
QVQLVESGGG LVQPGGSLRL SCAASGFTFS SYAMSWVRQA PGKGLEWVSA ISGRGSSTYY    60
ADSVKGRFTI SRDNSKNTLY LQMNSLRAED TAVYYCAKGY YDILTGSFFD YWGQGTLVTV    120
SS                                                                   122

SEQ ID NO: 265          moltype = DNA  length = 321
FEATURE                 Location/Qualifiers
misc_feature            1..321
```

|                  |                                                                                                                                                                                          |     |
| ---------------- | ---------------------------------------------------------------------------------------------------------------------------------------------------------------------------------------- | --- |
|                  | note = The Description of the artificial sequence: base<br>  sequence encoding VL excluding signal sequence of MOG 314                                                                   |     |
| source           | 1..321                                                                                                                                                                                   |     |
|                  | mol_type = other DNA                                                                                                                                                                     |     |
|                  | organism = synthetic construct                                                                                                                                                           |     |

SEQUENCE: 265
```
gacatccagt tgacccagtc tccatcctcc ctgtctgcat ctgtaggaga cagagtcacc   60
atcacttgcc gggcaagtca gggcattagc agtgctttag cctggtatca gcagaaacca  120
gggaaagctc ctaagctcct gatctatgat gcctccagtt tggaaagtgg ggtcccatca  180
aggttcagcg gcagtggatc tgggacagat ttcactctca ccatcagcag cctgcagcct  240
gaagattttg caacttatta ctgtcaacag tttaatagtt acccgtacac ttttggccag  300
gggaccaagc tggagatcaa a                                            321
```

| SEQ ID NO: 266 | moltype = AA   length = 107                                                                                                                              |
| -------------- | -------------------------------------------------------------------------------------------------------------------------------------------------------- |
| FEATURE        | Location/Qualifiers                                                                                                                                      |
| REGION         | 1..107                                                                                                                                                   |
|                | note = The Description of the artificial sequence: amino<br>  acid sequence of VL excluding signal sequence of MOG 314                                   |
| source         | 1..107                                                                                                                                                   |
|                | mol_type = protein                                                                                                                                       |
|                | organism = synthetic construct                                                                                                                           |

SEQUENCE: 266
```
DIQLTQSPSS LSASVGDRVT ITCRASQGIS SALAWYQQKP GKAPKLLIYD ASSLESGVPS   60
RFSGSGSGTD FTLTISSLQP EDFATYYCQQ FNSYPYTFGQ GTKLEIK                107
```

| SEQ ID NO: 267 | moltype = DNA   length = 366                                                                                                                             |
| -------------- | -------------------------------------------------------------------------------------------------------------------------------------------------------- |
| FEATURE        | Location/Qualifiers                                                                                                                                      |
| misc_feature   | 1..366                                                                                                                                                   |
|                | note = The Description of the artificial sequence: base<br>  sequence encoding VH excluding signal sequence of MOG 315                                   |
| source         | 1..366                                                                                                                                                   |
|                | mol_type = other DNA                                                                                                                                     |
|                | organism = synthetic construct                                                                                                                           |

SEQUENCE: 267
```
gaggtgcagc tggtggagtc tgggggaggc ttggtacagc ctggggggtc cctgagactc   60
tcctgtgcag cctctggatt cacctttagc acctatgcca tgagctgggt ccgccaggct  120
ccagggaagg ggctggagtg ggtctcagct attagtggta gtggtgttag cacatactac  180
gcagactccg tgaagggccg gttcaccctc tccagagaca attccaagaa cacgctgtat  240
ctgcaaatga acagcctgag agccgaggac acggccgtat attactgtgc gaaagcgtat  300
tacgatattt tgactggtaa tttccttgac tactggggcc agggaaccct ggtcactgtc  360
tcctca                                                             366
```

| SEQ ID NO: 268 | moltype = AA   length = 122                                                                                                                              |
| -------------- | -------------------------------------------------------------------------------------------------------------------------------------------------------- |
| FEATURE        | Location/Qualifiers                                                                                                                                      |
| REGION         | 1..122                                                                                                                                                   |
|                | note = The Description of the artificial sequence: amino<br>  acid sequence of VH excluding signal sequence of MOG 315                                   |
| source         | 1..122                                                                                                                                                   |
|                | mol_type = protein                                                                                                                                       |
|                | organism = synthetic construct                                                                                                                           |

SEQUENCE: 268
```
EVQLVESGGG LVQPGGSLRL SCAASGFTFS TYAMSWVRQA PGKGLEWVSA ISGSGVSTYY   60
ADSVKGRFTL SRDNSKNTLY LQMNSLRAED TAVYYCAKAY YDILTGNFLD YWGQGTLVTV  120
SS                                                                 122
```

| SEQ ID NO: 269 | moltype = DNA   length = 321                                                                                                                             |
| -------------- | -------------------------------------------------------------------------------------------------------------------------------------------------------- |
| FEATURE        | Location/Qualifiers                                                                                                                                      |
| misc_feature   | 1..321                                                                                                                                                   |
|                | note = The Description of the artificial sequence: base<br>  sequence encoding VL excluding signal sequence of MOG 315                                   |
| source         | 1..321                                                                                                                                                   |
|                | mol_type = other DNA                                                                                                                                     |
|                | organism = synthetic construct                                                                                                                           |

SEQUENCE: 269
```
gccatccagt tgacccagtc tccatcctcc ctgtctgcat ctgtaggaga cagagtcacc   60
atcacttgcc gggcaagtca gggcattagc agtgctttag cctggtatca gcagaaacca  120
gggaaagctc ctaagctcct gatctatgat gcctccagtt tggaaagtgg ggtcccatca  180
aggttcagcg gcagtggatc tgggacagat ttcactctca ccatcagcag cctgcagcct  240
gaagattttg caacttatta ctgtcaacag tttaatagtt acccgctcac tttcggcgga  300
gggaccaagg tggaaatcaa a                                            321
```

| SEQ ID NO: 270 | moltype = AA   length = 107                                                                                                                              |
| -------------- | -------------------------------------------------------------------------------------------------------------------------------------------------------- |
| FEATURE        | Location/Qualifiers                                                                                                                                      |
| REGION         | 1..107                                                                                                                                                   |
|                | note = The Description of the artificial sequence: amino<br>  acid sequence of VL excluding signal sequence of MOG 315                                   |
| source         | 1..107                                                                                                                                                   |
|                | mol_type = protein                                                                                                                                       |
|                | organism = synthetic construct                                                                                                                           |

```
SEQUENCE: 270
AIQLTQSPSS LSASVGDRVT ITCRASQGIS SALAWYQQKP GKAPKLLIYD ASSLESGVPS    60
RFSGSGSGTD FTLTISSLQP EDFATYYCQQ FNSYPLTFGG GTKVEIK                 107

SEQ ID NO: 271             moltype = DNA   length = 366
FEATURE                    Location/Qualifiers
misc_feature               1..366
                           note = The Description of the artificial sequence: base
                            sequence encoding VH excluding signal sequence of MOG331
source                     1..366
                           mol_type = other DNA
                           organism = synthetic construct
SEQUENCE: 271
gaggtgcagc tggtggagtc cgggggaggc ttggtatagc ctgggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg attcaccatc tccagagaca attccaagaa cacactgtat   240
ctgcaaatga acagcctgag agccgaggac acggccgtat attactgtgc gaaagcgtat   300
tacgatattt tgactggttc cttctttgac tactggggcc agggaaccct ggtcactgtc   360
tcctca                                                              366

SEQ ID NO: 272             moltype = AA   length = 122
FEATURE                    Location/Qualifiers
REGION                     1..122
                           note = The Description of the artificial sequence: amino
                            acid sequence of VH excluding signal sequence of MOG331
source                     1..122
                           mol_type = protein
                           organism = synthetic construct
SEQUENCE: 272
EVQLVESGGG LVYPGGSLRL SCAASGFTFS SYAMSWVRQA PGKGLEWVSA ISGSGGSTYY    60
ADSVKGRFTI SRDNSKNTLY LQMNSLRAED TAVYYCAKAY YDILTGSFFD YWGQGTLVTV   120
SS                                                                  122

SEQ ID NO: 273             moltype = DNA   length = 321
FEATURE                    Location/Qualifiers
misc_feature               1..321
                           note = The Description of the artificial sequence: base
                            sequence encoding VL excluding signal sequence of MOG331
source                     1..321
                           mol_type = other DNA
                           organism = synthetic construct
SEQUENCE: 273
gaaatagtga tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag actggagcct   240
gaagattttg cagtgtatta ctgtcagcag tatggtagct caccgctcac tttcggcgga   300
gggaccaagc tggagatcaa a                                             321

SEQ ID NO: 274             moltype = AA   length = 107
FEATURE                    Location/Qualifiers
REGION                     1..107
                           note = The Description of the artificial sequence: amino
                            acid sequence of VL excluding signal sequence of MOG331
source                     1..107
                           mol_type = protein
                           organism = synthetic construct
SEQUENCE: 274
EIVMTQSPAT LSLSPGERAT LSCRASQSVS SYLAWYQQKP GQAPRLLIYD ASNRATGIPA    60
RFSGSGSGTD FTLTISRLEP EDFAVYYCQQ YGSSPLTFGG GTKLEIK                 107

SEQ ID NO: 275             moltype = DNA   length = 366
FEATURE                    Location/Qualifiers
misc_feature               1..366
                           note = The Description of the artificial sequence: base
                            sequence encoding VH excluding signal sequence of MOG357
source                     1..366
                           mol_type = other DNA
                           organism = synthetic construct
SEQUENCE: 275
gaggtgcagc tggtggagac tgggggaggc ttggtacagc ctgggggtc cctgagactc    60
tcctgtgcag cctctggatt cacctttagc agctatgcca tgagctgggt ccgccaggct   120
ccagggaagg ggctggagtg ggtctcagat attaatcata gtggtggtag cacatactac   180
gcagactccg tgaagggccg gttcaccatc tccagagaca attccaagca cacgctgtat   240
ctgcaaatga acagcctgag agccgaggac acggccgtat attactgtgc gaaagactat   300
tacgatattt tgactggttc cttctttgac tactggggcc agggaaccct ggtcactgtc   360
tcctca                                                              366
```

```
SEQ ID NO: 276           moltype = AA   length = 122
FEATURE                  Location/Qualifiers
REGION                   1..122
                         note = The Description of the artificial sequence: amino
                          acid sequence of VH excluding signal sequence of MOG 357
source                   1..122
                         mol_type = protein
                         organism = synthetic construct
SEQUENCE: 276
EVQLVETGGG LVQPGGSLRL SCAASGFTFS SYAMSWVRQA PGKGLEWVSD INHSGGSTYY    60
ADSVKGRFTI SRDNSKHTLY LQMNSLRAED TAVYYCAKDY YDILTGSFFD YWGQGTLVTV   120
SS                                                                 122

SEQ ID NO: 277           moltype = DNA   length = 321
FEATURE                  Location/Qualifiers
misc_feature             1..321
                         note = The Description of the artificial sequence: base
                          sequence encoding VL excluding signal sequence of MOG 357
source                   1..321
                         mol_type = other DNA
                         organism = synthetic construct
SEQUENCE: 277
gacatcgtga tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt acccgtggac gttcggccaa   300
gggaccaagg tggagatcaa a                                             321

SEQ ID NO: 278           moltype = AA   length = 107
FEATURE                  Location/Qualifiers
REGION                   1..107
                         note = The Description of the artificial sequence: amino
                          acid sequence of VL excluding signal sequence of MOG 357
source                   1..107
                         mol_type = protein
                         organism = synthetic construct
SEQUENCE: 278
DIVMTQSPSS LSASVGDRVT ITCRASQGIS SALAWYQQKP GKAPKLLIYD ASSLESGVPS    60
RFSGSGSGTD FTLTISSLQP EDFATYYCQQ FNSYPWTFGQ GTKVEIK                 107

SEQ ID NO: 279           moltype = DNA   length = 366
FEATURE                  Location/Qualifiers
misc_feature             1..366
                         note = The Description of the artificial sequence: base
                          sequence encoding VH excluding signal sequence of MOG 476
source                   1..366
                         mol_type = other DNA
                         organism = synthetic construct
SEQUENCE: 279
gaggtgcagc tggtggagtc tgggggaggc ttggtacagc ctgggggtc cctgagactc     60
tcctgtgcag cctctggatt cacttttagc agctatgcca tgaactgggt ccgccaggct   120
ccagggaagg ggctggagtg ggtctcagct attagttata gtggtcgtag cacatactac   180
gcagactccg tgaagggccg attcaccatc tccagagaca attccaagaa cacgctgtat   240
ctgcaaatga acagcctgag agccgaggac acggccgtat attactgtgc gaagggcctt   300
tacgatattt tgactggtgg cggatttgac tactggggcc agggaaccct ggtcaccgtc   360
tcttca                                                              366

SEQ ID NO: 280           moltype = AA   length = 122
FEATURE                  Location/Qualifiers
REGION                   1..122
                         note = The Description of the artificial sequence: amino
                          acid sequence of VH excluding signal sequence of MOG 476
source                   1..122
                         mol_type = protein
                         organism = synthetic construct
SEQUENCE: 280
EVQLVESGGG LVQPGGSLRL SCAASGFTFS SYAMNWVRQA PGKGLEWVSA ISYSGRSTYY    60
ADSVKGRFTI SRDNSKNTLY LQMNSLRAED TAVYYCAKGL YDILTGGGFD YWGQGTLVTV   120
SS                                                                 122

SEQ ID NO: 281           moltype = DNA   length = 321
FEATURE                  Location/Qualifiers
misc_feature             1..321
                         note = The Description of the artificial sequence: base
                          sequence encoding VL excluding signal sequence of MOG 476
source                   1..321
                         mol_type = other DNA
                         organism = synthetic construct
```

```
SEQUENCE: 281
gacatccaga tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt acccgtccac ttttggccag   300
gggacacgac tggagattaa a                                             321

SEQ ID NO: 282          moltype = AA  length = 107
FEATURE                 Location/Qualifiers
REGION                  1..107
                        note = The Description of the artificial sequence: amino
                         acid sequence of VL excluding signal sequence of MOG 476
source                  1..107
                        mol_type = protein
                        organism = synthetic construct
SEQUENCE: 282
DIQMTQSPSS LSASVGDRVT ITCRASQGIS SALAWYQQKP GKAPKLLIYD ASSLESGVPS    60
RFSGSGSGTD FTLTISSLQP EDFATYYCQQ FNSYPSTFGQ GTRLEIK                 107

SEQ ID NO: 283          moltype = DNA  length = 381
FEATURE                 Location/Qualifiers
misc_feature            1..381
                        note = The Description of the artificial sequence: base
                         sequence encoding VH excluding signal sequence of MOG 323
source                  1..381
                        mol_type = other DNA
                        organism = synthetic construct
SEQUENCE: 283
cggatcacct tgagggagtc tggtcctacg ctggtgaaac ccacacagac cctcacgctg    60
acctgcacct tctctgggtt ctcactcagc actagtggag tgggtgtggg ctggatccgt   120
cagcccccag gaaaggccct ggagtggctt gcactcattt ttgggatga tgatagtcac   180
tacagcccat ctctgaagag caggctcacc atcaccaagg acacctccaa aaaccaggtg   240
gtccttacaa tgaccaacat ggaccctgtg gacacagcca catattactg tgcacggtat   300
tactttggtt cggggagtta tttccctagc tactggtact cgatctctg gggccgtggc   360
accctggtca ccgtctcctc a                                             381

SEQ ID NO: 284          moltype = AA  length = 127
FEATURE                 Location/Qualifiers
REGION                  1..127
                        note = The Description of the artificial sequence: amino
                         acid sequence of VH excluding signal sequence of MOG 323
source                  1..127
                        mol_type = protein
                        organism = synthetic construct
SEQUENCE: 284
RITLRESGPT LVKPTQTLTL TCTFSGFSLS TSGVGVGWIR QPPGKALEWL ALIFWDDDSH    60
YSPSLKSRLT ITKDTSKNQV VLTMTNMDPV DTATYYCARY YFGSGSYFPS YWYFDLWGRG   120
TLVTVSS                                                             127

SEQ ID NO: 285          moltype = DNA  length = 321
FEATURE                 Location/Qualifiers
misc_feature            1..321
                        note = The Description of the artificial sequence: base
                         sequence encoding VL excluding signal sequence of MOG 323
source                  1..321
                        mol_type = other DNA
                        organism = synthetic construct
SEQUENCE: 285
gaaatagtga tgacgcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccac tttcggcgga   300
gggaccaagc tggagatcaa a                                             321

SEQ ID NO: 286          moltype = AA  length = 107
FEATURE                 Location/Qualifiers
REGION                  1..107
                        note = The Description of the artificial sequence: amino
                         acid sequence of VL excluding signal sequence of MOG 323
source                  1..107
                        mol_type = protein
                        organism = synthetic construct
SEQUENCE: 286
EIVMTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPPTFGG GTKLEIK                 107

SEQ ID NO: 287          moltype = DNA  length = 381
```

```
FEATURE                 Location/Qualifiers
misc_feature            1..381
                        note = The Description of the artificial sequence: base
                         sequence encoding VH excluding signal sequence of MOG 341
source                  1..381
                        mol_type = other DNA
                        organism = synthetic construct
SEQUENCE: 287
cggatcacct tgaaggagtc tggtcctacg ctggtgaaac ccacacagac cctcacgctg    60
acctgcacct tctctgggtt ctcactcagc actagtggag tgggtgtggg ctggatccgt   120
cagcccccag gaaaggccct ggagtggctt gcactcattt attgggatga tgataaacac   180
tacagcccca tctctgaagag caggctcacc atcaccaagg acacctccaa aaaccaggtg   240
gtccttacaa tgaccaacat ggaccctgtg gacacagcca catattactg tgcacggtat   300
tactttggtt cggggagtta ttcccctagc tactggtact cgatctctg ggccgtggc    360
accctggtca ctgtctcctc a                                              381

SEQ ID NO: 288          moltype = AA   length = 127
FEATURE                 Location/Qualifiers
REGION                  1..127
                        note = The Description of the artificial sequence: amino
                         acid sequence of VH excluding signal sequence of MOG 341
source                  1..127
                        mol_type = protein
                        organism = synthetic construct
SEQUENCE: 288
RITLKESGPT LVKPTQTLTL TCTFSGFSLS TSGVGVGWIR QPPGKALEWL ALIYWDDDKH    60
YSPSLKSRLT ITKDTSKNQV VLTMTNMDPV DTATYYCARY YFGSGSYSPS YWYFDLWGRG   120
TLVTVSS                                                              127

SEQ ID NO: 289          moltype = DNA   length = 321
FEATURE                 Location/Qualifiers
misc_feature            1..321
                        note = The Description of the artificial sequence: base
                         sequence encoding VL excluding signal sequence of MOG 341
source                  1..321
                        mol_type = other DNA
                        organism = synthetic construct
SEQUENCE: 289
gaaattgtgt tgacgcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccac tttcggcgga   300
gggaccaagg tggagatcaa a                                              321

SEQ ID NO: 290          moltype = AA   length = 107
FEATURE                 Location/Qualifiers
REGION                  1..107
                        note = The Description of the artificial sequence: amino
                         acid sequence of VL excluding signal sequence of MOG 341
source                  1..107
                        mol_type = protein
                        organism = synthetic construct
SEQUENCE: 290
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPPTFGG GTKVEIK                 107

SEQ ID NO: 291          moltype = DNA   length = 381
FEATURE                 Location/Qualifiers
misc_feature            1..381
                        note = The Description of the artificial sequence: base
                         sequence encoding VH excluding signal sequence of MOG 354
source                  1..381
                        mol_type = other DNA
                        organism = synthetic construct
SEQUENCE: 291
cggatcacct tgagggagtc tggtcctacg ctggtgaaac ccacacagac cctcacgctg    60
acctgcacct cctctgggct ctcactcagc actagtggag tgggtgtggg ctggatccgt   120
cagcccccag gaaaggccct ggagtggctt gcactcattt tttgggatga tgatacacac   180
tacagcccat ctctgaagag caggctcacc atcaccaagg acacctccaa aaaccaggtg   240
gtccttacaa tgaccaacat ggaccctgtg gacacagcca catattactg tgcacggtat   300
tactttggtt cggggagtta tttccctagc tactggtact cgatctctg ggccgtggc    360
accatggtca ccgtctcttc a                                              381

SEQ ID NO: 292          moltype = AA   length = 127
FEATURE                 Location/Qualifiers
REGION                  1..127
                        note = The Description of the artificial sequence: amino
                         acid sequence of VH excluding signal sequence of MOG 354
```

| | |
|---|---|
| source | 1..127<br>mol_type = protein<br>organism = synthetic construct |

SEQUENCE: 292
```
RITLRESGPT LVKPTQTLTL TCTSSGLSLS TSGVGVGWIR QPPGKALEWL ALIFWDDDTH    60
YSPSLKSRLT ITKDTSKNQV VLTMTNMDPV DTATYYCARY YFGSGSYFPS YWYFDLWGRG   120
TMVTVSS                                                             127
```

| | |
|---|---|
| SEQ ID NO: 293 | moltype = DNA  length = 321 |
| FEATURE | Location/Qualifiers |
| misc_feature | 1..321<br>note = The Description of the artificial sequence: base<br>sequence encoding VL excluding signal sequence of MOG 354 |
| source | 1..321<br>mol_type = other DNA<br>organism = synthetic construct |

SEQUENCE: 293
```
gaaatagtga tgacgcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccgctcac tttcggcgga   300
gggaccaagg tggaaatcaa a                                             321
```

| | |
|---|---|
| SEQ ID NO: 294 | moltype = AA  length = 107 |
| FEATURE | Location/Qualifiers |
| REGION | 1..107<br>note = The Description of the artificial sequence: amino<br>acid sequence of VL excluding signal sequence of MOG 354 |
| source | 1..107<br>mol_type = protein<br>organism = synthetic construct |

SEQUENCE: 294
```
EIVMTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPLTFGG GTKVEIK                 107
```

| | |
|---|---|
| SEQ ID NO: 295 | moltype = DNA  length = 381 |
| FEATURE | Location/Qualifiers |
| misc_feature | 1..381<br>note = The Description of the artificial sequence: base<br>sequence encoding VH excluding signal sequence of MOG 355 |
| source | 1..381<br>mol_type = other DNA<br>organism = synthetic construct |

SEQUENCE: 295
```
cggatcacct tgagggagtc tggtcctacg ctggtgaaac ccacacagac cctcacgctg    60
acctgcacct cctctgggct ctcactcagc actagtggag tgggtgtggg ctggatccgt   120
cagcccccag gaaaggccct ggagtggctt gcactcattt tttggatga tgatacacac   180
tacagcccat ctctgaagag caggctcacc atcaccaagg acacctccaa aaaccaggtg   240
gtccttacaa tgaccaacat ggaccctgtg acacagcca catattactg tgcacggtat   300
tactttggtt cggggagtta tttccctagc tactggtact cgatctctg gggccgtggc   360
accctggtca ctgtctcctc a                                             381
```

| | |
|---|---|
| SEQ ID NO: 296 | moltype = AA  length = 127 |
| FEATURE | Location/Qualifiers |
| REGION | 1..127<br>note = The Description of the artificial sequence: amino<br>acid sequence of VH excluding signal sequence of MOG 355 |
| source | 1..127<br>mol_type = protein<br>organism = synthetic construct |

SEQUENCE: 296
```
RITLRESGPT LVKPTQTLTL TCTSSGLSLS TSGVGVGWIR QPPGKALEWL ALIFWDDDTH    60
YSPSLKSRLT ITKDTSKNQV VLTMTNMDPV DTATYYCARY YFGSGSYFPS YWYFDLWGRG   120
TLVTVSS                                                             127
```

| | |
|---|---|
| SEQ ID NO: 297 | moltype = DNA  length = 321 |
| FEATURE | Location/Qualifiers |
| misc_feature | 1..321<br>note = The Description of the artificial sequence: base<br>sequence encoding VL excluding signal sequence of MOG 355 |
| source | 1..321<br>mol_type = other DNA<br>organism = synthetic construct |

SEQUENCE: 297
```
gaaatagtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
```

```
gaagattttg cagtttatta ctgtcagcag cgtagcaact ggccgctcac tttcggcgga    300
gggaccaagc tggagatcaa a                                               321
```

SEQ ID NO: 298        moltype = AA  length = 107
FEATURE              Location/Qualifiers
REGION               1..107
                       note = The Description of the artificial sequence: amino
                       acid sequence of VL excluding signal sequence of MOG 355
source               1..107
                       mol_type = protein
                       organism = synthetic construct
SEQUENCE: 298
```
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPLTFGG GTKLEIK                 107
```

SEQ ID NO: 299        moltype = DNA  length = 360
FEATURE              Location/Qualifiers
misc_feature       1..360
                       note = The Description of the artificial sequence: base
                       sequence encoding VH excluding signal sequence of MOG 308
source               1..360
                       mol_type = other DNA
                       organism = synthetic construct
SEQUENCE: 299
```
gaggtgcagc tggtgcagtc cggggctgag gtgaggaagt ctgggtcctc ggtgaaggtc    60
tcctgcaagg cttctggagg caccttcagc agatatgtca tcagctgggt gcgacaggcc   120
cctggacaag ggcttgagtg gatgggaggg atcatcccta tgtttagtac gacaaactac   180
gcacagaagt tccagggcag agtcacgatt accgcggacg aatccacgag cacagcctac   240
atggaactga gcagcctgag atctgaggac acggccgtgt attactgtgc gagagattgg   300
gcagtggctg gtatggggtt tgcctactgg ggccagggaa ccctggtcac cgtctcctca   360
```

SEQ ID NO: 300        moltype = AA  length = 120
FEATURE              Location/Qualifiers
REGION               1..120
                       note = The Description of the artificial sequence: amino
                       acid sequence of VH excluding signal sequence of MOG 308
source               1..120
                       mol_type = protein
                       organism = synthetic construct
SEQUENCE: 300
```
EVQLVQSGAE VRKSGSSVKV SCKASGGTFS RYAISWVRQA PGQGLEWMGG IIPMFSTTNY    60
AQKFQGRVTI TADESTSTAY MELSSLRSED TAVYYCARDW AVAGMGFAYW GQGTLVTVSS   120
```

SEQ ID NO: 301        moltype = DNA  length = 321
FEATURE              Location/Qualifiers
misc_feature       1..321
                       note = The Description of the artificial sequence: base
                       sequence encoding VL excluding signal sequence of MOG 308
source               1..321
                       mol_type = other DNA
                       organism = synthetic construct
SEQUENCE: 301
```
gaaatagtga tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggcactggg catcccagcc   180
aggttcagtg gcagtgggtc tgggacagac ttcactctca ccatcagcag cctagagcct   240
gaagattttg cagtttatta ctgtcagcag cgtagcaact ggcctccgac gttcggccaa   300
gggaccaaag tggatatcaa a                                             321
```

SEQ ID NO: 302        moltype = AA  length = 107
FEATURE              Location/Qualifiers
REGION               1..107
                       note = The Description of the artificial sequence: amino
                       acid sequence of VL excluding signal sequence of MOG 308
source               1..107
                       mol_type = protein
                       organism = synthetic construct
SEQUENCE: 302
```
EIVMTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPPTFGQ GTKVDIK                 107
```

SEQ ID NO: 303        moltype = DNA  length = 360
FEATURE              Location/Qualifiers
misc_feature       1..360
                       note = The Description of the artificial sequence: base
                       sequence encoding VH excluding signal sequence of MOG 316
source               1..360
                       mol_type = other DNA
                       organism = synthetic construct

```
SEQUENCE: 303
gaagtgcagc tggtgcagtc cggggctgag gtgaagaagc ctgggtcctc ggtgaaggtc    60
tcctgcaagg cttctggagg caccttcagc agatatgcta tcagctgggt gcgacaggcc   120
cctggacaag ggcttgagtg gatgggaggg atcatccta tgtttaatac agcaaactac    180
gcacagaagt tccagggcag agtcacgatt accgcggacg aatccacgag cacagcctac   240
atggagctga gcagcctgag atctgaggac acggccgtgt attactgtgc gagagattga   300
gcagtggctg gtatggggtt taactactgg ggccagggaa ccctggtcac cgtctcctca   360
```

| SEQ ID NO: 304 | moltype = AA   length = 120 |
|---|---|
| FEATURE | Location/Qualifiers |
| REGION | 1..120 |
| | note = The Description of the artificial sequence: amino acid sequence of VH excluding signal sequence of MOG 316 |
| source | 1..120 |
| | mol_type = protein |
| | organism = synthetic construct |

```
SEQUENCE: 304
EVQLVQSGAE VKKPGSSVKV SCKASGGTFS RYAISWVRQA PGQGLEWMGG IIPMFNTANY    60
AQKFQGRVTI TADESTSTAY MELSSLRSED TAVYYCARDW AVAGMGFNYW GQGTLVTVSS   120
```

| SEQ ID NO: 305 | moltype = DNA   length = 321 |
|---|---|
| FEATURE | Location/Qualifiers |
| misc_feature | 1..321 |
| | note = The Description of the artificial sequence: base sequence encoding VL excluding signal sequence of MOG 316 |
| source | 1..321 |
| | mol_type = other DNA |
| | organism = synthetic construct |

```
SEQUENCE: 305
gacatccaga tgacccagtc tccatcctcc ctgtctgcat ctgtaggaga cagagtcacc    60
atcacttgcc gggcaagtca gggcattaac agtgctttag cctggtatca gcagaaacca   120
gggaaagctc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt acccgatcac cttcggccaa   300
gggacacgac tggagattaa a                                             321
```

| SEQ ID NO: 306 | moltype = AA   length = 107 |
|---|---|
| FEATURE | Location/Qualifiers |
| REGION | 1..107 |
| | note = The Description of the artificial sequence: amino acid sequence of VL excluding signal sequence of MOG 316 |
| source | 1..107 |
| | mol_type = protein |
| | organism = synthetic construct |

```
SEQUENCE: 306
DIQMTQSPSS LSASVGDRVT ITCRASQGIN SALAWYQQKP GKAPKLLIYA ASSLQSGVPS    60
RFSGSGSGTD FTLTISSLQP EDFATYYCQQ YNSYPITFGQ GTRLEIK                 107
```

| SEQ ID NO: 307 | moltype = DNA   length = 360 |
|---|---|
| FEATURE | Location/Qualifiers |
| misc_feature | 1..360 |
| | note = The Description of the artificial sequence: base sequence encoding VH excluding signal sequence of MOG 319 |
| source | 1..360 |
| | mol_type = other DNA |
| | organism = synthetic construct |

```
SEQUENCE: 307
caggtgcagc tggtgcaatc tggggctgag gtgaagaagc ctgggtcctc ggtgaaggtc    60
tcctgcaagg cttctggagg caccttcagc agatatgcta tcagctgggt gcgacaggcc   120
cctggacaag ggcttgagtg gatgggaggg atcatccta tgtttagtac agcaaactac    180
gcacagaagt tccagggcag agtcacgatt accgcggacg aatccacgag cacagcctac   240
atggagctga gcagcctgag atctgacgac acggccgtgt attactgtgc gagagattgg   300
gcagtggctg gtatgggctt taactactgg ggccaggaa ccctggtcac tgtctcctca    360
```

| SEQ ID NO: 308 | moltype = AA   length = 120 |
|---|---|
| FEATURE | Location/Qualifiers |
| REGION | 1..120 |
| | note = The Description of the artificial sequence: amino acid sequence of VH excluding signal sequence of MOG 319 |
| source | 1..120 |
| | mol_type = protein |
| | organism = synthetic construct |

```
SEQUENCE: 308
QVQLVQSGAE VKKPGSSVKV SCKASGGTFS RYAISWVRQA PGQGLEWMGG IIPMFSTANY    60
AQKFQGRVTI TADESTSTAY MELSSLRSDD TAVYYCARDW AVAGMGFNYW GQGTLVTVSS   120
```

| SEQ ID NO: 309 | moltype = DNA   length = 324 |
|---|---|
| FEATURE | Location/Qualifiers |
| misc_feature | 1..324 |

```
                              note = The Description of the artificial sequence: base
                                sequence encoding VL excluding signal sequence of MOG 319
source                        1..324
                              mol_type = other DNA
                              organism = synthetic construct
SEQUENCE: 309
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccatt cactttcggc   300
cctgggacca aggtggaaat caaa                                          324

SEQ ID NO: 310           moltype = AA  length = 108
FEATURE                  Location/Qualifiers
REGION                   1..108
                         note = The Description of the artificial sequence: amino
                           acid sequence of VL excluding signal sequence of MOG 319
source                   1..108
                         mol_type = protein
                         organism = synthetic construct
SEQUENCE: 310
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPFTFG PGTKVEIK                108

SEQ ID NO: 311           moltype = DNA  length = 360
FEATURE                  Location/Qualifiers
misc_feature             1..360
                         note = The Description of the artificial sequence: base
                           sequence encoding VH excluding signal sequence of MOG 320
source                   1..360
                         mol_type = other DNA
                         organism = synthetic construct
SEQUENCE: 311
caggtgcagc tggtgcagtc tggggctgag gtgaagaagc ctgggtcctc ggtgaaggtc    60
tcctgcaagg cttctggagg caccttcagc agatatgcta tcaactgggt gcgacaggcc   120
cctggacaag gcttgagtg gatgggaggg atcatcccta tgtttagtac agtaaattac   180
gcacagaagt tccagggcag agtcacgatt accgcggacg aatccacgag cacagcctac   240
atggagctga gcagcctgag atctgaggac acggccgtgt attactgtgc gagagattgg   300
gcagtgctg gtatgggggtt tgactactgg ggccagggaa ccctggtcac cgtctcctca   360

SEQ ID NO: 312           moltype = AA  length = 120
FEATURE                  Location/Qualifiers
REGION                   1..120
                         note = The Description of the artificial sequence: amino
                           acid sequence of VH excluding signal sequence of MOG 320
source                   1..120
                         mol_type = protein
                         organism = synthetic construct
SEQUENCE: 312
QVQLVQSGAE VKKPGSSVKV SCKASGGTFS RYAINWVRQA PGQGLEWMGG IIPMFSTVNY    60
AQKFQGRVTI TADESTSTAY MELSSLRSED TAVYYCARDW AVAGMGFDYW GQGTLVTVSS   120

SEQ ID NO: 313           moltype = DNA  length = 324
FEATURE                  Location/Qualifiers
misc_feature             1..324
                         note = The Description of the artificial sequence: base
                           sequence encoding VL excluding signal sequence of MOG 320
source                   1..324
                         mol_type = other DNA
                         organism = synthetic construct
SEQUENCE: 313
gaaatagtgt tgacacagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccatt cactttcggc   300
cctgggacca aagtggatat caaa                                          324

SEQ ID NO: 314           moltype = AA  length = 108
FEATURE                  Location/Qualifiers
REGION                   1..108
                         note = The Description of the artificial sequence: amino
                           acid sequence of VL excluding signal sequence of MOG 320
source                   1..108
                         mol_type = protein
                         organism = synthetic construct
SEQUENCE: 314
EIVLTQSPGT LSLSPGERAT LSCRASQSVS SSYLAWYQQK PGQAPRLLIY GASSRATGIP    60
```

DRFSGSGSGT DFTLTISRLE PEDFAVYYCQ QYGSSPFTFG PGTKVDIK                108

SEQ ID NO: 315          moltype = DNA   length = 360
FEATURE                 Location/Qualifiers
misc_feature            1..360
                        note =  FThe Description of the artificial sequence: base
                          sequence encoding VH excluding signal sequence of MOG 338
source                  1..360
                        mol_type = other DNA
                        organism = synthetic construct
SEQUENCE: 315
caggtccagc tggtgcagtc tggggctgag gtgaagaagc ctgggtcctc ggtgaaggtc    60
tcctgcaagg cttctggagg caccttcagc agatatgcta tcagctgggt gcgacaggcc   120
cctggacaag ggcttgagtg gatgggaggg atcatcccta tgtttaatac agcaaactac   180
gcacagaagt tccagggcag agtcacgatt accgcggacg aatccacgag cacagcctac   240
atggagctga gcagcctgag atctgaggac acggccgtgt attactgtgc gagagattgg   300
gcagtggctg gtatggggtt tgaccccctgg ggccagggaa ccctggtcac tgtctcctca   360

SEQ ID NO: 316          moltype = AA   length = 120
FEATURE                 Location/Qualifiers
REGION                  1..120
                        note = The Description of the artificial sequence: amino
                          acid sequence of VH excluding signal sequence of MOG 338
source                  1..120
                        mol_type = protein
                        organism = synthetic construct
SEQUENCE: 316
QVQLVQSGAE VKKPGSSVKV SCKASGGTFS RYAISWVRQA PGQGLEWMGG IIPMFNTANY    60
AQKFQGRVTI TADESTSTAY MELSSLRSED TAVYYCARDW AVAGMGFDPW GQGTLVTVSS   120

SEQ ID NO: 317          moltype = DNA   length = 321
FEATURE                 Location/Qualifiers
misc_feature            1..321
                        note = The Description of the artificial sequence: base
                          sequence encoding VL excluding signal sequence of MOG 338
source                  1..321
                        mol_type = other DNA
                        organism = synthetic construct
SEQUENCE: 317
gaaattgtgt tgacgcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtaacaact ggcctctcac tttcggcgga   300
gggaccaagc tggagatcaa a                                             321

SEQ ID NO: 318          moltype = AA   length = 107
FEATURE                 Location/Qualifiers
REGION                  1..107
                        note = The Description of the artificial sequence: amino
                          acid sequence of VL excluding signal sequence of MOG 338
source                  1..107
                        mol_type = protein
                        organism = synthetic construct
SEQUENCE: 318
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RNNWPLTFGG GTKLEIK                 107

SEQ ID NO: 319          moltype = DNA   length = 360
FEATURE                 Location/Qualifiers
misc_feature            1..360
                        note = The Description of the artificial sequence: base
                          sequence encoding VH excluding signal sequence of MOG352
source                  1..360
                        mol_type = other DNA
                        organism = synthetic construct
SEQUENCE: 319
gaggtgcagc tggtgcagtc cggggctgag gtgaagaagc ctgggtcctc ggtgaaggtc    60
tcctgcaagg cttctggagg caccttcagc agatatgcta tcaactgggt gcgacaggcc   120
cctggacaag ggcttgagtg gatgggaggg atcatcccta tgtttagtac agtaaactac   180
gcacagaagt tccagggcag agtcacgatt accgcggacg aatccacgag cacagcctac   240
atggagctga gcagcctgag atctgaggac acggccgtgt attactgtgc gagagattgg   300
gcagtggctg gtatggggtt tgactactgg ggccagggaa ccctggtcac tgtctcctca   360

SEQ ID NO: 320          moltype = AA   length = 120
FEATURE                 Location/Qualifiers
REGION                  1..120
                        note = The Description of the artificial sequence: amino
                          acid sequence of VH excluding signal sequence of MOG352

```
source                          1..120
                                mol_type = protein
                                organism = synthetic construct
SEQUENCE: 320
EVQLVQSGAE VKKPGSSVKV SCKASGGTFS RYAINWVRQA PGQGLEWMGG IIPMFSTVNY    60
AQKFQGRVTI TADESTSTAY MELSSLRSED TAVYYCARDW AVAGMGFDYW GQGTLVTVSS   120

SEQ ID NO: 321                  moltype = DNA   length = 321
FEATURE                         Location/Qualifiers
misc_feature                    1..321
                                note = The Description of the artificial sequence: base
                                 sequence encoding VL excluding signal sequence of MOG352
source                          1..321
                                mol_type = other DNA
                                organism = synthetic construct
SEQUENCE: 321
gccatccaga tgacccagtc tccatcttcc gtgtctgcat ctgtaggaga cagagtcacc    60
atcacttgtc gggcgagtca gggtattagc agctggttag cctggtatca gcataaacca   120
gggaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt acccgctcac tttcggcgga   300
gggaccaaag tggatatcaa a                                             321

SEQ ID NO: 322                  moltype = AA   length = 107
FEATURE                         Location/Qualifiers
REGION                          1..107
                                note = The Description of the artificial sequence: amino
                                 acid sequence of VL excluding signal sequence of MOG 352
source                          1..107
                                mol_type = protein
                                organism = synthetic construct
SEQUENCE: 322
AIQMTQSPSS VSASVGDRVT ITCRASQGIS SWLAWYQHKP GKAPKSLIYA ASSLQSGVPS    60
RFSGSGSGTD FTLTISSLQP EDFATYYCQQ YNSYPLTFGG GTKVDIK                 107

SEQ ID NO: 323                  moltype = DNA   length = 360
FEATURE                         Location/Qualifiers
misc_feature                    1..360
                                note = The Description of the artificial sequence: base
                                 sequence encoding VH excluding signal sequence of MOG 359
source                          1..360
                                mol_type = other DNA
                                organism = synthetic construct
SEQUENCE: 323
gaggtccagc tggtgcagtc tggggctgag gtgaagaagc ctgggtcctc ggtgaaggtc    60
tcctgcaagg cttctggagg caccttcagc agatatgcta tcagctgggt gcgacaggcc   120
cctggacagg gcttgagtg gatgggaggg atcatcccta tgtttaatac agcaaactac   180
gcacagaagt tccagggcag agtcacgatt accgcggacg aatccacgag cacagcctac   240
atggagctga gcagcctgag atctgaggac acggccgtgt attactgtgc gagagattgg   300
gcagtggctg gtatggggtt taactactgg ggccagggaa ccctggtcac tgtctcctca   360

SEQ ID NO: 324                  moltype = AA   length = 120
FEATURE                         Location/Qualifiers
REGION                          1..120
                                note = The Description of the artificial sequence: amino
                                 acid sequence of VH excluding signal sequence of MOG 359
source                          1..120
                                mol_type = protein
                                organism = synthetic construct
SEQUENCE: 324
EVQLVQSGAE VKKPGSSVKV SCKASGGTFS RYAISWVRQA PGQGLEWMGG IIPMFNTANY    60
AQKFQGRVTI TADESTSTAY MELSSLRSED TAVYYCARDW AVAGMGFNYW GQGTLVTVSS   120

SEQ ID NO: 325                  moltype = DNA   length = 324
FEATURE                         Location/Qualifiers
misc_feature                    1..324
                                note = The Description of the artificial sequence: base
                                 sequence encoding VL excluding signal sequence of MOG 359
source                          1..324
                                mol_type = other DNA
                                organism = synthetic construct
SEQUENCE: 325
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgct cactttcggc   300
ggagggacca agctggagat caaa                                          324
```

```
SEQ ID NO: 326              moltype = AA  length = 108
FEATURE                     Location/Qualifiers
REGION                      1..108
                            note = The Description of the artificial sequence: amino
                             acid sequence of VL excluding signal sequence of MOG 359
source                      1..108
                            mol_type = protein
                            organism = synthetic construct
SEQUENCE: 326
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPLTFG GGTKLEIK                108

SEQ ID NO: 327              moltype = DNA  length = 360
FEATURE                     Location/Qualifiers
misc_feature                1..360
                            note = The Description of the artificial sequence: base
                             sequence encoding VH excluding signal sequence of MOG 478
source                      1..360
                            mol_type = other DNA
                            organism = synthetic construct
SEQUENCE: 327
gaggtccagc tggtacagtc tggggctgag gtgaagaagc ctgggtcctc ggtgaaggtc    60
tcctgcaagg cttctggagg cacccttcag agatatgcta tcagctgggt gcgacaggcc   120
cctggacaag gccttgagtg gatgggaggg atcatcccta tgtttgctac agcaaactac   180
gcacagaagt tccaggccag agtcacgatt accgcggacg aaaccacgag cacagcctac   240
atggagctga gcagcctgag atctgaggac acgggcgtgt attactgtgc gagagattgg   300
gcagtggctg ctatggggtt tgcccactgg ggccagggaa ccctggtcac tgtctcctca   360

SEQ ID NO: 328              moltype = AA  length = 120
FEATURE                     Location/Qualifiers
REGION                      1..120
                            note = The Description of the artificial sequence: amino
                             acid sequence of VH excluding signal sequence of MOG 478
source                      1..120
                            mol_type = protein
                            organism = synthetic construct
SEQUENCE: 328
EVQLVQSGAE VKKPGSSVKV SCKASGGTFS RYAISWVRQA PGQGLEWMGG IIPMFATANY    60
AQKFQARVTI TADETTSTAY MELSSLRSED TGVYYCARDW AVAAMGFAHW GQGTLVTVSS   120

SEQ ID NO: 329              moltype = DNA  length = 324
FEATURE                     Location/Qualifiers
misc_feature                1..324
                            note = The Description of the artificial sequence: base
                             sequence encoding VL excluding signal sequence of MOG 478
source                      1..324
                            mol_type = other DNA
                            organism = synthetic construct
SEQUENCE: 329
gaaatagtga tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgat caccttcggc   300
caagggacac gactggagat taaa                                          324

SEQ ID NO: 330              moltype = AA  length = 108
FEATURE                     Location/Qualifiers
REGION                      1..108
                            note = The Description of the artificial sequence: amino
                             acid sequence of VL excluding signal sequence of MOG 478
source                      1..108
                            mol_type = protein
                            organism = synthetic construct
SEQUENCE: 330
EIVMTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPITFG QGTRLEIK                108

SEQ ID NO: 331              moltype = DNA  length = 357
FEATURE                     Location/Qualifiers
misc_feature                1..357
                            note = The Description of the artificial sequence: base
                             sequence encoding VH excluding signal sequence of MOG 470
source                      1..357
                            mol_type = other DNA
                            organism = synthetic construct
SEQUENCE: 331
caggtgcagc tggtggagtc tgggggaggc ttggtacagc cggggggtc cctgagactc     60
tcctgtgcag cctctggatt cacctttagc agctatgcca tgaactgggt ccgccaggct   120
```

-continued

```
ccagggaagg ggctggagtg ggtctcagct attagtggta gtggtggtag cacatactac    180
gcagactccg tgaagggccg gttcaccatc tccagagaca attccaagaa cacgctgtat    240
ctgcaagtga acagcctgag agccgaggac acggccgttt attactgtgc gagagactac    300
ggtggtatct cccccttttga ctactggggc cagggaaccc tggtcaccgt ctcctca      357

SEQ ID NO: 332          moltype = AA   length = 119
FEATURE                 Location/Qualifiers
REGION                  1..119
                        note = The Description of the artificial sequence: amino
                         acid sequence of VH excluding signal sequence of MOG 470
source                  1..119
                        mol_type = protein
                        organism = synthetic construct
SEQUENCE: 332
QVQLVESGGG LVQPGGSLRL SCAASGFTFS SYAMNWVRQA PGKGLEWVSA ISGSGGSTYY    60
ADSVKGRFTI SRDNSKNTLY LQVNSLRAED TAVYYCARDY GGISPFDYWG QGTLVTVSS     119

SEQ ID NO: 333          moltype = DNA   length = 321
FEATURE                 Location/Qualifiers
misc_feature            1..321
                        note = The Description of the artificial sequence: base
                         sequence encoding VL excluding signal sequence of MOG 470
source                  1..321
                        mol_type = other DNA
                        organism = synthetic construct
SEQUENCE: 333
gaaatagtga tgacacagtc tccagccacc ctgtctttgt ctccagggga aagagccacc    60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag actggagcct    240
gaagattttg cagtgtatta ctgtcagcag tatggtagct caccgtacac ttttggccag    300
gggacacgac tggagattaa a                                              321

SEQ ID NO: 334          moltype = AA   length = 107
FEATURE                 Location/Qualifiers
REGION                  1..107
                        note = The Description of the artificial sequence: amino
                         acid sequence of VL excluding signal sequence of MOG 470
source                  1..107
                        mol_type = protein
                        organism = synthetic construct
SEQUENCE: 334
EIVMTQSPAT LSLSPGERAT LSCRASQSVS SYLAWYQQKP GQAPRLLIYD ASNRATGIPA    60
RFSGSGSGTD FTLTISRLEP EDFAVYYCQQ YGSSPYTFGQ GTRLEIK                  107

SEQ ID NO: 335          moltype = DNA   length = 366
FEATURE                 Location/Qualifiers
misc_feature            1..366
                        note = The Description of the artificial sequence: base
                         sequence encoding VH excluding signal sequence of MOG 418
source                  1..366
                        mol_type = other DNA
                        organism = synthetic construct
SEQUENCE: 335
caggtgtagc tggtgcagtc tgggggaggc ctggtcaagc ctgggggggtc cctgagactc    60
tcctgtgcag cctctggatt cacccttcagt agctatagca tgcactgggt ccgccaggct   120
ccagggaagg ggctggagtg ggtctcatcc attagtcata gtagtagtta catatcctac    180
gcagactcag tgaagggccg attcaccatc tccagagaca cgccaagaa ttcactgtat     240
ctgcaaatga acagcctgag agccgaggac acggctgtgt attactgtgc gaaagggtat    300
tacgatatt tgactggttc tcttctttgac tactggggcc agggaaccct ggtcaccgtc    360
tcctca                                                               366

SEQ ID NO: 336          moltype = AA   length = 122
FEATURE                 Location/Qualifiers
REGION                  1..122
                        note = The Description of the artificial sequence: amino
                         acid sequence of VH excluding signal sequence of MOG 418
source                  1..122
                        mol_type = protein
                        organism = synthetic construct
SEQUENCE: 336
QVYLVQSGGG LVKPGGSLRL SCAASGFTFS SYSMHWVRQA PGKGLEWVSS ISHSSSYISY    60
ADSVKGRFTI SRDNAKNSLY LQMNSLRAED TAVYYCAKGY YDILTGSLFD YWGQGTLVTV    120
SS                                                                   122

SEQ ID NO: 337          moltype = DNA   length = 321
FEATURE                 Location/Qualifiers
misc_feature            1..321
                        note = The Description of the artificial sequence: base
```

```
                    sequence encoding VL excluding signal sequence of MOG 418
source              1..321
                    mol_type = other DNA
                    organism = synthetic construct
SEQUENCE: 337
gaaattgtgt tgacgcagtc tccagccacc ctgtctttgt ctccagggga aagagccacc   60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag actggagcct  240
gaagattttg cagtgtatta ctgtcagcag tatggtagct caccattcac tttcggccct  300
gggaccaaag tggatatcaa a                                            321

SEQ ID NO: 338      moltype = AA  length = 107
FEATURE             Location/Qualifiers
REGION              1..107
                    note = The Description of the artificial sequence: amino
                    acid sequence of VL excluding signal sequence of MOG 418
source              1..107
                    mol_type = protein
                    organism = synthetic construct
SEQUENCE: 338
EIVLTQSPAT LSLSPGERAT LSCRASQSVS SYLAWYQQKP GQAPRLLIYD ASNRATGIPA   60
RFSGSGSGTD FTLTISRLEP EDFAVYYCQQ YGSSPFTFGP GTKVDIK                107

SEQ ID NO: 339      moltype = AA  length = 146
FEATURE             Location/Qualifiers
source              1..146
                    mol_type = protein
                    organism = Homo sapiens
SEQUENCE: 339
MNLGLSLIFL ALILKGVQCQ VQLQQSGAGL LKPSETLSLT CAVSGGSFSG YYWTWIRQRP   60
GKGLEWIGEI NHRGSTDYNP SLKSRVTMSI DTSKSQFSLN LKSVTAADTA VYYCARAAWG  120
SCYDGTCYPA EYFQYWGQGT LVTVSS                                       146

SEQ ID NO: 340      moltype = AA  length = 130
FEATURE             Location/Qualifiers
source              1..130
                    mol_type = protein
                    organism = Homo sapiens
SEQUENCE: 340
MKLPVRLLVL MFWIPASSSQ SALTQPASVS GSPGQSITIS CTGTSRDVGG YNYVSWYQQH   60
PGKAPKLMIY DVNNRPSGVS NRFSGSKSGN TASLTISGLQ AEDEADYFCS SYTSSSTPVV  120
FGGGTKLTVL                                                         130

SEQ ID NO: 341      moltype = AA  length = 141
FEATURE             Location/Qualifiers
source              1..141
                    mol_type = protein
                    organism = Homo sapiens
SEQUENCE: 341
MNLGLSLIFL ALILKGVQCQ VQLQESGPGL VKSSETLSLT CAVSGHSISS AYYWGWIRQP   60
PGKGLEWLGS IYHSGNTYYN PSLKSRVTIS VDTSKNQFSL RLTSVTAADT AVYYCARGRG  120
YSGYDSGMDV WGQGTTVTVS S                                            141

SEQ ID NO: 342      moltype = AA  length = 129
FEATURE             Location/Qualifiers
source              1..129
                    mol_type = protein
                    organism = Homo sapiens
SEQUENCE: 342
MKLPVRLLVL MFWIPASSSS YVLTQPPSAS GTPGQRVTIS CSGTSSNIGI NSVNWYQQLP   60
GMAPKLVIYS RDQRPSGVPD RFSGSQSGTS ASLAINGLQS EDEADYWCST WDDSLNGWVF  120
GGGTKLTVL                                                          129

SEQ ID NO: 343      moltype = AA  length = 138
FEATURE             Location/Qualifiers
source              1..138
                    mol_type = protein
                    organism = Homo sapiens
SEQUENCE: 343
MNLGLSLIFL ALILKGVQCQ VQLVQSGAEV KKPGASVKVS CQASGYTFTG DYIHWVRQAP   60
GQGLEYLGWI NPDRGFTYYT QKFQGRVTMT RDTSSNTAYM ELSSLRSDDT AMYYCTRENP  120
RAYFFDLWGQ GTLVTVSS                                                138

SEQ ID NO: 344      moltype = AA  length = 127
FEATURE             Location/Qualifiers
source              1..127
                    mol_type = protein
                    organism = Homo sapiens
```

```
SEQUENCE: 344
MKLPVRLLVL MFWIPASSSE IVLTQSPGTL SLSPGERATL SCRASQSISG SYVTWYQQKP      60
GQAPRLLIYA TSNRAIGIPD KFSGGGSGRD FTLTINRLEP EDFAVYYCQQ SVSSPYTFGQ     120
GTKVEIK                                                              127

SEQ ID NO: 345          moltype = AA   length = 137
FEATURE                 Location/Qualifiers
source                  1..137
                        mol_type = protein
                        organism = synthetic construct
SEQUENCE: 345
MYRMQLLSCI ALSLALVTNS QVQLVESGGG LVQTGGSLRL SCAASGSMFS TMGWFRQAPG      60
NQRELVAIMS SGGTANYADS VKGRFTISGD NVKNTVTLQM NSLNPEDTAV YYCRFTGWVK     120
SSFSTYWGQG TQVTVSS                                                   137

SEQ ID NO: 346          moltype = AA   length = 245
FEATURE                 Location/Qualifiers
source                  1..245
                        mol_type = protein
                        organism = Rattus norvegicus
SEQUENCE: 346
MAGVWSLSLP SCLLSLLLLL QLSRSYAGQF RVIGPGHPIR ALVGDEAELP CRISPGKNAT      60
GMEVGWYRSP FSRVVHLYRN GKDQDAEQAP EYRGRTELLK ESIGEGKVAL RIQNVRFSDE     120
GGYTCFFRDH SYQEEAAVEL KVEDPFYWIN PGVLALIALV PMLLLQVSVG LVFLFLQHRL     180
RGKLRAEVEN LHRTFDPHFL RVPCWKITLF VIVPVLGPLV ALIICYNWLH RRLAGQFLEE     240
LRNPF                                                                245

SEQ ID NO: 347          moltype = AA   length = 388
FEATURE                 Location/Qualifiers
source                  1..388
                        mol_type = protein
                        organism = synthetic construct
SEQUENCE: 347
MAGVWSLSLP SCLLSLLLLL QLSRSYAGQF RVIGPGHPIR ALVGDEAELP CRISPGKNAT      60
GMEVGWYRSP FSRVVHLYRN GKDQDAEQAP EYRGRTELLK ESIGEGKVAL RIQNVRFSDE     120
GGYTCFFRDH SYQEEAAVEL KVEDPFYWSR ADYKDDDDKT SDKTHTCPPC PAPELLGGPS     180
VFLFPPKPKD TLMISRTPEV TCVVVDVSHE DPEVKFNWYV DGVEVHNAKT KPREEQYNST     240
YRVVSVLTVL HQDWLNGKEY KCKVSNKALP APIEKTISKA KGQPREPQVY TLPPSRDELT     300
KNQVSLTCLV KGFYPSDIAV EWESNGQPEN NYKTTPPVLD SDGSFFLYSK LTVDKSRWQQ     360
GNVFSCSVMH EALHNHYTQK SLSLSPGK                                       388

SEQ ID NO: 348          moltype = AA   length = 378
FEATURE                 Location/Qualifiers
source                  1..378
                        mol_type = protein
                        organism = synthetic construct
SEQUENCE: 348
MAGVWSLSLP SCLLSLLLLL QLSRSYAGQF RVIGPGHPIR ALVGDEAELP CRISPGKNAT      60
GMEVGWYRSP FSRVVHLYRN GKDQDAEQAP EYRGRTELLK ESIGEGKVAL RIQNVRFSDE     120
GGYTCFFRDH SYQEEAAVEL KVEDPFYWGT LEVLFQGPMS PILGYWKIKG LVQPTRLLLE     180
YLEEKYEEHL YERDEGDKWR NKKFELGLEF PNLPYYIDGD VKLTQSMAII RYIADKHNML     240
GGCPKERAEI SMLEGAVLDI RYGVSRIAYS KDFETLKVDF LSKLPEMLKM FEDRLCHKTY     300
LNGDHVTHPD FMLYDALDVV LYMDPMCLDA FPKLVCFKKR IEAIPQIDKY LKSSKYIAWP     360
LQGWQATFGG GDHPPKSD                                                  378

SEQ ID NO: 349          moltype = AA   length = 247
FEATURE                 Location/Qualifiers
source                  1..247
                        mol_type = protein
                        organism = Mus musculus
SEQUENCE: 349
MACLWSFSWP SCFLSLLLLL LLQLSCSYAG QFRVIGPGYP IRALVGDEAE LPCRISPGKN      60
ATGMEVGWYR SPFSRVVHLY RNGKDQDAEQ APEYRGRTEL LKETISEGKV TLRIQNVRFS     120
DEGGYTCFFR DHSYQEEAAM ELKVEDPFYW VNPGVLTLIA LVPTILLQVS VGLVFLFLQH     180
RLRGKLRAEV ENLHRTFDPH FLRVPCWKIT LFVIVPVLGP LVALIICYNW LHRRLAGQFL     240
EELRNPF                                                              247

SEQ ID NO: 350          moltype = AA   length = 247
FEATURE                 Location/Qualifiers
source                  1..247
                        mol_type = protein
                        organism = Macaca fascicularis
SEQUENCE: 350
MASLSRPSLP SCLCSFLLLL LLQVSSSYAG QFRVIGPRQP IRALVGDEVE LPCRISPGKN      60
ATGMEVGWYR PPFSRVVHLY RNGRDQDGEQ APEYRGRTEL LKDAIGEGKV TLRIRNVRFS     120
DEGGFTCFFR DHSYQEEAAI ELKVEDPFYW VSPAVLVLLA VLPVLLQIT VGLVFLCLQY     180
RLRGKLRAEI ENLHRTFDPH FLRVPCWKIT LFVIVPVLGP LVALIICYNW LHRRLAGQFL     240
EELRNPF                                                              247
```

```
SEQ ID NO: 351          moltype = AA   length = 247
FEATURE                 Location/Qualifiers
source                  1..247
                        mol_type = protein
                        organism = Homo sapiens
SEQUENCE: 351
MASLSRPSLP  SCLCSFLLLL  LLQVSSSYAG  QFRVIGPRHP  IRALVGDEVE  LPCRISPGKN   60
ATGMEVGWYR  PPFSRVVHLY  RNGKDQDGDQ  APEYRGRTEL  LKDAIGEGKV  TLRIRNVRFS  120
DEGGFTCFFR  DHSYQEEAAM  ELKVEDPFYW  VSPGVLVLLA  VLPVLLLQIT  VGLVFLCLQY  180
RLRGKLRAEI  ENLHRTFDPH  FLRVPCWKIT  LFVIVPVLGP  LVALIICYNW  LHRRLAGQFL  240
EELRNPF                                                                247

SEQ ID NO: 352          moltype = AA   length = 879
FEATURE                 Location/Qualifiers
source                  1..879
                        mol_type = protein
                        organism = synthetic construct
SEQUENCE: 352
MELAALCRWG  LLLALLPPGA  ASTQVCTGTD  MKLRLPASPE  THLDMLRHLY  QGCQVVQGNL   60
ELTYLPTNAS  LSFLQDIQEV  QGYVLIAHNQ  VRQVPLQRLR  IVRGTQLFED  NYALAVLDNG  120
DPLNNTTPVT  GASPGGLREL  QLRSLTEILK  GGVLIQRNPQ  LCYQDTILWK  DIFHKNNQLA  180
LTLIDTNRSR  ACHPCSPMCK  GSRCWGESSE  DCQSLTRTVC  AGGCARCKGP  LPTDCCHEQC  240
AAGCTGPKHS  DCLACLHFNH  SGICELHCPA  LVTYNTDTFE  SMPNPEGRYT  FGASCVTACP  300
YNYLSTDVGS  CTLVCPLHNQ  EVTAEDGTQR  CEKCSKPCAR  VCYGLGMEHL  REVRAVTSAN  360
IQEFAGCKKI  FGSLAFLPES  FDGDPASNTA  PLQPEQLQVF  ETLEEITGYL  YISAWPDSLP  420
DLSVFQNLQV  IRGRILHNGA  YSLTLQGLGI  SWLGLRSLRE  LGSGLALIHH  NTHLCFVHTV  480
PWDQLFRNPH  QALLHTANRP  EDECVGEGLA  CHQLCARGHC  WGPGPTQCVN  CSQFLRGQEC  540
VEECRVLQGL  PREYVNARHC  LPCHPECQPQ  NGSVTCFGPE  ADQCVACAHY  KDPPFCVARC  600
PSGVKPDLSY  MPIWKFPDEE  GACQPCPINC  THSCVDLDDK  GCPAEQRASG  TLEVLFQGPM  660
SPILGYWKIK  GLVQPTRLLL  EYLEEKYEEH  LYERDEGDKW  RNKKFELGLE  FPNLPYYIDG  720
DVKLTQSMAI  IRYIADKHNM  LGGCPKERAE  ISMLEGAVLD  IRYGVSRIAY  SKDFETLKVD  780
FLSKLPEMLK  MFEDRLCHKT  YLNGDHVTHP  DFMLYDALDV  VLYMDPMCLD  AFPKLVCFKK  840
RIEAIPQIDK  YLKSSKYIAW  PLQGWQATFG  GGDHPPKSD                          879
```

The invention claimed is:

1. A nucleic acid molecule comprising a nucleotide sequence encoding an antibody which binds to myelin oligodendrocyte glycoprotein (MOG) or an antibody fragment thereof, wherein the antibody comprises an antibody in which the amino acid sequences of complementarity determining regions (CDRs) 1 to 3 of the heavy chain variable region (VH) of the antibody comprise the amino acid sequences of SEQ ID NOs: 4, 5 and 6, respectively, and in which the amino acid sequences of CDRs 1 to 3 of the light chain variable region (VL) of the antibody comprise the amino acid sequences of SEQ ID NOs: 10, 11 and 12, respectively.

2. The nucleic acid molecule according to claim 1, wherein the antibody comprises an antibody in which the amino acid sequence of VH comprises the amino acid sequence of SEQ ID NO: 3 and in which the amino acid sequence of VL comprises the amino acid sequence of SEQ ID NO: 9.

3. The nucleic acid molecule according to claim 1, wherein the antibody fragment is selected from the group consisting of Fab, Fab', F(ab')2, a single chain antibody (scFv), a dimerized V region (diabody), a disulfide-stabilized V region (dsFv), VHH, and a peptide comprising CDR.

4. The nucleic acid molecule according to claim 1, wherein the antibody is selected from the group consisting of a chimeric antibody, a humanized antibody, and a human antibody.

5. A vector comprising the nucleic acid molecule according to claim 1.

6. The vector according to claim 5, wherein the vector is an expression vector.

7. A transformant cell comprising the vector according to claim 5.

8. A transformant cell comprising the vector according to claim 6.

9. The transformant cell according to claim 7, wherein the cell is an *E. coli* cell, a yeast cell, an insect cell, or an animal cell.

10. The transformant cell according to claim 8, wherein the cell is an *E. coli* cell, a yeast cell, an insect cell, or an animal cell.

11. A method for producing an antibody which binds to MOG or an antibody fragment thereof, comprising culturing the transformant cell according to claim 9 and collecting the antibody or the antibody fragment from a culture solution.

12. A method for producing an antibody which binds to MOG or an antibody fragment thereof, comprising culturing the transformant cell according to claim 10 and collecting the antibody or the antibody fragment from a culture solution.

* * * * *